(12) United States Patent
Shen et al.

(10) Patent No.: US 10,285,989 B2
(45) Date of Patent: May 14, 2019

(54) PYRIMIDINONE AMIDE COMPOUNDS AS PDE2 INHIBITORS

(71) Applicant: Merck Sharp & Dohme Corp., Rahway, NJ (US)

(72) Inventors: Dong-Ming Shen, Edison, NJ (US); Deping Wang, Furlong, PA (US); XiaoXia Qian, New York, NY (US); Bart Harper, New York, NY (US); Meng Yang, Westfield, NJ (US); Yingjian Bo, Beijing (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/573,858

(22) PCT Filed: May 10, 2016

(86) PCT No.: PCT/US2016/031559
§ 371 (c)(1),
(2) Date: Nov. 14, 2017

(87) PCT Pub. No.: WO2016/186888
PCT Pub. Date: Nov. 24, 2016

(65) Prior Publication Data
US 2018/0256575 A1    Sep. 13, 2018

(30) Foreign Application Priority Data

May 15, 2015 (WO) ................ PCT/CN2015/079091

(51) Int. Cl.
| | | |
|---|---|---|
| *C07D 403/12* | (2006.01) | |
| *A61K 31/513* | (2006.01) | |
| *C07D 401/12* | (2006.01) | |
| *C07D 403/04* | (2006.01) | |
| *C07D 405/12* | (2006.01) | |
| *C07D 239/38* | (2006.01) | |
| *C07D 239/42* | (2006.01) | |
| *C07D 239/52* | (2006.01) | |
| *C07D 487/04* | (2006.01) | |
| *A61P 25/28* | (2006.01) | |
| *A61P 25/22* | (2006.01) | |
| *A61P 25/18* | (2006.01) | |
| *A61P 25/16* | (2006.01) | |
| *A61P 25/06* | (2006.01) | |

(52) U.S. Cl.
CPC ............ *A61K 31/513* (2013.01); *A61P 25/06* (2018.01); *A61P 25/16* (2018.01); *A61P 25/18* (2018.01); *A61P 25/22* (2018.01); *A61P 25/28* (2018.01); *C07D 239/38* (2013.01); *C07D 239/42* (2013.01); *C07D 239/52* (2013.01); *C07D 401/12* (2013.01); *C07D 403/04* (2013.01); *C07D 403/12* (2013.01); *C07D 405/12* (2013.01); *C07D 487/04* (2013.01)

(58) Field of Classification Search
CPC .................................................. A61K 31/513
See application file for complete search history.

(56) References Cited

U.S. PATENT DOCUMENTS

| | | |
|---|---|---|
| 5,312,823 A | 5/1994 | Petersen et al. |
| 6,573,263 B2 | 6/2003 | Niewohner et al. |
| 8,598,155 B2 | 12/2013 | Helal et al. |
| 8,680,116 B2 | 3/2014 | DeLeon et al. |
| 2004/0180944 A1 | 9/2004 | Bunnage et al. |
| 2007/0135457 A1 | 6/2007 | Beyer et al. |
| 2009/0253677 A1 | 10/2009 | Beaulieu et al. |
| 2012/0022045 A1 | 1/2012 | Venkatraman et al. |
| 2012/0214791 A1 | 8/2012 | Helal et al. |

FOREIGN PATENT DOCUMENTS

| | | |
|---|---|---|
| EP | 1097706 A1 | 5/2001 |
| EP | 1097707 A1 | 5/2001 |
| WO | WO2005061497 | 12/2003 |
| WO | WO2005041957 | 10/2004 |
| WO | WO2006024640 | 3/2006 |
| WO | WO2006072615 | 7/2006 |
| WO | WO2006127530 A2 | 11/2006 |
| WO | WO2007097931 A2 | 8/2007 |
| WO | WO2008002671 | 1/2008 |
| WO | WO2009016498 | 2/2009 |
| WO | WO2010136493 | 12/2010 |
| WO | WO2012114222 | 8/2012 |
| WO | WO2013034758 | 9/2012 |
| WO | WO2013034761 | 9/2012 |
| WO | WO2012168817 | 12/2012 |

(Continued)

OTHER PUBLICATIONS

Ahlstrom et al., Inactivation of Atrial Natriuretic Factor-Stimulated, Biochemical Pharmacology, 2000, 1133-1139, 59.

(Continued)

*Primary Examiner* — Paul V Ward
(74) *Attorney, Agent, or Firm* — Sylvia A. Ayler; John C. Todaro

(57) ABSTRACT

The present invention is directed to pyrimidinone amide compounds which may be useful as therapeutic agents for the treatment of central nervous system and/or peripheral disorders associated with phosphodiesterase 2 (PDE2). The present invention also relates to the use of such compounds for treating neurological and psychiatric disorders, such as schizophrenia, psychosis, Alzheimer's, cognitive impairment, anxiety, depression, migraines, or Huntington's disease, Parkinson's disease, Parkinson's disease dementia (PDD), and other diseases associated with striatal hypofunction or basal ganglia dysfunction.

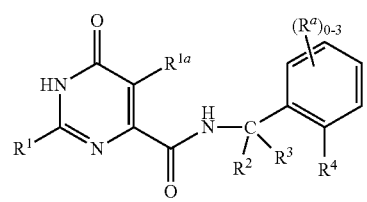

18 Claims, No Drawings

(56) References Cited

FOREIGN PATENT DOCUMENTS

| WO | WO201300924 | 1/2013 |
|---|---|---|
| WO | WO2013034755 | 3/2013 |
| WO | WO2013098373 | 7/2013 |
| WO | 2013161913 | 10/2013 |
| WO | WO2014010732 | 1/2014 |
| WO | WO2014019979 | 2/2014 |
| WO | WO2014139983 | 9/2014 |
| WO | WO2015012328 | 1/2015 |
| WO | WO2015060368 | 4/2015 |
| WO | WO2005063723 | 7/2017 |

OTHER PUBLICATIONS

Arulomozhi et al., Migraine: Current Therapeutic Targets and Future Avenues, Current Vascular Pharmacology, 2006, 117-128, 4.

Beavo et al., Cyclic GMP as Substrate and Regulator of Cyclic Nucleotide Phosphodiesterases (PDEs), Rev. Physio Biochem Pharm, 1999, 67-104, 135.

Bernard et al., PDE2 Is a Novel Target for Attenuating Tumor Formation in a Mouse Model of UVB-Induced Skin Carcinogenesis, Plos One, 2014, 1-8, 9.

Biftu et al., Omarigliptin (MK-3102): A Novel Long-Acting DPP-4 Inhibitor for Once-Weekly Treatment of Type 2 Diabetes, J. of Medicinal Chemistry, 2014, 3205-3212, 57.

Boess et al., Inhibition of phosphodiesterase 2 increases neuronal cGMP, synaptic plasticity and memory, Neuropharmacology, 2004, 1081-92, 47.

Brandon et al., Potential CNS Applications for, Annual Reports in Medicinal Chemistry, 2007, 3-11, 42.

Bubb et al., Inhibition of Phosphodiesterase 2 Augments cGMP and, Circulation, 2014, 496-507, 268.

Clark, Rapid Calculation of Polar Molecular Surface Area and Its Application to the Prediction of Transprt Phenomena. 2. Prediction of Blood-Brain Barrier Penetration, J. of Pharmaceutical Sciences, 1999, 815-821, 88.

Colman, Abkommlinge der Cinchomeronsaure II, Berichte der deutschen chemischen Gesellschaft, 1902, 2831-2852, 35.

Cote et al., Comparative Involvement of Cyclic Nucleotide, Endocrinology, 1999, 3594-3601, 140.

Demaria et al., Highlights of the Year in JACC 2013, j. aMER. cOLL. cARD, 2014, 570-602, 63, (6).

Desai et al., Integration of in Silico and in Vitro Tools for Scaffold Optimization During Drug Discovery: Predicting P-Glycoprotein Efflux, Molecular Pharmaceutics, 2013, 1249-1261, 10.

Dickinson et al., Activation of cGMP-stimulated phosphodiesterase by nitroprusside limits, Biochem J., 1997, 371-377, 323.

Ding et al., Protective effects of phosphodiesterase 2 inhibitor on depression- and -Anxiety-Like Behaviors: Involvement of antioxidant and anti-apotoic Mechanisms, Behaviorual Brain Research, 2014, 150-158, 268.

Doan et al., Passive Permeability and P-Glycoprotein-Mediated Efflux Differentiate Central Nervous System (CNS) and Non-CNS Marketed Drugs, J. Pharmacology and Experimental Therapeutics, 2002, 1029-1037, 303.

Domek-Lopacinska et al., The Effect of Selective Inhibition of Cyclic GMP Hydrolyzing Phosphodiesterases 2 and 5 on Learning and Memory Processes and Nitric Oxide Synthase Activity, Brain Research, 2008, 68-77, 1216.

Ducrot et al, CoMFA and CoMSIA 3D-Quantitative Structure-Activity Relationship Model on Benzodiaepine Derivatives, Inhibitors of Phosphodiesterase IV, J. of Computer Aided Molecular Designs, 2001, 767-785, 15.

Duran et al., The NO cascade, eNOS Location, and Microvascular Permeability, Cardiovascular Research, 2010, 254-261, 87.

Favot et al., VEGF-Induced HUVEC Migration and Proliferation, Schattauer GmbH Stuttgart, 2003, 3443-343, 90.

Gergega et al., Systematic Effect of Benzo-Annelation on Oxo-Hydroxy Tautomerism of Heterocyclic, J. Phys. Chem A., 2007, 4934-4943, 111.

Giuliano et al., Correction to Tautomerism in 4-Hydroxypyrimidine, S-Methyl-2-thiouracil, and 2-Thiouracil, The Journal of Physical Chemistry A, 2011, 8178-8179, 115.

Giuliano et al., Tautomerism in 4-Hydroxypyrimidine, S-Methyl-2-thiouracil, and 2-Thiouracil, J. Phys. Chem. A, 2010, 12725-12730, 114.

Ha et al., Mini Review on Molecular Modeling of P-Glycoprotein(Pgp), Current Topics in Medicinal Chemistry, 2007, 1525-1529, 7.

Haynes et al., Erythro-9-(2-Hydroxy-3-Nonyl) Adenine Inhibits Cyclic-3',5' Guanosine Monophosphate-Stimulated Phosphodiesterase to Reverse Hypoxic Pulmonary Vasoconstriction in the Perfused Rat Lung, The J. of Pharmacology, 1996, 752-757, 276.

He et al., Utility of Unbound Plasma Drug Levels and P-Glycoprotein Transport Data in Prediction of Central Nervous System Exposure, Xenobiotica, 2009, 687-693, 39.

Herring et al., NO-cGMP Pathway Increases the Hyperpolarisation-Activated Current ,I, and Heart Rate During Adrenergic Stimulation, Cardiovascular Research, 2001, 446-453, 52.

Hiramoto et al., Role of Phosphodiesterase 2 in Growth and Invasion of HUman Maligant Melanoma, Cellular Signaling, 2014, 1807-1817, 26.

Hochman et al., Establishment of P-Glycoprotein Structure Transport Realtionships to Optimize CNS exposure of CNS Drug Discovery, Blood Brain Barriers in Drug Discovery, 2015, 113-124, Chaper 6.

Huang et al., A Fluroescence Polarization Assay for Cyclic Nucleotide Phosphodiesterases, J. of Biomolecular Screening, 2002, pp. 215-222, 7.

Jorgensen et al., Selective Inhibitors of PDE2, PDE9, and PDE10: Modulators of Activity of the Central Nervous System, Annual Reports in Medicinal Chemistry, 2013, pp. 37-55, 48.

Keravis et al., Cyclic Nucleotide Hydrolysis in Bovine Aortic Endothelial Cells in Culture: Differential Regulation in Cobblestone and Spindle Phenotypes, J. Vasc. Res, 2000, 235-249, 37.

Kheifets et al., Structure and Amide-Amide Tautomerism of 4-Hydroxypyrimidines. Determination of the Tautomeric Composition by 13C NMR Spectroscopy, Russ. J. of Organic Chemistry, 2000, 1373-1387, 36, 9.

Lieberman et al., Effectiveness of Antipsychotic Drugs in Patients with Chronic Schizophrenia, New England J. of Medicine, Sep. 22, 2005, pp. 1209-1223, 353, US.

Lopez et al., Solution and solid state (CPMAS) NMR Studies of the Tautomerism of Six-Membered Heterocyclic Compounds Related to 2-Pyridones, Spectroscopy, 2000, pp. 121-126, 14.

Masood et al., Anxiolytic Effects of Phosphodiesterase-2 Inhibitors Associated with Increased cGMP Signaling, J. of Pharmacology, 2009, 690-699, 331.

Masood et al., Reversal of Oxidative Stress-Induced Anxiety by Inhibition of Phosphodiesterase-2 in Mice, J. of Pharmacology and Experimental Therapeutics, 2008, 369-379, 326.

Michie et al., Rapid Regulation of PDE-2 and PDE-4 Cyclic AMP Phosphodiesterase Activity Folloiwng Ligation of the T Cell Antigen Receptor on Thymocytes: Analysis Using theSelctive Inhibitors Erythro-9-(2-Hydroxy-3Nonyl)-Adenine (EHNA) and Rolipram, Cell Signal, 1996, 97-110, 8.

Morita et al., Characterization of Phosphodiesterase 2A in Human Malignant Melanoma PMP Cells, Oncology Reports, 2013, 1275-1284, 29.

Mosser et al., Automation of In Vitro Dose-Inhibition Assays Utlizing the Tecan Genesis and an Integratd Software Package to Support the Drug Discovery Process, JALA, 2003, pp. 54-63, 8, Sage Publications.

Netherton et al., Vascular Endothelial Cell Cyclic Nucleotide phosphodiesterases and Regulated Cell Migration: IMplications in Angiogenesis, Molecular Pharmacology, 2005, 263-272, 67.

P. C. Tfelt-Hansen et al., One Hundred Years of Migraine Research: Major Clinical and, Headache, 2011, 752-778, 51.

Paget et al., Synthesis and Antibacterial, Biorganic & Medicinal Chemistry Letters 13, 2003, 4173-4177, 13.

(56) References Cited

OTHER PUBLICATIONS

Plummer et al., Discovery of Poten, Selective, Bioavailable Phosphodiesterase 2 (PDE2) Inhibitors Active in an Osteoarthritis Pain Model, Part I: Transformation of Selective Pyrazolodiazepinone Phosphodiesterase 4 (PDE4) Inhibitors into Selective PDE2 Inhibitors, Biorganic & Medicinal Chemistry Letters, 2013, 3438-3442, 23.

Plummer et al., Discovery of potent selective bioavailable phosphodiesterase, Bioorganic & Medicinal Chemistry Letters, 2013, 3443-3447, 23.

Reierson et al., Repeated antidepressant therapy increases cyclic GMP signaling, Neurosci Letter, 2009, 149-153, 466 (3).

Rivet-Bastide et al., cGMP-stimulated Cyclic Nucleotide Phosphodiesterase Regulates the Basal, J. Clin. Invest, 1997, 2710-2718, 99.

Sadhu et al., Differential Expression of the Cyclic GMP-Stimulated Phosphodiesterase PDE2A in HUman Venous and Capillary Endothelial Cells, J. of Histochemistry & Cytochemistry, 1999, 895-905, 47.

Sanchez et al., Gas-Phase Tautomeric Equilibrium of 4-Hydroxypyrimidine, J. Am. Chem Soc., 2007, 6287-6290, 129.

Savai et al., Targeting Cancer with Phosphodiesterase Inhibitors, Expert Opinion, 2010, 117-131, 19.

Surapisitchat et al., Differential Regulation of Endothelial Cell Permeability by cGMP via Phosphodiesterases 2 and 3, Circulation Research, 2007, 811-818, 101.

Suvrana et al., Hydrolysis of N-Methyl-D-aspartate Receptor-Stimulated cAMP, J. of Pharmacology, 2002, 249-256, 302.

Van Staveren et al., The effects of phosphodiesterase inhibition on cyclic GMP and cyclic, Brain Research, 2001, 275-286, 888.

Vandecasteele, Cyclic GMP regulation of the L-type Ca2+ channel current, J. of Physiology, 2001, 329-340, 533.

Velardez et al., Role of Phosphodiesterase and Protein Kinase G on Nitric Oxide-Induced Inhibition of Prolactin Relase from the Rat Anterior Pituitary, Europe J. of Endocrinology, 2000, 279-284, 143.

Wakabayashi et al., Involvement of Phosphodiesterase Isozymes in Osteoblastic, J. of Bone and Mineral Research, 2002, 249-253, 17.

PYRIMIDINONE AMIDE COMPOUNDS AS PDE2 INHIBITORS

CROSS REFERENCE TO RELATED APPLICATIONS

This application is the National Stage of International Application No. PCT/US2016/0031559 filed on May 10, 2016, which claims the benefit under International Application PCT/CN2015/079091 filed on May 15, 2015.

FIELD OF THE INVENTION

The invention relates generally to compounds which act as inhibitors of the phosphodiesterase (PDE) 2 enzyme, compositions and therapeutic uses thereof.

BACKGROUND OF THE INVENTION

Schizophrenia is a debilitating disorder affecting the psychic and motor functions of the brain. It is typically diagnosed in individuals in their early to mid-twenties and symptoms include hallucinations and delusions or at the other extreme, anhedonia or social withdrawal. Across the spectrum, the symptoms are indicative of cognitive impairment and functional disabilities. Notwithstanding improvements in antipsychotic treatments, current therapies, including typical (haloperidol) and atypical (clozapine or olanzapine) antipsychotics, have been less than acceptable and result in an extremely high rate of noncompliance or discontinuation of medication. Dissatisfaction with therapy is attributed to lack of efficacy or intolerable and unacceptable side effects. The side effects have been associated with significant metabolic, extrapyramidal, prolactic and cardiac adverse events. See, Lieberman et al., N. Engl. J. Med. (2005) 353:1209-1223.

While multiple pathways are believed to be involved with the pathogenesis of schizophrenia leading to psychosis and cognition deficits, much attention has focused on the role of glutamate/NMDA dysfunction associated with cyclic guanosine monophosphate (cGMP) levels and the dopaminergic receptors associated with cyclic adenosine monophosphate (cAMP). These ubiquitous secondary messengers are responsible for altering the function of many intracellular proteins. Cyclic AMP is thought to regulate the activity of cAMP-dependent protein kinase (PKA), which in turn phosphorylates and regulates many types of proteins including ion channels, enzymes and transcription factors. Similarly, cGMP is also responsible for downstream regulation of kinases and ion channels.

One pathway for affecting the levels of cyclic nucleotides, such as cAMP and cGMP, is to alter or regulate the enzymes that degrade these secondary messengers, known as 3', 5'-cyclic nucleotide specific phosphodiesterases (PDEs). The PDE superfamily includes twenty-one genes that encode for eleven families of PDEs. These families are further subdivided based on catalytic domain homology and substrate specificity and include the 1) cAMP specific, PDE4A-D, 7A and 7B, and 8A and 8B, 2) cGMP specific, PDE 5A, 6A-C, and 9A, and 3) those that are dual substrate, PDE 1A-C, 2A, 3A and 3B, 10A, and 11A. The homology between the families, ranging from 20% to 45%, suggests that it may be possible to develop selective inhibitors for each of these families.

PDE2 is highly expressed in the brain, but is also found in many other tissues as well, and therefore has a broad array of function and utility (J. A. Beavo, et al., Rev. Physio. Biochem. Pharm., 135, 67 (1999)). Amongst others, PDE2 has been shown to have therapeutic potential in neuronal development, learning, and memory (W. C. G. van Staveren, et al., Brain Res., 888, 275 (2001) and J. O'Donnell, et al., J. Pharm. Exp. Ther., 302, 249 (2002)); prolactin and aldosterone secretion (M. O. Velardez, et al., Eur. J. Endo., 143, 279 (2000) and N. Gallo-Payet, et al., Endo., 140, 3594 (1999)); bone cell differentiation, growth, and bone resorption (C. Allardt-Lamberg, et al., Biochem. Pharm., 59, 1133 (2000) and S. Wakabayashi, et al., J. Bone, Miner. Res., 17, 249 (2002); immunological response (M. D. Houslay, et al., Cell. Signal., 8, 97 (1996); vascular angiogenesis (T. Keravis, et al., J. Vasc. Res., 37, 235 (2000); inflammatory cell transit (S. L. Wolda, et al., J. Histochem. Cytochem., 47, 895 (1999); cardiac contraction (R. Fischmeister, et al., J. Clin. Invest., 99, 2710 (1997), P. Donzeau-Gouge, et al., J. Physiol., 533, 329 (2001), and D. J. Paterson, et al., Card. Res., 52, 446 (2001); platelet aggregation (R. J. Haslam, et al., Biochem. J., 323, 371 (1997); female sexual arousal disorder (C. P. Wayman, et al., EP Patent Publications EP10977707 and EP1097706); osteoarthritis pain (M. Plummer et. al., Bioorganic & Medicinal Chemistry Letters, 23(11), 3438-3442 and 3443-3447(2013)); malignant melanoma (H. Morita, et al., Oncology Reports, 29, 1275-1284, 2013; Hiramoto, et al., Cell. Signal., 26(9), 1807-1817, 2014; and J. J. Bernard, et al., PloS ONE 9(10): e109862, 2014); heart failure (A. N. DeMaria, et al., J. Amer. Coll. Card. 63 (6), 570-602, 2014); pulmonary hypertension (K. J, Bubb, et al., Circulation, 130, 496-508, 2014); depression and anxiety (L. Ding, et al., Behav. Brain Res. 268, 150-158, 2014); and hypoxic pulmonary vasoconstriction (J. Haynes, et. al., J. Pharm. Exp. Ther., 276, 752 (1996). See also US2007135457 and WO2015060368.

Inhibition of PDE2 (e.g., PDE2A) has been shown to enhance cognitive function across multiple preclinical models of cognitive performance that reflect improvements in recognition memory, social interactions and working memory, which are all deficient in schizophrenia (Boess et al., *Inhibition of Phosphodiesterase 2 Increases Neuronal cGMP, Synaptic Plasticity and Memory Performance*, Neuropharmacology, 47(7): 1081-92, 2004). PDE2A inhibition was also shown to improve cognitive deficits that develop in aging and Alzheimer's disease (Domek-Lopacinska and Strosznajder, *The Effect of Selective Inhibition of Cyclic GMP Hydrolyzing Phosphodiesterases 2 and 5 on Learning and Memory Processes and Nitric Oxide Synthetase Activity in Brain During Aging*, Brain Research, 1216:68-77, 2008). The role of PDE2 inhibition in cognitive disorders was also shown in Brandon et al., *Potential CNS Applications for Phosphodiesterase Enzyme Inhibitors*, Annual Reports in Medicinal Chemistry 42: 4-5, 2007 (compound BAY 60-7550 was reported to have significant potency at other PDE isoforms, had high clearance and limited brain penetration). See also Jorgenson, et al, Annual Reports in Medicinal Chemistry 48: 37-55, 2013. "Selective Inhibitors of PDE2, PDE9, and PDE10: Modulators of Activity of the Central Nervous System".

PDE2 inhibitors have also been shown to have efficacy in preclinical models of anxiety and depression (Masood et al., Anxiolytic Effects of Phosphodiesterase-2 Inhibitors Associated with Increased cGMP Signaling, JPET 331(2):690-699, 2009; Masood et al., Reversal of Oxidative Stress-Induced Anxiety by Inhibition of Phosphodiesterase-2 in Mice, JPET 326(2):369-379, 2008; Reierson et al., Repeated Antidepressant Therapy Increases Cyclic GMP Signaling in Rat Hippocampus, Neurosci. Lett., 466(3):149-53, 2009). See also Ducrot et al., CoMFA and CoMSIA 3D-quantitative structure-activity relationship model on benzodiazepine derivatives, inhibitors of phosphodieserase IV, J Computer-Aided Molecular Design, 15: 767785, 2001; US20120214791; WO2012168817; WO2013034755; WO2013034758; WO2013034761; WO2005041957; WO2005061497; WO2006024640; WO2013161913; WO2010136493; WO 2013098373; WO 2009016498; U.S. Pat. Nos. 6,573,263; 8,598,155; and 8,680,116; WO2015012328; WO2014139983; WO2014019979; WO2014010732; WO2013000924; WO2012114222; WO2006072615; WO2005063723; M. Plummer et al., Bioorg Med Chem Lett 23(11), 3438, 2013; and M. Plummer et al., Bioorg Med Chem Lett 23(11), 3443, 2013.

An increase in vascular permeability has been shown to be attributable to increased activity of PDE2. PDE2 and PDE3 in the endothelium can act as a sensor or switch to detect normal versus pathological concentrations of cGMP and thus regulate endothelial permeability accordingly with potential relevance to migraine. See Surapisitchat et al., *Differential Regulation of Endothelial Cell Permeability by cGMP via Phosphodieserase 2 and 3*, Circulation Research, 2007; 101, pgs.: 811-818 and Duran et al., *The NO Cascade, eNOS Location and Microvascular Permeability*, Cardiovascular Res. (2010) 87, 254-261. Cerebral vasodilation is considered a major cause of migraine. See P. C. Tfelt-Hansen and P. J. Koehler, *One hundred years of migraine research: major clinical and scientific observations from 1910 to 2010*, Headache, 2011. 51(5), 752-578 and D. K. Arulmozhi et al., *Migraine: current therapeutic targets and future avenues*, Current Vascular Pharmacology, 2006, 4(2), 117-128. Therefore, PDE2 inhibition may have utility as a treatment or prophylactic for migraine.

The need for new and improved PDE2 modulators believed to be useful for treating diseases or disorders associated with PDE2 such as Alzheimer's disease, cognitive impairment associated with schizophrenia, depression, migraines, and the like continues to exist. Inhibitors of PDE2 are not only believed to be useful in treating schizophrenia but also a wide variety of conditions or disorders that would benefit from increasing levels of cAMP and/or cGMP within neurons, including a variety of neurological, psychotic, anxiety and/or movement disorders. Accordingly, agents that inhibit PDE2 and PDE2A would be desirable as therapeutics for neurological and psychiatric disorders.

SUMMARY OF THE INVENTION

The present invention is directed to pyrimidinone amide compounds which may be useful as therapeutic agents for the treatment of central nervous system and/or peripheral disorders associated with phosphodiesterase 2 (PDE2). The present invention also relates to the use of such compounds for treating neurological and psychiatric disorders, such as schizophrenia, psychosis, Alzheimer's, cognitive impairment, anxiety, depression, migraines, or Huntington's disease, Parkinson's disease, Parkinson's disease dementia (PDD), and other diseases associated with striatal hypofunction or basal ganglia dysfunction.

DETAILED DESCRIPTION OF THE INVENTION

The present invention is directed to pyrimidinone amide compounds of formula I:

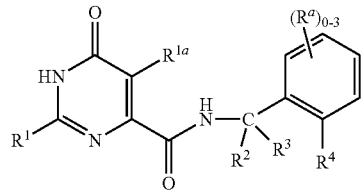

or a pharmaceutically acceptable salt thereof, wherein:

$R^1$ is linked to the pyrimidinone via an atom other than carbon and is selected from the group consisting of halo, —OR, $O(CH_2)_{1\text{-}3}OR$, $O(CH_2)_{1\text{-}3}N(R)_2$, $O(CH_2)_nC(R)_2OR$, $O—(CH_2)_nC_{4\text{-}10}$heterocyclyl, $O—(CH_2)_{1\text{-}3}OC_{6\text{-}10}$aryl, $O—C_{6\text{-}10}$aryl, $N(R^x)_2$, —$NRC_{5\text{-}10}$heterocyclyl, —$NRC_{6\text{-}10}$aryl, —$NRC_{3\text{-}10}$cycloalkyl, SR, said alkyl, cycloalkyl, heterocyclyl and aryl optionally substituted with one to three groups of $R^a$;

$R^{1a}$ represents H, or $C_{1\text{-}6}$ alkyl, said alkyl optionally substituted with OH or halo, $R^2$ and $R^3$ are independently selected from the group consisting of hydrogen, $C_{1\text{-}6}$alkyl, $(CH_2)_nCN$, $C(O)R$, $C(O)OR$, $CF_3$, —$C_{3\text{-}10}$ cycloalkyl, $C_{6\text{-}10}$aryl, $C_{5\text{-}10}$heteroaryl, said alkyl, cycloalkyl, aryl and heteroaryl optionally substituted with one to three groups of $R^b$;

$R^2$ and $R^3$ can combine with the carbon atom to which they are attached to form a $C_{3\text{-}6}$ cycloalkyl, said cycloalkyl optionally interrupted with 1-2 heteroatoms selected from O, S, or N and optionally substituted with one to three groups of $R^b$ $R^4$ represents hydrogen, halo, or $C_{1\text{-}6}$ alkyl; or alternatively, $R^2$ and $R^3$ along with the carbon atom to which they are attached and the $R^4$ on the phenyl ring can combine to form a $C_{6\text{-}10}$ bicyclic ring which includes the phenyl ring, said bicyclic ring optionally interrupted with 1-2 heteroatoms selected from O, S, and N and optionally substituted with one to three groups of $R^b$;

R represents H, or $C_{1\text{-}6}$ alkyl;

$R^a$ is selected from the group consisting of H, halo, CN, $C_{1\text{-}6}$alkyl, $(CH_2)_nOR$, $(O)_pC_{1\text{-}4}$haloalkyl, $S(O)_sCF_3$, $S(O)_s$ R, $SF_5$, $C_{3\text{-}10}$cycloalkyl, said alkyl and cycloalkyl optionally substituted with one to three groups of $R^b$;

$R^b$ is selected from the group consisting of H, halo, $C_{1\text{-}6}$alkyl, $SO_2C_{1\text{-}6}$alkyl, and $(O)_pC_{1\text{-}4}$haloalkyl;

each occurring $R^x$ independently represents H, or $C_{1\text{-}6}$ alkyl, or two adjacent $R^x$ groups can combined together with the nitrogen atom to which they are attached to form a $C_{4\text{-}10}$heterocyclyl optionally substituted with one to three groups of $R^b$;

n represents 0, 1, 2, 3, or 4;

s represents 0, 1, or 2; and p represents 0 or 1.

An embodiment of the invention of formula I is realized when $R^{1a}$ is hydrogen.

Another embodiment of the invention is realized when $R^{1a}$ is $C_{1\text{-}6}$alkyl.

Another embodiment of the invention of the formula I is realized when the heterocyclyl of $R^1$ is selected from the group consisting of optionally substituted oxetanyl, tetrahydrofuranyl, piperidinyl, pyrrolidinyl, morpholinyl, dihydropyrrolopyrazolyl, dihydropyrrolopyrimindyl, tetrahydropyranyl, pyrazolyl, and azetidinyl.

Another embodiment of the invention of the formula I is realized when the aryl of $R^1$ is phenyl.

Still another embodiment of the invention of formula I is realized when the cycloalkyl of $R^1$ is selected from the group consisting of optionally substituted cyclopropyl, cyclobutyl, cyclopentyl, and cyclohexyl.

An embodiment of the invention of formula I is realized when $R^1$ is selected from the group consisting of OR, $O(CH_2)_{1-3}OR$, $O(CH_2)_nC(R)_2OR$, and $O(CH_2)_{1-3}N(R)_2$.

Another embodiment of the invention of formula I is realized when $R^1$ is selected from the group $O-(CH_2)_nC_{4-10}$heterocyclyl said heterocyclyl optionally substituted with one to three groups of $R^a$.

Another embodiment of the invention of formula I is realized when $R^1$ is selected from the group $O-(CH_2)_{1-3}OC_{6-10}$aryl and $O-C_{6-10}$aryl, said aryl optionally substituted with one to three groups of $R^a$.

Another embodiment of the invention of formula I is realized when $R^1$ is selected from the group $N(R^x)_2$, $-NRC_{5-10}$heterocyclyl, $-NRC_{6-10}$aryl, and $NRC_{3-10}$cycloalkyl, said cycloalkyl, aryl and heterocyclyl optionally substituted with one to three groups of $R^a$. A subembodiment of this aspect the invention is realized when $R^1$ is $N(R^x)_2$. Still another subembodiment of this aspect of the invention is realized when two adjacent $R^x$ groups combine together with the nitrogen atom to which they are attached to form a $C_{4-10}$ heterocyclyl and optionally substituted with one to three groups of $R^b$. Yet another subembodiment of this aspect of the invention is realized when two adjacent $R^x$ groups combine together with the nitrogen atom to which they are attached to form a $C_{4-10}$ heterocyclyl selected from the group consisting of optionally substituted pyrrolidinyl, pyrazolyl, azetidinyl, piperidinyl, morpholinyl, dihydropyrrolopyrazolyl, dihydropyrrolopyrimidinyl, and dihydropyrrolopyridinyl.

Still another embodiment of the invention of formulas I is realized when $R^1$ is SR.

An embodiment of the invention of formula I is realized when $R^1$ is selected from the group consisting of $SCH_3$, $-N(CH_3)_2$, $N(CH_3)(CH_2CH_3)$, $N(CH_2CH_3)_2$, $-NH_2$, $-NHCH_3$, NH-cyclobutyl, NH-cyclopentyl, NH-cyclopropyl, NH-pyridyl, $-OR$, $-O$-phenyl, $-O(CH_2)_2OCH_3$, $-O(CH_2)_3OCH_3$, $-O(CH_2)_3OCH(CH_3)_2$, $-O(CH_2)_2N(CH_3)_2$, $-O(CH_2)_2C(CH_3)_2OCH_3$, $-OCH_2$oxetanyl, $-O(CH_2)_4OCH_3$, $-O(CH_2)_3NHCH_3$, $-O$-tetrahydrofuranyl, $-O$-piperidinyl, $-O$-oxetanyl, $-O(CH_2)_3O$phenyl, $O(CH_2)_2CH(CH_3)OCH_3$, $-O$-tetrahydropyranyl, $O$-pyrrolidinyl, and N linked pyrazolyl, N linked azetidinyl, N linked pyrrolidinyl, and N linked piperidinyl, said cyclobutyl, cyclopentyl, cyclopropyl, phenyl, oxetanyl, tetrahydrofuranyl, piperidinyl, tetrahydropyranyl, pyrollidinyl, pyrazolyl, and azetidinyl optionally substituted with one to three groups of $R^a$. A subembodiment of the invention of formula I when $R^1$ is selected from the group consisting of $-N(CH_3)_2$, $NH_2$, $NHCH_3$, $O(CH_2)_3NHCH_3$, and optionally substituted O-tetrahydrofuranyl, N linked piperidinyl, N linked pyrrolidinyl, O-pyrrolidinyl, N linked pyrazolyl, or O-piperidinyl.

Another subembodiment of the invention of formula I is realized when $R^1$ is $-N(CH_3)_2$. Another subembodiment of the invention of formula I is realized when $R^1$ is $-NH_2$. Another subembodiment of the invention of formula I is realized when $R^1$ is $-NH(CH_3)$. Another subembodiment of the invention of formula I is realized when $R^1$ is $O(CH_2)_3NHCH_3$. Another subembodiment of the invention of formula I is realized when $R^1$ is optionally substituted N-linked pyrazolyl. Another subembodiment of the invention of formula I is realized when $R^1$ is optionally substituted N-linked piperidinyl, or O-piperidinyl (e.g., 3- or 4-O-piperidinyl).

Another subembodiment of the invention of formula I is realized when $R^1$ is optionally substituted N-linked pyrrolidinyl, or O-(3-pyrrolidinyl).

Another embodiment of the invention of formula I is realized when both of $R^2$ and $R^3$ are $C_{1-6}$alkyl, said alkyl optionally substituted with one to three groups of $R^b$.

Another embodiment of the invention of formula I is realized when one of $R^2$ and $R^3$ is hydrogen or $CH_3$ and the other is $C_{1-6}$alkyl or $C_{3-10}$ cycloalkyl, said alkyl and cycloalkyl optionally substituted with one to three groups of $R^b$. A subembodiment of this aspect of the invention is realized when the alkyl is selected from the group consisting of $CH_3$, $CH(CH_3)_2$, $CH_2CH_3$, $C(CH_3)_3$. Another subembodiment of this aspect of the invention is realized when the alkyl is $CH_3$. Another subembodiment of this aspect of the invention is realized when the alkyl is $CH(CH_3)_2$. Another subembodiment of this aspect of the invention is realized when the alkyl is $C(CH_3)_3$. Another subembodiment of this aspect of the invention is realized when the alkyl is $CH_2CH_3$. An aspect of this embodiment of the invention of formula I is realized when one of $R^2$ and $R^3$ is hydrogen and the other is $CH_3$. An aspect of this embodiment of the invention of formula I is realized when one of $R^2$ and $R^3$ is hydrogen and the other is $CH_2CH_3$. An aspect of this embodiment of the invention of formula I is realized when one of $R^2$ and $R^3$ is hydrogen and the other is $C(CH_3)_3$. Still another aspect of this embodiment of the invention of formula I is realized when one of $R^2$ and $R^3$ is hydrogen and the other is $CH(CH_3)_2$.

Another embodiment of the invention of formula I is realized when one of $R^2$ and $R^3$ is hydrogen and the other is optionally substituted $C_{3-10}$ cycloalkyl. An aspect of this embodiment of the invention is realized when the cycloalkyl is selected from the group consisting of cyclopropyl, cyclobutyl, and cyclopentyl. A subembodiment of this aspect of the invention is realized when the cycloalkyl is cyclopropyl. Another subembodiment of this aspect of the invention is realized when the cycloalkyl is cyclobutyl. Another subembodiment of this aspect of the invention is realized when the cycloalkyl is cyclopentyl.

Another embodiment of the invention of formula I is realized when one of $R^2$ and $R^3$ is hydrogen and the other is optionally substituted $C_{6-10}$ aryl, said aryl optionally substituted with one to three groups of $R^b$.

Another embodiment of the invention of formula I is realized when one of $R^2$ and $R^3$ is hydrogen and the other is optionally substituted $C_{5-10}$ heteroaryl, said heteroaryl optionally substituted with one to three groups of $R^b$.

Another embodiment of the invention of formula I is realized when one of $R^2$ and $R^3$ is hydrogen and the other is selected from $(CH_2)_nCN$, $C(O)R$, $C(O)OR$, and $CF_3$.

Still another embodiment of the invention of formula I is realized when $R^2$ and $R^3$ combine with the carbon atom to which they are attached to form a $C_{3-10}$ cycloalkyl, said cycloalkyl optionally substituted with one to three groups of $R^b$. An aspect of this embodiment of the invention is realized when the optionally substituted cycloalkyl is selected from the group consisting of cyclopropyl, cyclobutyl, and cyclopentyl. A subembodiment of this aspect of the invention is realized when the cycloalkyl is cyclopropyl. Another subembodiment of this aspect of the invention is realized when the cycloalkyl is cyclobutyl. Another subembodiment of this aspect of the invention is realized when the cycloalkyl is cyclopentyl.

An embodiment of the invention of formula I is realized when $R^2$ and $R^3$ along with the carbon atom to which they are attached and the $R^4$ on the phenyl ring combine to form a $C_{6-10}$ bicyclic ring which includes the phenyl ring, said bicyclic ring optionally interrupted with 1-2 heteroatoms selected from O, S, and N and optionally substituted.

An embodiment of the invention of formula I is realized when $R^a$ is selected from OH, halo, $CH_3$, optionally substituted cyclopropyl, $(CH_2)_nOCH_3$, $CF_2R$, $CH_2F$, $(CH_2)_nCF_3$, $OCHF_2$, $OCF_3$, $SCH_3$, $SCF_3$, $SF_5$, $SOCF_3$, $SO_2CF_3$, $SO_2CH_3$, $CH_2NH_2$, and $(CH_2)_nN(CH_3)_2$. An aspect of this embodiment of the invention is realized when $R^a$ is selected from $(CH_2)_nOCH_3$, $CH_2F$, $(CH_2)_nCF_3$, $OCHF_2$, $OCF_3$, $SCH_3$, $SCF_3$, and $SF_5$.

Another embodiment of the invention of formula I is realized when n is 0. Another embodiment of the invention of formula I is realized when n is 1. Another embodiment of the invention of formula I is realized when n is 2. Another embodiment of the invention of formula I and II is realized when n is 3. Still another embodiment of the invention of formula I is realized when n of $R^a$ is 0-1, 0-2, or 0-3.

Still another embodiment of the invention of formula I is represented by structural formula II:

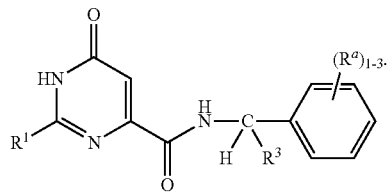

II or a pharmaceutically acceptable salt thereof, wherein $R^1$ is selected from the group consisting of —$N(CH_3)_2$, $NH_2$, $NHCH_3$, $O(CH_2)_3NHCH_3$, and optionally substituted O-tetrahydrofuranyl, N linked pyrazolyl, N linked pyrrolidinyl, O-(3-pyrrolidinyl), O-(3-piperidinyl), or O-(4-piperidinyl), $R^3$ is selected from the group consisting of $CH_3$, $CH(CH_3)_2$, $CH_2CH_3$, $C(CH_3)_3$ and optionally substituted cyclopropyl, and $R^a$ is selected from the group consisting of $SCF_3$, $CF_3$, $OCHF_2$, $OCF_3$, and $CH_2CF_3$. A subembodiment of this aspect of the invention of formula II is realized when $R^1$ is selected from the group consisting of —$N(CH_3)_2$, $NH_2$, $NHCH_3$, and optionally substituted 1-pyrrolidinyl, $R^3$ is selected from the group consisting of $CH_3$, $CH(CH_3)_2$, $CH_2CH_3$, $C(CH_3)_3$ and optionally substituted cyclopropyl, and $R^a$ is $CF_3$.

The invention is also directed to a method for the treatment of central nervous system disorders associated with phosphodiesterase 2 (PDE2) using the compounds of Formula I and II. More specifically, the present invention relates to the use of such compounds for treating neurological and psychiatric disorders, such as schizophrenia, psychosis, Alzheimer's, cognitive impairment, anxiety, depression, migraines, or Huntington's disease, Parkinson's disease, Parkinson's disease dementia, and other diseases associated with striatal hypofunction or basal ganglia dysfunction using the compounds of formula I and II.

Examples of compounds of the invention can be found throughout the specification as illustrated by Examples 1 through 212.

The invention also encompasses pharmaceutical compositions containing a compound of formula I and II and methods for treatment or prevention of phosphodiesterase mediated diseases using compounds of formula I and II.

Where a variable occurs more than once in any formula of the invention, or in a substituent thereof, the individual occurrences of that variable are independent of each other, unless otherwise specified. Also, combinations of substituents/or variables are permissible only if such combinations result in stable compounds and valency is permissible.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six atoms. Exemplary alkyl groups include methyl, ethyl, n-propyl, isopropyl, n-butyl, isobutyl, tert-butyl, pentyl, hexyl, and the like. $C_0$ alkyl means a bond.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, spirocycles, and bridged and fused ring carbocycles.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantyl and norbornyl. Exemplary fused cycloalkyl groups include decahydronaphthalene.

As used herein, the term "aryl," by itself or as part of another substituent, means an aromatic cyclic hydrocarbon radical. Preferred aryl groups have from six to ten carbons atoms. The term "aryl" includes multiple ring systems as well as single ring systems. Preferred aryl groups for use in the invention include phenyl and naphthyl.

The term "aryl" also includes fused cyclic hydrocarbon rings which are partially aromatic (i.e., one of the fused rings is aromatic and the other is non-aromatic). An exemplary aryl group which is partially aromatic is indanyl.

The term heterocyclyl, heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocyclyl, heterocycle or heterocyclic includes heteroaryl moieties. Examples of such heterocyclic elements include, but are not limited to, azepinyl, benzodioxolyl, benzimidazolyl, benzisoxazolyl, benzofurazanyl, benzopyranyl, benzothiopyranyl, benzofuryl, benzothiazolyl, benzothienyl, benzotriazolyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyrazolopyridinyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl, and triazolyl. The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure.

When a heterocyclyl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

As used herein, the term "halo" or "halogen" includes fluoro, chloro, bromo and iodo. The term "haloalkyl" means an alkyl, as defined above, wherein one or more of the bonding positions on the alkyl moiety typically occupied by hydrogen atoms are instead occupied by a halo group, perhaloalkyl (or "fully halogenated" alkyl) means that all bonding positions not participating in bonding the alkyl substituent to a substrate are occupied by a halogen, for example, where the alkyl is selected to be methyl, the term perfluoroalkyl means —$CF_3$.

It should be appreciated by any one skilled in the art that the compounds of this invention can exist in several tautomeric forms as shown below:

it is intended that the invention embrace both solvated and unsolvated forms. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates and the like. "Hydrate" is a solvate wherein the solvent molecule is $H_2O$.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of the compound bound to PDE2 enzyme, of crystalline products or crystalline intermediates that are derivatized, if necessary, with a reagent containing an asymmetric center of known absolute configuration.

The compounds of the invention may have one or more asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of the invention. The present invention includes all stereoisomers of formulae (I) and pharmaceutically acceptable salts thereof.

If desired, racemic mixtures of the compounds may be separated so that the individual enantiomers or diastereomers are isolated. The separation can be carried out by methods well known in the art, such as the coupling of a racemic mixture of compounds to an enantiomerically pure

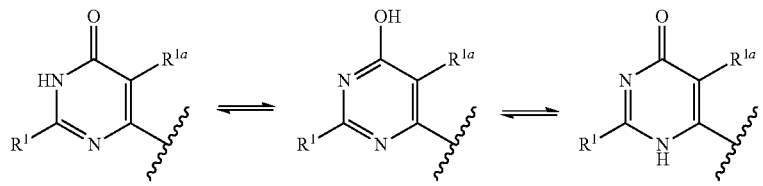

Previous researchers have studied similar compounds and found that one of these tautomers can exist as the predominant form depending on structures and conditions. See B. M. Giuliano, et al. J. Phys. Chem. A, 114, 12725-12730, 2010; B. M. Giuliano, et al. J. Phys. Chem. A, 115, 8178-8179, 2011; A. Gerega, et al. J. Phys. Chem. A, 111, 4934-4943, 2007; R. Sanchez, et al., J. Amer. Chem. Soc., 129(19), 6287-6290, 2007; C. Lopez, et al., Spectroscopy 14, 121-126, 2000; and G. M. Kheifets, et al., Russ. J. Org. Chem., 36(9), 1373-1387, 2000. For brevity and simplicity, we have represented the compounds of the present invention using Formula I and II and they are intended to represent all possible tautomeric forms for these compounds without regard to what actually is the predominant tautomeric form in existence for a particular compound.

One or more compounds of the invention may exist in unsolvated as well as solvated forms with pharmaceutically acceptable solvents such as water, ethanol, and the like, and compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

In the compounds of the invention the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic formulas I and Ia. For example, isotopic forms of hydrogen (H), including protium ($^1$H) and deuterium ($^2$H); isotopic forms of carbon, including $^{11}$C; and isotopic forms of fluorine, including $^{18}$F. Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. While $^{12}$C and $^{19}$F are the predominant isotopes of carbon and fluorine found in nature, enriching for $^{11}$C or $^{18}$F may afford advantages, particularly for use in imaging via positron emission tomography (PET). In general, one of ordinary skill in the art would appreciate that a preferred substance for potential use as a PET imaging agent would effectively inhibit the PDE2 enzyme with a Ki value less than or about 0.5 nM, where compounds tested are comprised of naturally occurring isotopes. Such preferred substances, when enriched with $^{11}$C or $^{18}$F, may be therefore be useful as PET imaging agents. Isotopically enriched compounds within generic formula I and II can be prepared without undue experimentation by conventional techniques well known to those skilled in the art or by processes analogous to those described in the Schemes and Examples herein using appropriate isotopically enriched reagents and/or intermediates.

The term "substantially pure" means that the isolated material is at least 90% pure, and preferably 95% pure, and even more preferably 99% pure as assayed by analytical techniques known in the art.

For purposes of this specification, the following abbreviations have the indicated meanings:
Ac=acetyl
ACN=acetonitrile
AcO=acetate
BOC=t-butyloxycarbonyl
CBZ=carbobenzoxy
CDI=carbonyldiimidazole
DBU=1,8-Diazabicycloundec-7-ene
DCC=1,3-dicyclohexylcarbodiimide
DCE=1,2-dichloroethane
(dF(CF$_3$)ppy)=2-(2,4-difluorophenyl)-5-trifluoromethyl-pyridine
DI=de-ionized
DIAD=Diisopropyl azodicarboxylate
DIBAL=diisobutyl aluminum hydride
DIPEA or DIEA=N,N-diisoproylethylamine, also known as Hunig's base
DMA=dimethylacetamide
DMAP=4-(dimethylamino)pyridine
DMF=dimethylformamide
DMP=Dess-Martin periodinane
DPPA=Diphenylphosphoryl azide
DPPP=1,3-bis(diphenylphosphino)propane
Dtbbpy=4,4'-di-tert-butyl-2,2'-dipyridyl
EDC or EDCI=1-(3-dimethylaminopropyl)-3-ethylcarbodiimide hydrochloride
EDTA=ethylenediaminetetraacetic acid, tetrasodium salt
EtOAc=ethyl acetate
FA=Formic Acid
FAB=fast atom bombardment
FMOC=9-fluorenylmethoxycarbonyl
HATU=O-(7-Azabenzotriazol-1-yl)-N,N,N',N'-tetramethyluronium hexafluorophosphate
HBTU=O-(Benzotriazol-1-yl)N,N,N',N'-tetramethyluronium hexafluorophosphate
HMPA=hexamethylphosphoramide
HOAt=1-Hydroxy-7-azabenzotriazole or 3H-[1,2,3]triazolo[4,5-b]pyridin-3-ol
HOBt=1-hydroxybenzotriazole
HRMS=high resolution mass spectrometry
IBCF=isobutyl chloroformate
KHMDS=potassium hexamethyldisilazane
LC-MS=Liquid chromatography-mass spectrometry
LDA=lithium diisopropylamide
LiHMDS=lithium hexamethyldisilazane
MCPBA=metachloroperbenzoic acid
MMPP=magnesium monoperoxyphthlate hexahydrate
Ms=methanesulfonyl=mesyl
MsO=methanefulfonate=mesylate
MTBE=Methyl t-butyl ether
NBS=N-bromosuccinimide
NMM=4-methylmorpholine
NMP=N-methylpyrrolidinone
NMR=Nuclear magnetic resonance
PCC=pyridinium chlorochromate
PDC=pyridinium dichromate
Ph=phenyl
PPTS=pyridinium p-toluene sulfonate
pTSA=p-toluene sulfonic acid
PyH.Br3=pyridine hydrobromide perbromide
r.t./RT=room temperature
rac.=racemic
T3P=2,4,6-Tripropyl-1,3,5,2,4,6-trioxatriphosphinane 2,4,6-trioxide
TBTU=O-(Benzotriazol-1-yl)N,N,N',N'-tetramethyluronium tetrafluoroborate
TEA=triethylamine
TFA=trifluoroacetic acid
TfO=trifluoromethanesulfonate=triflate
THF=tetrahydrofuran
TLC=thin layer chromatography
TMSCl=trimethylsilyl chloride The compounds of the present invention may contain one or more stereogenic centers and can thus occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

All patents, patent applications and publications cited herein, whether supra or infra, are hereby incorporated by reference in their entirety and are deemed representative of the prevailing state of the art.

It will be understood that, as used herein, references to the compounds of present invention are meant to also include the pharmaceutically acceptable salts, and also salts that are not pharmaceutically acceptable when they are used as precursors to the free compounds or in other synthetic manipulations. The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, cupric, cuprous, ferric, ferrous, lithium, magnesium, manganic, manganous, potassium, sodium, zinc and the like salts. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments are citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

Exemplifying the invention are the specific compounds disclosed in the Examples and herein. The subject compounds may be useful in a method of treating a neurological or psychiatric disorder associated with PDE2 dysfunction in a patient such as a mammal in need of such inhibition comprising the administration of an effective amount of the compound. In addition to primates, especially humans, a variety of other mammals can be treated according to the method of the present invention. The subject compounds may be useful in a method of inhibiting PDE2 activity in a patient such as a mammal in need of such inhibition comprising the administration of an effective amount of the compound. The subject compounds also may be useful for treating a neurological or psychiatric disorder associated with striatal hypofunction or basal ganglia dysfunction in a mammalian patient in need thereof. In addition to primates, especially humans, a variety of other mammals can be treated according to the method of the present invention.

The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for treating a neurological or psychiatric disorder associated with PDE2 function in a mammalian patient in need thereof. The present invention is further directed to a use of a compound of the present invention or a pharmaceutically acceptable salt thereof for the manufacture of a medicament for treating a neurological or psychiatric disorder associated with striatal hypofunction or basal ganglia dysfunction in a mammalian patient in need thereof.

"Treating" or "treatment of" a disease state includes: 1) inhibiting the disease state, i.e., arresting the development of the disease state or its clinical symptoms; 2) or relieving the disease state, i.e., causing temporary or permanent regression of the disease state or its clinical symptoms. "Treating" or "treatment of" does not include curing or preventing the disease from occurring.

The subject treated in the present methods is generally a mammal, in particular, a human being, male or female, in whom therapy is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention.

Applicants propose that inhibitors of PDE2, including PDE2A, will provide therapeutic benefit to those individuals suffering from psychiatric and cognitive disorders. The unique and exclusive distribution of PDE2A in the medium spiny projection neurons of the striatum, which form the principle site for cortical and dopaminergic input within basal ganglia, suggests that it may be possible and desirable to identify inhibitors of PDE2 to enhance cellular signaling. Without wishing to be bound by any theory, applicants believe that inhibition of PDE2A in the striatum will result in increased cAMP/cGMP signaling and striatal output, which has the potential to restore behavioral inhibition that is impaired in cognitive disease such as schizophrenia. Regulation and integration of glutamatergic and dopaminergic inputs will enhance cognitive behavior, while suppressing or reducing unwanted behavior. Thus, in one embodiment, compounds of the invention provide a method for treating or ameliorating diseases or conditions in which striatal hypofunction is a prominent feature or ones in which basal ganglia dysfunction plays a role, such as, Parkinson's disease, Parkinson's disease dementia (PDD), Huntington's disease, schizophrenia, obsessive-compulsive disorders, addiction and psychosis. Other conditions for which the inhibitors described herein may have a desirable and useful effect include those requiring a reduction in activity and reduced response to psychomotor stimulants or where it would be desirable to reduce conditional avoidance responses, which is often predictive of clinical antipsychotic activity.

In another embodiment the compounds of this invention there is provided a method for treating or ameliorating diseases or conditions in neuronal development, learning, and memory, prolactin and aldosterone secretion, bone cell differentiation, growth, and bone resorption, immunological response, vascular angiogenesis, inflammatory cell transit, cardiac contraction, platelet aggregation, female sexual arousal disorder, and hypoxic pulmonary vasoconstriction.

As used herein, the term "selective PDE2 inhibitor" refers to an organic molecule that effectively inhibits an enzyme from the PDE2 family to a greater extent than enzymes from the PDE 1, and 3-11 families. In one embodiment, a selective PDE2 inhibitor is an organic molecule having a Ki for inhibition of PDE2 that is less than or about one-tenth that for a substance that is an inhibitor for another PDE enzyme. In other words, the organic molecule inhibits PDE2 activity to the same degree at a concentration of about one-tenth or less than the concentration required for any other PDE enzyme. Preferably, a selective PDE2 inhibitor is an organic molecule, having a Ki for inhibition of PDE2 that is less than or about one-hundredth that for a substance that is an inhibitor for another PDE enzyme. In other words, the organic molecule inhibits PDE2 activity to the same degree at a concentration of about one-hundredth or less than the concentration required for any other PDE enzyme. Preferably, a selective PDE2 inhibitor is an organic molecule, having a Ki for inhibition of PDE2 that is less than or about five-hundredth that for a substance that is an inhibitor for another PDE enzyme. In other words, the organic molecule inhibits PDE2 activity to the same degree at a concentration of about five-hundredth or less than the concentration required for any other PDE enzyme. A "selective PDE2 inhibitor" can be identified, for example, by comparing the ability of an organic molecule to inhibit PDE2 activity to its ability to inhibit PDE enzymes from the other PDE families. For example, an organic molecule may be assayed for its ability to inhibit PDE2 activity, as well as PDE1A, PDE1B, PDE1C, PDE3A, PDE3B, PDE4A, PDE4B, PDE4C, PDE4D, PDE5A, PDE6A, PDE6B, PDE6C, PDE7A, PDE7B, PDE8A, PDE8B, PDE9A, PDE10 and/or PDE11A.

Phosphodiesterase enzymes including PDE2 have been implicated in a wide range of biological functions. This has suggested a potential role for these enzymes in a variety of disease processes in humans or other species. The compounds of the present invention may have utility in treating a variety of neurological and psychiatric disorders.

In a specific embodiment, compounds of the present invention provide a method for treating schizophrenia or psychosis comprising administering to a patient in need thereof an effective amount of a compound of the present invention. The Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, cannabis, cocaine, hallucinogens, inhalants, opioids, phencyclidine, ketamine and other dissociative anaesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, the compounds of the present invention provide a method for treating cognitive disorders comprising administering to a patient in need thereof an effective amount of a compound of the present invention. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Parkinson's disease dementia (PDD), Huntington's disease, Pick's disease, Creutzfeldt Jacob disease, perinatal hypoxia, other general medical conditions or substance abuse), Alzheimer's disease, multi-infarct dementia, AIDS-related dementia, and Fronto temporal dementia, delirium, amnestic disorders or age related cognitive decline.

In another specific embodiment, compounds of the present invention provide a method for treating anxiety disorders comprising administering to a patient in need thereof an effective amount of a compound of the present invention. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another specific embodiment, compounds of the present invention provide a method for treating substance-related disorders and addictive behaviors comprising administering to a patient in need thereof an effective amount of a compound of the present invention. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, cannabis, cocaine, hallucinogens, inhalants, nicotine, opioids, phencyclidine, sedatives, hypnotics or anxiolytics.

In another specific embodiment, compounds of the present invention provide a method for treating obesity or eating disorders associated with excessive food intake, and complications associated therewith, comprising administering to a patient in need thereof an effective amount of a compound of the present invention. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-2 and DSM-IV-TR and the term is intended to include similar disorders described in other sources. Disorders and conditions encompassed herein include, but are not limited to, obesity, bulimia nervosa and compulsive eating disorders.

In another specific embodiment, compounds of the present invention provide a method for treating mood and depressive disorders comprising administering to a patient in need thereof an effective amount of a compound of the present invention. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with post-partum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder, mood disorders due to a general medical condition, and substance-induced mood disorders.

In another specific embodiment, compounds of the present invention provide a method for treating pain comprising administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In other specific embodiments, compounds of the invention provide methods for treating other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with cerebral trauma, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, Parkinson's disease dementia (PDD), drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemiballism), myoclonus (including, generalised myoclonus and focal myoclonus), tics (including, simple tics, complex tics and symptomatic tics), dystonia (including, generalised, iodiopathic, drug-induced, symptomatic, paroxymal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy.

Of the disorders above, the treatment of schizophrenia, bipolar disorder, depression, including unipolar depression, seasonal depression and post-partum depression, premenstrual syndrome (PMS) and premenstrual dysphoric disorder, learning disorders, pervasive developmental disorders, including autistic disorder, attention disorders including Attention-Deficit/Hyperactivity Disorder, autism, tic disorders including Tourette's disorder, anxiety disorders including phobia and post-traumatic stress disorder, cognitive disorders associated with dementia, AIDS dementia, Alzheimer's, Parkinson's disease, Parkinson's disease dimentia, Huntington's disease, spasticity, myoclonus, muscle spasm, tinnitus and hearing impairment and loss are of particular importance.

Angiogenesis is the physiological process through which new blood vessels form, and agents that inhibit this process have been shown to be effective treatments for some cancers. As initiation of angiogenesis involves migration and proliferation of vascular endothelial cells, and agents that elevate cAMP inhibit these processes, PDE2 inhibition may have utility as a treatment for cancer. See Savai, et al, *Targeting cancer with phosphodiesterase inhibitors*, Expert Opin. Investig. Drugs (2010) 19(1):117-131. PDE2 has been shown to be expressed in human vascular endothelial cells (VECs) and inhibition of PDE2 by treatment with selective inhibitors inhibited VEGF promoted migration of VECs. See Netherton and Maurice, *Vascular Endothelial Cell Cyclic Nucleotide Phosphodiesterases and Regulated Cell Migration: Implications in Angiogenesis*, Mol Pharmacol (2005) 67:263-272 and Favot, et al, *VEGF-induced HUVEC migration and proliferation are decreased by PDE2 and PDE4 inhibitors*. Thromb Haemost (2003) 90:334-343. Reduction of PDE2 activity with either small molecule inhibitors or PDE2A siRNA suppressed cell growth and invasion in a human malignant melanoma PMP cell line. See Hiramoto, et al, *Role of phosphodiesterase 2 in growth and invasion of human malignant melanoma cells*, Cellular Signalling (2014), 26:1807-1817. Reduction of PDE2 activity with a small molecule inhibitor attenuated tumor formation in a mouse model of ultraviolet light B-induced tumorigenesis. See Bernard, et al, *PDE2 is a Novel Target for Attenuating Tumor Formation in a Mouse Model of UVB-Induced Skin Carcinogenesis*, PLoS ONE (2014), 9(10):e109862. Thus, in another specific embodiment, compounds of the invention provide methods for treating, preventing, controlling, and/or reducing, attenuating cancers, such as malignant melanomas, skin cancer, and the like.

The subject compounds may be further useful in a method for the prevention, treatment, control, amelioration, or reduction of risk of the diseases, disorders and conditions noted herein. The subject compounds are further useful in a method for the prevention, treatment, control, amelioration, or reduction of risk of the aforementioned diseases, disorders and conditions in combination with other agents. The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention may be desirable. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, AChEis (such as Aricept (donepezil) and Exelon (rivastigmine)) and NMDA blocker Namenda (memantine), beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, atypical antipsychotics, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MAO-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an antidepressant or antianxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-$HT_{1A}$ agonists or antagonists, especially 5-$HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

The compounds of the present invention may be administered by oral, parenteral (e.g., intramuscular, intraperitoneal, intravenous, ICV, intracistemal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The terms "administration of" and or "administering a" compound should be understood to mean providing a compound of the invention or a prodrug of a compound of the invention to the individual in need of treatment.

In another specific embodiment, compounds of the present invention may be suitable as PET imaging agents. An aspect of the invention is realized when the PET imaging compounds of the instant invention are those that effectively inhibit the PDE2 enzyme with a Ki value less than or about 0.5 nM. Another aspect of the invention is realized when the compounds of the invention are enriched with $^{11}C$ or $^{18}F$. Still another aspect of the invention is realized when the compounds of Examples 1 through 212 are enriched with $^{11}C$ or $^{18}F$. Yet another aspect of the invention is realized when Examples 30, 47, 149, 89, 90. 91, 165, 150, 96, 97, 98, 1, 112, 2, 100, 31, 34, 35, 101, 102, 103, 37, 38, 41, 42, 43, 168, 169, 14, 170, 176, 177, 124, 54, 128, 57, 58, 60, 71, 73, 75, 76, 77 are enriched with $^{11}C$ or $^{18}F$.

The term "composition" as used herein is intended to encompass a product comprising specified ingredients in predetermined amounts or proportions, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by mixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art. By "pharmaceutically acceptable" it is meant the carrier, diluent or excipient must be compatible with the other ingredients of the formulation and not deleterious to the recipient thereof.

The subject compounds are further useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.001 to 10 mg/kg of body weight daily are administered to the patient, e.g., humans and elderly humans. The dosage range will generally be about 0.5 mg to 1.0 g per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Several methods, schemes, and examples for preparing representative compounds of this invention are illustrated below. Starting materials and the requisite intermediates are in some cases commercially available, or can be prepared according to literature procedures or as illustrated herein. The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing conditions as shown in the schemes and examples herein, as well as using other standard manipulations such as ester hydrolysis, cleavage of protecting groups, etc., as may be known in the literature or exemplified in the experimental procedures. Starting materials are made according to procedures known in the art or as illustrated herein.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood.

The representative examples of the compounds of the invention are illustrated in the following non-limiting schemes and Examples.

General

Starting materials used were obtained from commercial sources or prepared in other examples, unless otherwise noted.

The progress of reactions was often monitored by TLC or LC-MS. The identity of the products was often confirmed by LC-MS. The LC-MS was recorded using one of the following methods.

Method A: Supelco Ascentis Express C18, 3×50 mm, 2.7 um column. 2.0 uL injection, 1.25 ml/min flow rate, 170-900 amu scan range, 200-400 nm UV range, 10-99% (over 2.0 min) gradient with MeCN (0.05% TFA) and water (0.05%); 3 minute total run time.

Method B: Supelco Ascentis Express C18, 3×100 mm, 2.7 um column. 2.0 uL injection, 1.00 ml/min flow rate, 170-900 amu scan range, 200-400 nm UV range, 10-99% (over 4.0 min) gradient with MeCN (0.05% TFA) and water (0.05%); 5 minute total run time.

Method C: Waters Acquity UPLC, HSS C18, 1.8 um, 2.1×50 mm, MeCN and water with 0.1% TFA, 1 mL/min flow rate, gradient 5%-100% MeCN over 1.4 min.

Method D: Waters Acquity UPLC, HSS C18, 1.8 um, 2.1×50 mm, MeCN and water with 0.1% FA, 1 mL/min flow rate, gradient 5%-100% MeCN over 1.4 min.

Method E: XBridge Shield RP18: 2.5×50 mm, 3.5 um, 1.0 uL injection, 1.00 mL/min flow rate, 90-900 amu scan range, 190-400 nm UV range, 10-95% (over 2.2 min) gradient with MeCN and water (0.04% aq. $NH_3$), hold 1 min; 3.6 minute total run time.

Method F: Shimadzu: 3.0×50 mm, 2.2 um, 1.0 uL injection, 1.00 mL/min flow rate, 90-900 amu scan range, 190-400 nm UV range, 5-100% (over 2.2 min) gradient with MeCN (0.05% TFA) and water (0.05% TFA), hold 1 min; 3.6 minute total run time.

Method G: Titan C18: 2.1×50 mm, 1.9 um, 1.0 uL injection, 0.80 mL/min flow rate, 90-900 amu scan range, 190-400 nm UV range, 5-100% (over 2.1 min) gradient with MeCN (0.05% TFA) and water (0.05% TFA), hold 0.5 min; 3.0 minute total run time.

Method H: ZORBAX Eclipse Plus C18: 3.0×50 mm, 1.8 um, 1.0 uL injection, 1.00 mL/min flow rate, 90-900 amu scan range, 190-400 nm UV range, 5-100% (over 2.1 min) gradient with MeCN (0.1% FA) and water (0.1% FA), hold 0.5 min; 3.0 minute total run time.

Method I: XBridge C18: 4.6×50 mm, 3.5 um, 1.0 uL injection, 1.50 mL/min flow rate, 90-900 amu scan range, 190-400 nm UV range, 10-95% (over 2.2 min) gradient with MeCN and water (5 μM NH₄HCO₃), hold 1 min; 3.6 minute total run time.

NMR was recorded at room temperature unless noted otherwise on Varian Inova 400 or 500 MHz spectrometers with the residual solvent peak used as the reference or on Bruker 300 or 400 MHz spectrometers with the TMS peak used as an internal reference.

The methods used for the preparation of the compounds of this invention are illustrated by the following schemes. Often it involves an amide coupling of a carboxylic acid and an enantiomerically pure or enriched amine or its HCl salt to yield the desired product. When a racemic amine is used, the resulting enantiomers are separated by chiral chromatography when desired. Unless specified otherwise, the acids and amines or amines salts used are commercially available. Schemes A-F illustrate several conditions used for coupling of acid 1 and amine 2 to afford amide 3. Persons with ordinary skills in the art will be able to find many other coupling reagents to prepare amides from acids or their derivatives plus amines.

Scheme A

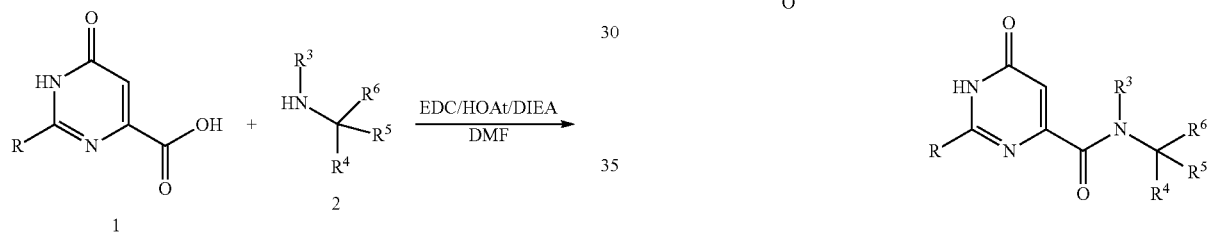

Scheme B

Scheme C

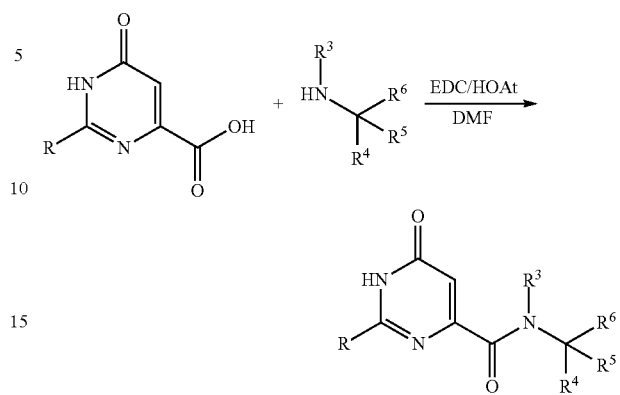

Scheme D

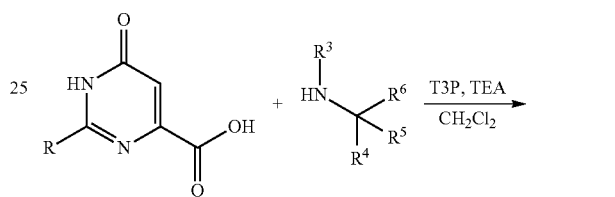

Scheme E

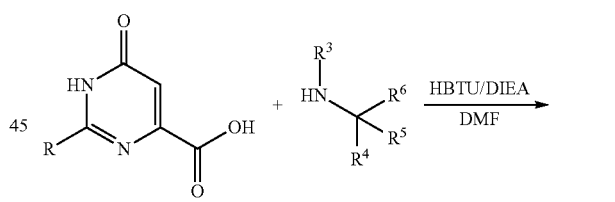

Scheme F

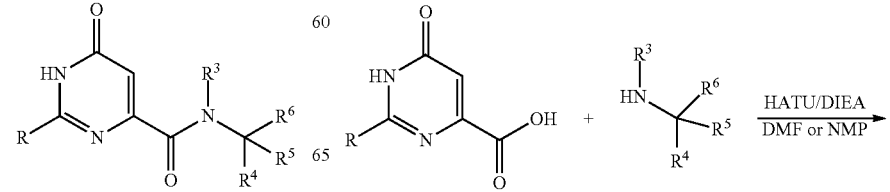

-continued

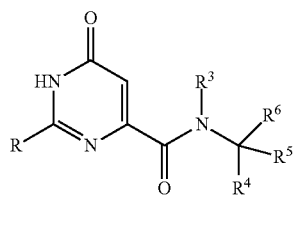
5

Another approach to prepare the compounds of this invention is to activate a 2-thiomethyl group of pyrimidinone 4 by oxidation to 2-methylsulfonyl group followed by substituting this sulfone with amine as shown in Scheme G in a one-pot procedure to give product 5. Alternatively, this sulfone intermediate 6 can be isolated and reacted with an amine 7 in the presence of a variety of bases or without additional base to form the 2-amino compounds 5 in a variety of solvents as shown in Schemes H-N. Similar substitutions can occur using alcohols, phenols, or hydroxide as nucleophiles instead of amines (Schemes O-T).

Scheme G

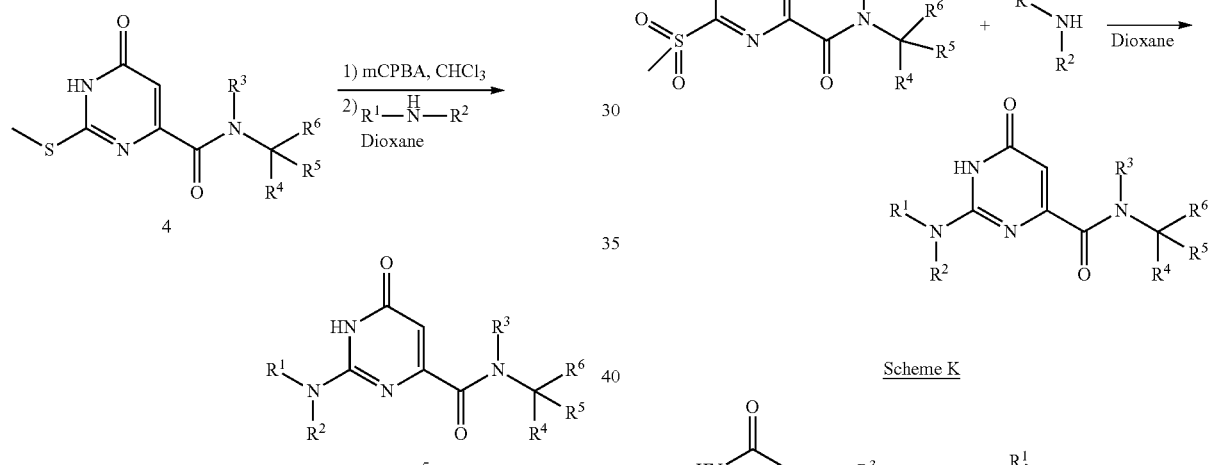

Scheme H

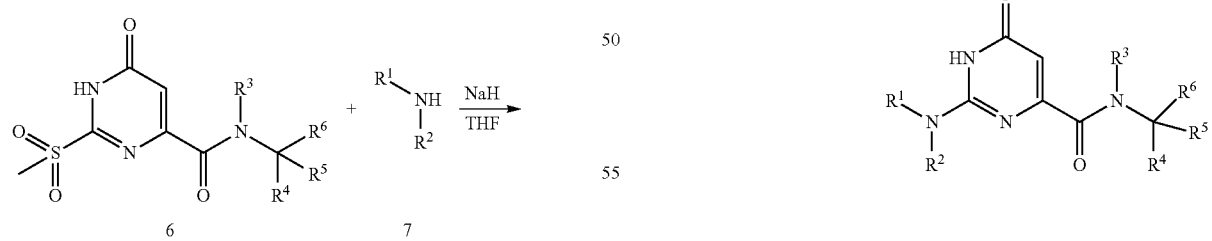

Scheme I

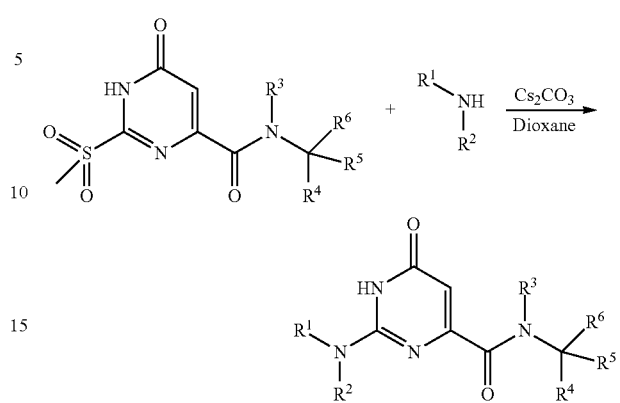

Scheme J

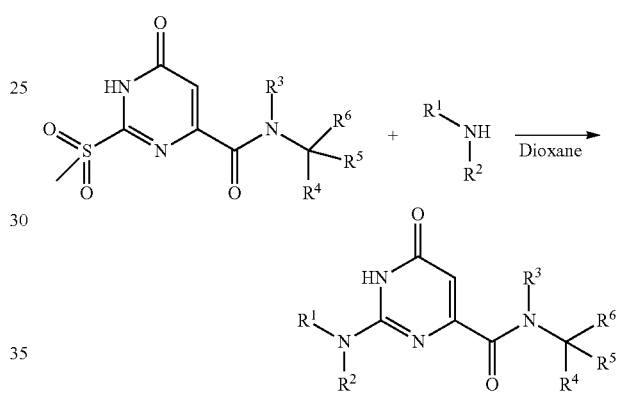

Scheme K

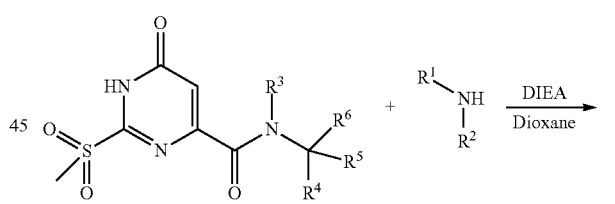

Scheme L

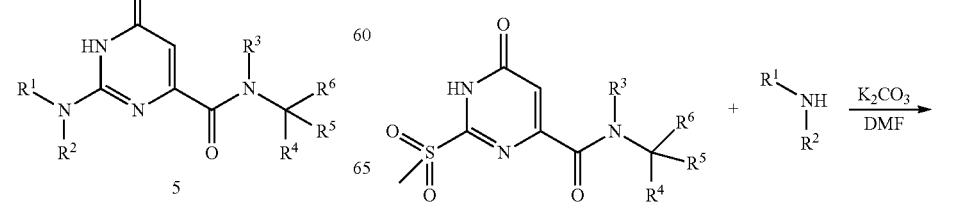

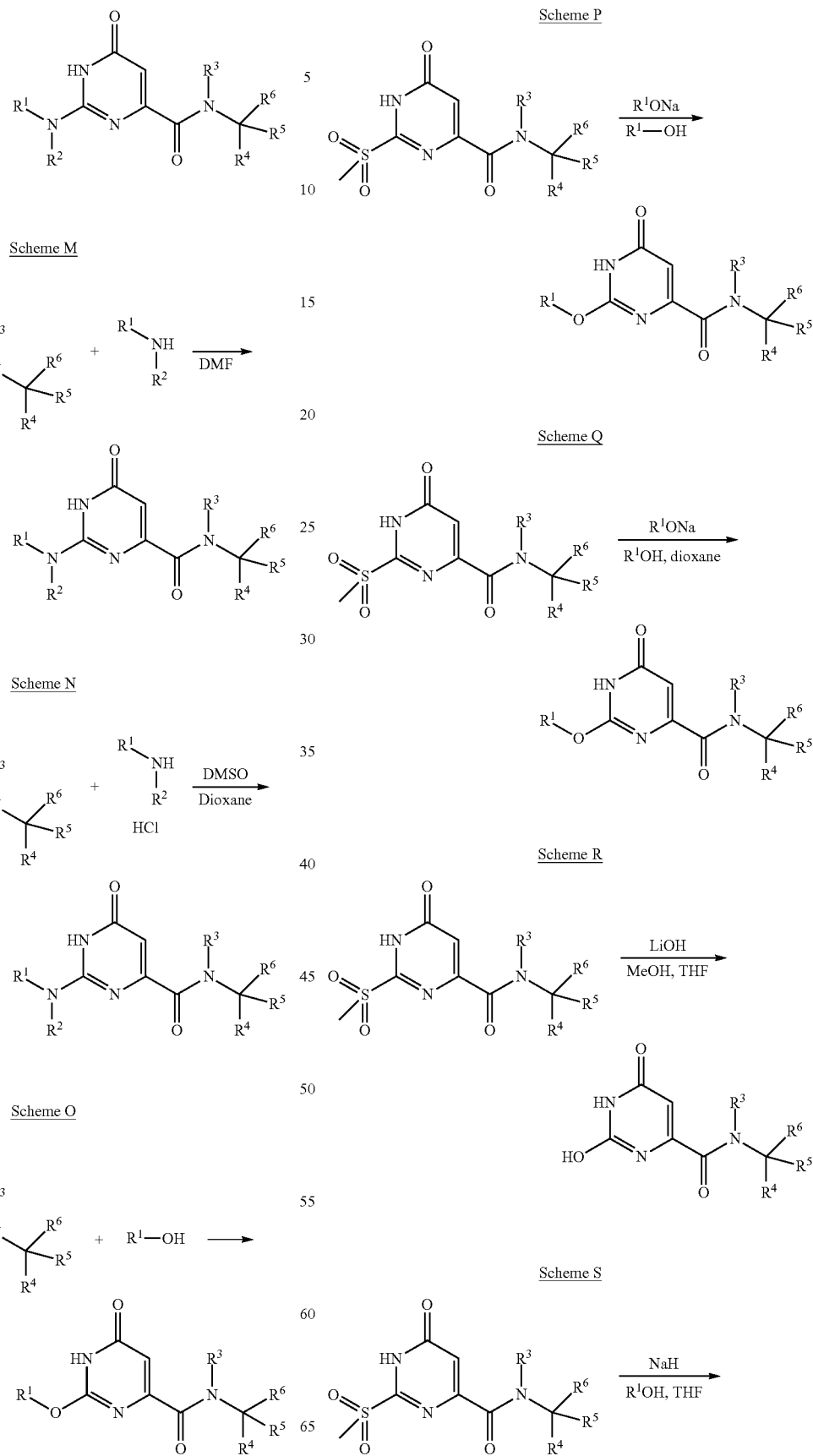

-continued

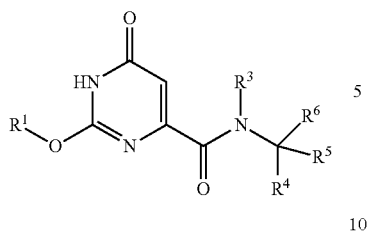

Scheme T

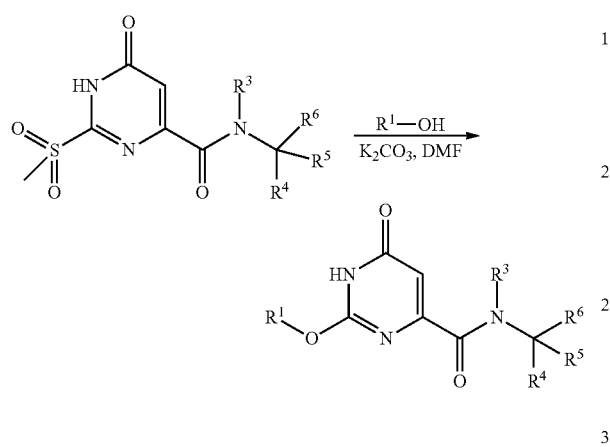

Scheme U

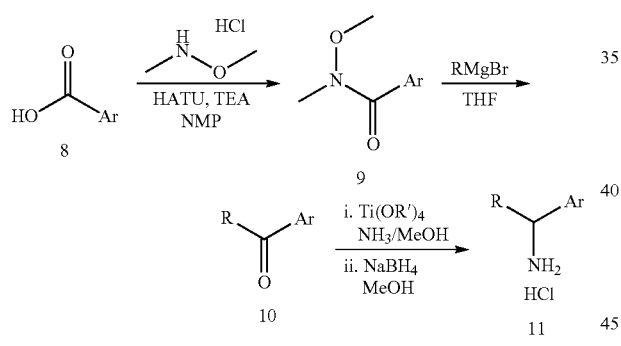

Scheme U illustrates one procedure for the syntheses of amines such as 11. The coupling of aryl carboxylic acid 8 and N,O-dimethylhydroxylamine hydrochloride gives Weinreb amide 9. The ketone 10 is obtained by addition of a Grignard reagent RMgBr to the Weinreb amide 9. The ketone 10 is converted to amine 11 via a reductive amination using Ti(OR')$_4$, NH$_3$ and NaBH$_4$.

Scheme V

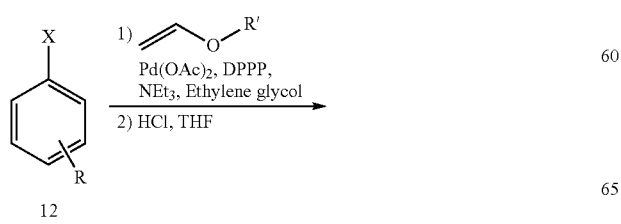

-continued

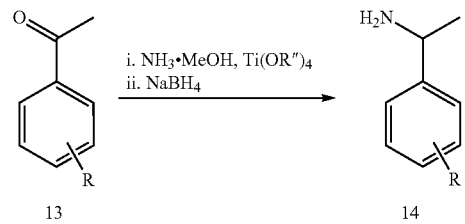

Scheme V illustrates another procedure for the syntheses of amines such as 14. Aryl halide 12 is converted to ketone 13 using a Heck reaction followed by hydrolysis. The ketone 13 is converted to amine 14 via a reductive amination reaction using Ti(OR')$_4$, NH$_3$ and NaBH$_4$.

Scheme W

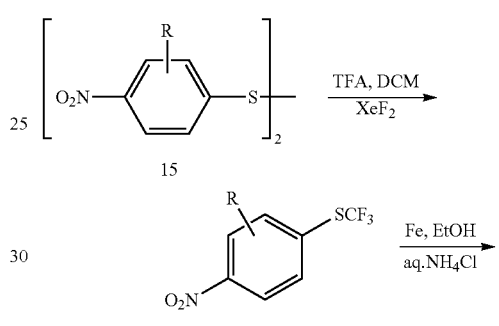

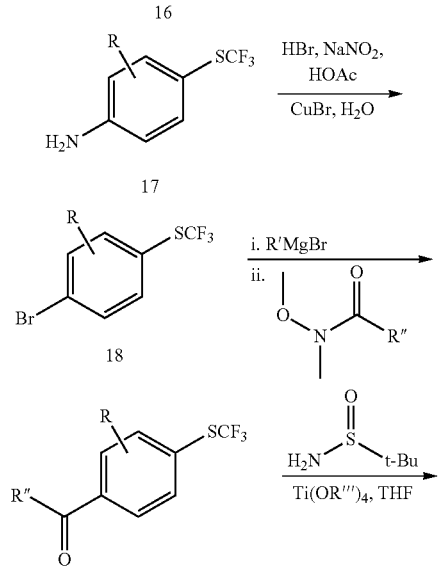

-continued

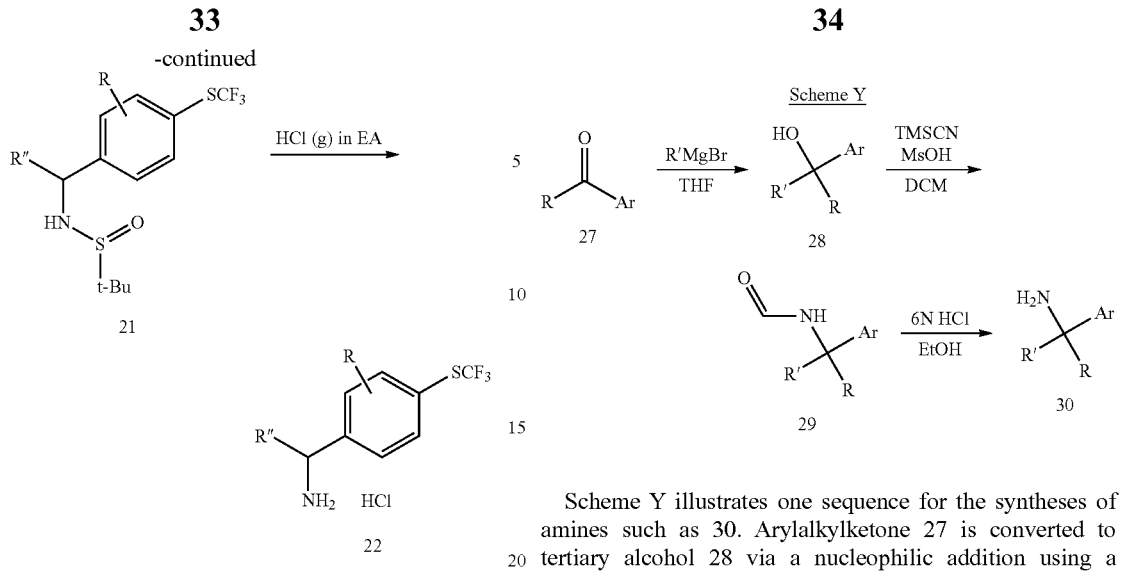

Scheme W illustrates a procedure for the syntheses of amines such as 22. Disulfane compound 15 is prepared according to the methods described by Kirsch et al. in *European Journal of Organic Chemistry*, 2005, 14, 3095-3100. Nitrobenzene compound 16 is prepared from disulfane compound 15 by treatment with TFA and XeF$_2$. Reduction of nitrobenzene compound 16 using iron and ammonium chloride forms aniline 16. Aniline 17 is converted to aryl bromide 18 through a Sandmeyer reaction. Transmetalation of aryl halide 18 using a Grignard reagent followed by the addition of a Weinreb amide leads to ketone 19. The condensation of ketone 19 and tert-butanesulfinamide in the presence of Ti(OR''')$_4$ in THF gives sulfinimine 20. The sulfinimine 20 was reduced by NaBH$_4$ in MeOH to give sulfinamide 21. The sulfinyl group is readily removed under acidic conditions to give amine 22.

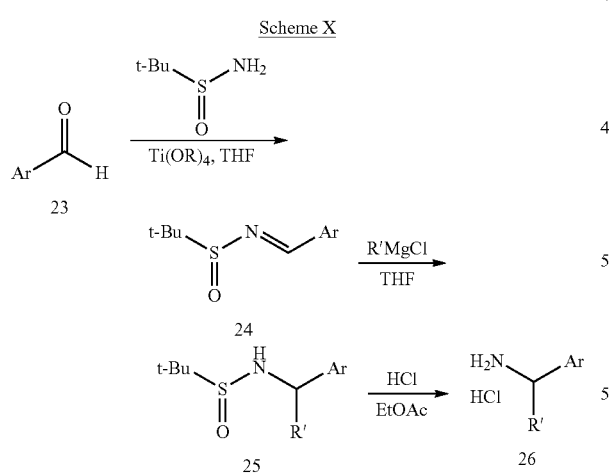

Scheme X illustrates another sequence for the syntheses of amines such as 26. The condensation of aldehyde 23 and tert-butanesulfinamide in the presence of Ti(OR)$_4$ in THF gives sulfinimine 24. Addition of a Grignard reagent R'MgCl to sulfinimine 24 in THF leads to sulfinamide 25. The sulfinyl group is readily removed under acidic conditions to give amine 26.

Scheme Y illustrates one sequence for the syntheses of amines such as 30. Arylalkylketone 27 is converted to tertiary alcohol 28 via a nucleophilic addition using a Grignard reagent R'MgBr. The alcohol 28 is converted to formamide 29 via a Ritter reaction using TMSCN under acidic conditions. The formamide 27 is hydrolyzed under acidic conditions to afford the amine 30.

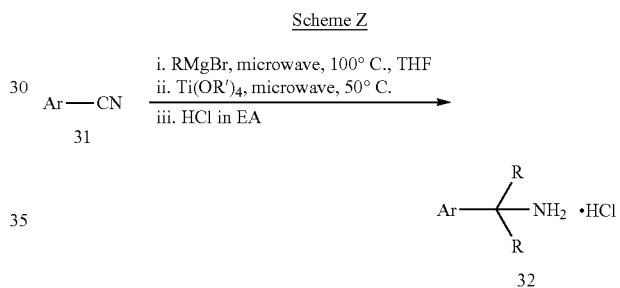

Scheme Z illustrates another sequence for the syntheses of α,α-disubstituted amines 32. Addition of a Grignard reagent RMgBr to aromatic nitrile 31 gives a magnesium-imine complex, to which a second equivalent of a Grignard reagent RMgBr is added mediated by Ti(OR')$_4$ to form α,α-disubstituted amine 32.

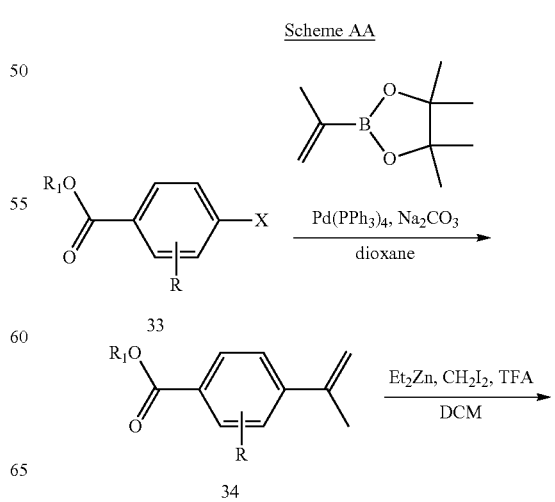

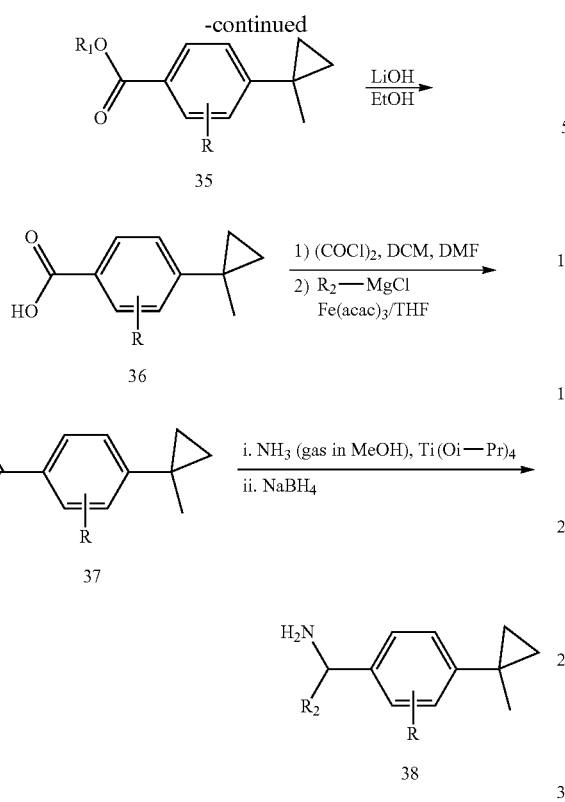

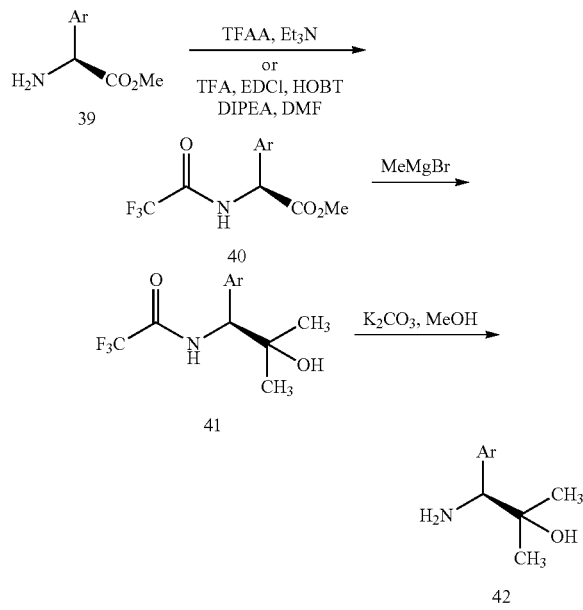

Scheme AA illustrates one sequence for the syntheses of amines such as 38. Aryl halide 33 is converted to olefin 34 by a Suzuki coupling. Cyclopropanation of olefin 34 using Et₂Zn and CH₂I₂ affords ester 35. Then ester 33 is hydrolyzed to acid 36. The acid 36 is converted to acyl chloride, which is converted to ketone 35 by a Grignard addition in the presence of tris(acetylacetonate)iron(III). The ketone 37 is converted to amine 38 via a reductive amination using Ti(OR')₄, NH₃ and NaBH₄.

Scheme AB outlines the procedure for the synthesis the 2-methylpropan-2-ol benzyl amines 42 from commercially available (S)-aminoesters 39. The amine is first protected as the trifluoroacetamide 40 which is then treated with an excess of Grinard reagent. Once isolated, the trifluoroacetamide 41 can be deprotected with base to yield the desired 2-methylpropan-2-ol benzyl amine 42. In some cases, minor racemazation (5-15%) was observed and the enantiomers can be separated via chiral column chromatography.

PREPARATORY EXAMPLE 1

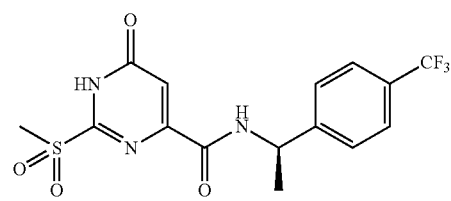 [SMILES: C[C@@H](NC(=O)c1cc(=O)[nH]c(S(C)(=O)=O)n1)c1ccc(C(F)(F)F)cc1]

(R)-2-(methylsulfonyl)-6-oxo-N-(1-(4-(trifluoromethyl)phenyl)ethyl)-16-dihydropyrimidine-4-carboxamide To a stirred mixture of (R)-2-(methylthio)-6-oxo-N-(1-(4-(trifluoromethyl)phenyl)ethyl)-1,6-dihydro-pyrimidine-4-carboxamide from Example 15 (0.59 g, 1.651 mmol) in MeOH (45 mL) was added a solution of oxone (3.05 g, 4.95 mmol) in water (14 mL). The resulting suspension was stirred at RT overnight. Solvent was removed under reduced pressure. The residue was diluted with water (25 mL) and extracted with DCM twice. The combined organic layers were washed with water, brine, dried over sodium sulfate, and concentrated under reduced pressure to yield the title compound, which was used in the next step without further purification. LC-MS: 390.0 (M+H).

PREPARATORY EXAMPLE 2

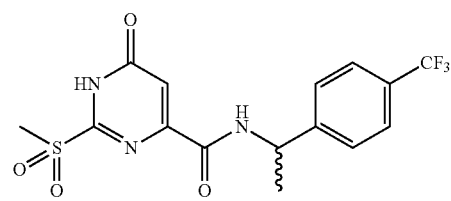 [SMILES: CC(NC(=O)c1cc(=O)[nH]c(S(C)(=O)=O)n1)c1ccc(C(F)(F)F)cc1]

2-(Methylsulfonyl)-6-oxo-N-(1-(4-(trifluoromethyl)phenyl)ethyl)-16-dihydropyrimidine-4-carboxamide (racemic)

The title compound was prepared from racemic 2-(methylthio)-6-oxo-N-(1-(4-(trifluoromethyl)-phenyl)-ethyl)-1,6-dihydropyrimidine-4-carboxamide obtained as described in Example 15, Method A by oxidation as described in Preparatory Example 1.

TABLE 1

The compounds in the following Table were prepared using amide coupling procedures similar to those described in Example 15 Method B and followed by oxidation described in Preparatory Example 1, except for Preparatory Example 5, where the amide coupling step was carried out using conditions described in Example 1 (Scheme A).

| Preparatory Example Number | Structure | IUPAC Name | Exact Mass [M + H]+ |
|---|---|---|---|
| 3 | 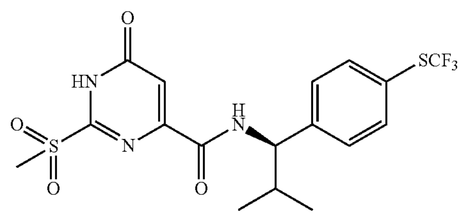 | (R)-N-(2-methyl-1-(4-(trifluoromethoxy)phenyl)propyl)-2-(methylsulfonyl)-6-oxo-1,6-dihydropyrimidine-4-carboxamide | 471.9 (M + Na) and 450.0 |
| 4 | 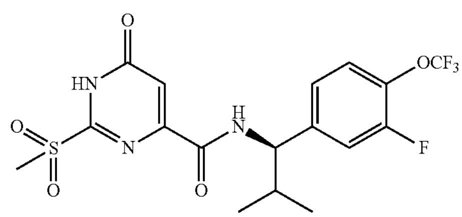 [SMILES: CC(C)[C@@H](NC(=O)c1cc(=O)[nH]c(S(C)(=O)=O)n1)c1ccc(OC(F)(F)F)c(F)c1] | (R)-N-(1-(3-fluoro-4-(trifluoromethoxy)phenyl)-2-methylpropyl)-2-(methylsulfonyl)-6-oxo-1,6-dihydropyrimidine-4-carboxamide | 452.0 |
| 5 | 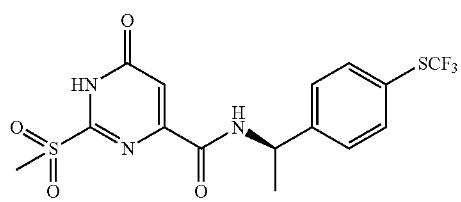 | (R)-2-(methylsulfonyl)-6-oxo-N-(1-(4-((trifluoromethyl)thio)phenyl)ethyl)-1,6-dihydropyrimidine-4-carboxamide | 443.9 (M + Na) and 421.9 |
| 6 | 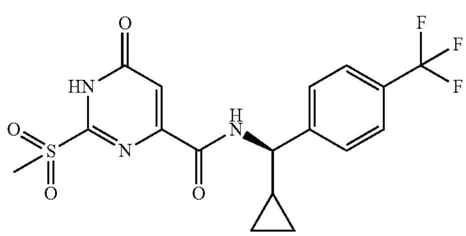 [SMILES: CS(=O)(=O)c1nc(C(=O)N[C@@H](c2ccc(C(F)(F)F)cc2)C2CC2)cc(=O)[nH]1] | (R)-N-(cyclopropyl(4-(trifluoromethyl)phenyl)methyl)-2-(methylsulfonyl)-6-oxo-1,6-dihydropyrimidine-4-carboxamide | 415.9 |
| 7 | 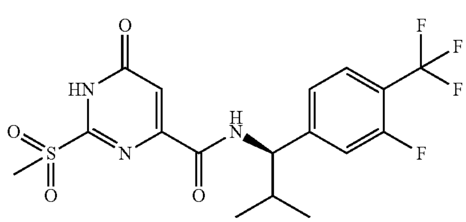 [SMILES: CC(C)[C@@H](NC(=O)c1cc(=O)[nH]c(S(C)(=O)=O)n1)c1ccc(C(F)(F)F)c(F)c1] | (R)-N-(1-(3-fluoro-4-(trifluoromethyl)phenyl)-2-methylpropyl)-2-(methylsulfonyl)-6-oxo-1,6-dihydropyrimidine-4-carboxamide | 436.0 |
| 8 | 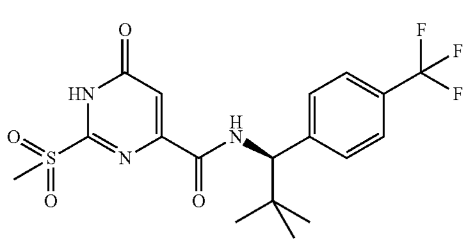 [SMILES: CC(C)(C)[C@@H](NC(=O)c1cc(=O)[nH]c(S(C)(=O)=O)n1)c1ccc(C(F)(F)F)cc1] | (R)-N-(2,2-dimethyl-1-(4-(trifluoromethyl)phenyl)propyl)-2-(methylsulfonyl)-6-oxo-1,6-dihydropyrimidine-4-carboxamide | 432.0 |

| Preparatory Example Number | Structure | IUPAC Name | Exact Mass [M + H]+ |
|---|---|---|---|
| 9 | ![structure] | (R)-N-(1-(3-fluoro-4-((trifluoromethyl)thio)phenyl)-2-methylpropyl)-2-(methylsulfonyl)-6-oxo-1,6-dihydropyrimidine-4-carboxamide | 490.0 (M + Na) |

PREPARATORY EXAMPLE 10

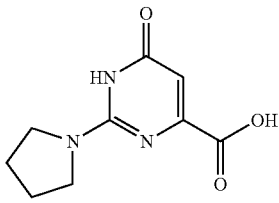 [SMILES: O=C(O)c1cc(=O)[nH]c(N2CCCC2)n1]

6-Oxo-2-(pyrrolidin-1-yl)-1,6-dihydropyrimidine-4-carboxylic acid

To a stirred mixture of sodium (Z)-1,4-diethoxy-1,4-dioxobut-2-en-2-olate (2 g, 9.52 mmol) and amino(pyrrolidin-1-yl)methaniminium iodide (2.52 g, 10.47 mmol) was added a solution of NaOH (0.761 g, 19.03 mmol) in water (19.03 ml). The mixture was stirred at RT overnight under $N_2$. The resulting reaction mixture was concentrated to give title compound, which was used in the next step without further purification. MS: 210.1 (M+H).

PREPARATORY EXAMPLE 11

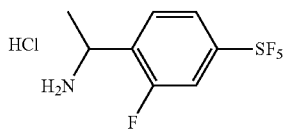

1-(2-Fluoro-4-(pentafluorothio)phenyl)ethanamine hydrochloride (Scheme U)

Step 1. 4-(Pentafluorothio)-2-fluoro-N-methoxy-N-methylbenzamide

HATU (0.590 g, 1.6 mmol) was added to a stirred solution of 4-(pentafluorothio)-2-fluorobenzoic acid (0.400 g, 1.3 mmol) in NMP (4 mL) at 0° C. The reaction solution was stirred at 0° C. for 10 min. To the solution were added N,O-dimethylhydroxylamine hydrochloride (0.189 g, 1.9 mmol) and TEA (0.54 mL, 3.9 mmol) at 0° C. The reaction suspension was stirred at room temperature for 16 h. The resulting suspension was diluted with water (100 mL) and extracted with EtOAc (3×20 mL). The combined organic layers were washed with brine (50 mL), dried with anhydrous $Na_2SO_4$ and filtered. The filtrate was concentrated under reduced pressure. The residue was purified by column chromatography over silica gel eluting with 50% ethyl acetate in petroleum ether. The fractions containing desired product were combined and concentrated. The title compound was obtained as a liquid. MS (+ESI) m/z=310.0.

Step 2.
1-(2-Fluoro-4-(pentafluorothio)phenyl)ethanone

Methyl magnesium bromide (1.0 M in THF, 2.56 mL, 2.6 mmol) was added dropwise to a stirred solution of 4-(pentafluorothio)-2-fluoro-N-methoxy-N-methylbenzamide (0.450 g, 1.2 mmol) in THF (5 mL) at 0° C. The reaction solution was stirred at 0° C. for 2 h. The resulting suspension was diluted with sat'd aqueous $NH_4Cl$ (40 mL) and extracted with $Et_2O$ (3×20 mL). The combined organic layers were washed with brine (50 mL), dried with anhydrous $Na_2SO_4$ and filtered. The filtrate was concentrated under reduced pressure. The residue was purified by column chromatography over silica gel eluting with 10% ethyl acetate in petroleum ether. The fractions containing desired product were combined and concentrated. The title compound was obtained as a liquid. MS (+EI) m/z=264.0. (GCMS)

Step 3.
1-(2-Fluoro-4-(pentafluorothio)phenyl)ethanamine hydrochloride

To a solution of sat'd $NH_3$ in MeOH (3 mL) were added 1-(2-fluoro-4-(pentafluorothio)phenyl)-ethanone (0.165 g, 0.6 mmol) and $Ti(OEt)_4$ (0.37 mL, 1.3 mmol) at room temperature. The reaction mixture was stirred at 60° C. for 2 h. The resulting suspension was cooled. $NaBH_4$ (35.0 mg, 0.9 mmol) was added to the suspension at 0° C. and the reaction mixture was stirred at 0° C. for 30 min. The resulting mixture was concentrated under reduced pressure. The residue was diluted with water (30 mL) and the pH value of the mixture was adjusted to 12 with sat'd NaOH. The mixture was extracted with ethyl acetate (3×15 mL). The combined organic layers were washed with brine (30 mL), dried with anhydrous $Na_2SO_4$ and filtered. The filtrate was concentrated under reduced pressure. The residue was diluted with EtOAc (5 mL) and treated with a sat'd solution of HCl in EtOAc. The resulting precipitate was collected, washed with EtOAc (3×1 mL) and dried. The title compound was obtained as a solid and used in the next step without further purification. MS (+ESI) m/z=266.0.

PREPARATORY EXAMPLE 12

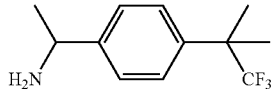

1-(4-(1,1,1-Trifluoro-2-methylpropan-2-yl)phenyl)ethanamine (Scheme V)

Step 1. 1-(4-(1,1,1-Trifluoro-2-methylpropan-2-yl)phenyl)ethanone

Palladium(II) acetate (27.7 mg, 0.1 mmol), DPPP (10.2 mg, 0.03 mmol), n-butyl vinyl ether (0.34 g, 3.4 mmol) and triethylamine (0.39 mL, 2.8 mmol) were added to the solution of 1-bromo-4-(1,1,1-trifluoro-2-methylpropan-2-yl)-benzene (0.30 g, 1.1 mmol) in ethylene glycol (2.0 mL). The mixture was purged with nitrogen 3 times and stirred at 145° C. for 4 h under nitrogen. The mixture was cooled and diluted with ethyl acetate (50 mL). The mixture was washed with water (4×20 mL), brine (20 mL), dried with anhydrous Na$_2$SO$_4$ and filtered. The filtrate was concentrated under reduced pressure. The residue was diluted with tetrahydrofuran (2 mL). Then hydrochloric acid (6.0 M, 3.0 mL) was added. The reaction mixture was stirred at 25° C. for 2 h. The resulting mixture was extracted with dichloromethane (3×10 mL). The combined organic fractions were washed with water (2×5 mL), dried with anhydrous Na$_2$SO$_4$, filtered and concentrated. The residue was purified by column chromatography over silica gel eluting with 15% ethyl acetate in petroleum ether. The fractions containing desired product were combined and concentrated. The title compound was obtained as a liquid. $^1$H NMR (300 MHz, CDCl$_3$) δ: 7.95 (d, J=8.4 Hz, 2H), 7.59 (d, J=8.4 Hz, 2H), 2.61 (s, 3H), 1.61 (s, 6H).

Step 2. 1-(4-(1,1,1-Trifluoro-2-methylpropan-2-yl)phenyl)ethanamine

The title compound was prepared as described for Preparatory Example 11 step 3 using 1-(4-(1,1,1-trifluoro-2-methylpropan-2-yl)phenyl)ethanone to give the title compound as a solid, which was used in the next step without further purification. $^1$H NMR (300 MHz, CDCl$_3$) δ: 7.45 (d, J=8.4 Hz, 2H), 7.36 (d, J=8.4 Hz, 2H), 3.98 (q, J=6.9 Hz, 1H), 2.21-2.18 (br, 2H), 1.53 (s, 6H), 1.18 (d, J=7.2 Hz, 3H).

PREPARATORY EXAMPLE 13

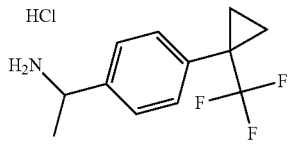

1-(4-(1-(trifluoromethyl)cyclopropyl)phenyl)ethanamine hydrochloride

The title compound was prepared using procedures similar to those described in Preparatory Example 12 using appropriate starting materials. MS (+ESI) m/z=230.1.

PREPARATORY EXAMPLE 14

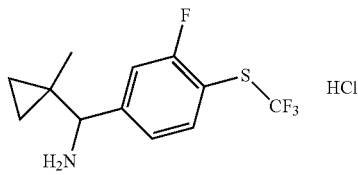 [SMILES: CC1(C(N)c2ccc(SC(F)(F)F)c(F)c2)CC1 ; Cl]

(3-Fluoro-4-((trifluoromethyl)thio)phenyl)(1-methylcyclopropyl)methanamine hydrochloride (Scheme W)

Step 1. (2-Fluoro-4-nitrophenyl)(trifluoromethyl)sulfane

To a solution of 2,2,2-trifluoroacetic acid (19.9 g, 0.174 mol) and 1,2-bis(2-fluoro-4-nitrophenyl)-disulfane (3.00 g, 8.7 mmol; prepared according to procedures from Kirsch et al. in European Journal of Organic Chemistry, 2005, 14, 3095-3100) in DCM (30.0 mL) was added difluoroxenon (3.69 g, 21.8 mmol). The reaction mixture was stirred at 30° C. for 1 h. The resulting mixture was dissolved in 100 mL of DCM and washed with brine (2×50 mL). The organic layer was dried over anhydrous Na$_2$SO$_4$, filtered and concentrated. The residue was purified by column chromatography over silica gel eluting with 1% ethyl acetate in petroleum ether. The fractions containing desired product were combined and concentrated. The title compound was obtained as a liquid. $^1$H NMR (400 MHz, DMSO-d$_6$) δ: 8.42-8.34 (m, 1H), 8.24-8.16 (m, 1H), 8.16-8.03 (m, 1H).

Step 2. 3-Fluoro-4-((trifluoromethyl)thio)aniline

To a stirred mixture of (2-fluoro-4-nitrophenyl)(trifluoromethyl)sulfane (2.70 g, 11.2 mmol) and sat'd ammonium chloride (15.0 mL) in EtOH (30.0 mL) was added iron powder (3.13 g, 56.0 mmol). The reaction mixture was stirred at 100° C. for 1 h. The resulting mixture was cooled, diluted with ethyl acetate (500 mL) and washed with brine (2×250 mL). The organic layer was dried over anhydrous Na$_2$SO$_4$ and filtered. Volatiles were evaporated and residue obtained was purified by column chromatography over silica gel eluting with 30% ethyl acetate in petroleum ether. The fractions containing desired product were combined and concentrated. The title compound was obtained as a liquid. MS (+ESI) m/z=212.0.

Step 3. (4-Bromo-2-fluorophenyl)(trifluoromethyl)sulfane

To a solution of 3-fluoro-4-((trifluoromethyl)thio)aniline (1.00 g, 4.7 mmol) in acetic acid (20 mL) was added HBr (20 mL, 0.177 mol). An aqueous solution of sodium nitrite (0.343 g, 5.0 mmol) in water (1 mL) was then added dropwise to the reaction mixture and the resulting mixture was stirred at 0° C. for 10 min. The resulting mixture was added dropwise to a solution of copper(I) bromide (1.36 g, 9.5 mmol) in HBr (20.0 mL, 177 mmol) at 0° C. The reaction solution was stirred at 0° C. for 30 min. The resulting solution was diluted with water (300 mL) and extracted with dichloromethane (3×50 mL). The combined organic layers were washed with brine (200 mL), dried with anhydrous Na$_2$SO$_4$, filtered and concentrated. The residue was purified by column chromatography over silica gel using hexane as eluent. The fractions containing desired product were combined and concentrated. The title compound was obtained as a liquid. $^1$H NMR (400 MHz, CDCl$_3$) δ: 7.76-7.53 (m, 1H), 7.45-7.39 (m, 2H).

Step 4. (3-Fluoro-4-((trifluoromethyl)thio)phenyl)(1-methylcyclopropyl)methanone Isopropylmagnesium bromide (3.0 M in THF, 0.5 mL, 1.5 mmol) was added dropwise to a solution of (4-bromo-2-fluorophenyl)(trifluoromethyl)sulfane (0.340 g, 1.2 mmol) in THF (3.0 mL) at −78° C. and stirred at room temperature for 1 h. To the reaction solution was added dropwise a solution of N-methoxy-N,1-dimethylcyclopropanecarboxamide (0.168 g, 1.2 mmol) in THF (2.0 mL) at −78° C. and stirred at room temperature for 16 h. The resulting solution was diluted with sat'd NH$_4$Cl (10.0 mL) and extracted with Et$_2$O (3×5.0 mL). The combined organic layers were washed with brine (10 mL), dried with anhydrous Na$_2$SO$_4$, filtered and concentrated. The residue was purified by column chromatography over silica gel using hexane as eluent. The fractions containing desired product were combined and concentrated. The title compound was obtained as a liquid. $^1$H NMR (400 MHz, DMSO-d$_6$) δ: 7.78-7.74 (m, 1H), 7.61-7.54 (m, 2H), 1.46 (s, 3H), 1.38-1.34 (m, 2H), 0.90-0.83 (m, 2H).

Step 5. (Z)—N-((3-fluoro-4-((trifluoromethyl)thio)phenyl)(1-methylcyclopropyl)methylene)-2-methylpropane-2-sulfinamide To a solution of (3-fluoro-4-((trifluoromethyl)thio)phenyl)(1-methylcyclopropyl)methanone (40.0 mg, 0.1 mmol) in THF (0.5 mL) was added 2-methylpropane-2-sulfinamide (34.8 mg, 0.3 mmol) and titanium(IV) ethoxide (0.131 g, 0.6 mmol). The reaction mixture was stirred at 70° C. for 16 h. The resulting solution was cooled, diluted with ethyl acetate (8.0 mL) and quenched with water (0.5 mL). The mixture was filtered. The filter cake was washed with ethyl acetate (3×0.5 mL). The combined filtrates was washed with brine (5 mL), dried with anhydrous Na$_2$SO$_4$ and filtered. Volatiles were evaporated and residue obtained was purified by Prep-TLC over silica gel eluting with 5% ethyl acetate in petroleum ether. The fractions containing desired product were combined and concentrated. The title compound was obtained as a liquid. MS (+ESI) m/z=382.2.

Step 6. N-((3-fluoro-4-((trifluoromethyl)thio)phenyl)(1-methylcyclopropyl)methyl)-2-methylpropane-2-sulfinamide NaBH$_4$ (45.0 mg, 1.2 mmol) was added to a solution of (Z)—N-((3-fluoro-4-((trifluoromethyl)thio)-phenyl)(1-methylcyclopropyl)methylene)-2-methylpropane-2-sulfinamide (0.45 g, 1.2 mmol) in MeOH (5.0 mL). The reaction solution was stirred at 0° C. for 30 min. The resulting solution was concentrated under reduced pressure. The residue was purified by column chromatography over silica gel using 35-50% gradient of ethyl acetate in petroleum ether as eluent. The fractions containing desired product were combined and concentrated. The title compound was obtained as a liquid. MS (+ESI) m/z=384.2.

Step 7. (3-Fluoro-4-((trifluoromethyl)thio)phenyl)(1-methylcyclopropyl)methanamine hydrochloride Hydrochloric acid in ethyl acetate (0.5 mL, 0.8 mmol) was added dropwise to a stirred solution of N-((3-fluoro-4-((trifluoromethyl)thio)phenyl)(1-methylcyclopropyl)methyl)-2-methylpropane-2-sulfinamide (0.320 g, 0.8 mmol) in ethyl acetate (8.0 mL). The resulting suspension was stirred at room temperature for 2 h and was filtered. The filter cake was washed with diethyl ether (3×2.0 mL) and dried to give the title compound as a solid which was used in the next step without further purification. $^1$H NMR (400 MHz, DMSO-d$_6$) δ: 8.80-8.68 (br, 3H), 7.93 (m, 1H), 7.65 (d, J=10.4 Hz, 1H), 7.48 (d, J=8.0 Hz, 1H), 3.96-3.87 (m, 1H), 0.92 (s, 3H), 0.92-0.91 (m, 1H), 0.83-0.78 (m, 1H), 0.58-0.55 (m, 1H), 0.38-0.32 (m, 1H).

PREPARATORY EXAMPLE 15

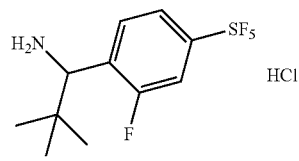

1-(2-Fluoro-4-(pentafluorosulfanyl)phenyl)-2,2-dimethylpropan-1-amine hydrochloride (Scheme X)

Step 1. N-(2-fluoro-4-(pentafluorosulfanyl)benzylidene)-2-methylpropane-2-sulfinamide The title compound was prepared using procedures similar to those described in step 5 of Preparatory Example 14 using 2-fluoro-4-(pentafluorosulfanyl)benzaldehyde to afford the title compound as a liquid. MS (+ESI) m/z=354.1.

Step 2. N-(1-(2-fluoro-4-(pentafluorosulfanyl)phenyl)-2,2-dimethylpropyl)-2-methylpropane-2-sulfinamide To a stirred solution of N-(2-fluoro-4-(pentafluorosulfanyl)benzylidene)-2-methylpropane-2-sulfinamide (0.220 g, 0.6 mmol) in THF (3 mL) was added dropwise tert-butylmagnesium chloride (1.0 M in THF, 1.30 mL, 1.3 mmol) at 0° C. The reaction solution was stirred at 0° C. for 2 h. The resulting solution was quenched with sat'd NH$_4$Cl (5 mL) and extracted with EtOAc (3×2 mL). The combined organic layers were washed with brine (5 mL), dried with anhydrous Na$_2$SO$_4$ and filtered. The filtrate was concentrated under reduced pressure. The residue was purified by column chromatography over silica gel using 0-40% gradient of ethyl acetate in petroleum ether as eluent. The combined organic fractions containing desired product were combined and concentrated under reduced pressure to give the crude product which was further purified by column chromatography over C18 silica gel using 70-95% gradient of methanol in water as eluent. The title compound was obtained as a solid. MS (+ESI) m/z=412.2.

Step 3. 1-(2-Fluoro-4-(pentafluorosulfanyl)phenyl)-2,2-dimethylpropan-1-amine hydrochloride The title compound was prepared using procedures similar to those described in step 7 of Preparatory Example 14 using N-(1-(2-fluoro-4-(pentafluorosulfanyl)phenyl)-2,2-dimethylpropyl)-2-methylpropane-2-sulfinamide to afford the title compound as a solid, which was used in next step without further purification. MS (+ESI) m/z=308.1.

PREPARATORY EXAMPLE 16

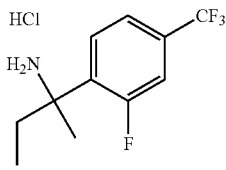

2-(2-Fluoro-4-(trifluoromethyl)phenyl)butan-2-amine hydrochloride (Scheme Y)

Step 1.
2-(2-Fluoro-4-(trifluoromethyl)phenyl)butan-2-ol

To a solution of 1-(2-fluoro-4-(trifluoromethyl)phenyl)ethanone (0.650 g, 3.2 mmol) in THF (6 mL) was added dropwise ethyl magnesium bromide (1.0 M in THF, 9.46 mL, 9.5 mmol) with stirring under nitrogen atmosphere at 0° C. The reaction mixture was stirred under nitrogen atmosphere for 2 h at 0° C. and stirred for another 2 h at room temperature. The resulting mixture was quenched with brine (30 mL) at 0° C. and extracted with ethyl acetate (3×30 mL). The combined organic layers were dried over anhydrous $Na_2SO_4$ and filtered. The filtrate was concentrated under vacuum. The residue was purified by column chromatography over silica gel eluting with 10% ethyl acetate in petroleum ether. The fractions containing desired product were combined and concentrated. The title compound was obtained as a liquid. MS (−ESI) m/z=234.9.

Step 2. N-(2-(2-fluoro-4-(trifluoromethyl)phenyl)butan-2-yl)formamide

To a stirred solution of 2-(2-fluoro-4-(trifluoromethyl)phenyl)butan-2-ol (0.300 g, 0.64 mmol) and trimethylsilyl cyanide (0.17 mL, 1.3 mmol) in dichloromethane (5 mL) was added dropwise methanesulfonic acid (0.8 mL, 12.3 mmol) at 0° C. The reaction solution was stirred at room temperature for 16 h. The resulting solution was cooled, diluted with aqueous $Na_2CO_3$ (2 M, 50 mL) and extracted with DCM (3×20 mL). The combined organic layers were washed with brine (50 mL), dried with anhydrous $Na_2SO_4$ and filtered. The filtrate was concentrated under reduced pressure. The residue was purified by column chromatography over silica gel using 0-100% gradient of ethyl acetate in petroleum ether as eluent. The fractions containing desired product were combined and concentrated. The title compound was obtained as a solid. MS (+ESI) m/z=264.1.

Step 3. 2-(2-Fluoro-4-(trifluoromethyl)phenyl)butan-2-amine hydrochloride

To a stirred suspension of N-(2-(2-fluoro-4-(trifluoromethyl)phenyl)butan-2-yl)formamide (0.100 g, 0.4 mmol) in EtOH (3 mL) was added portions of HCl (6 M, 1 mL, 6.0 mmol) at room temperature. The reaction suspension was stirred at 60° C. for 3 h. The resulting solution was cooled and concentrated under reduced pressure. The crude title compound was obtained as a solid and used for next step directly without further purification. MS (+ESI) m/z=235.7.

PREPARATORY EXAMPLE 17

2-(4-(Pentafluorosulfanyl)phenyl)propan-2-amine hydrochloride (Scheme Z)

A 20 mL Biotage microwave tube with stir bar was charged with 4-(pentafluorosulfanyl)benzonitrile (0.100 g, 0.4 mmol) and THF (5 ml) followed by methylmagnesium bromide (1.0 M in THF, 1.53 mL, 1.5 mmol). The resulting mixture was heated at 100° C. under microwave irradiation for 10 min. The resulting reaction mixture was cooled to 25° C., then titanium(IV) isopropoxide (0.124 g, 0.4 mmol) was added. After heating at 50° C. under microwave irradiation for 1 h, brine (10 mL) was added. The resulting mixture was extracted with ethyl acetate (3×15 mL). The combined organic fractions were dried over anhydrous $Na_2SO_4$ and filtered. HCl (1.0 N) in EtOAc was added to the filtrate and the filtrate was concentrated under reduced pressure. The crude product was triturated with EtOAc to afford the title compound as a solid and used for next step directly without further purification. MS (+ESI) m/z=262.1.

PREPARATORY EXAMPLE 18

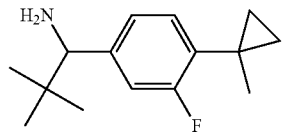 [SMILES: CC1(c2ccc(C(N)C(C)(C)C)cc2F)CC1]

1-(3-Fluoro-4-(1-methylcyclopropyl)phenyl)-2,2-dimethylpropan-1-amine (Scheme AA)

Step 1. Methyl 3-fluoro-4-(prop-1-en-2-yl)benzoate

Aqueous sodium carbonate (2.0 M, 32.2 mL, 64.4 mmol) was added to a solution of methyl 4-bromo-3-fluorobenzoate (5.0 g, 21.5 mmol) and 4,4,5,5-tetramethyl-2-(prop-1-en-2-yl)-1,3,2-dioxaborolane (4.69 g, 27.9 mmol) in 1,4-dioxane (150 mL) at RT. The reaction mixture was purged with nitrogen 3 times, then to the mixture was added tetrakis (triphenylphosphine) palladium(0) (1.24 g, 1.1 mmol). The resulting mixture was purged with nitrogen 3 times again and stirred under nitrogen atmosphere at 110° C. for 3 h. The reaction mixture was cooled and concentrated under reduced pressure. The residue was diluted with water (300 mL) and extracted with DCM (3×100 mL). The combined organic layers were washed with brine (3×200 mL), dried with anhydrous $Na_2SO_4$ and filtered. The filtrate was concentrated under reduced pressure. The residue was purified by column chromatography over silica gel using hexane as eluent. The fractions containing desired product were combined and concentrated. The title compound was obtained as a liquid. MS (+ESI): m/z=195.1.

Step 2. Methyl 3-fluoro-4-(1-methylcyclopropyl)benzoate

A solution of 2,2,2-trifluoroacetic acid (2.98 mL, 38.6 mmol) in DCM (10.0 mL) was added dropwise to a solution of diethylzinc (1.0 M in hexane, 38.6 mL, 38.6 mmol) in DCM (150 mL) at 0° C. The reaction suspension was stirred at 0° C. for 15 min. Then to the reaction suspension was added a solution of diiodomethane (3.12 mL, 38.6 mmol) in DCM (10 mL) at 0° C. The reaction suspension was stirred at 0° C. for 15 min. To the reaction suspension was added dropwise a solution of methyl 3-fluoro-4-(prop-1-en-2-yl) benzoate (3.00 g, 15.5 mmol) in DCM (10 mL) at 0° C. The reaction mixture was stirred at 0° C. for 30 min and warmed to room temperature, stirred for additional 16 h. The resulting suspension was quenched with sat'd $NH_4Cl$ (200 mL) and extracted with DCM (3×100 mL). The combined organic layers were washed with brine (1×300 mL), dried with anhydrous $Na_2SO_4$ and filtered. The filtrate was concentrated under reduced pressure. The residue was purified by column chromatography over silica gel using hexane as eluent. The fractions containing desired product were combined and concentrated. The title compound was obtained as a liquid: MS (+ESI): m/z=209.1.

Step 3. 3-Fluoro-4-(1-methylcyclopropyl)benzoic acid

Lithium hydroxide (2.0 M in water, 30.0 mL, 60.0 mmol) was added to a solution of methyl 3-fluoro-4-(1-methylcyclopropyl)benzoate (3.10 g, 14.9 mmol) in ethanol (60.0 mL). The reaction mixture was stirred at 20° C. for 16 h. The pH value of the resulting mixture was adjusted to 5 with aqueous hydrochloric acid solution (1.0 M). The resulting mixture was washed with brine (200 mL).

The separated aqueous phase was extracted with ethyl acetate (3×200 mL). The combined organic layers were dried with anhydrous $Na_2SO_4$ and filtered. The filtrate was concentrated. The title compound was obtained as a solid and used for next step directly without further purification. MS (−ESI): m/z=192.9.

Step 4. 1-(3-Fluoro-4-(1-methylcyclopropyl)phenyl)-2,2-dimethylpropan-1-one

Oxalyl dichloride (0.216 g, 1.7 mmol) was added to a solution of 3-fluoro-4-(1-methylcyclopropyl)-benzoic acid (0.150 g, 0.8 mmol) and DMF (0.6 µl, 7.7 µmol) in DCM (4.0 mL) dropwise with stirring at 0° C. The reaction mixture was stirred under nitrogen atmosphere at 0° C. for 2 h. Then the reaction mixture was concentrated to give 3-fluoro-4-(1-methylcyclopropyl)benzoyl chloride as a liquid. The residue was dissolved in THF (4.0 mL) and was added iron(III) acetylacetonate (8.2 mg, 0.02 mmol). This was followed by dropwise addition of tert-butylmagnesium chloride (1.0 M in THF, 0.77 mL, 0.77 mmol) with stirring at 0° C. in 5 min. The reaction mixture was stirred under nitrogen atmosphere at room temperature for 1 h. The resulting mixture was quenched with brine (20 mL) and extracted with ethyl acetate (3×20 mL). The combined organic layers were washed with brine (3×50 mL), dried with anhydrous $Na_2SO_4$, filtered and concentrated. The title compound was obtained as a liquid and used for next step directly without further purification. MS (+ESI) m/z=235.1.

Step 5. 1-(3-Fluoro-4-(1-methylcyclopropyl)phenyl)-2,2-dimethylpropan-1-amine The title compound was prepared using procedures similar to those described in Preparatory Example 11 step 3 using 1-(3-fluoro-4-(1-methylcyclopropyl)phenyl)-2,2-dimethylpropan-1-one to afford the tile compound as a liquid. MS (+ESI) m/z=236.2.

PREPARATORY EXAMPLE 19

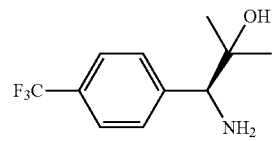

(S)-1-amino-2-methyl-1-(4-(trifluoromethyl)phenyl) propan-2-ol (Scheme AB)

Step 1: methyl (S)-2-(2,2,2-trifluoroacetamido)-2-(4-(trifluoromethyl)phenyl)acetate To a solution of (S)-methyl 2-amino-2-(4-(trifluoromethyl)phenyl)acetate hydrochloride (360 mg, 1.335 mmol) and DIEA (0.3 mL, 1.67 mmol) in DCM (2 mL) was added trifluoroacetic anhydride (0.23 mL, 1.60 mmol) and the resulting solution stirred at RT for 2 hours. The reaction was quenched with 1N HCl solution (2 mL) and diluted with DCM (5 mL). The organic layer was separated, washed with saturated aqueous solution of sodium bicarbonate (2 mL) and then brine (2 mL). The organic layer was dried over anhydrous sodium sulfate, filtered and then the filtrate concentrated under reduced pressure. The residue was purified via preparative TLC plates (3×1000 µM, silica gel) developing with 25% ethyl acetate in hexanes. The bands containing the product were removed from the plates and the product eluted with ethyl acetate. The solvent was removed under reduced pressure to afford the title compound as a solid. LC-MS (+ESI) m/z=330. $^1$H NMR (500 MHz, CD$_3$OD) δ: 7.70 (d, J=8.2 Hz, 2H), 7.53 (d, J=8.2 Hz, 2H), 5.63 (d, J=6.6 Hz, 1H), 3.82 (s, 3H).

Step 2: (S)-2,2,2-trifluoro-N-(2-hydroxy-2-methyl-1-(4 (trifluoromethyl)phenyl)propyl)acetamide To a stirring solution of methyl (S)-2-(2,2,2-trifluoroacetamido)-2-(4-(trifluoromethyl)phenyl)acetate (400 mg, 1.215 mmol) in THF (6 mL) cooled to 0° C. via ice/water bath under nitrogen atmosphere was added via syringe a 3.0 M solution of methylmagnesium bromide in THF (4.05 mL, 12.15 mmol) and the resulting solution stirred for 2 hours at 0° C. TLC and LC-MS showed that reaction was complete. The reaction mixture was quenched with saturated aqueous ammonium chloride solution (7 mL) and diluted with ethyl acetate (10 mL). The biphasic solution was separated and the aqueous layer washed with ethyl acetate (2×10 mL). The organics were combined, dried over anhydrous sodium sulfate, filtered and the filtrate concentrate to dryness under reduced pressure. The residue was taken up in 2 mL DCM and purified via prep TLC plates (2×1000 µM, silica gel) developing with 25% ethyl acetate in hexanes. The bands containing the product were removed from the plates and the product eluted off with ethyl acetate. The solvent was removed under reduced pressure to afford the compound as a solid. LC-MS (+ESI) m/z=330 and 312 (M+H—H$_2$O)$^+$. $^1$H NMR (500 MHz, CD$_3$OD) δ: 7.65 (d, J=8.1 Hz, 2H), 7.48 (d, J=8.1 Hz, 2H), 4.83 (d, J=8.6 Hz, 1H), 1.42 (s, 3H), 1.08 (s, 3H).

Step 3: (S)-1-amino-2-methyl-1-(4-(trifluoromethyl) phenyl)propan-2-ol

To a solution of (S)-2,2,2-trifluoro-N-(2-hydroxy-2-methyl-1-(4-(trifluoromethyl)phenyl)propyl)acetamide (130 mg, 0.395 mmol) in methanol/water (7:3) was added K$_2$CO$_3$ and the resulting suspension heated to 60° C. using an oil bath. All material went into solution after 30 minutes and then the homogeneous solution was stirred for another 16 hours at 60° C. Aliquot of reaction was run through LC-MS to prove that the reaction was complete. The solvent was removed under reduced pressure and the aqueous phase was then extracted with ethyl acetate (3×5 mL). The organics were then combined, dried over anhydrous sodium sulfate, filtered and the filtrate concentrate to dryness under reduced pressure to afford the title compound. The material was used for the next reaction without further purification. LC-MS (+ESI) m/z=234. $^1$H NMR (500 MHz, CD$_3$OD) δ: 7.60 (d, J=8.3 Hz, 2H), 7.48 (d, J=8.3 Hz, 2H), 3.90 (s, 1H), 1.25 (s, 3H), 1.05 (s, 3H).

PREPARATORY EXAMPLE 20

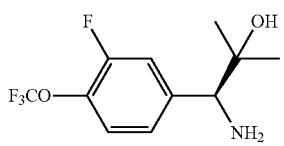

(S)-1-Amino-1-[3-fluoro-4-(trifluoromethoxy)phenyl]-2-methylpropan-2-ol

The title compound was prepared using procedures described in Preparatory Example 19. LC-MS (+ESI) m/z=268.0.

PREPARATORY EXAMPLE 21

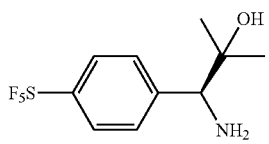

(S)-1-Amino-2-methyl-1-[4-(pentafluoro-λ$^6$-sulfanyl) phenyl]propan-2-ol

The title compound was prepared using procedures described in Preparatory Example 19. LC-MS (+ESI) m/z=292.1.

PREPARATORY EXAMPLE 22

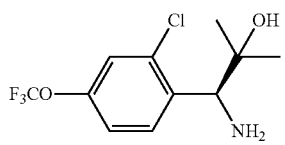 [SMILES: CC(C)(O)[C@@H](N)c1ccc(OC(F)(F)F)cc1Cl]

(S)-1-Amino-1-(2-chloro-4-(trifluoromethoxy)phenyl)-2-methylpropan-2-ol

The title compound was prepared using procedures described in Preparatory Example 19. LC-MS (+ESI) m/z=284.0/265.9.

EXAMPLE 1

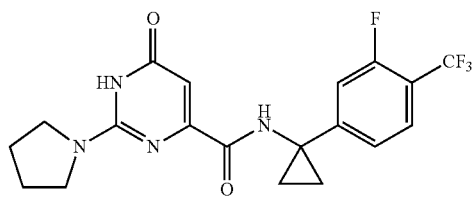 [SMILES: O=C(NC1(c2ccc(C(F)(F)F)c(F)c2)CC1)c1cc(=O)[nH]c(N2CCCC2)n1]

N-(1-(3-fluoro-4-(trifluoromethyl)phenyl)cyclopropyl)-6-oxo-2-(pyrrolidin-1-yl)-1,6-dihydropyrimidine-4-carboxamide (Scheme A)

To a stirred mixture of 6-oxo-2-(pyrrolidin-1-yl)-1,6-dihydropyrimidine-4-carboxylic acid (50 mg, 0.239 mmol) in DMF (1.2 mL) was added HOAt (35.8 mg, 0.263 mmol), 1-(3-fluoro-4-(trifluoro-methyl)phenyl)cyclopropan-1-amine hydrochloride (52 mg, 0.203 mmol) and DIEA (0.125 mL, 0.717 mmol). After stirring for 10 min, EDC (54.4 mg, 0.263 mmol) was added. The resulting mixture was stirred at RT overnight. The reaction was filtered. The filtrate was purified by RP-HPLC with Waters Sunfire C18 column (5 u, 19×100 mm) eluting with 35-70% acetonitrile in water with 0.1% FA to give the title compound. MS: 411.2 (M+1). $^1$H NMR (499 MHz, DMSO-d$_6$) δ 9.11 (s, 1 H), 7.68 (m, 1 H), 7.18 (m, 2 H), 6.04 (s, 1H), 3.54 (s, 1H), 2.54 (m, 4H), 1.91 (m, 4 H), 1.43 (m, 2 H), 1.38 (m, 2 H).

EXAMPLE 2

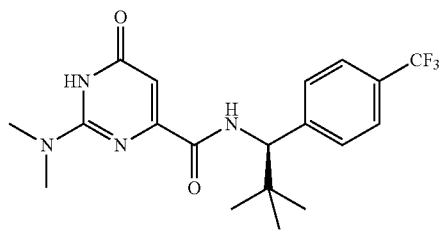 [SMILES: CN(C)c1nc(C(=O)N[C@@H](c2ccc(C(F)(F)F)cc2)C(C)(C)C)cc(=O)[nH]1]

(R)—N-(2,2-dimethyl-1-(4-(trifluoromethyl)phenyl) propyl)-2-(dimethylamino)-6-oxo-1,6-dihydropyrimidine-4-carboxamide (Scheme B)

To a stirred mixture of 2-(dimethylamino)-6-oxo-1,6-dihydropyrimidine-4-carboxylic acid (50 mg, 0.273 mmol)

in DMA (294 μl) was added (R)-2,2-dimethyl-1-(4-(trifluoromethyl)phenyl)propan-1-amine hydrochloride (73.1 mg, 0.273 mmol), HOAt (18.58 mg, 0.136 mmol), and EDC (78 mg, 0.409 mmol). The resulting mixture was stirred at RT under $N_2$ overnight. The mixture was filtered and purified by RP-HPLC with an XTerra C18 column eluting with 10-100% acetonitrile in water containing 0.1% TFA to afford the title compound. LC-MS: 397.0 (M+1). $^1$H NMR (500 MHz, CD$_3$OD) δ 8.87 (d, J=8.6 Hz, 1H), 7.64 (d, J=8.1 Hz, 2H), 7.50 (d, J=8.0 Hz, 2H), 6.29 (s, 1H), 4.85 (d, J=9.0 Hz, 1H), 3.24 (s, 6H), 1.01 (s, 9H).

EXAMPLE 3

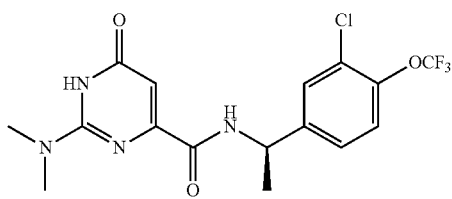 [SMILES: C[C@@H](NC(=O)c1cc(=O)[nH]c(N(C)C)n1)c1ccc(OC(F)(F)F)c(Cl)c1]

(R)—N-(1-(3-chloro-4-(trifluoromethoxy)phenyl) ethyl)-2-(dimethylamino)-6-oxo-1,6-dihydropyrimidine-4-carboxamide (Scheme C)

To a stirred mixture of 2-(dimethylamino)-6-oxo-1,6-dihydropyrimidine-4-carboxylic acid (50 mg, 0.273 mmol) in DMF (1 mL) was added HOAt (37.2 mg, 0.273 mmol) and (R)-1-(3-chloro-4-(trifluoromethoxy)phenyl)ethanamine HCl salt (83 mg, 0.3 mmol). After stirring the mixture for 10 min, EDC (78 mg, 0.409 mmol) was added. The resulting mixture was stirred at RT under $N_2$ overnight. The mixture was filtered and purified by preparative RP-HPLC (C-18), eluting with 5-95% acetonitrile in water with 0.05% TFA to give the title compound. MS: 405.1 (M+1). $^1$H NMR (500 MHz, CD$_3$OD) δ 7.61 (d, J=2.0 Hz, 1H), 7.43-7.41 (m, 2H), 6.32 (s, 1H), 5.16 (q, J=7.1 Hz, 1H), 3.20 (s, 6H), 1.60 (d, J=7.0 Hz, 3H).

EXAMPLE 4

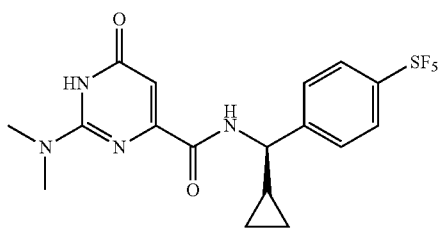

(R)—N-(cyclopropyl(4-(pentafluoro-λ$^6$-sulfanyl) phenyl)methyl)-2-(dimethylamino)-6-oxo-1,6-dihydropyrimidine-4-carboxamide (Scheme D)

To a stirred mixture of 2-(dimethylamino)-6-oxo-1,6-dihydropyrimidine-4-carboxylic acid (23.73 mg, 0.110 mmol) in CH$_2$Cl$_2$ (1.1 mL) was added (R)-cyclopropyl(4-(pentafluoro-λ$^6$-sulfanyl)phenyl)-methanamine hydrochloride (30 mg, 0.097 mmol) and TEA (33.3 mg, 46 uL, 0.329 mmol), followed by addition of T3P (50% in DMF, 77 mg, 0.121 mmol). The reaction mixture was stirred at RT for 2 h. The mixture was concentrated under reduced pressure. The resulting crude reaction mixture was diluted with DMSO and filtered. The filtrate was purified by RP-HPLC on a Waters Sunfire C18 column (5 u, 19×100 mm) eluting with 15-80% acetonitrile in water containing 0.1% TFA to give the title compound. MS: 439.1 (M+1). $^1$H NMR (499 MHz, DMSO-d$_6$) δ 8.83 (s, 1H), 7.88 (d, J=8.4 Hz, 2 H), 7.67 (d, J=8.3 Hz, 2 H), 6.07 (br, s, 1H), 4.32-4.26 (m, 1H), 3.15 (s, 3H), 2.53 (s, 3H), 1.50-1.44 (m, 1H), 0.62-0.55 (m, 2H), 0.49-0.44 (m, 1H), 0.38-0.33 (m, 1H).

EXAMPLE 5

(R)-2-(dimethylamino)-6-oxo-N-(1-(4-(pentafluoro-λ$^6$-sulfanyl)phenyl)propyl)-1,6-dihydropyrimidine-4-carboxamide (Scheme E)

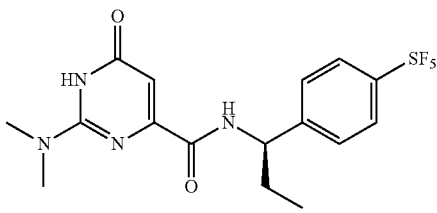

To a stirred mixture of 2-(dimethylamino)-6-oxo-1,6-dihydropyrimidine-4-carboxylic acid (25 mg, 0.136 mmol) in DMF (1.3 mL) was added (R)-1-(4-(pentafluoro-λ$^6$-sulfanyl)phenyl)propan-1-amine hydrochloride (43 mg, 0.14 mmol) and DIEA (0.072 mL, 0.409 mmol). After stirring for 10 min, HBTU (104 mg, 0.273 mmol) was added. The resulting mixture was stirred at RT overnight. The mixture was filtered and purified by RP-HPLC on a Waters XBridge C18 column (5 u, 30×100 mm) eluting with 15-50% acetonitrile in water with NH$_4$OH modifier to give the title compound. MS: 427.2 (M+1).

EXAMPLE 6

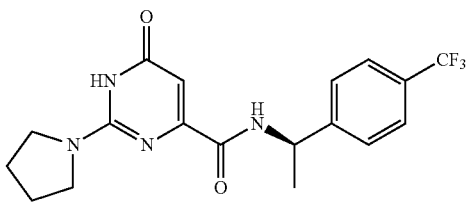 [SMILES: C[C@@H](NC(=O)c1cc(=O)[nH]c(N2CCCC2)n1)c1ccc(C(F)(F)F)cc1]

(R)-6-oxo-2-(pyrrolidin-1-yl)-N-(1-(4-(trifluoromethyl)phenyl)ethyl)-1,6-dihydropyrimidine-4-carboxamide (Scheme G)

A microwave reaction vessel was charged with (R)-2-(methylthio)-6-oxo-N-(1-(4-(trifluoromethyl)-phenyl) ethyl)-1,6-dihydropyrimidine-4-carboxamide (30 mg, 0.084 mmol) and anhydrous CHCl$_3$ (400 uL), followed by addition of mCPBA (56.4 mg, 0.252 mmol). Mixture was stirred under $N_2$ for 24 h. Chloroform was removed under reduced pressure. The resulting mixture was redissolved in anhydrous dioxane (400 uL), followed by addition of pyrrolidine (69.4 μl, 0.840 mmol) and stirred under N₂ at 75° C. After 24 h, reaction mixture was allowed to cool to RT and diluted with water.

Aqueous layer was extracted with EtOAc (3×). The combined organic layer was dried over MgSO₄, filtered and concentrated. The crude product was purified by RP-HPLC with an XTerra C18 column eluted with 10-100% acetonitrile in water containing 0.1% TFA to give the title compound. LC-MS: 381.1 (M+1). ¹H NMR (500 MHz, CD₃OD) δ 7.64 (d, J=8.1 Hz, 2H), 7.56 (d, J=8.0 Hz, 2H), 6.33 (s, 1H), 5.22-5.18 (m, 1H), 3.59 (br s, 4H), 2.04 (br s, 4H), 1.59 (d, J=7.0 Hz, 3H).

EXAMPLE 7

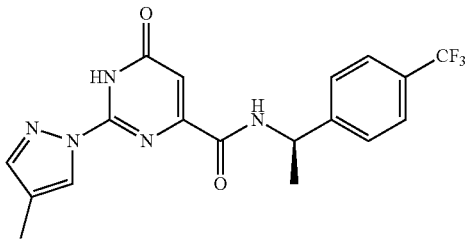 [SMILES: Cc1cnn(-c2nc(C(=O)N[C@H](C)c3ccc(C(F)(F)F)cc3)cc(=O)[nH]2)c1]

(R)-2-(4-methyl-1H-pyrazol-1-yl)-6-oxo-N-(1-(4-(trifluoromethyl)phenyl)ethyl)-1,6-dihydropyrimidine-4-carboxamide (Scheme H)

To a stirred solution of (R)-2-(methylsulfonyl)-6-oxo-N-(1-(4-(trifluoromethyl)phenyl)ethyl)-1,6-dihydropyrimidine-4-carboxamide (100 mg, 0.257 mmol) in THF (2 mL), was added NaH (30.8 mg, 0.771 mmol, 60%) and 4-methylpyrazole (63.3 mg, 0.771 mmol). The resulting mixture was stirred at 80° C. for 1.5 h. The mixture was cooled, quenched with 1N HCl, followed by sat'd NH₄Cl. The mixture was diluted with ethyl acetate and stirred overnight. The mixture was extracted with ethyl acetate twice. The combined organic layer was washed with brine, dried over Na₂SO₄, filtered and concentrated. The residue was purified by prep-TLC, eluted with 4% MeOH in CH₂Cl₂, then further purified by preparative RP-HPLC (C-18), eluted with 10-90% acetonitrile in water with 0.1% TFA, to give the title compound as a solid. MS: 392.2 (M+1). ¹H NMR (500 MHz, CD₃OD) δ 9.74 (br, 1H), 8.52 (s, 1H), 7.75 (s, 1H), 7.66-7.62 (m, 4H), 7.10 (s, 1H), 5.33-5.29 (m, 1H), 2.20 (s, 3H), 1.66 (d, J=7.1 Hz, 3H).

EXAMPLE 8

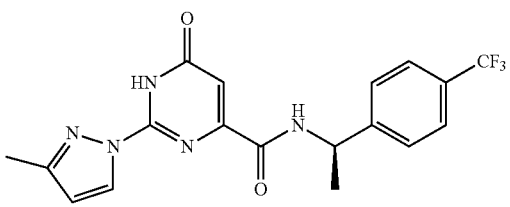 [SMILES: Cc1ccn(-c2nc(C(=O)N[C@H](C)c3ccc(C(F)(F)F)cc3)cc(=O)[nH]2)n1]

(R)-2-(3-methyl-1H-pyrazol-1-yl)-6-oxo-N-(1-(4-(trifluoromethyl)phenyl)ethyl)-1,6-dihydropyrimidine-4-carboxamide (Scheme I)

To a stirred mixture of 3-methylpyrazole (63.3 mg, 0.771 mmol) in dioxane (2 mL) at 80° C. was added (R)-2-(methylsulfonyl)-6-oxo-N-(1-(4-(trifluoromethyl)phenyl)ethyl)-1,6-dihydropyrimidine-4-carboxamide (100 mg, 0.257 mmol), Cs₂CO₃ (502 mg, 1.541 mol), and 3-methylpyrazole (63.3 mg, 0.771 mmol). The resulting mixture was stirred at 80° C. for 1.5 h. The same work-up as described in Example 7 afforded the title compound as a solid. MS: 392.2 (M+H). ¹H NMR (500 MHz, CD₃OD) δ 9.90 (br, 1H), 8.64 (d, J=2.4 Hz, 1H), 7.67-7.63 (m, 4H), 7.12 (s, 1H), 6.46 (d, J=2.8 Hz, 1H), 5.36-5.30 (m, 1H), 2.44 (s, 3H), 1.68 (d, J=7.1 Hz, 3H).

EXAMPLE 9

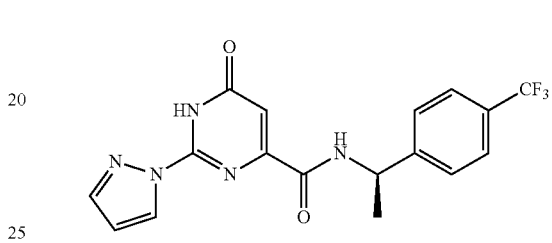

(R)-6-oxo-2-(1H-pyrazol-1-yl)-N-(1-(4-(trifluoromethyl)phenyl)ethyl)-1,6-dihydropyrimidine-4-carboxamide The title compound was prepared using the procedure described in Example 8 above. MS: 378.2 (M+1).

EXAMPLE 10

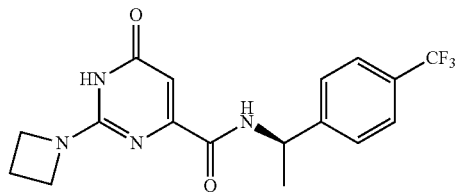 [SMILES: C[C@@H](NC(=O)c1cc(=O)[nH]c(N2CCC2)n1)c1ccc(C(F)(F)F)cc1]

(R)-2-(azetidin-1-yl)-6-oxo-N-(1-(4-(trifluoromethyl)phenyl)ethyl)-1,6-dihydropyrimidine-4-carboxamide (Scheme J)

A reaction vessel was charged with (R)-2-(methylsulfonyl)-6-oxo-N-(1-(4-(trifluoromethyl)-phenyl)ethyl)-1,6-dihydropyrimidine-4-carboxamide (39 mg, 0.100 mmol) and anhydrous dioxane (1002 μl). The reaction mixture was evacuated and purge with N₂, followed by addition of azetidine (67.5 μl, 1.002 mmol). The resulting mixture was stirred at 75° C. under N₂ overnight. It was allowed to cool to RT and quenched with water. The same work-up as described in Example 6 afforded the title compound. MS: 367.1 (M+H).

EXAMPLE 11

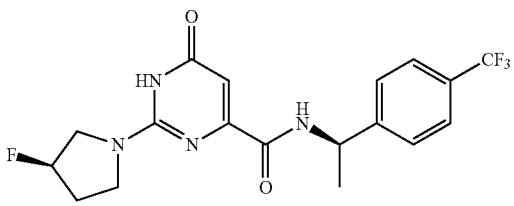 [SMILES: C[C@@H](NC(=O)c1cc(=O)[nH]c(N2CC[C@@H](F)C2)n1)c1ccc(C(F)(F)F)cc1]

2-((R)-3-fluoropyrrolidin-1-yl)-6-oxo-N—((R)-1-(4-(trifluoromethyl)phenyl)ethyl)-1,6-dihydropyrimidine-4-carboxamide (Scheme K)

A reaction vessel was charged with (R)-2-(methylsulfonyl)-6-oxo-N-(1-(4-(trifluoromethyl)phenyl)-ethyl)-1,6-dihydropyrimidine-4-carboxamide (30 mg, 0.077 mmol), (R)-3-fluoropyrrolidine hydrochloride (97 mg, 0.771 mmol), and anhydrous dioxane (771 µl). The reaction mixture was evacuated and purged with N₂ then following by addition of DIEA (135 µl, 0.771 mmol). The reaction mixture was stirred at 75° C. overnight. Additional DIEA (135 µl, 0.771 mmol) was added and the reaction mixture was stirred at 100° C. for additional 3 h. The same work-up as described in Example 6 afforded the title compound. MS: 399.1 (M+1). ¹H NMR (500 MHz, CD₃OD) δ7.64 (d, J=7.6 Hz, 2H), 7.57 (d, J=7.9 Hz, 2H), 6.36 (s, 1H), 5.38 (d, J=52.5 Hz, 1H), 5.23-5.18 (m, 1H), 3.97-3.61 (m, 4H), 2.41-2.14 (m, 2H), 1.60 (d, J=7.0 Hz, 3H).

EXAMPLE 12

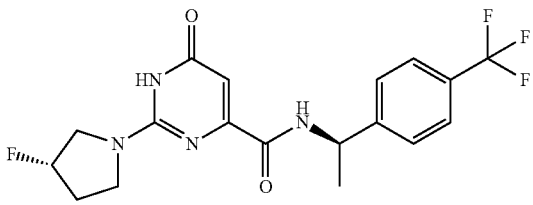 [SMILES: C[C@@H](NC(=O)c1cc(=O)[nH]c(N2CC[C@H](F)C2)n1)c1ccc(C(F)(F)F)cc1]

2-((S)-3-fluoropyrrolidin-1-yl)-6-oxo-N—((R)-1-(4-(trifluoromethyl)phenyl)ethyl)-1,6-dihydropyrimidine-4-carboxamide The title compound was prepared using the procedure described in Example 11 above. MS: 399.1 (M+1).

EXAMPLE 13

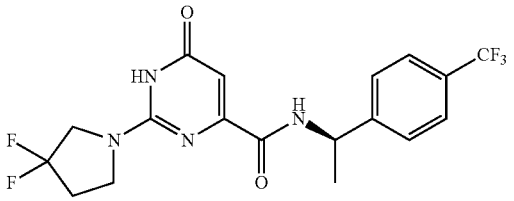 [SMILES: C[C@@H](NC(=O)c1cc(=O)[nH]c(N2CCC(F)(F)C2)n1)c1ccc(C(F)(F)F)cc1]

(R)-2-(3,3-difluoropyrrolidin-1-yl)-6-oxo-N-(1-(4-(trifluoromethyl)phenyl)ethyl)-16-dihydropyrimidine-4-carboxamide (Scheme L)

A microwave reaction vessel was charge with (R)-2-(methylsulfonyl)-6-oxo-N-(1-(4-(trifluoro-methyl)-phenyl) ethyl)-1,6-dihydropyrimidine-4-carboxamide (30 mg, 0.077 mmol)), 3,3-difluoro-pyrrolidine hydrochloride (111 mg, 0.771 mmol), and anhydrous DMF (1541 µl), followed by addition of K₂CO₃ (106 mg, 0.771 mmol). The reaction mixture was evacuated and purged with N₂, then stirred at 180° C. in microwave for 30 min. The same work-up as described in Example 6 afforded the title compound. MS: 417.1 (M+1). ¹H NMR (500 MHz, CD₃OD) δ7.65 (d, J=8.1 Hz, 2H), 7.58 (d, J=8.2 Hz, 2H), 6.42 (s, 1H), 5.25-5.22 (m, 1H), 4.02 (t, J=12.7 Hz, 2H), 3.84 (t, J=7.4 Hz, 2H), 2.59-2.51 (tt, J=7.0 and 13.4 Hz, 2H), 1.61 (d, J=7.1 Hz, 3H).

EXAMPLE 14

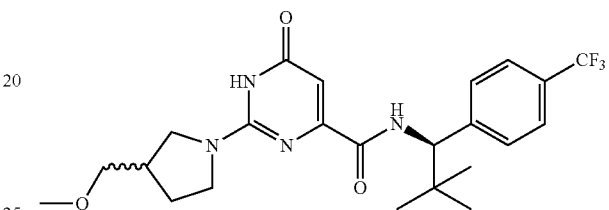

N—((R)-2,2-dimethyl-1-(4-(trifluoromethyl)phen) propyl)-2-(3-(methoxymethyl)pyrrolidin-1-yl)-6-oxo-1,6-dihydropyrimidine-4-carboxamide (Scheme M)

To a stirred solution of (R)—N-(2,2-dimethyl-1-(4-(trifluoromethyl)phenyl)propyl)-2-(methylsulfonyl)-6-oxo-1,6-dihydropyrimidine-4-carboxamide (30 mg, 0.070 mmol) in anhydrous DMF (695 µl) in a microwave reaction vial was added 3-(methoxymethyl)pyrrolidine (80 mg, 0.695 mmol). The reaction mixture was stirred at 150° C. for 15 min. The crude reaction mixture was purified by RP-HPLC on an XTerra C18 column (19×100 mm) eluting with 10-100% acetonitrile in water containing 0.1% TFA to give the title compound. MS: 467.0 (M+1).

EXAMPLE 15

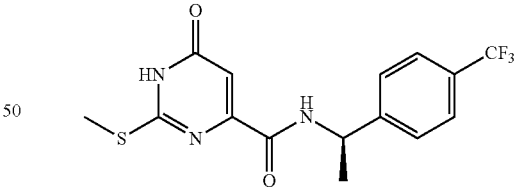

(R)-2-(methylthio)-6-oxo-N-(1-(4-(trifluoromethyl) phenyl)ethyl)-1,6-dihydropyrimidine-4-carboxamide Method A (Scheme F)

To a stirred mixture of 2-(methylthio)-6-oxo-1,6-dihydropyrimidine-4-carboxylic acid (5.0 g, 26.9 mmol) in DMF (60 mL) was added 1-(4-(trifluoromethyl)phenyl)ethanamine (5.59 g, 29.5 mmol), HATU (15.32 g, 40.3 mmol) and DIEA (18.76 mL, 107 mmol). The resulting mixture was stirred at RT overnight. The reaction mixture was diluted with EtOAc and sat'd NH₄Cl. The combined organic layers were washed with water, brine and dried over anhydrous sodium sulfate and concentrated under reduced pressure.

The residue was purified by column chromatography on silica gel eluting with 10 to 90% EtOAc in hexanes to yield the racemic product, which was resolved on a ChiralPak OJ column with 15% MeOH in CO₂ to yield the title compound as the slower-eluting enantiomer.

LC-MS: 399.1 (M+MeCN+H) and 358.1 (M+H).

Method B (Scheme A)

To a stirred mixture of 2-(methylthio)-6-oxo-1,6-dihydropyrimidine-4-carboxylic acid (6.23 g, 33.5 mmol) in DMF (130 mL) was added (R)-1-(4-(trifluoromethyl)phenyl) ethanamine (7.28 g, 38.5 mmol), HOAt (5.47 g, 40.2 mmol), and DIEA (11.69 mL, 66.9 mmol). After stirring for 10 min, EDC (7.70 g, 40.2 mmol) was added. The resulting mixture was stirred at RT overnight. The mixture was diluted with saturated aqueous NH₄Cl (200 mL), extracted with EtOAc (2×200 mL). The combined organic layers were washed with water (3×150 mL), brine, then dried over Na₂SO₄, filtered, and concentrated under reduced pressure. The residue was purified by column chromatography on silica gel, eluting with 0-4% MeOH in DCM to give the title compound as a solid. LC-MS: 399.0 (M+MeCN+H).

EXAMPLE 16

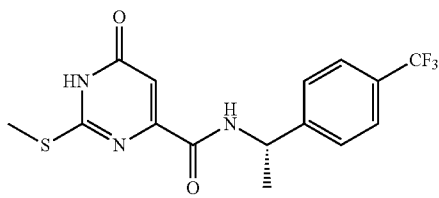 [SMILES: CSc1nc(C(=O)N[C@@H](C)c2ccc(C(F)(F)F)cc2)cc(=O)[nH]1]

(S)-2-(methylthio)-6-oxo-N-(1-(4-(trifluoromethyl) phenyl)ethyl)-1,6-dihydropyrimidine-4-carboxamide The title compound was obtained as the faster-eluting enantiomer from Example 15 Method A. LC-MS: 358.1 (M+H).

EXAMPLE 17

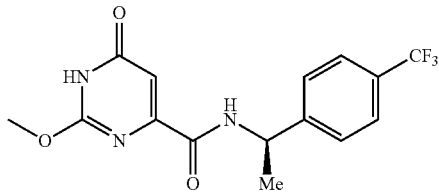 [SMILES: COc1nc(C(=O)N[C@H](C)c2ccc(C(F)(F)F)cc2)cc(=O)[nH]1]

(R)-2-methoxy-6-oxo-N-(1-(4-(trifluoromethyl)phenyl)ethyl)-1,6-dihydropyrimidine-4-carboxamide (Scheme O)

A stirred solution of (R)-2-(methylsulfonyl)-6-oxo-N-(1-(4-(trifluoromethyl)phenyl)ethyl)-1,6-dihydropyrimidine-4-carboxamide (30 mg, 0.077 mmol) in methanol (0.312 mL) was heated at 75° C. overnight. The reaction mixture was concentrated under reduced pressure and the resulting residue was purified by RP-HPLC as described in Example 14 to afford the title compound. MS: 342.1 (M+1).

EXAMPLE 18

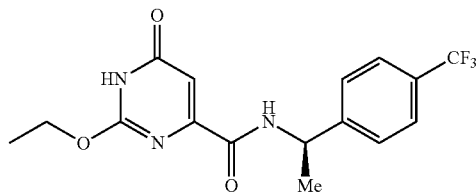 [SMILES: CCOc1nc(C(=O)N[C@H](C)c2ccc(C(F)(F)F)cc2)cc(=O)[nH]1]

(R)-2-ethoxy-6-oxo-N-(1-(4-(trifluoromethyl)phenyl)ethyl)-1,6-dihydropyrimidine-4-carboxamide (Scheme P)

A stirred solution of (R)-2-(methylsulfonyl)-6-oxo-N-(1-(4-(trifluoromethyl)phenyl)ethyl)-1,6-dihydropyrimidine-4-carboxamide (30 mg, 0.077 mmol) in ethanol (0.450 mL) was heated at 75° C. overnight. A solution of sodium ethoxide (21%, 0.288 mL, 0.77 mmol) was added and the reaction mixture was stirred at 75° C. for 1 h. The reaction mixture was worked up as described in Example 17 to afford the title compound. MS: 356.1 (M+1).

EXAMPLE 19

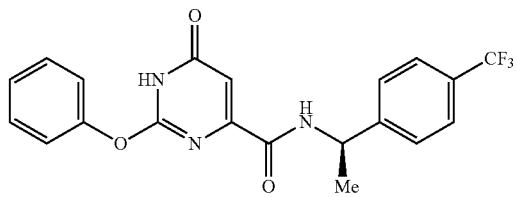 [SMILES: C[C@@H](NC(=O)c1cc(=O)[nH]c(Oc2ccccc2)n1)c1ccc(C(F)(F)F)cc1]

(R)-6-oxo-2-phenoxy-N-(1-(4-(trifluoromethyl)phenyl)ethyl)-1,6-dihydropyrimidine-4-carboxamide (Scheme Q)

To a stirred solution of (R)-2-(methylsulfonyl)-6-oxo-N-(1-(4-(trifluoromethyl)phenyl)ethyl)-1,6-dihydropyrimidine-4-carboxamide (30 mg, 0.077 mmol) in dioxane (0.771 mL) was added phenol (73 mg, 0.77 mmol). The reaction mixture was stirred at 75° C. overnight. Sodium phenoxide (89 mg, 0.77 mmol) was added and heating continued at 100° C. for 3 hr. The reaction mixture was worked up as described in Example 17 to afford the title compound. MS: 404.1 (M+1). ¹H NMR (500 MHz, CD₃OD) δ7.61 (d, J=8.1 Hz, 2H), 7.50-7.47 (m, 2H), 7.38-7.33 (m, 3H), 7.30 (d, J=7.9 Hz, 2H), 6.80 (br s, 1H), 5.06 (q, J=6.8 Hz, 1H), 1.42 (d, J=6.9 Hz, 3H).

EXAMPLE 20

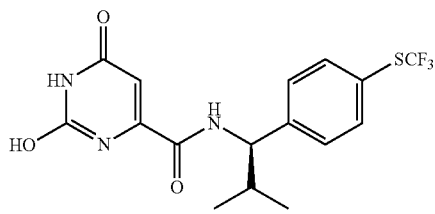

(R)-2-hydroxy-N-(2-methyl-1-(4-((trifluoromethyl)thio)phenyl)propyl)-6-oxo-1,6-dihydropyrimidine-4-carboxamide (Scheme R)

To a stirred solution of (R)—N-(2-methyl-1-(4-((trifluoromethyl)thio)phenyl)propyl)-2-(methylsulfonyl)-6-oxo-1, 6-dihydropyrimidine-4-carboxamide (55 mg, 0.122 mmol) in a 3:1 solution of tetrahydrofuran/methanol (1.467 mL) was added 1N aqueous lithium hydroxide (0.367 mL, 0.367 mmol). The resulting mixture was stirred at RT for 1 h. The solution was concentrated to remove volatiles and then diluted with 1N HCl (2 mL). The result mixture was extracted with 3:1 solution of chloroform/IPA (2 mL×3) dried over magnesium sulfate, filtered and concentrated under reduced pressure. The resulting residue was purified by RP-HPLC on an XTerra C18 column eluted with 10-100% acetonitrile in water containing 0.1% TFA to afford the title compound. MS: 428.8 (M+MeCN+H). $^1$H NMR (500 MHz, CD$_3$OD) δ7.67 (d, J=7.1 Hz, 2H), 7.48 (d, J=7.1 Hz, 2H), 6.17 (s, 1H), 4.67 (d, J=9.5 Hz, 1H), 2.21-2.12 (m, 1H), 1.09 (d, J=6.2 Hz, 3H), 0.78 (d, J=6.4 Hz, 3H).

EXAMPLE 21

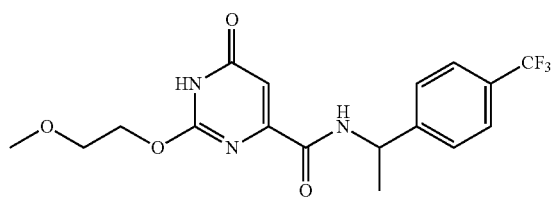 [SMILES: COCCOc1nc(C(=O)NC(C)c2ccc(C(F)(F)F)cc2)cc(=O)[nH]1]

2-(2-Methoxyethoxy)-6-oxo-N-(1-(4-(trifluoromethyl)phenyl)ethyl)-1,6-dihydropyrimidine-4-carboxamide (Scheme S)

To a stirring solution of 2-(methylsulfonyl)-6-oxo-N-(1-(4-(trifluoromethyl)phenyl)ethyl)-1,6-dihydropyrimidine-4-carboxamide (60 mg, 0.154 mmol) in THF (1541 µl), was added 60% NaH oil dispersion (61.6 mg, 1.54 mmol) at 0° C. Reaction mixture was stirred at 0° C. for 30 minutes, then 2-methoxyethan-1-ol (59 mg, 0.776 mmol) was added and stirred at RT overnight. The reaction mixture was quenched with water at 0° C., extracted with ethyl acetate three times. The combined organic layers were washed with brine, dried over Na$_2$SO$_4$, filtered and concentrate. The resulting residue was purified by RP-HPLC on a Waters Sunfire C18 column (5 u, 19×100 mm) eluting with 30-65% acetonitrile in water with 0.1% TFA to afford the title compound. MS: 386.1 (M+1).

EXAMPLE 22

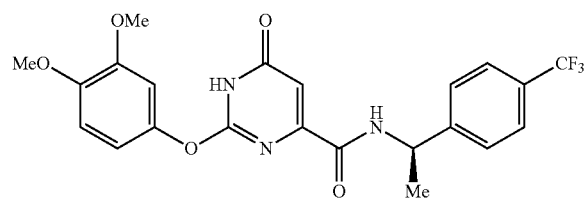 [SMILES: COc1ccc(Oc2nc(C(=O)N[C@H](C)c3ccc(C(F)(F)F)cc3)cc(=O)[nH]2)cc1OC]

(R)-2-(3,4-dimethoxyphenoxy)-6-oxo-N-(1-(4-(trifluoromethyl)phenyl)ethyl)-1,6-dihydropyrimidine-4-carboxamide (Scheme T)

To a stirred solution of (R)-2-(methylsulfonyl)-6-oxo-N-(1-(4-(trifluoromethyl)phenyl)ethyl)-1,6-dihydropyrimidine-4-carboxamide (20 mg, 0.051 mmol) and anhydrous DMF (1027 µl) in a microwave reaction vial was added 3,4-dimethoxyphenol (79 mg, 0.514 mmol) followed by potassium carbonate (71.0 mg, 0.514 mmol). The reaction mixture was evacuated and purged with N$_2$ and then stirred at 180° C. in a microwave reactor for 30 minutes. The reaction was quenched with water, then extracted with EtOAc (3×). The combined organic layers were dried over anhydrous MgSO$_4$, filtered and concentrated. The resulting residue was purified as described in Example 17 to afford the title compound. MS: 464.1 (M+1). $^1$H NMR (500 MHz, CD$_3$OD) δ7.62 (d, J=8.2 Hz, 2H), 7.36 (d, J=8.0 Hz, 2H), 7.01 (d, J=8.7 Hz, 1H), 6.96 (d, J=2.2 Hz, 1H), 6.82 (dd, J=2.4 and 8.7 Hz, 1H), 6.75 (br s, 1H), 5.08 (q, J=6.5 Hz, 1H), 3.86 (s, 3H), 3.77 (s, 3H), 1.44 (d, J=6.7 Hz, 3H).

EXAMPLE 23

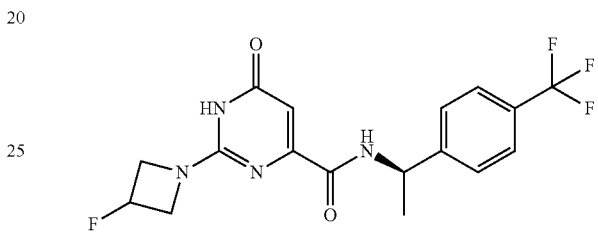

2-(3-Fluoroazetidin-1-yl)-6-oxo-N-{(1R)-1-[4-(trifluoromethyl)phenyl]ethyl}-1,6-dihydropyrimidine-4-carboxamide (Scheme N)

A solution of (R)-2-(methylsulfonyl)-6-oxo-N-(1-(4-(trifluoro-methyl)-phenyl)ethyl)-1,6-dihydro-pyrimidine-4-carboxamide (50 mg, 0.128 mmol) in anhydrous dioxane was purged with nitrogen followed by addition of 3-fluoroazetidine hydrochloride (143 mg, 1.28 mmol). The reaction mixture was heated at 75° C. for 4 hr without much conversion. DMSO (0.50 mL) was added to this suspension and the mixture was heated at 75° C. overnight. The same work-up as described in Example 14 afforded the title compound. MS: 385.1 (M+1).

EXAMPLE 24

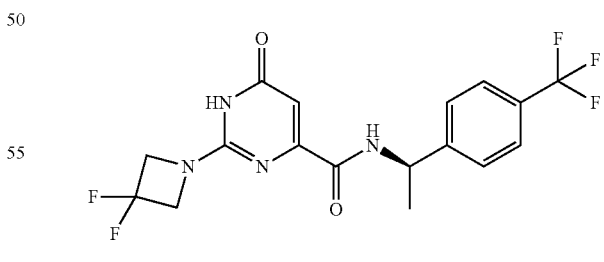

2-(3,3-Difluoroazetidin-1-yl)-6-oxo-N-{(1R)-1-[4-(trifluoromethyl)phenyl]ethyl}-1,6-dihydropyrimidine-4-carboxamide The title compound was prepared using the procedure described in Example 23 above. MS: 403.1 (M+1).

TABLE 2

Examples 25-30 in the following table were prepared using similar conditions as described in Example 1 and Scheme A from appropriate starting materials.

| Example Number | Structure | IUPAC Name | Exact Mass [M + H]+ |
|---|---|---|---|
| 25 | 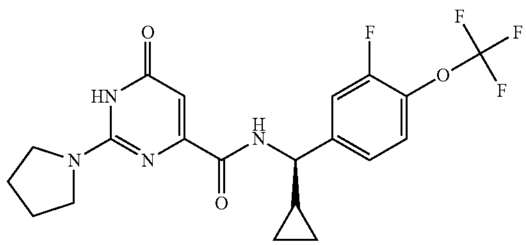 [SMILES: O=C(N[C@@H](c1ccc(OC(F)(F)F)c(F)c1)C1CC1)c1cc(=O)[nH]c(N2CCCC2)n1] | N-{(R)-cyclopropyl[3-fluoro-4-(trifluoromethoxy)phenyl]methyl}-6-oxo-2-pyrrolidin-1-yl-1,6-dihydropyrimidine-4-carboxamide | 441.2 |
| 26 | 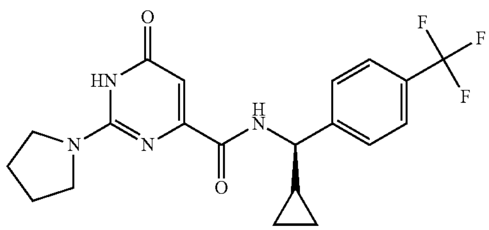 [SMILES: O=C(N[C@@H](c1ccc(C(F)(F)F)cc1)C1CC1)c1cc(=O)[nH]c(N2CCCC2)n1] | N-{(R)-cyclopropyl[4-(trifluoromethyl)phenyl-1-methyl}-6-oxo-2-pyrrolidin-1-yl-1,6-dihydropyrimidine-4-carboxamide | 407.2 |
| 27 | 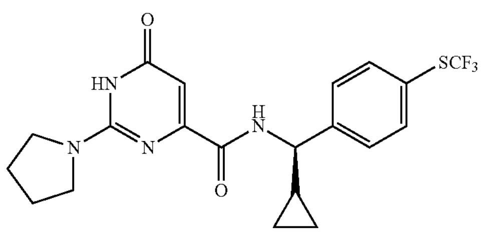 | N-[(R)-cyclopropyl{4-[(trifluoromethyl)sulfanyl]phenyl}methyl]-6-oxo-2-pyrrolidin-1-yl-1,6-dihydropyrimidine-4-carboxamide | 439.2 |
| 28 | 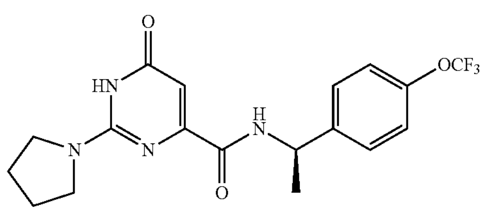 [SMILES: C[C@@H](NC(=O)c1cc(=O)[nH]c(N2CCCC2)n1)c1ccc(OC(F)(F)F)cc1] | 6-oxo-2-pyrrolidin-1-yl-N-{(1R)-1-[4-(trifluoromethoxy)phenyl]ethyl}-1,6-dihydropyrimidine-4-carboxamide | 397.2 |
| 29 | 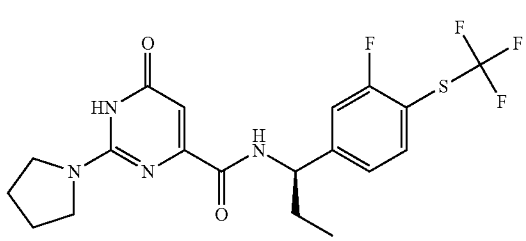 [SMILES: CC[C@@H](NC(=O)c1cc(=O)[nH]c(N2CCCC2)n1)c1ccc(SC(F)(F)F)c(F)c1] | N-[(1R)-1-{3-fluoro-4-[(trifluoromethyl)sulfanyl]phenyl}propyl]-6-oxo-2-pyrrolidin-1-yl-1,6-dihydropyrimidine-4-carboxamide | 445.2 |

TABLE 3

Examples 30-84 in the following table were prepared using similar conditions as described in Example 2 and Scheme B from appropriate starting materials.

| Example Number | Structure | IUPAC Name | Exact Mass [M + H]+ |
|---|---|---|---|
| 30 | 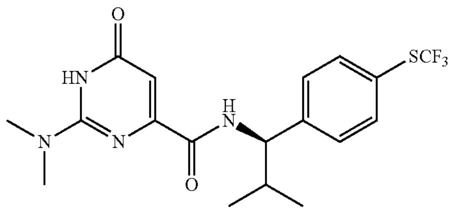 | 2-(dimethylamino)-N-[(1R)-2-methyl-1-{4-[(trifluoromethyl)sulfanyl]phenyl}propyl]-6-oxo-1,6-dihydropyrimidine-4-carboxamide | Calc'd 415.1, found 415.0 |
| 31 | 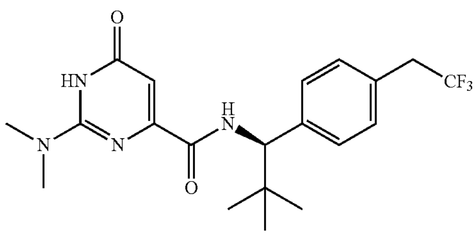 [SMILES: CN(C)c1nc(C(=O)N[C@@H](c2ccc(CC(F)(F)F)cc2)C(C)(C)C)cc(=O)[nH]1] | 2-(dimethylamino)-N-{(1R)-2,2-dimethyl-1-[4-(2,2,2-trifluoroethyl)phenyl]propyl}-6-oxo-1,6-dihydropyrimidine-4-carboxamide | Calc'd 411.2, found 411.1 |
| 32 | 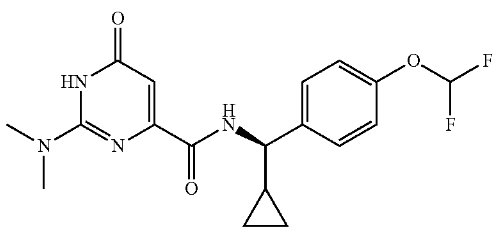 [SMILES: CN(C)c1nc(C(=O)N[C@@H](c2ccc(OC(F)F)cc2)C2CC2)cc(=O)[nH]1] | N-{(R)-cyclopropyl[4-(difluoromethoxy)phenyl]methyl}-2-(dimethylamino)-6-oxo-1,6-dropyrimidine-4-carboxamide | Calc'd 379.2, found 379.1 |
| 33 | 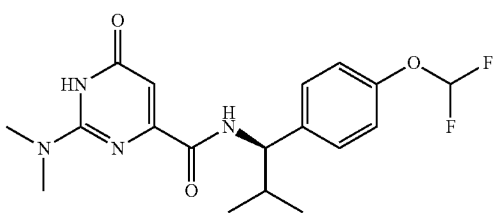 [SMILES: CC(C)[C@@H](NC(=O)c1cc(=O)[nH]c(N(C)C)n1)c1ccc(OC(F)F)cc1] | N-{(1R)-1-[4-(difluoromethoxy)phenyl]-2-methylpropyl}-2-(dimethylamino)-6-oxo-1,6-dihydropyrimidine-4-carboxamide | Calc'd 381.2, found 381.1 |
| 34 | 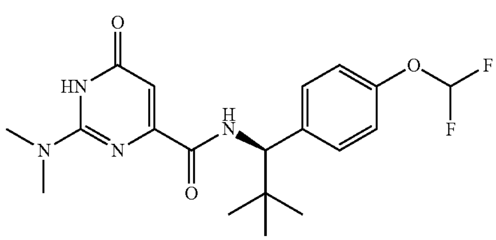 [SMILES: CN(C)c1nc(C(=O)N[C@@H](c2ccc(OC(F)F)cc2)C(C)(C)C)cc(=O)[nH]1] | N-{(1R)-1-[4-(difluoromethoxy)phenyl]-2,2-dimethylpropyl}-2-(dimethylamino)-6-oxo-1,6-dihydropyrimidine-4-carboxamide | Calc'd 395.2, found 395.1 |
| 35 | 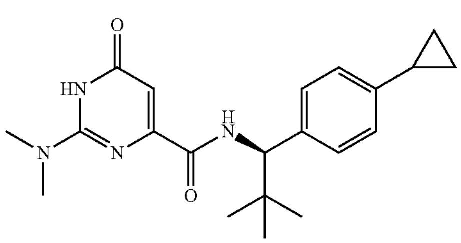 [SMILES: CN(C)c1nc(C(=O)N[C@@H](c2ccc(C3CC3)cc2)C(C)(C)C)cc(=O)[nH]1] | N-[(1R)-1-(4-cyclopropylphenyl)-2,2-dimethylpropyl]-2-(dimelhylamino)-6-oxo-1,6-dihydropyrimidine-4-carboxamide | Calc'd 369.2, found 369.2 |

TABLE 3-continued

Examples 30-84 in the following table were prepared using similar conditions as described in Example 2 and Scheme B from appropriate starting materials.

| Example Number | Structure | IUPAC Name | Exact Mass [M + H]+ |
|---|---|---|---|
| 36 | 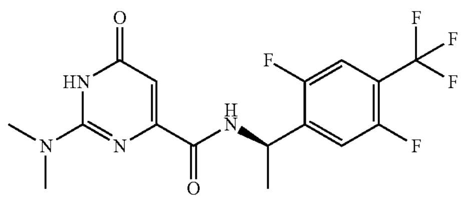 [SMILES: C[C@@H](NC(=O)c1cc(=O)[nH]c(N(C)C)n1)c1cc(F)c(C(F)(F)F)cc1F] | N-{(1R)-1-[2,5-difluoro-4-(trifluoromethyl)phenyl]ethyl}-2-(dimethylamino)-6-oxo-1,6-dihydropyrimidine-4-carboxamide | Calc'd 391.1, found 391.0 |
| 37 | 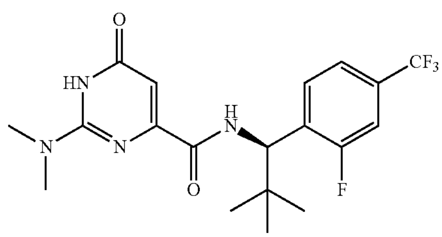 [SMILES: CN(C)c1nc(C(=O)N[C@@H](c2ccc(C(F)(F)F)cc2F)C(C)(C)C)cc(=O)[nH]1] | 2-(dimethylamino)-N-{(1R)-1-[2-fluoro-4-(trifluoromethyl)phenyl]-2,2-dimethylpropyl}-6-oxo-1,6-dihydropyrimidine-4-carboxamide | Calc'd 415.2, found 415.1 |
| 38 | 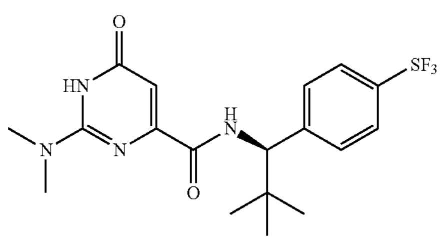 | 2-(dimethylamino)-N-{(1R)-2,2-dimethyl-1-[4-(pentafluoro-$\lambda^6$-sulfanyl)phenyl]propyl}-6-oxo-1,6-dihydropyrimidine-4-carboxamide | Calc'd 455.2, found 455.1 |
| 39 | 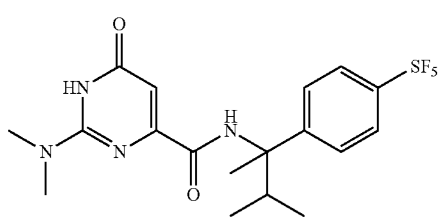 | 2-(dimethylamino)-N-{1,2-dimethyl-1-[4-(pentafluoro-$\lambda^6$-sulfanyl)phenyl]propyl}-6-oxo-1,6-dihydropyrimidine-4-carboxamide | Calc'd 455.2, found 455.1 |
| 40 | 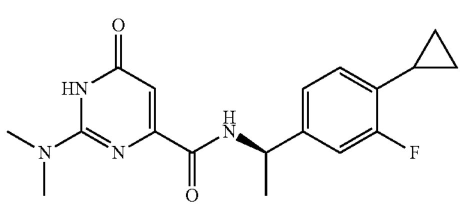 [SMILES: C[C@@H](NC(=O)c1cc(=O)[nH]c(N(C)C)n1)c1ccc(C2CC2)c(F)c1] | N-[(1R)-1-(4-cyclopropyl-3-fluorophenyl)ethyl]-2-(dimethylamino)-6-oxo-1,6-dihydropyrimidine-4-carboxamide | Calc'd 345.2, found 345.2 |
| 41 | 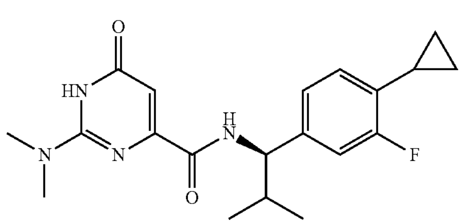 [SMILES: CC(C)[C@@H](NC(=O)c1cc(=O)[nH]c(N(C)C)n1)c1ccc(C2CC2)c(F)c1] | N-[(1R)-1-(4-cyclopropyl-3-fluorophenyl)-2-methylpropyl]-2-(dimethylamino)-6-oxo-1,6-dihydropyrimidine-4-carboxamide | Calc'd 373.2, found 373.2 |

TABLE 3-continued

Examples 30-84 in the following table were prepared using similar conditions as described in Example 2 and Scheme B from appropriate starting materials.

| Example Number | Structure | IUPAC Name | Exact Mass [M + H]+ |
|---|---|---|---|
| 42 | 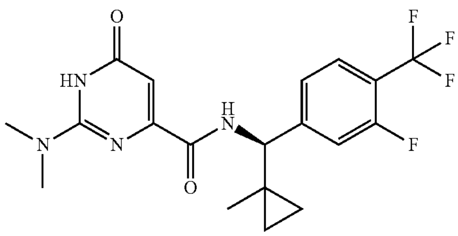 [SMILES: CN(C)c1nc(C(=O)N[C@@H](c2ccc(C(F)(F)F)c(F)c2)C2(C)CC2)cc(=O)[nH]1] | 2-(dimethylamino)-N-[(R)-[3-fluoro-4-(trifluoromethyl)phenyl](1-methylcyclopropyl)methyl]-6-oxo-1,6-dihydropyrimidine-4-carboxamide | Calc'd 413.2, found 413.1 |
| 43 | 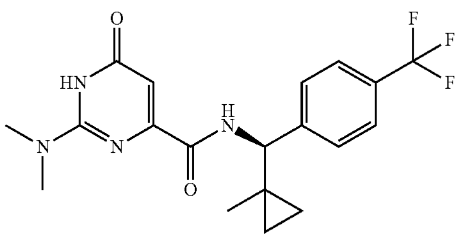 [SMILES: CN(C)c1nc(C(=O)N[C@@H](c2ccc(C(F)(F)F)cc2)C2(C)CC2)cc(=O)[nH]1] | 2-(dimethylamino)-N-{(R)-(1-methylcyclopropyl)[4-(trifluoromethyl)phenyl]methyl}-6-oxo-1,6-dihydropyrimidine-4-carboxamide | Calc'd 395.2, found 395.1 |
| 44 | 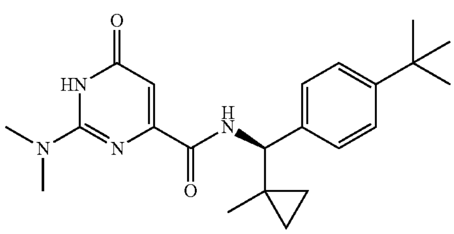 [SMILES: CN(C)c1nc(C(=O)N[C@@H](c2ccc(C(C)(C)C)cc2)C2(C)CC2)cc(=O)[nH]1] | N-[(R)-(4-tert-butylphenyl)(1-methylcyclopropyl)methyl]-2-(dimethylamino)-6-oxo-1,6-dihydropyrimidine-4-carboxamide | Calc'd 383.2, found 383.1 |
| 45 | 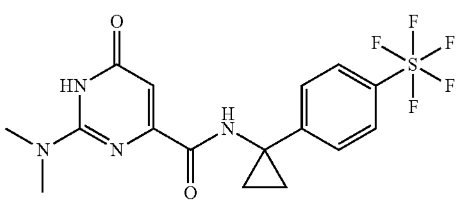 [SMILES: CN(C)c1nc(C(=O)NC2(c3ccc(S(F)(F)(F)(F)F)cc3)CC2)cc(=O)[nH]1] | 2-(dimethylamino)-6-oxo-N-{1-[4-(pentafluoro-$\lambda^6$-sulfanyl)phenyl]cyclopropyl}-1,6-dihydropyrimidine-4-carboxamide | Calc'd 425.1, found 425.0 |
| 46 | 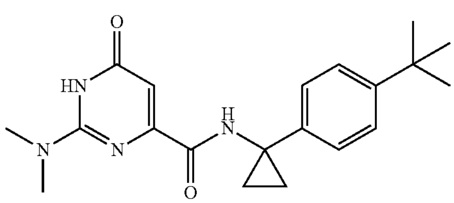 [SMILES: CN(C)c1nc(C(=O)NC2(c3ccc(C(C)(C)C)cc3)CC2)cc(=O)[nH]1] | N-[1-(4-tert-butylphenyl)cyclopropyl]-2-(dimethylamino)-6-oxo-1,6-dihydropyrimidine-4-carboxamide | Calc'd 355.2, found 355.2 |
| 47 | 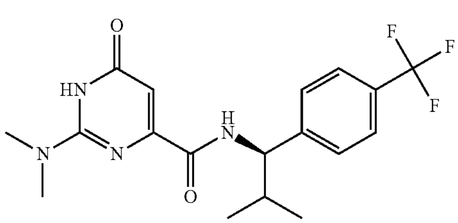 [SMILES: CC(C)[C@@H](NC(=O)c1cc(=O)[nH]c(N(C)C)n1)c1ccc(C(F)(F)F)cc1] | 2-(dimethylamino)-N-{(1R)-2-methyl-1-[4-(trifluoromethyl)phenyl]propyl}-6-oxo-1,6-dihydropyrimidine-4-carboxamide | Calc'd 383.2, found 383.0 |

TABLE 3-continued

Examples 30-84 in the following table were prepared using similar conditions as described in Example 2 and Scheme B from appropriate starting materials.

| Example Number | Structure | IUPAC Name | Exact Mass [M + H]+ |
|---|---|---|---|
| 48 | 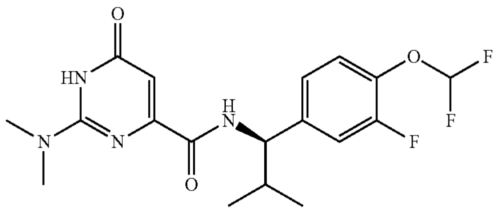 [SMILES: CC(C)[C@@H](NC(=O)c1cc(=O)[nH]c(N(C)C)n1)c1ccc(OC(F)F)c(F)c1] | N-{(1R)-1-[4-(difluoromethoxy)-3-fluorophenyl]-2-methylpropyl}-2-(dimethylamino)-6-oxo-1,6-dihydropyrimidine-4-carboxamide | Calc'd 399.2, found 399.1 |
| 49 | 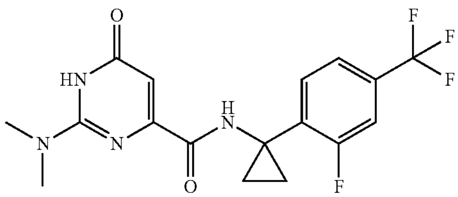 [SMILES: CN(C)c1nc(C(=O)NC2(c3ccc(C(F)(F)F)cc3F)CC2)cc(=O)[nH]1] | 2-(dimethylamino)-N-{1-[2-fluoro-4-(trifluoromethyl)phenyl]cyclopropyl}-6-oxo-1,6-dihydropyrimidine-4-carboxamide | Calc'd 385.1, found 384.9 |
| 50 | 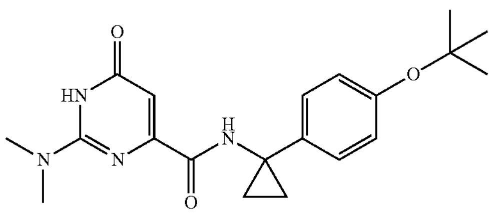 [SMILES: CN(C)c1nc(C(=O)NC2(c3ccc(OC(C)(C)C)cc3)CC2)cc(=O)[nH]1] | N-[1-(4-tert-butoxyphenyl)cyclopropyl]-2-(dimethylamino)-6-oxo-1,6-dihydropyrimidine-4-carboxamide | Calc'd 371.2, found 371.0 |
| 51 | 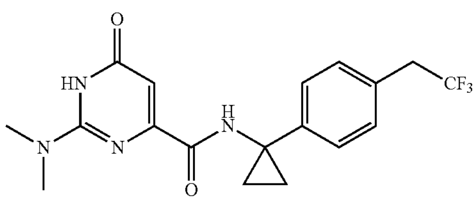 [SMILES: CN(C)c1nc(C(=O)NC2(c3ccc(CC(F)(F)F)cc3)CC2)cc(=O)[nH]1] | 2-(dimethylamino)-6-oxo-N-{1-[4-(2,2,2-trifluoroethyl)phenyl]cyclopropyl}-1,6-dihydropyrimidine-4-carboxamide | Calc'd 381.2, found 381.0 |
| 52 | 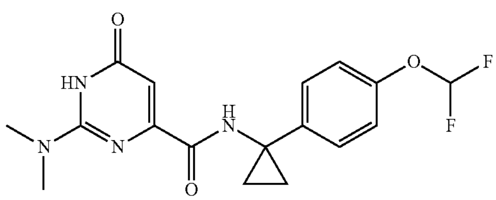 [SMILES: CN(C)c1nc(C(=O)NC2(c3ccc(OC(F)F)cc3)CC2)cc(=O)[nH]1] | N-{1-[4-(difluoromethoxy)phenyl]cyclopropyl}-2-(dimethylamino)-6-oxo-1,6-dihydropyrimidine-4-carboxamide | Calc'd 365.1, found 365.1 |
| 53 | 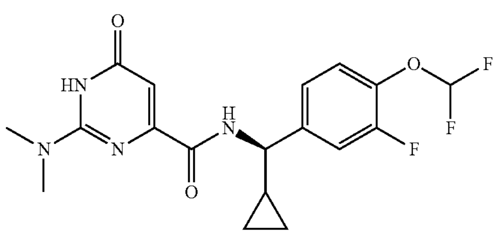 [SMILES: CN(C)c1nc(C(=O)N[C@@H](c2ccc(OC(F)F)c(F)c2)C2CC2)cc(=O)[nH]1] | N-{(R)-cyclopropyl[4-(difluoromethoxy)-3-fluorophenyl]methyl}-2-(dimethylamino)-6-oxo-1,6-dihydropyrimidine-4-carboxamide | Calc'd 397.1, found 397.0 |
| 54 | 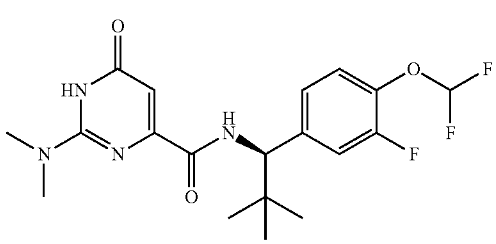 [SMILES: CN(C)c1nc(C(=O)N[C@@H](c2ccc(OC(F)F)c(F)c2)C(C)(C)C)cc(=O)[nH]1] | N-{(1R)-1-[4-(difluoromethoxy)-3-fluorophenyl]-2,2-dimethylpropyl}-2-(dimethylamino)-6-oxo-1,6-dihydropyrimidine-4-carboxamide | Calc'd 413.2, found 413.2 |

TABLE 3-continued

Examples 30-84 in the following table were prepared using similar conditions as described in Example 2 and Scheme B from appropriate starting materials.

| Example Number | Structure | IUPAC Name | Exact Mass [M + H]+ |
|---|---|---|---|
| 55 | 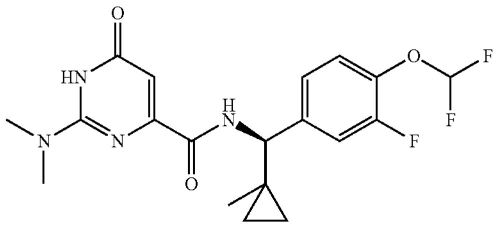 [SMILES: CN(C)c1nc(C(=O)N[C@@H](c2ccc(OC(F)F)c(F)c2)C2(C)CC2)cc(=O)[nH]1] | N-[(R)-[4-(difluoromethoxy)-3-fluorophenyl](1-methylcyclopropyl)methyl]-2-(dimethylamino)-6-oxo-1,6-dihydropyrimidine-4-carboxamide | Calc'd 411.2, found 411.1 |
| 56 | 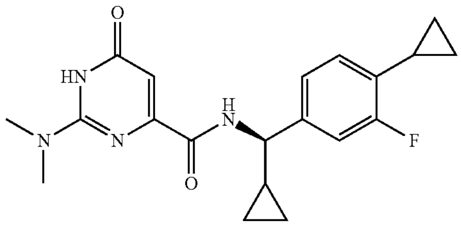 [SMILES: CN(C)c1nc(C(=O)N[C@@H](c2ccc(C3CC3)c(F)c2)C2CC2)cc(=O)[nH]1] | N-[(R)-cyclopropyl(4-cyclopropyl-3-fluorophenyl)methyl]-2-(dimethylamino)-6-oxo-1,6-dihydropyrimidine-4-carboxamide | Calc'd 371.2, found 371.1 |
| 57 | 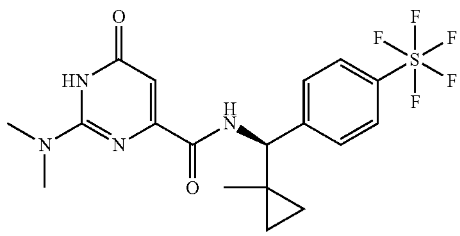 [SMILES: CN(C)c1nc(C(=O)N[C@@H](c2ccc(S(F)(F)(F)(F)F)cc2)C2(C)CC2)cc(=O)[nH]1] | 2-(dimethylamino)-N-{(R)-(1-methylcyclopropyl)[4-(pentafluoro-$\lambda^6$-sulfanyl)phenyl]methyl}-6-oxo-1,6-dihydropyrimidine-4-carboxamide | Calc'd 453.1, found 453.0 |
| 58 | 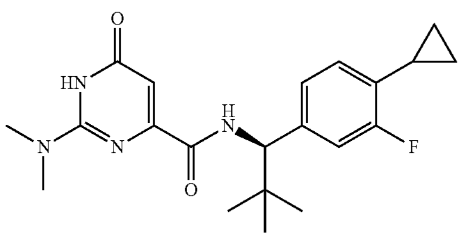 [SMILES: CN(C)c1nc(C(=O)N[C@@H](c2ccc(C3CC3)c(F)c2)C(C)(C)C)cc(=O)[nH]1] | N-[(1R)-1-(4-cyclopropyl-3-fluorophenyl)-2,2-dimethylpropyl]-2-(dimethylamino)-6-oxo-1,6-dihydropyrimidine-4-carboxamide | Calc'd 387.2, found 387.1 |
| 59 | 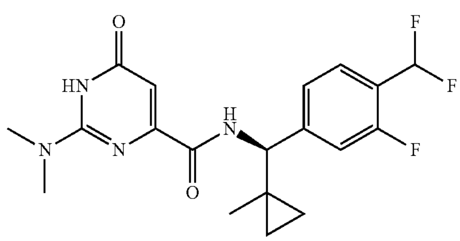 [SMILES: CN(C)c1nc(C(=O)N[C@@H](c2ccc(C(F)F)c(F)c2)C2(C)CC2)cc(=O)[nH]1] | N-[(R)-[4-(difluoromethyl)-3-fluorophenyl](1-methylcyclopropyl)methyl]-2-(dimethylamino)-6-oxo-1,6-dihydropyrimidine-4-carboxamide | Calc'd 395.2, found 395.1 |
| 60 | 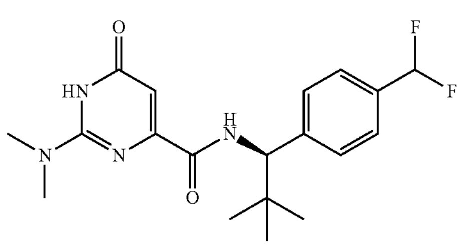 [SMILES: CN(C)c1nc(C(=O)N[C@@H](c2ccc(C(F)F)cc2)C(C)(C)C)cc(=O)[nH]1] | N-{(1R)-1-[4-(difluoromethyl)phenyl]-2,2-dimethylpropyl}-2-(dimethylamino)-6-oxo-1,6-dihydropyrimidine-4-carboxamide | Calc'd 379.2, found 379.2 |

TABLE 3-continued

Examples 30-84 in the following table were prepared using similar conditions as described in Example 2 and Scheme B from appropriate starting materials.

| Example Number | Structure | IUPAC Name | Exact Mass [M + H]+ |
|---|---|---|---|
| 61 | 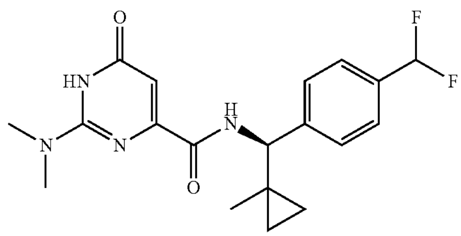 [SMILES: CN(C)c1nc(C(=O)N[C@@H](c2ccc(C(F)F)cc2)C2(C)CC2)cc(=O)[nH]1] | N-[(R)-[4-(difluoromethyl)phenyl](1-methylcyclopropyl)methyl]-2-(dimethylamino)-6-oxo-1,6-dihydropyrimidine-4-carboxamide | Calc'd 377.2, found 377.1 |
| 62 | 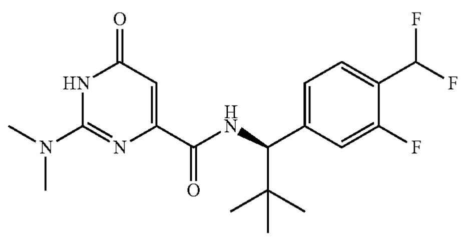 [SMILES: CN(C)c1nc(C(=O)N[C@@H](c2ccc(C(F)F)c(F)c2)C(C)(C)C)cc(=O)[nH]1] | N-{(1R)-1-[4-(difluoromethyl)-3-fluorophenyl]-2,2-dimethylpropyl}-2-(dimethylamino)-6-oxo-1,6-dihydropyrimidine-4-carboxamide | Calc'd 397.2, found 397.1 |
| 63 | 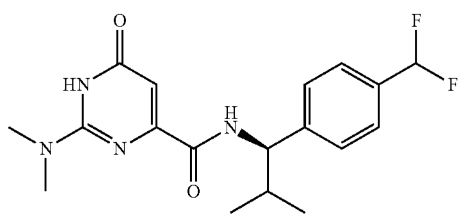 [SMILES: CC(C)[C@@H](NC(=O)c1cc(=O)[nH]c(N(C)C)n1)c1ccc(C(F)F)cc1] | N-{(1R)-1-[4-(difluoromethyl)phenyl]-2-methylpropyl}-2-(dimethylamino)-6-oxo-1,6-dihydropyrimidine-4-carboxamide | Calc'd 365.2, found 364.9 |
| 64 | 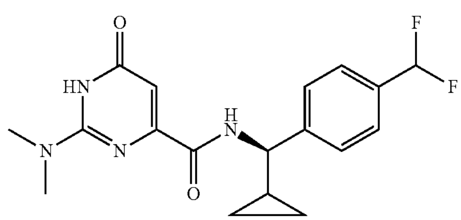 [SMILES: CN(C)c1nc(C(=O)N[C@@H](c2ccc(C(F)F)cc2)C2CC2)cc(=O)[nH]1] | N-{(R)-cyclopropyl[4-(difluoromethyl)phenyl]methyl}-2-(dimethylamino)-6-oxo-1,6-dihydropyrimidine-4-carboxamide | Calc'd 363.2, found 362.8 |
| 65 | 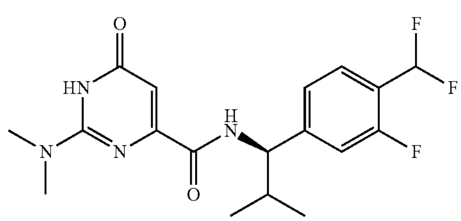 [SMILES: CC(C)[C@@H](NC(=O)c1cc(=O)[nH]c(N(C)C)n1)c1ccc(C(F)F)c(F)c1] | N-{(1R)-1-[4-(difluoromethyl)-3-fluorophenyl]-2-methylpropyl}-2-(dimethylamino)-6-oxo-1,6-dihydropyrimidine-4-carboxamide | Calc'd 383.2, found 382.8 |
| 66 | 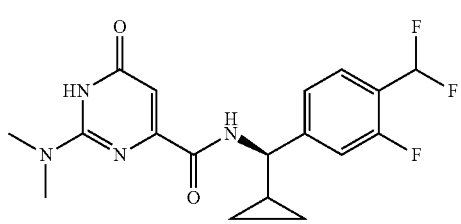 [SMILES: CN(C)c1nc(C(=O)N[C@@H](c2ccc(C(F)F)c(F)c2)C2CC2)cc(=O)[nH]1] | N-{(R)-cyclopropyl[4-(difluoromethyl)-3-fluorophenyl]methyl}-2-(dimethylamino)-6-oxo-1,6-dihydropyrimidine-4-carboxamide | Calc'd 381.2, found 381.1 |

TABLE 3-continued

Examples 30-84 in the following table were prepared using similar conditions as described in Example 2 and Scheme B from appropriate starting materials.

| Example Number | Structure | IUPAC Name | Exact Mass [M + H]+ |
|---|---|---|---|
| 67 | 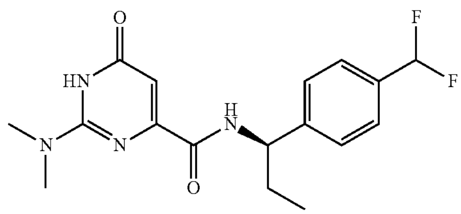 [SMILES: CC[C@@H](NC(=O)c1cc(=O)[nH]c(N(C)C)n1)c1ccc(C(F)F)cc1] | N-{(1R)-1-[4-(difluoromethyl)phenyl]propyl}-2-(dimethylamino)-6-oxo-1,6-dihydropyrimidine-4-carboxamide | Calc'd 351.2, found 351.1 |
| 68 | 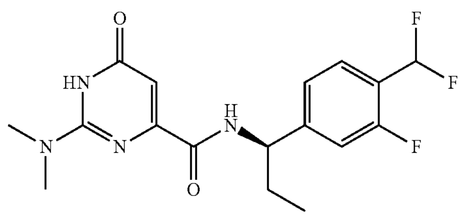 [SMILES: CC[C@@H](NC(=O)c1cc(=O)[nH]c(N(C)C)n1)c1ccc(C(F)F)c(F)c1] | N-{(1R)-1-[4-(difluoromethyl)-3-fluorophenyl]propyl}-2-(dimethylamino)-6-oxo-1,6-dihydropyrimidine-4-carboxamide | Calc'd 369.2, found 369.1 |
| 69 | 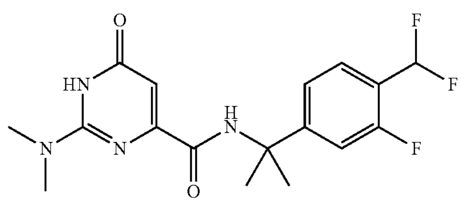 [SMILES: CN(C)c1nc(C(=O)NC(C)(C)c2ccc(C(F)F)c(F)c2)cc(=O)[nH]1] | N-{1-[4-(difluoromethyl)-3-fluorophenyl]-1-methylethyl}-2-(dimethylamino)-6-oxo-1,6-dihydropyrimidine-4-carboxamide | Calc'd 369.2, found 369.1 |
| 70 | 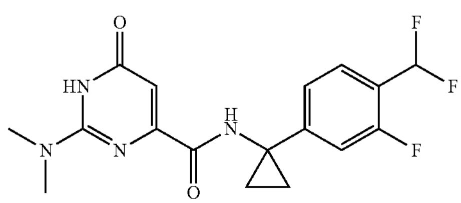 [SMILES: CN(C)c1nc(C(=O)NC2(c3ccc(C(F)F)c(F)c3)CC2)cc(=O)[nH]1] | N-{1-[4-(difluoromethyl)-3-fluorophenyl]cyclopropyl}-2-(dimethylamino)-6-oxo-1,6-dihydropyrimidine-4-carboxamide | Calc'd 367.1, found 367.1 |
| 71 | 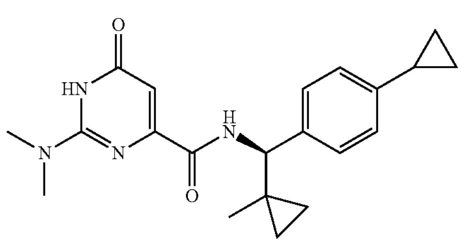 [SMILES: CN(C)c1nc(C(=O)N[C@@H](c2ccc(C3CC3)cc2)C2(C)CC2)cc(=O)[nH]1] | N-[(R)-(4-cyclopropylphenyl)(1-methylcyclopropyl)methyl]-2-(dimethylamino)-6-oxo-1,6-dihydropyrimidine-4-carboxamide | Calc'd 367.2, found 366.9 |
| 72 | 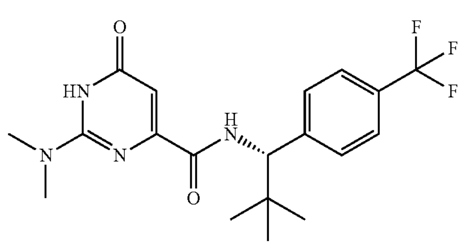 [SMILES: CN(C)c1nc(C(=O)N[C@H](c2ccc(C(F)(F)F)cc2)C(C)(C)C)cc(=O)[nH]1] | 2-(dimethylamino)-N-{(1S)-2,2-dimethyl-1-[4-(trifluoromethyl)phenyl]propyl}-6-oxo-1,6-dihydropyrimidine-4-carboxamide | Calc'd 397.2, found 396.8 |

TABLE 3-continued

Examples 30-84 in the following table were prepared using similar conditions as described in Example 2 and Scheme B from appropriate starting materials.

| Example Number | Structure | IUPAC Name | Exact Mass [M + H]⁺ |
|---|---|---|---|
| 73 | 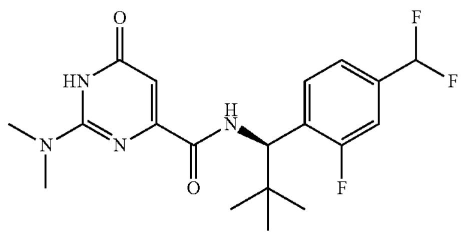 [SMILES: CN(C)c1nc(C(=O)N[C@@H](c2ccc(C(F)F)cc2F)C(C)(C)C)cc(=O)[nH]1] | N-{(1R)-1-[4-(difluoromethyl)-2-fluorophenyl]-2,2-dimethylpropyl}-2-(dimethylamino)-6-oxo-1,6-dihydropyrimidine-4-carboxamide | Calc'd 397.2, found 397.1 |
| 74 | 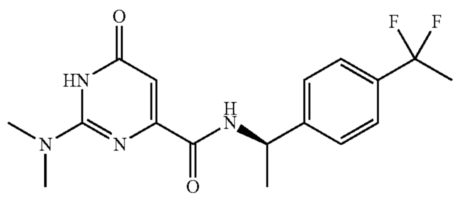 [SMILES: C[C@@H](NC(=O)c1cc(=O)[nH]c(N(C)C)n1)c1ccc(C(C)(F)F)cc1] | N-{(1R)-1-[4-(1,1-difluoroethyl)phenyl]ethyl}-2-(dimelhylamino)-6-oxo-1,6-dihydropyrimidine-4-carboxamide | Calc'd 351.2, found 350.9 |
| 75 | 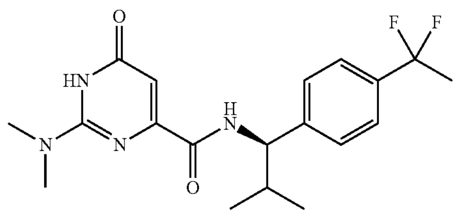 [SMILES: CC(C)[C@@H](NC(=O)c1cc(=O)[nH]c(N(C)C)n1)c1ccc(C(C)(F)F)cc1] | N-{(1R)-1-[4-(1,1-difluoroethyl)phenyl]-2-methylpropyl}-2-(dimethylamino)-6-oxo-1,6-dihydropyrimidine-4-carboxamide | Calc'd 379.2, found 379.2 |
| 76 | 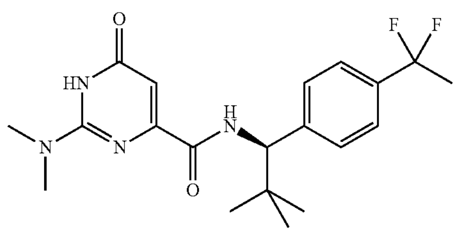 [SMILES: CN(C)c1nc(C(=O)N[C@@H](c2ccc(C(C)(F)F)cc2)C(C)(C)C)cc(=O)[nH]1] | N-{(1R)-1-[4-(1,1-difluoroethyl)phenyl]-2,2-dimethylpropyl}-2-(dimethylamino)-6-oxo-1,6-dihydropyrimidine-4-carboxamide | Calc'd 393.2, found 393.2 |
| 77 | 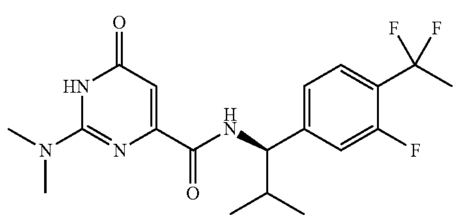 [SMILES: CC(C)[C@@H](NC(=O)c1cc(=O)[nH]c(N(C)C)n1)c1ccc(C(C)(F)F)c(F)c1] | N-{(1R)-1-[4-(1,1-difluoroethyl)-3-fluorophenyl]-2-methylpropyl}-2-(dimethylamino)-6-oxo-1,6-dihydropyrimidine-4-carboxamide | Calc'd 397.2, found 397.0 |
| 78 | 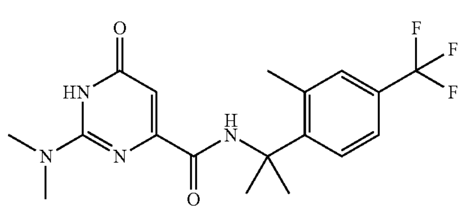 [SMILES: Cc1cc(C(F)(F)F)ccc1C(C)(C)NC(=O)c1cc(=O)[nH]c(N(C)C)n1] | 2-(dimethylamino)-N-{1-methyl-1-[2-methyl-4-(trifluoromethyl)phenyl]ethyl}-6-oxo-1,6-dihydropyrimidine-4-carboxamide | Calc'd 383.2, found 383.1 |

TABLE 3-continued

Examples 30-84 in the following table were prepared using similar conditions as described in Example 2 and Scheme B from appropriate starting materials.

| Example Number | Structure | IUPAC Name | Exact Mass [M + H]+ |
|---|---|---|---|
| 79 | 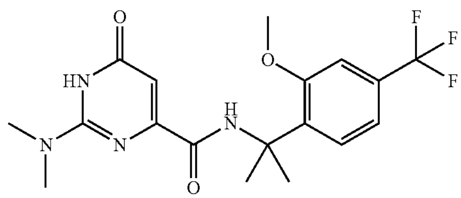 [SMILES: COc1cc(C(F)(F)F)ccc1C(C)(C)NC(=O)c1cc(=O)[nH]c(N(C)C)n1] | 2-(dimethylamino)-N-{1-[2-methoxy-4-(trifluoromethyl)phenyl]-1-methylethyl}-6-oxo-1,6-dihydropyrimidine-4-carboxamide | Calc'd 399.2, found 399.0 |
| 80 | 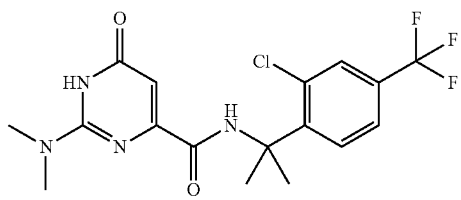 [SMILES: CN(C)c1nc(C(=O)NC(C)(C)c2ccc(C(F)(F)F)cc2Cl)cc(=O)[nH]1] | N-{1-[2-chloro-4-(trifluoromethyl)phenyl]-1-methylethyl}-2-(dimethylamino)-6-oxo-1,6-dihydropyrimidine-4-carboxamide | Calc'd 403.1, found 403.0 |
| 81 | 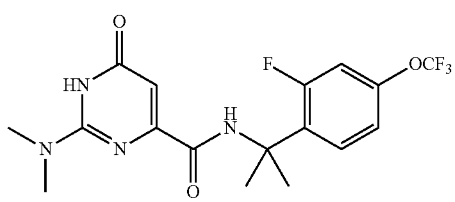 [SMILES: CN(C)c1nc(C(=O)NC(C)(C)c2ccc(OC(F)(F)F)cc2F)cc(=O)[nH]1] | 2-(dimethylamino)-N-{1-[2-fluoro-4-(trifluoromethoxy)phenyl]-1-methylethyl}-6-oxo-1,6-dihydropyrimidine-4-carboxamide | Calc'd 403.1, found 402.9 |
| 82 | 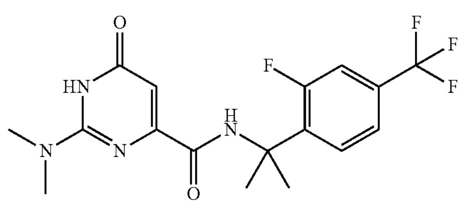 | 2-(dimethylamino)-N-{1-[2-fluoro-4-(trifluoromethyl)phenyl]-1-methylethyl}-6-oxo-1,6-dihydropyrimidine-4-carboxamide | Calc'd 387.1, found 387.0 |
| 83 | 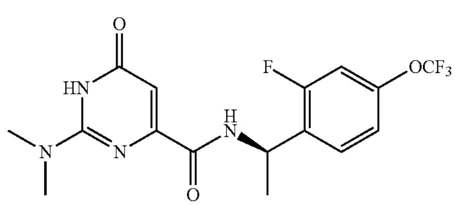 [SMILES: C[C@@H](NC(=O)c1cc(=O)[nH]c(N(C)C)n1)c1ccc(OC(F)(F)F)cc1F] | 2-(dimethylamino)-N-{(1R)-1-[2-fluoro-4-(trifluoromethoxy)phenyl]ethyl}-6-oxo-1,6-dihydropyrimidine-4-carboxamide | Calc'd 389.1, found 388.9 |
| 84 | 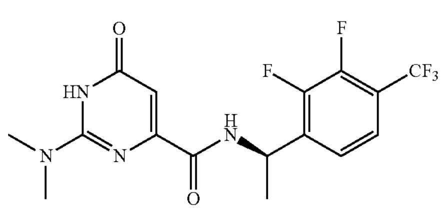 [SMILES: C[C@@H](NC(=O)c1cc(=O)[nH]c(N(C)C)n1)c1ccc(C(F)(F)F)c(F)c1F] | N-{(1R)-1-[2,3-difluoro-4-(trifluoromethyl)phenyl]ethyl}-2-(dimethylamino)-6-oxo-1,6-dihydropyrimidine-4-carboxamide | Calc'd 391.1, found 390.9 |

TABLE 4

Examples 85-98 in the following table were prepared using similar conditions as described in Example 3 and Scheme C from appropriate starting materials.

| Example Number | Structure | IUPAC Name | Exact Mass [M + H]+ |
|---|---|---|---|
| 85 | 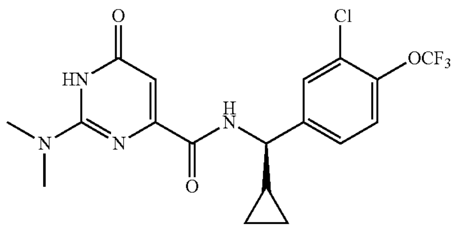 [SMILES: CN(C)c1nc(C(=O)N[C@@H](c2ccc(OC(F)(F)F)c(Cl)c2)C2CC2)cc(=O)[nH]1] | N-[(R)-[3-chloro-4-(trifluoromethoxy)phenyl](cyclopropyl)methyl]-2-(dimethylamino)-6-oxo-1,6-dihydropyrimidine-4-carboxamide | 431.1 |
| 86 | 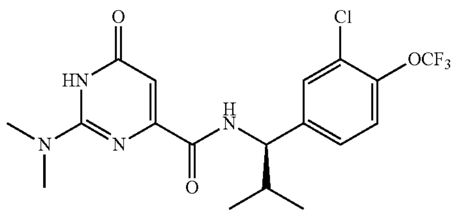 [SMILES: CC(C)[C@@H](NC(=O)c1cc(=O)[nH]c(N(C)C)n1)c1ccc(OC(F)(F)F)c(Cl)c1] | N-{(1R)-1-[3-chloro-4-(trifluoromethoxy)phenyl]-2-methylpropyl}-2-(dimethylamino)-6-oxo-1,6-dihydropyrimidine-4-carboxamide | 433.1 |
| 87 | 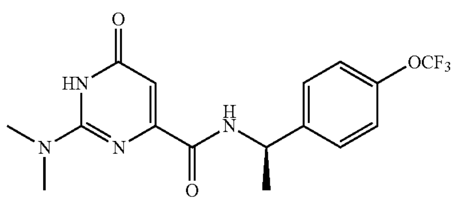 [SMILES: C[C@@H](NC(=O)c1cc(=O)[nH]c(N(C)C)n1)c1ccc(OC(F)(F)F)cc1] | 2-(dimethylamino)-6-oxo-N-{(1R)-1-[4-(trifluoromethoxy)phenyl]ethyl}-1,6-dihydropyrimidine-4-carboxamide | 371.2 |
| 88 | 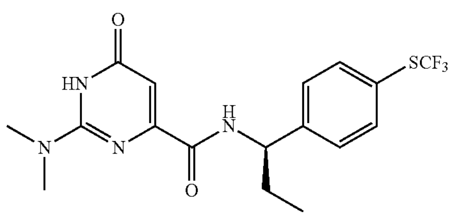 | 2-(dimethylamino)-6-oxo-N-[(1R)-1-{4-[(trifluoromethyl)sulfanyl]phenyl}propyl]-1,6-dihydropyrimidine-4-carboxamide | 401.3 |
| 89 | 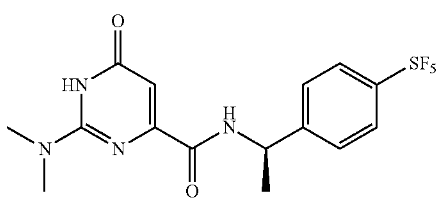 | 2-(dimethylamino)-6-oxo-N-{(1R)-1-[4-(pentafluoro-λ$^6$-sulfanyl)phenyl]ethyl}-1,6-dihydropyrimidine-4-carboxamide | 413.2 |
| 90 | 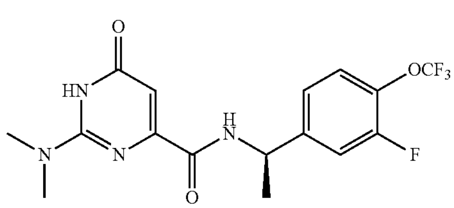 [SMILES: C[C@@H](NC(=O)c1cc(=O)[nH]c(N(C)C)n1)c1ccc(OC(F)(F)F)c(F)c1] | 2-(dimethylamino)-N-{(1R)-1-[3-fluoro-4-(trifluoromethoxy)phenyl]ethyl}-6-oxo-1,6-dihydropyrimidine-4-carboxamide | 389.2 |
| 91 | 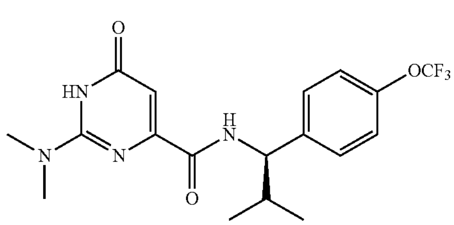 [SMILES: CC(C)[C@@H](NC(=O)c1cc(=O)[nH]c(N(C)C)n1)c1ccc(OC(F)(F)F)cc1] | 2-(dimethylamino)-N-{(1R)-2-methyl-1-[4-(trifluoromethoxy)phenyl]propyl}-6-oxo-1,6-dihydropyrimidine-4-carboxamide | 399.2 |

TABLE 4-continued

Examples 85-98 in the following table were prepared using similar conditions as described in Example 3 and Scheme C from appropriate starting materials.

| Example Number | Structure | IUPAC Name | Exact Mass [M + H]+ |
|---|---|---|---|
| 92 | 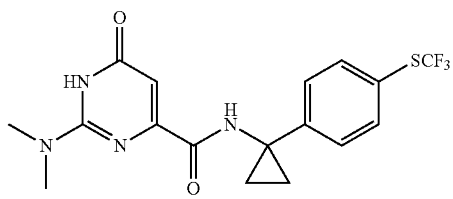 | 2-(dimethylamino)-6-oxo-N-(1-{4-[(trifluoromethyl)sulfanyl]phenyl}cyclopropyl)-1,6-dihydropyrimidine-4-carboxamide | 399.2 |
| 93 | 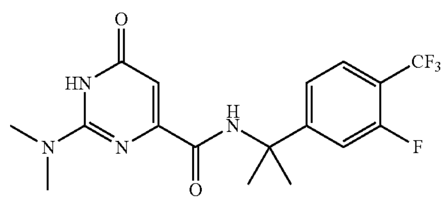 [SMILES: CN(C)c1nc(C(=O)NC(C)(C)c2ccc(C(F)(F)F)c(F)c2)cc(=O)[nH]1] | 2-(dimethylamino)-N-{1-[3-fluoro-4-(trifluoromethyl)phenyl]-1-methylethyl}-6-oxo-1,6-dihydropyrimidine-4-carboxamide | 387.3 |
| 94 | 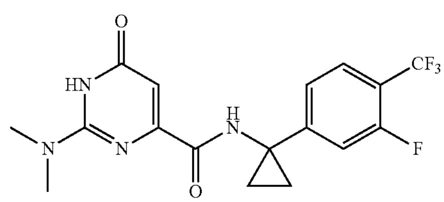 [SMILES: CN(C)c1nc(C(=O)NC2(c3ccc(C(F)(F)F)c(F)c3)CC2)cc(=O)[nH]1] | 2-(dimethylamino)-N-{1-[3-fluoro-4-(trifluoromethyl)phenyl]cyclopropyl}-6-oxo-1,6-dihydropyrimidine-4-carboxamide | 385.2 |
| 95 | 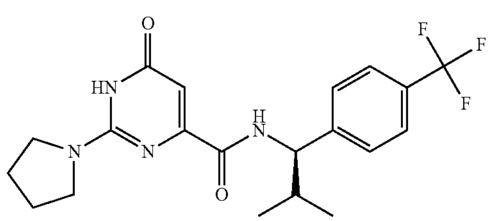 [SMILES: CC(C)[C@@H](NC(=O)c1cc(=O)[nH]c(N2CCCC2)n1)c1ccc(C(F)(F)F)cc1] | N-{(1R)-2-methyl-1-[4-(trifluoromethyl)phenyl]propyl}-6-oxo-2-pyrrolidin-1-yl-1,6-dihydropyrimidine-4-carboxamide | 409.2 |
| 96 | 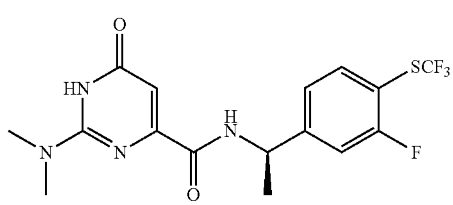 | 2-(dimethylamino)-N-[(1R)-1-{3-fluoro-4-[(trifluoromethyl)sulfanyl]phenyl}ethyl]-6-oxo-1,6-dihydropyrimidine-4-carboxamide | 405.1 |
| 97 | 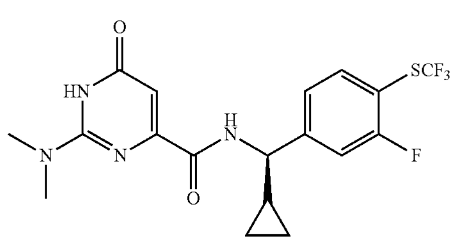 | N-[(R)-cyclopropyl{3-fluoro-4-[(trifluoromethyl)sulfanyl]phenyl}methyl]-2-(dimethylamino)-6-oxo-1,6-dihydropyrimidine-4-carboxamide | 431.2 |
| 98 | 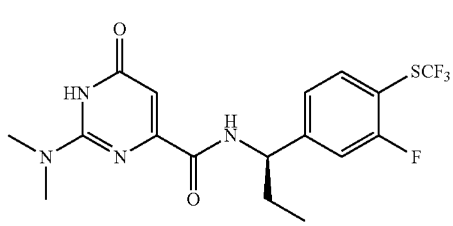 | 2-(dimethylamino)-N-[(1R)-1-{3-fluoro-4-[(trifluoromethyl)sulfanyl]phenyl}propyl]-6-oxo-1,6-dihydropyrimidine-4-carboxamide | 419.3 |

TABLE 5

Examples 99-103 in the following table were prepared using similar conditions as described in Example 4 and Scheme D from appropriate starting materials.

| Example Number | Structure | IUPAC Name | Exact Mass [M + H]+ |
|---|---|---|---|
| 99 | 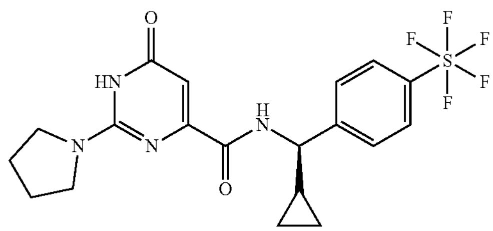 [SMILES: O=C(N[C@@H](c1ccc(S(F)(F)(F)(F)F)cc1)C1CC1)c1cc(=O)[nH]c(N2CCCC2)n1] | N-{(R)-cyclopropyl[4-(pentafluoro-λ$^6$-sulfanyl)phenyl]methyl}-6-oxo-2-pyrrolidin-1-yl-1,6-dihydropyrimidine-4-carboxamide | 465.2 |
| 100 | 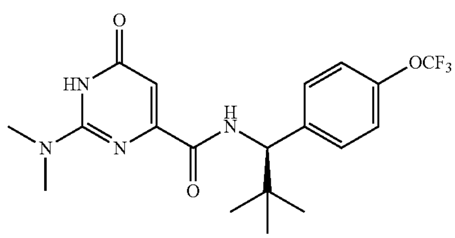 [SMILES: CN(C)c1nc(C(=O)N[C@@H](c2ccc(OC(F)(F)F)cc2)C(C)(C)C)cc(=O)[nH]1] | 2-(dimethylamino)-N-{(1R)-2,2-dimethyl-1-[4-(trifluoromethoxy)phenyl]propyl}-6-oxo-1,6-dihydropyrimidine-4-carboxamide | 413.2 |
| 101 | 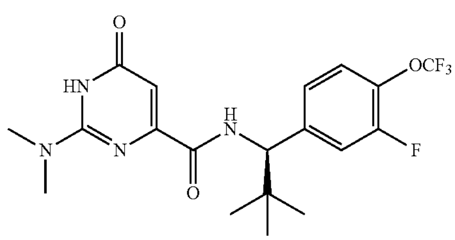 [SMILES: CN(C)c1nc(C(=O)N[C@@H](c2ccc(OC(F)(F)F)c(F)c2)C(C)(C)C)cc(=O)[nH]1] | 2-(dimethylamino)-N-{(1R)-1-[3-fluoro-4-(trifluoromethoxy)phenyl]-2,2-dimethylpropyl}-6-oxo-1,6-dihydropyrimidine-4-carboxamide | 431.2 |
| 102 | 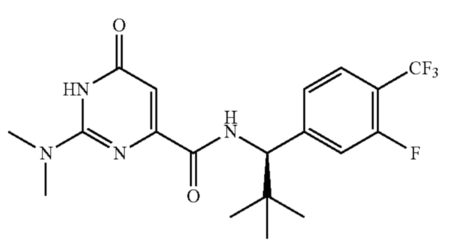 [SMILES: CN(C)c1nc(C(=O)N[C@@H](c2ccc(C(F)(F)F)c(F)c2)C(C)(C)C)cc(=O)[nH]1] | 2-(dimethylamino)-N-{(1R)-1-[3-fluoro-4-(trifluoromethyl)phenyl]-2,2-dimethylpropyl}-6-oxo-1,6-dihydropyrimidine-4-carboxamide | 415.2 |
| 103 | 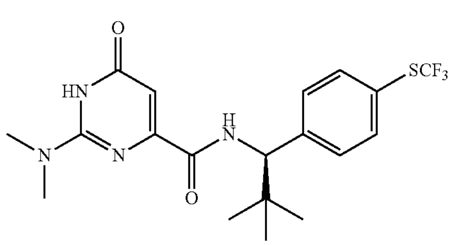 | 2-(dimethylamino)-N-[(1R)-2,2-dimethyl-1-{4-[(trifluoromethyl)sulfanyl]phenyl}propyl]-6-oxo-1,6-dihydropyrimidine-4-carboxamide | 429.1 |

TABLE 6

Examples 104-115 in the following table were prepared using similar conditions as described in Example 5 and Scheme E from appropriate starting materials. For the last example in this Table, TBTU was used as the coupling agent instead of HBTU under otherwisely similar conditions.

| Example Number | Structure | IUPAC Name | Exact Mass [M + H]+ |
|---|---|---|---|
| 104 | 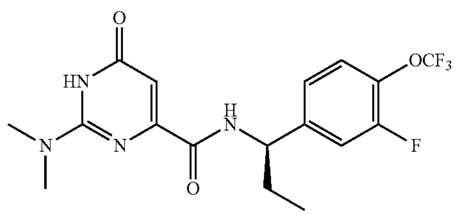 [SMILES: CC[C@@H](NC(=O)c1cc(=O)[nH]c(N(C)C)n1)c1ccc(OC(F)(F)F)c(F)c1] | 2-(dimethylamino)-N-{(1R)-1-[3-fluoro-4-(trifluoromethoxy)phenyl]propyl}-6-oxo-1,6-dihydropyrimidine-4-carboxamide | 403.2 |
| 105 | 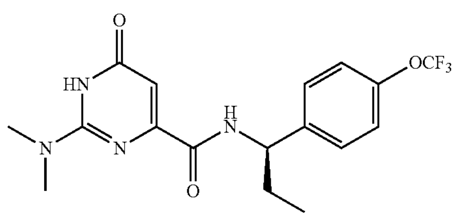 [SMILES: CC[C@@H](NC(=O)c1cc(=O)[nH]c(N(C)C)n1)c1ccc(OC(F)(F)F)cc1] | 2-(dimethylamino)-6-oxo-N-{(1R)-1-[4-(trifluoromethoxy)phenyl]propyl}-1,6-dihydropyrimidine-4-carboxamide | 385.2 |
| 106 | 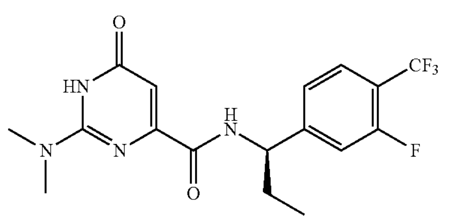 [SMILES: CC[C@@H](NC(=O)c1cc(=O)[nH]c(N(C)C)n1)c1ccc(C(F)(F)F)c(F)c1] | 2-(dimethylamino)-N-{(1R)-1-[3-fluoro-4-(trifluoromethyl)phenyl]propyl}-6-oxo-1,6-dihydropyrimidine-4-carboxamide | 387.2 |
| 107 | 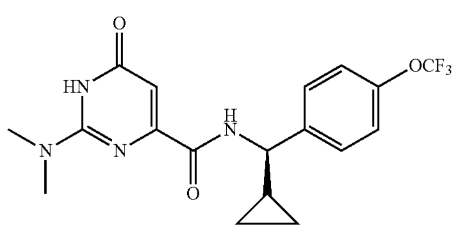 [SMILES: CN(C)c1nc(C(=O)N[C@@H](c2ccc(OC(F)(F)F)cc2)C2CC2)cc(=O)[nH]1] | N-{(1R)-cyclopropyl[4-(trifluoromethoxy)phenyl]methyl}-2-(dimethylamino)-6-oxo-1,6-dihydropyrimidine-4-carboxamide | 397.2 |
| 108 | 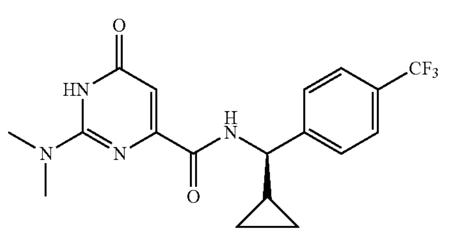 [SMILES: CN(C)c1nc(C(=O)N[C@@H](c2ccc(C(F)(F)F)cc2)C2CC2)cc(=O)[nH]1] | N-{(1R)-cyclopropyl[4-(trifluoromethyl)phenyl]methyl}-2-(dimethylamino)-6-oxo-1,6-dihydropyrimidine-4-carboxamide | 381.2 |
| 109 | 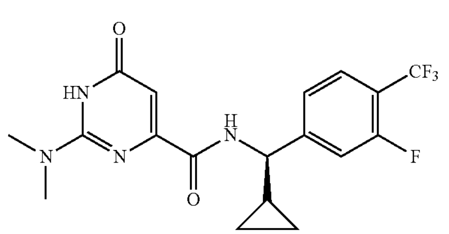 [SMILES: CN(C)c1nc(C(=O)N[C@@H](c2ccc(C(F)(F)F)c(F)c2)C2CC2)cc(=O)[nH]1] | N-{(1R)-cyclopropyl[3-fluoro-4-(trifluoromethyl)phenyl]methyl}-2-(dimethylamino)-6-oxo-1,6-dihydropyrimidine-4-carboxamide | 399.2 |

TABLE 6-continued

Examples 104-115 in the following table were prepared using similar conditions as described in Example 5 and Scheme E from appropriate starting materials. For the last example in this Table, TBTU was used as the coupling agent instead of HBTU under otherwisely similar conditions.

| Example Number | Structure | IUPAC Name | Exact Mass [M + H]+ |
| --- | --- | --- | --- |
| 110 | 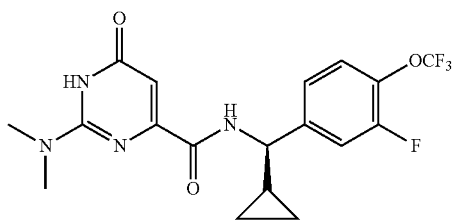 [SMILES: CN(C)c1nc(C(=O)N[C@@H](c2ccc(OC(F)(F)F)c(F)c2)C2CC2)cc(=O)[nH]1] | N-{(1R)-cyclopropyl[3-fluoro-4-(trifluoromethoxy)phenyl]methyl}-2-(dimethylamino)-6-oxo-1,6-dihydropyrimidine-4-carboxamide | 415.2 |
| 111 | 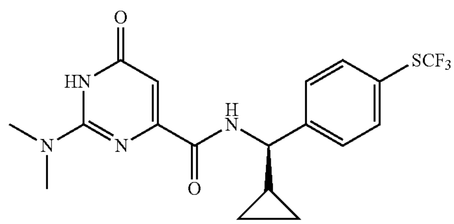 | N-[(R)-cyclopropyl{4-[(trifluoromethyl)sulfanyl]phenyl}methyl]-2-(dimethylamino)-6-oxo-1,6-dihydropyrimidine-4-carboxamide | 413.2 |
| 112 | 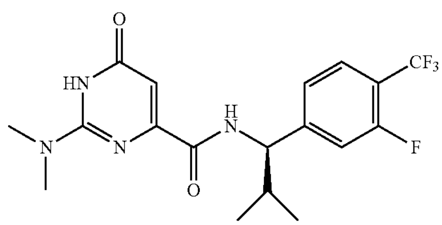 [SMILES: CC(C)[C@@H](NC(=O)c1cc(=O)[nH]c(N(C)C)n1)c1ccc(C(F)(F)F)c(F)c1] | 2-(dimethylamino)-N-{(1R)-1-[3-fluoro-4-(trifluoromethyl)phenyl]-2-methylpropyl}-6-oxo-1,6-dihydropyrimidine-4-carboxamide | 401.3 |
| 113 | 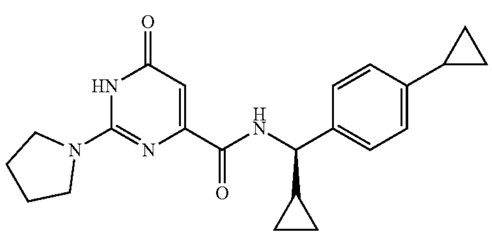 [SMILES: O=C(N[C@@H](c1ccc(C2CC2)cc1)C1CC1)c1cc(=O)[nH]c(N2CCCC2)n1] | N-[(R)-cyclopropyl(4-cyclopropylphenyl)methyl]-6-oxo-2-pyrrolidine-1-yl-1,6-dihydropyrimidine-4-carboxamide | 379.3 |
| 114 | 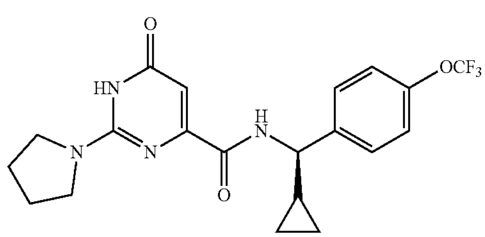 [SMILES: O=C(N[C@@H](c1ccc(OC(F)(F)F)cc1)C1CC1)c1cc(=O)[nH]c(N2CCCC2)n1] | N-{(R)-cyclopropyl[4-(trifluoromethoxy)phenyl]methyl}-6-oxo-2-pyrrolidin-1-yl-1,6-dihydropyrimidine-4-carboxamide | 423.2 |
| 115 | 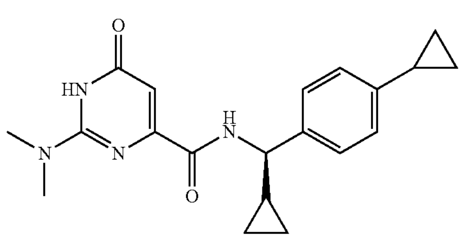 [SMILES: CN(C)c1nc(C(=O)N[C@@H](c2ccc(C3CC3)cc2)C2CC2)cc(=O)[nH]1] | N-[(R)-cyclopropyl(4-cyclopropylphenyl)methyl]-2-(dimethylamino)-6-oxo-1,6-dihydropyrimidine-4-carboxamide | 353.2 |

EXAMPLES 116 and 117

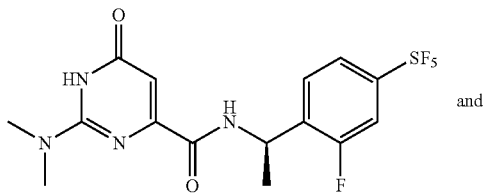

and

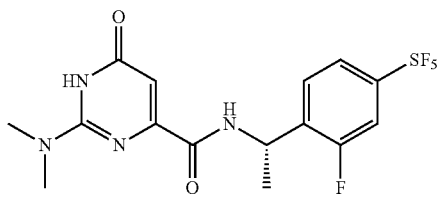

(R)-2-(dimethylamino)-N-(1-(4-(pentafluorothio)-2-fluorophenyl)ethyl)-6-oxo-1,6-dihydropyrimidine-4-carboxamide and (S)-2-(dimethylamino)-N-(1-(4-(pentafluorothio)-2-fluorophenyl)ethyl)-6-oxo-1,6-dihydropy-rimidine-4-carboxamide (Scheme F)

Step 1. 2-(Dimethylamino)-N-(1-(4-(pentafluorothio)-2-fluorophenyl)ethyl)-6-oxo-1,6-dihydro-pyrimidine-4-carboxamide To a mixture of 2-(dimethylamino)-6-oxo-1,6-dihydropyrimidine-4-carboxylic acid (42.5 mg, 0.2 mmol) in NMP (1 mL) was added HATU (57.3 mg, 0.2 mmol) at RT. The reaction mixture was stirred at RT for 5 min. To the mixture were added 1-(2-fluoro-4-(pentafluorothio)phenyl)ethanamine hydrochloride (35.0 mg, 0.1 mmol) and TEA (0.049 mL, 0.3 mmol). The reaction mixture was stirred at RT for 1 h. The resulting mixture was diluted with water (10 mL) and extracted with EtOAc (3×10 mL). The combined organic layers were washed with brine (20 mL), dried with anhydrous $Na_2SO_4$, and filtered. The filtrate was concentrated under reduced pressure. The residue was purified by reverse phase column chromatography over C18 silica gel eluting with 25-40% gradient of methanol in water as eluent. The fractions containing the desired product were combined and concentrated. The title compound was obtained as a solid. MS (ESI) m/z=431.2.

Step 2. (R)- and (S)-2-(dimethylamino)-N-(1-(4-(pentafluorothio)-2-fluorophenyl)ethyl)-6-oxo-1,6-dihydropyrimidine-4-carboxamide 2-(Dimethylamino)-N-(1-(4-(pentafluorothio)-2-fluorophenyl)ethyl)-6-oxo-1,6-dihydropyrimidine-4-carboxamide (35.0 mg, 0.08 mmol) was separated by chiral Prep-HPLC under the following conditions: Column: ChiralPak IC 2×25 cm, 5 um; Mobile Phase A: Hexane, Mobile Phase B: EtOH; Flow rate: 17 mL/min; Gradient: 50% B isocratic in 18 min; 254/220 nm. The faster-eluting enantiomer of the title compound (EXAMPLE 116) was obtained at 9.72 min as a solid. MS (ESI) m/z=431.2. $^1$H NMR (400 MHz, $CDCl_3$) δ: 8.29 (br s, 1H), 7.55-7.46 (m, 3H), 6.60 (s, 1H), 5.42-5.36 (m, 1H), 3.27 (s, 6H), 1.63 (d, J=6.8 Hz, 3H). The slower-eluting enantiomer of the title compound (Example 117) was obtained at 16.46 min as a solid. MS (ESI) m/z=431.2. $^1$H NMR (400 MHz, $CDCl_3$) δ: 8.31 (br s, 1H), 7.54-7.47 (m, 3H), 6.62 (s, 1H), 5.45-5.36 (m, 1H), 3.28 (s, 6H), 1.63 (d, J=5.2 Hz, 3H).

EXAMPLES 118

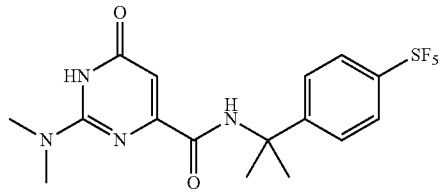

2-(Dimethylamino)-N-{1-methyl-1-[4-(pentafluoro-$\lambda^6$-sulfanyl)phenyl]ethyl}-6-oxo-1,6-dihydropyrimidine-4-carboxamide The title compound was prepared using procedures similar to those described in Step 1 of Examples 116 and 117 using appropriate starting materials (Scheme F). MS (ESI) m/z=426.9.

TABLE 7

Examples 119-130 in the following table were prepared using procedures similar to those described in Step 1 of Examples 116 and 117 using appropriate starting materials (Scheme F). Racemic products were separated using chiral columns specified in the table. For those pairs of enantiomers, the fast-eluting isomer is always list first in this table and this convention is used in all other tables in this application where chiral HPLC was used for resolving enantiomers or diastereomers.

| Example Number | Structure | IUPAC Name | Exact Mass [M + H]$^+$ | Chiral Column |
|---|---|---|---|---|
| 119 | 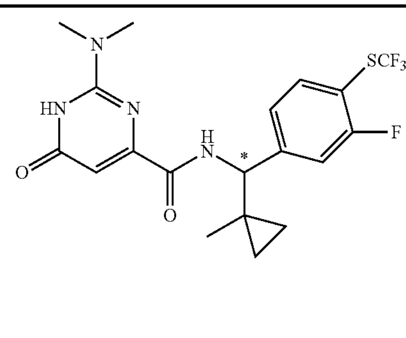 | (S)- or (R)-2-(dimethylamino)-N-[{3-fluoro-4-[(trifluoromethyl)sulfanyl]phenyl}(1-methylcyclopropyl)methyl]-6-oxo-1,6-dihydropyrimidine-4-carboxamide | Calc'd 445.1, found 445.2 | ChiralPak IC |

TABLE 7-continued

Examples 119-130 in the following table were prepared using procedures similar to those
described in Step 1 of Examples 116 and 117 using appropriate starting materials (Scheme F).
Racemic products were separated using chiral columns specified in the table. For those pairs of
enantiomers, the fast-eluting isomer is always list first in this table and this convention is used in all
other tables in this application where chiral HPLC was used for resolving enantiomers or diastereomers.

| Example Number | Structure | IUPAC Name | Exact Mass [M + H]+ | Chiral Column |
|---|---|---|---|---|
| 120 | 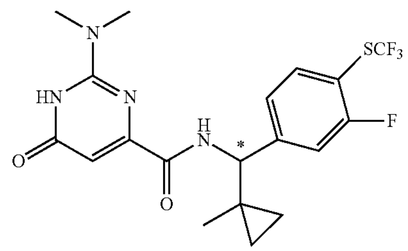 | (R)- or (S)-2-(dimethylamino)-N-[{3-fluoro-4-[(trifluoromethyl)sulfanyl]phenyl}(1-methylcyclopropyl)methyl]-6-oxo-1,6-dihydropyrimidine-4-carboxamide | Calc'd 445.1, found 445.2 | ChiralPak IC |
| 121 | 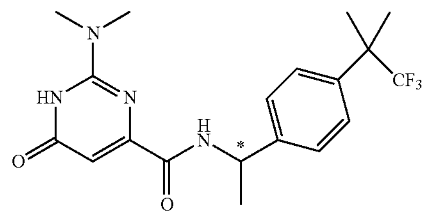 [SMILES: CC(NC(=O)c1cc(=O)[nH]c(N(C)C)n1)c1ccc(C(C)(C)C(F)(F)F)cc1] | (S)- or (R)-2-(dimethylamino)-6-oxo-N-{1-[4-(2,2,2-trifluoro-1,1-dimethylethyl)phenyl]ethyl}-1,6-dihydropyrimidine-4-carboxamide | Calc'd 397.2, found 397.2 | Lux ChiralPak IA-3 |
| 122 | 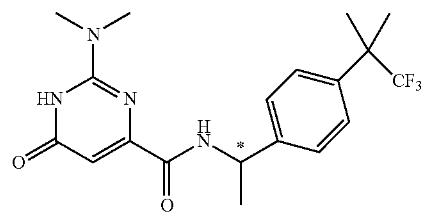 [SMILES: CC(NC(=O)c1cc(=O)[nH]c(N(C)C)n1)c1ccc(C(C)(C)C(F)(F)F)cc1] | (R)- or (S)-2-(dimethylamino)-6-oxo-N-{1-[4-(2,2,2-trifluoro-1,1-dimethylethyl)phenyl]ethyl}-1,6-dihydropyrimidine-4-carboxamide | Calc'd 397.2, found 397.2 | Lux ChiralPak IA-3 |
| 123 | 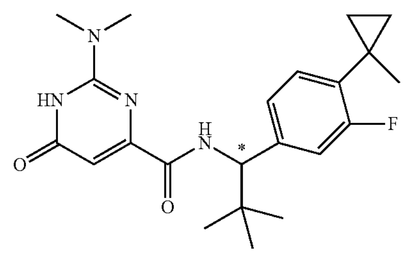 [SMILES: CN(C)c1nc(C(=O)NC(c2ccc(C3(C)CC3)c(F)c2)C(C)(C)C)cc(=O)[nH]1] | (S)- or (R)-2-(dimethylamino)-N-{1-[3-fluoro-4-(1-methylcyclopropyl)phenyl]-2,2-dimethylpropyl}-6-oxo-1,6-dihydropyrimidine-4-carboxamide | Calc'd 401.2, found 401.3 | ChiralPak IC |
| 124 | 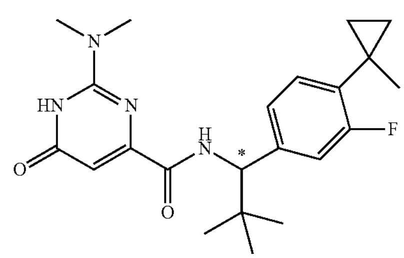 [SMILES: CN(C)c1nc(C(=O)NC(c2ccc(C3(C)CC3)c(F)c2)C(C)(C)C)cc(=O)[nH]1] | (R)- or (S)-2-(dimethylamino)-N-{1-[3-fluoro-4-(1-methylcyclopropyl)phenyl]-2,2-dimethylpropyl}-6-oxo-1,6-dihydropyrimidine-4-carboxamide | Calc'd 401.2, found 401.3 | ChiralPak IC |
| 125 | 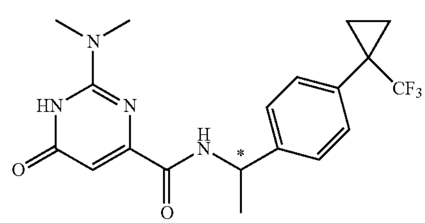 [SMILES: CC(NC(=O)c1cc(=O)[nH]c(N(C)C)n1)c1ccc(C2(C(F)(F)F)CC2)cc1] | (S)- or (R)-2-(dimethylamino)-6-oxo-N-[1-{4-[1-(trifluoromethyl)cyclopropyl]phenyl}ethyl]-1,6-dihydropyrimidine-4-carboxamide | Calc'd 395.2, found 395.2 | ChiralPak IC |

TABLE 7-continued

Examples 119-130 in the following table were prepared using procedures similar to those described in Step 1 of Examples 116 and 117 using appropriate starting materials (Scheme F). Racemic products were separated using chiral columns specified in the table. For those pairs of enantiomers, the fast-eluting isomer is always list first in this table and this convention is used in all other tables in this application where chiral HPLC was used for resolving enantiomers or diastereomers.

| Example Number | Structure | IUPAC Name | Exact Mass [M + H]$^+$ | Chiral Column |
|---|---|---|---|---|
| 126 | 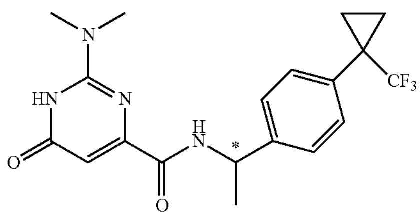 [SMILES: CC(NC(=O)c1cc(=O)[nH]c(N(C)C)n1)c1ccc(C2(C(F)(F)F)CC2)cc1] | (R)- or (S)-2-(dimethylamino)-6-oxo-N-[1-{4-[1-(trifluoromethyl)cyclopropyl]phenyl}ethyl]-1,6-dihydropyrimidine-4-carboxamide | Calc'd 395.2, found 395.1 | ChiralPak IC |
| 127 | 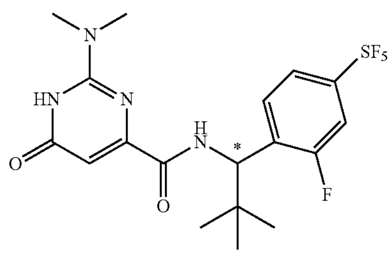 | (S)- or (R)-2-(dimethylamino)-N-{1-[2-fluoro-4-(pentafluoro-$\lambda^6$-sulfanyl)phenyl]-2,2-dimethylpropyl}-6-oxo-1,6-dihydropyrimidine-4-carboxamide | Calc'd 473.1, found 473.3 | ChiralPak IA |
| 128 | 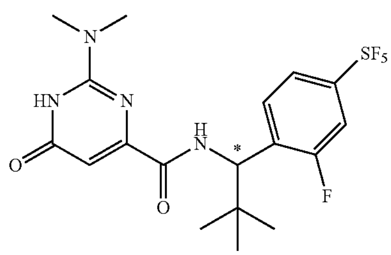 | (R)- or (S)-2-(dimethylamino)-N-{1-[2-fluoro-4-(pentafluoro-$\lambda^6$-sulfanyl)phenyl]-2,2-dimethylpropyl}-6-oxo-1,6-dihydropyrimidine-4-carboxamide | Calc'd 473.1, found 473.3 | ChiralPak IA |
| 129 | 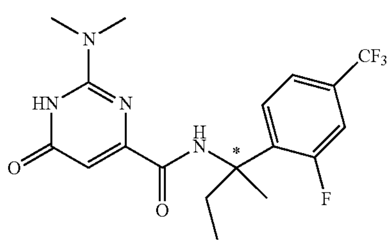 [SMILES: CCC(C)(NC(=O)c1cc(=O)[nH]c(N(C)C)n1)c1ccc(C(F)(F)F)cc1F] | (S)- or (R)-2-(dimethylamino)-N-{1-[2-fluoro-4-(trifluoromethyl)phenyl]-1-methylpropyl}-6-oxo-1,6-dihydropyrimidine-4-carboxamide | Calc'd 401.2, found 401.2 | ChiralPak IC |
| 130 | 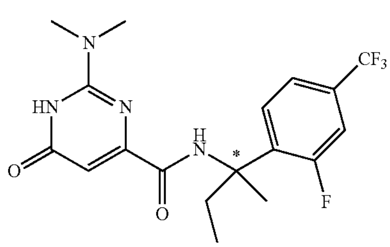 [SMILES: CCC(C)(NC(=O)c1cc(=O)[nH]c(N(C)C)n1)c1ccc(C(F)(F)F)cc1F] | (R)- or (S)-2-(dimethylamino)-N-{1-[2-fluoro-4-(trifluoromethyl)phenyl]-1-methylpropyl}-6-oxo-1,6-dihydropyrimidine-4-carboxamide | Calc'd 401.2, found 401.2 | ChiralPak IC |

TABLE 8

Examples 131-158 in the following table were prepared using similar conditions as described in Example 10 and Scheme J from appropriate starting materials. The synthesis of the amine starting material for Example 137 was described in J. Med. Chem. 2014, 57(8), 3205. The reaction temperature were tailored and modified according to the structures of the reactants and can range as high as 180° C. Similarly, the ratios of amine to sulfone starting materials vary from about 10 to about 25 depending on substrates.

| Example Number | Structure | IUPAC Name | Exact Mass [M + H]$^+$ |
|---|---|---|---|
| 131 | 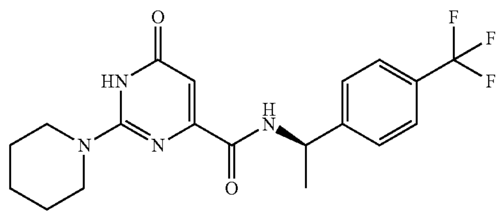 [SMILES: C[C@@H](NC(=O)c1cc(=O)[nH]c(N2CCCCC2)n1)c1ccc(C(F)(F)F)cc1] | 6-oxo-2-piperidin-1-yl-N-{(1R)-1-[4-(trifluoromethyl)phenyl]ethyl}-1,6-dihydropyrimidine-4-carboxamide | Calc'd 395.2, found 395.1 |
| 132 | 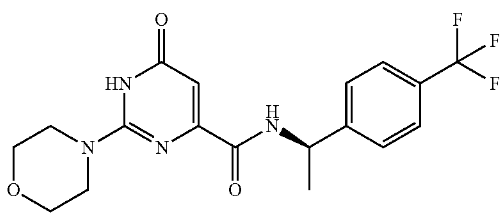 [SMILES: C[C@@H](NC(=O)c1cc(=O)[nH]c(N2CCOCC2)n1)c1ccc(C(F)(F)F)cc1] | 2-morpholin-4-yl-6-oxo-N-{(1R)-1-[4-(trifluoromethyl)phenyl]ethyl}-1,6-dihydropyrimidine-4-carboxamide | Calc'd 397.1, found 397.0 |
| 133 | 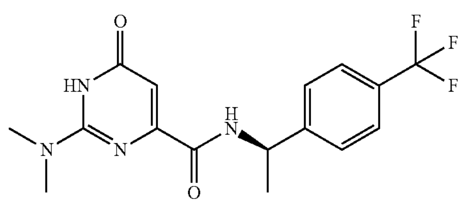 [SMILES: C[C@@H](NC(=O)c1cc(=O)[nH]c(N(C)C)n1)c1ccc(C(F)(F)F)cc1] | 2-(dimethylamino)-6-oxo-N-{(1R)-1-[4-(trifluoromethyl)phenyl]ethyl}-1,6-dihydropyrimidine-4-carboxamide | Calc'd 355.1, found 355.1 |
| 134 | 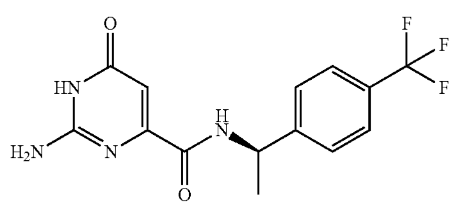 [SMILES: C[C@@H](NC(=O)c1cc(=O)[nH]c(N)n1)c1ccc(C(F)(F)F)cc1] | 2-amino-6-oxo-N-{(1R)-1-[4-(trifluoromethyl)phenyl]ethyl}-1,6-dihydropyrimidine-4-carboxamide | Calc'd 327.1, found 327.1 |
| 135 | 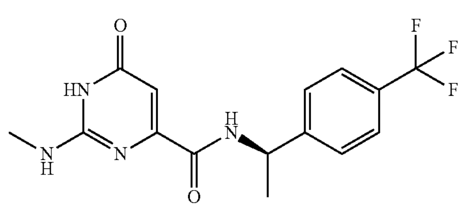 [SMILES: CNc1nc(C(=O)N[C@H](C)c2ccc(C(F)(F)F)cc2)cc(=O)[nH]1] | 2-(methylamino)-6-oxo-N-{(1R)-1-[4-(trifluoromethyl)phenyl]ethyl}-1,6-dihydropyrimidine-4-carboxamide | Calc'd 341.1, found 341.1 |
| 136 | 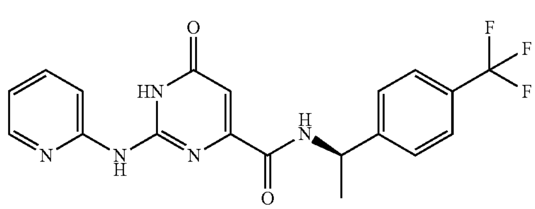 [SMILES: C[C@@H](NC(=O)c1cc(=O)[nH]c(Nc2ccccn2)n1)c1ccc(C(F)(F)F)cc1] | 6-oxo-2-(pyridin-2-ylamino)-N-{(1R)-1-[4-(trifluoromethyl)phenyl]ethyl}-1,6-dihydropyrimidine-4-carboxamide | Calc'd 404.1, found 404.1 |

TABLE 8-continued

Examples 131-158 in the following table were prepared using similar conditions as described in Example 10 and Scheme J from appropriate starting materials. The synthesis of the amine starting material for Example 137 was described in J. Med. Chem. 2014, 57(8), 3205. The reaction temperature were tailored and modified according to the structures of the reactants and can range as high as 180° C. Similarly, the ratios of amine to sulfone starting materials vary from about 10 to about 25 depending on substrates.

| Example Number | Structure | IUPAC Name | Exact Mass $[M + H]^+$ |
|---|---|---|---|
| 137 | 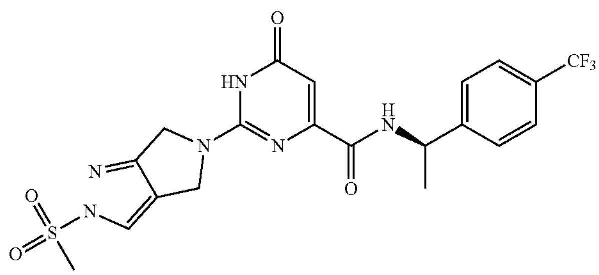 [SMILES: C[C@@H](NC(=O)c1cc(=O)[nH]c(N2CC(=N)/C(=C\NS(C)(=O)=O)C2)n1)c1ccc(C(F)(F)F)cc1] | 2-[2-(methylsulfonyl)-2,6-dihydropyrazolo[3,4-c]pyrazol-5(4H)-yl]-6-oxo-N-{(1R)-1-[4-(trifluoromethyl)phenyl]ethyl}-1,6-dihydropyrimidine-4-carboxamide | Calc'd 497.1, found 497.1 |
| 138 | 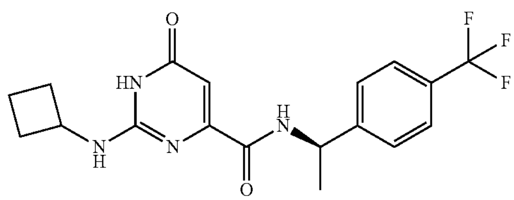 [SMILES: C[C@@H](NC(=O)c1cc(=O)[nH]c(NC2CCC2)n1)c1ccc(C(F)(F)F)cc1] | 2-(cyclobutylamino)-6-oxo-N-{(1R)-1-[4-(trifluoromethyl)phenyl]ethyl}-1,6-dihydropyrimidine-4-carboxamide | Calc'd 381.2, found 381.1 |
| 139 | 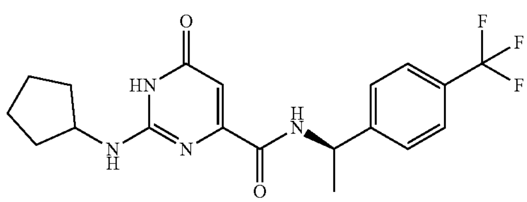 [SMILES: C[C@@H](NC(=O)c1cc(=O)[nH]c(NC2CCCC2)n1)c1ccc(C(F)(F)F)cc1] | 2-(cyclopentylamino)-6-oxo-N-{(1R)-1-[4-(trifluoromethyl)phenyl]ethyl}-1,6-dihydropyrimidine-4-carboxamide | Calc'd 395.2, found 395.1 |
| 140 | 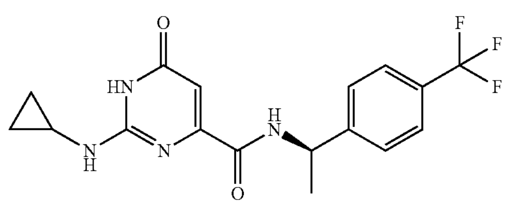 [SMILES: C[C@@H](NC(=O)c1cc(=O)[nH]c(NC2CC2)n1)c1ccc(C(F)(F)F)cc1] | 2-(cyclopropylamino)-6-oxo-N-{(1R)-1-[4-(trifluoromethyl)phenyl]ethyl}-1,6-dihydropyrimidine-4-carboxamide | Calc'd 367.1, found 367.1 |
| 141 | 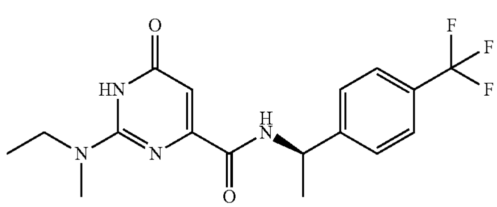 [SMILES: CCN(C)c1nc(C(=O)N[C@H](C)c2ccc(C(F)(F)F)cc2)cc(=O)[nH]1] | 2-[ethyl(methyl)amino]-6-oxo-N-{(1R)-1-[4-(trifluoromethyl)phenyl]ethyl}-1,6-dihydropyrimidine-4-carboxamide | Calc'd 369.2, found 369.1 |
| 142 | 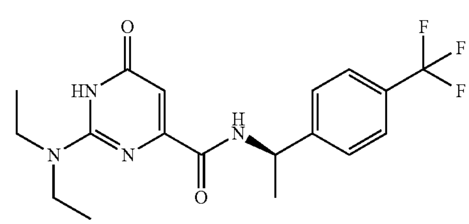 [SMILES: CCN(CC)c1nc(C(=O)N[C@H](C)c2ccc(C(F)(F)F)cc2)cc(=O)[nH]1] | 2-(diethylamino)-6-oxo-N-{(1R)-1-[4-(trifluoromethyl)phenyl]ethyl}-1,6-dihydropyrimidine-4-carboxamide | Calc'd 383.2, found 383.1 |

TABLE 8-continued

Examples 131-158 in the following table were prepared using similar conditions as described in Example 10 and Scheme J from appropriate starting materials. The synthesis of the amine starting material for Example 137 was described in J. Med. Chem. 2014, 57(8), 3205. The reaction temperature were tailored and modified according to the structures of the reactants and can range as high as 180° C. Similarly, the ratios of amine to sulfone starting materials vary from about 10 to about 25 depending on substrates.

| Example Number | Structure | IUPAC Name | Exact Mass [M + H]+ |
|---|---|---|---|
| 143 | 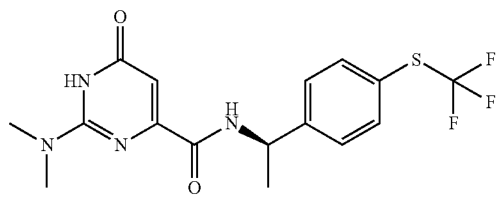 [SMILES: C[C@@H](NC(=O)c1cc(=O)[nH]c(N(C)C)n1)c1ccc(SC(F)(F)F)cc1] | 2-(dimethylamino)-6-oxo-N-[(1R)-1-{4-[(trifluoromethyl)sulfanyl]phenyl}ethyl]-1,6-dihydropyrimidine-4-carboxamide | Calc'd 387.1, found 387.1 |
| 144 | 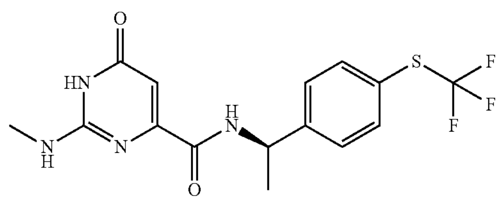 [SMILES: CNc1nc(C(=O)N[C@H](C)c2ccc(SC(F)(F)F)cc2)cc(=O)[nH]1] | 2-(methylamino)-6-oxo-N-[(1R)-1-{4-[(trifluoromethyl)sulfanyl]phenyl}ethyl]-1,6-dihydropyrimidine-4-carboxamide | Calc'd 373.1, found 373.1 |
| 145 | 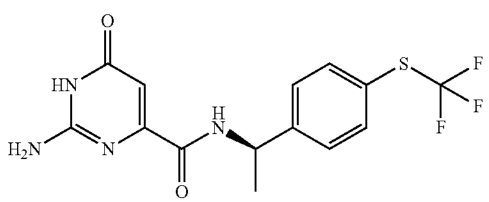 [SMILES: C[C@@H](NC(=O)c1cc(=O)[nH]c(N)n1)c1ccc(SC(F)(F)F)cc1] | 2-amino-6-oxo-N-[(1R)-1-{4-[(trifluoromethyl)sulfanyl]phenyl}ethyl]-1,6-dihydropyrimidine-4-carboxamide | Calc'd 359.1, found 359.0 |
| 146 | 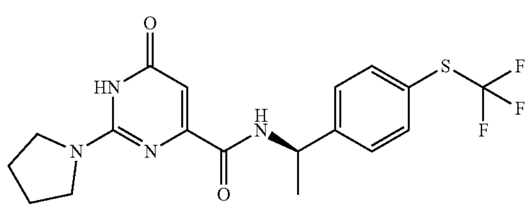 [SMILES: C[C@@H](NC(=O)c1cc(=O)[nH]c(N2CCCC2)n1)c1ccc(SC(F)(F)F)cc1] | 6-oxo-2-pyrrolidin-1-yl-N-[(1R)-1-{4-[(trifluoromethyl)sulfanyl]phenyl}ethyl]-1,6-dihydropyrimidine-4-carboxamide | Calc'd 413.1, found 413.1 |
| 147 | 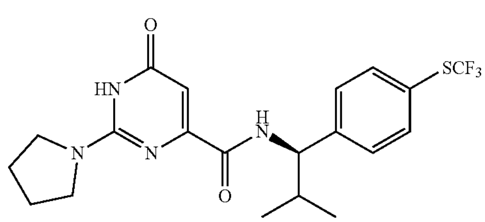 | N-[(1R)-2-methyl-1-{4-[(trifluoromethyl)sulfanyl]phenyl}propyl]-6-oxo-2-pyrrolidin-1-yl-1,6-dihydropyrimidine-4-carboxamide | Calc'd 441.2, found 441.2 |
| 148 | 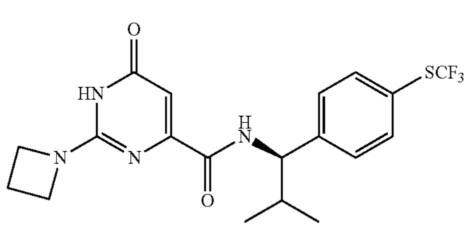 | 2-azetidin-1-yl-N-[(1R)-2-methyl-1-{4-[(trifluoromethyl)sulfanyl]phenyl}propyl]-6-oxo-1,6-dihydropyrimidine-4-carboxamide | Calc'd 427.1, found 427.1 |

TABLE 8-continued

Examples 131-158 in the following table were prepared using similar conditions as described in Example 10 and Scheme J from appropriate starting materials. The synthesis of the amine starting material for Example 137 was described in J. Med. Chem. 2014, 57(8), 3205. The reaction temperature were tailored and modified according to the structures of the reactants and can range as high as 180° C. Similarly, the ratios of amine to sulfone starting materials vary from about 10 to about 25 depending on substrates.

| Example Number | Structure | IUPAC Name | Exact Mass [M + H]+ |
|---|---|---|---|
| 149 | 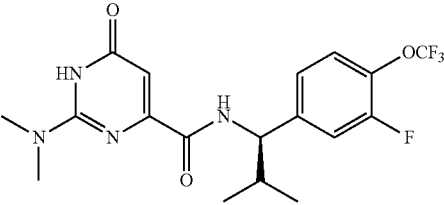 [SMILES: CC(C)[C@@H](NC(=O)c1cc(=O)[nH]c(N(C)C)n1)c1ccc(OC(F)(F)F)c(F)c1] | 2-(dimethylamino)-N-{(1R)-1-[3-fluoro-4-(trifluoromethoxy)phenyl]-2-methylpropyl}-6-oxo-1,6-dihydropyrimidine-4-carboxamide | Calc'd 417.2, found 417.1 |
| 150 | 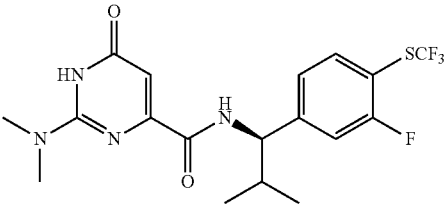 | 2-(dimethylamino)-N-[(1R)-1-{3-fluoro-4-[(trifluoromethyl)sulfanyl]phenyl}-2-methylpropyl]-6-oxo-1,6-dihydropyrimidine-4-carboxamide | Calc'd 433.1, found 433.1 |
| 151 | 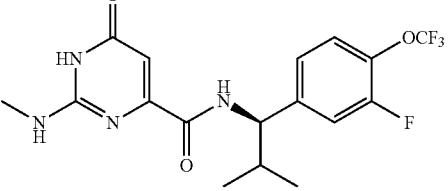 | N-{(1R)-1-[3-fluoro-4-(trifluoromethoxy)phenyl]-2-methylpropyl}-2-(methylamino)-6-oxo-1,6-dihydropyrimidine-4-carboxamide | Calc'd 403.1, found 403.1 |
| 152 | 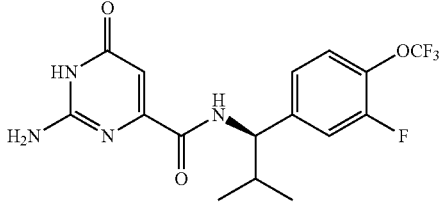 | 2-amino-N-{(1R)-1-[3-fluoro-4-(trifluoromethoxy)phenyl]-2-methylpropyl}-6-oxo-1,6-dihydropyrimidine-4-carboxamide | Calc'd 389.1, found 389.1 |
| 153 | 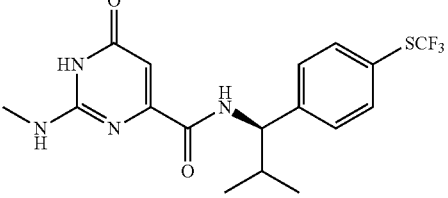 | 2-(methylamino)-N-[(1R)-2-methyl-1-{4-[(trifluoromethyl)sulfanyl]phenyl}propyl]-6-oxo-1,6-dihydropyrimidine-4-carboxamide | Calc'd 401.1, found 401.0 |
| 154 | 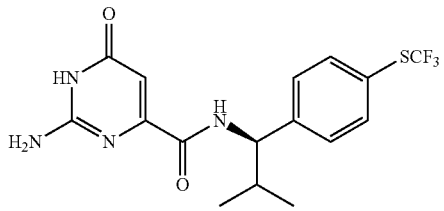 | 2-amino-N-[(1R)-2-methyl-1-{4-[(trifluoromethyl)sulfanyl]phenyl}propyl]-6-oxo-1,6-dihydropyrimidine-4-carboxamide | Calc'd 387.1, found 387.0 |

TABLE 8-continued

Examples 131-158 in the following table were prepared using similar conditions as described in Example 10 and Scheme J from appropriate starting materials. The synthesis of the amine starting material for Example 137 was described in J. Med. Chem. 2014, 57(8), 3205. The reaction temperature were tailored and modified according to the structures of the reactants and can range as high as 180° C. Similarly, the ratios of amine to sulfone starting materials vary from about 10 to about 25 depending on substrates.

| Example Number | Structure | IUPAC Name | Exact Mass [M + H]⁺ |
|---|---|---|---|
| 155 | 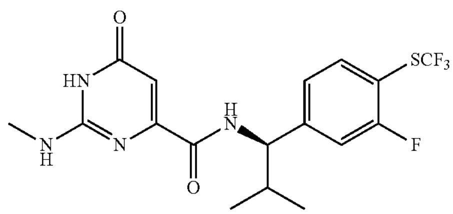 | N-[(1R)-1-{3-fluoro-4-[(trifluoromethyl)sulfanyl]phenyl}-2-methylpropyl]-2-(methylamino)-6-oxo-1,6-dihydropyrimidine-4-carboxamide | Calc'd 419.1, found 419.1 |
| 156 | 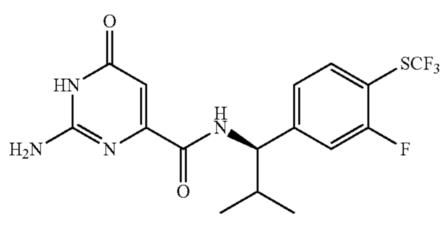 | 2-amino-N-[(1R)-1-{3-fluoro-4-[(trifluoromethyl)sulfanyl]phenyl}-2-methylpropyl]-6-oxo-1,6-dihydropyrimidine-4-carboxamide | Calc'd 405.1, found 405.1 |
| 157 | 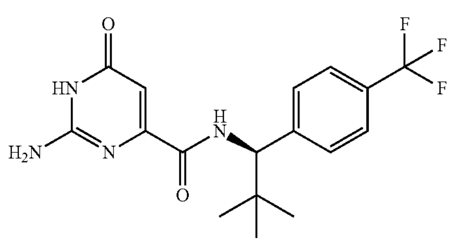 [SMILES: CC(C)(C)[C@@H](NC(=O)c1cc(=O)[nH]c(N)n1)c1ccc(C(F)(F)F)cc1] | 2-amino-N-{(1R)-2,2-dimethyl-1-[4-(trifluoromethyl)phenyl]propyl}-6-oxo-1,6-dihydropyrimidine-4-carboxamide | Calc'd 369.2, found 369.1 |
| 158 | 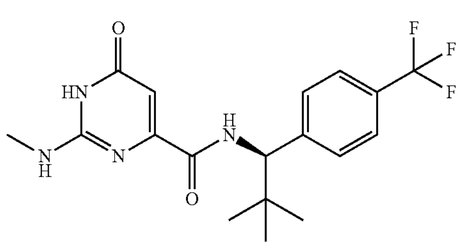 [SMILES: CNc1nc(C(=O)N[C@@H](c2ccc(C(F)(F)F)cc2)C(C)(C)C)cc(=O)[nH]1] | N-{(1R)-2,2-dimethyl-1-[4-(trifluoromethyl)phenyl]propyl}-2-(methylamino)-6-oxo-1,6-dihydropyrimidine-4-carboxamide | Calc'd 383.2, found 383.1 |

TABLE 9

Examples 159-171 in the following table were prepared using similar conditions as described in Example 13 and Scheme L from appropriate starting materials. The amine starting materials for Examples 159 and 161 were prepared according to methods described in WO2006/127530 and WO2007097931. The amine starting material for Example 160 can be prepared from methods described in the literature, such as Chemische Berichte, 1902, 35, 2845; Bioorg. Med. Chem. Lett., 2003, 13(23), 4173, or U.S. Pat. No. 5,312,823 May 17, 1994. The amine used in the substitution reaction for Example 166 was O-protected derivative (R)-3-((tert-butyldimethylsilyl)oxy)pyrrolidine. The TBDMS protecting group was lost during the reaction in situ.

| Example Number | Structure | IUPAC Name | Exact Mass [M + H]+ |
|---|---|---|---|
| 159 | 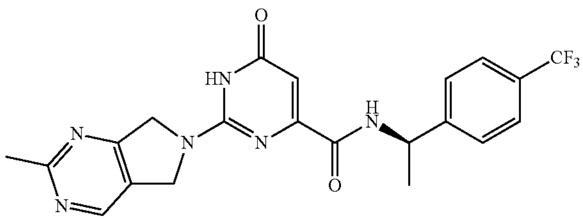 [SMILES: Cc1ncc2c(n1)CN(c1nc(C(=O)N[C@H](C)c3ccc(C(F)(F)F)cc3)cc(=O)[nH]1)C2] | 2-(2-methyl-5,7-dihydro-6H-pyrrolo[3,4-d]pyrimidin-6-yl)-6-oxo-N-{(1R)-1-[4-(trifluoromethyl)phenyl]ethyl}-1,6-dihydropyrimidine-4-carboxamide | Calc'd 445.2, found 445.1 |
| 160 | 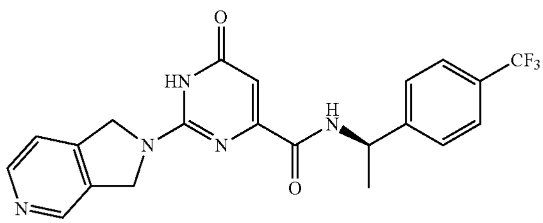 [SMILES: C[C@@H](NC(=O)c1cc(=O)[nH]c(N2Cc3ccncc3C2)n1)c1ccc(C(F)(F)F)cc1] | 2-(1,3-dihydro-2H-pyrrolo[3,4-c]pyridin-2-yl)-6-oxo-N-{(1R)-1-[4-(trifluoromethyl)phenyl]ethyl}-1,6-dihydropyrimidine-4-carboxamide | Calc'd 430.1, found 430.1 |
| 161 | 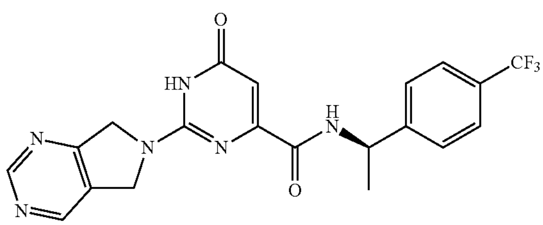 [SMILES: C[C@@H](NC(=O)c1cc(=O)[nH]c(N2Cc3cncnc3C2)n1)c1ccc(C(F)(F)F)cc1] | 2-(5,7-dihydro-6H-pyrrolo[3,4-d]pyrimidin-6-yl)-6-oxo-N-{(1R)-1-[4-(trifluoromethyl)phenyl]ethyl}-1,6-dihydropyrimidine-4-carboxamide | Calc'd 431.1, found 431.1 |
| 162 | 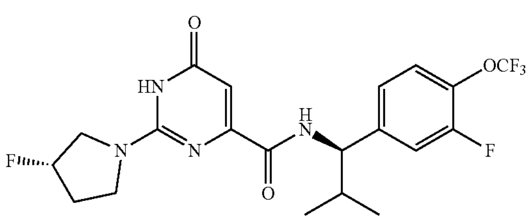 [SMILES: CC(C)[C@@H](NC(=O)c1cc(=O)[nH]c(N2CC[C@H](F)C2)n1)c1ccc(OC(F)(F)F)c(F)c1] | 2-[(3S)-3-fluoropyrrolidin-1-yl]-N-{(1R)-1-[3-fluoro-4-(trifluoromethoxy)phenyl]-2-methylpropyl}-6-oxo-1,6-dihydropyrimidine-4-carboxamide | Calc'd 461.2, found 461.1 |
| 163 | 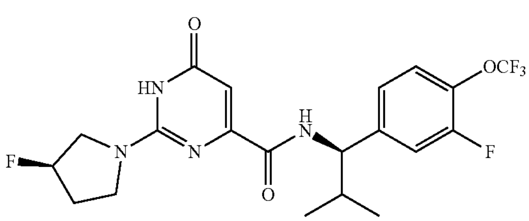 [SMILES: CC(C)[C@@H](NC(=O)c1cc(=O)[nH]c(N2CC[C@@H](F)C2)n1)c1ccc(OC(F)(F)F)c(F)c1] | 2-[(3R)-3-fluoropyrrolidin-1-yl]-N-{(R)-1-[3-fluoro-4-(trifluoromethoxy)phenyl]-2-methylpropyl}-6-oxo-1,6-dihydropyrimidine-4-carboxamide | Calc'd 461.2, found 461.1 |
| 164 | 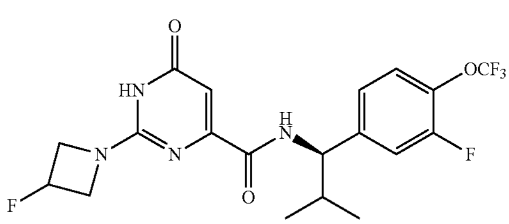 [SMILES: CC(C)[C@@H](NC(=O)c1cc(=O)[nH]c(N2CC(F)C2)n1)c1ccc(OC(F)(F)F)c(F)c1] | 2-(3-fluoroazetidin-1-yl)-N-{(1R)-1-[3-fluoro-4-(trifluoromethoxy)phenyl]-2-methylpropyl}-6-oxo-1,6-dihydropyrimidine-4-carboxamide | Calc'd 447.1, found 447.1 |

TABLE 9-continued

Examples 159-171 in the following table were prepared using similar conditions as described in Example 13 and Scheme L from appropriate starting materials. The amine starting materials for Examples 159 and 161 were prepared according to methods described in WO2006/127530 and WO2007097931. The amine starting material for Example 160 can be prepared from methods described in the literature, such as Chemische Berichte, 1902, 35, 2845; Bioorg. Med. Chem. Lett., 2003, 13(23), 4173, or U.S. Pat. No. 5,312,823 May 17, 1994. The amine used in the substitution reaction for Example 166 was O-protected derivative (R)-3-((tert-butyldimethylsilyl)oxy)pyrrolidine. The TBDMS protecting group was lost during the reaction in situ.

| Example Number | Structure | IUPAC Name | Exact Mass [M + H]+ |
| --- | --- | --- | --- |
| 165 | 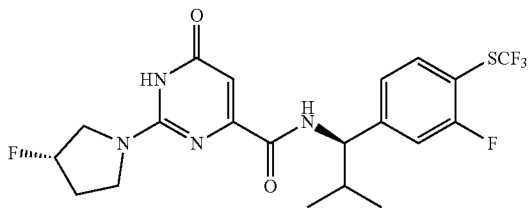 | 2-[(3S)-3-fluoropyrrolidin-1-yl]-N-[(1R)-1-{3-fluoro-4-[(trifluoromethyl)sulfanyl]phenyl}-2-methylpropyl]-6-oxo-1,6-dihydropyrimidine-4-carboxamide | Calc'd 477.1, found 477.0 |
| 166 | 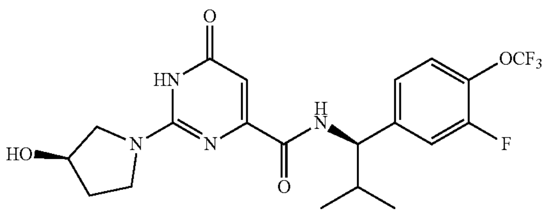 [SMILES: CC(C)[C@@H](NC(=O)c1cc(=O)[nH]c(N2CC[C@@H](O)C2)n1)c1ccc(OC(F)(F)F)c(F)c1] | N-{(1R)-1-[3-fluoro-4-(trifluoromethoxy)phenyl]-2-methylpropyl}-2-[(3R)-3-hydroxypyrrolidin-1-yl]-6-oxo-1,6-dihydropyrimidine-4-carboxamide | Calc'd 459.2, found 459.1 |
| 167 | 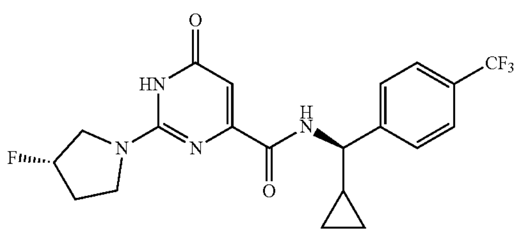 [SMILES: O=C(N[C@@H](c1ccc(C(F)(F)F)cc1)C1CC1)c1cc(=O)[nH]c(N2CC[C@H](F)C2)n1] | N-{(R)-cyclopropyl[4-(trifluoromethyl)phenyl]methyl}-2-[(3S)-3-fluoropyrrolidin-1-yl]-6-oxo-1,6-dihydropyrimidine-4-carboxamide | Calc'd 425.2, found 424.9 |
| 168 | 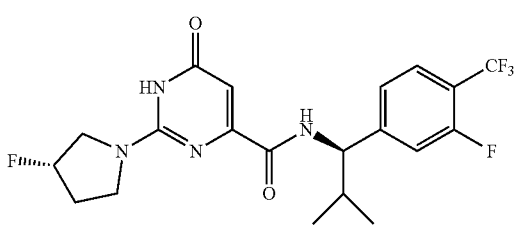 [SMILES: CC(C)[C@@H](NC(=O)c1cc(=O)[nH]c(N2CC[C@H](F)C2)n1)c1ccc(C(F)(F)F)c(F)c1] | 2-[(3S)-3-fluoropyrrolidin-1-yl]-N-{(1R)-1-[3-fluoro-4-(trifluoromethyl)phenyl]-2-methylpropyl}-6-oxo-1,6-dihydropyrimidine-4-carboxamide | Calc'd 445.2, found 445.0 |
| 169 | 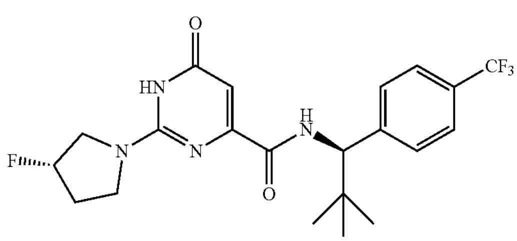 [SMILES: CC(C)(C)[C@@H](NC(=O)c1cc(=O)[nH]c(N2CC[C@H](F)C2)n1)c1ccc(C(F)(F)F)cc1] | N-{(1R)-2,2-dimethyl-1-[4-(trifluoromethyl)phenyl]propyl}-2-[(3S)-3-fluoropyrrolidin-1-yl]-6-oxo-1,6-dihydropyrimidine-4-carboxamide | Calc'd 441.2, found 441.1 |
| 170 | 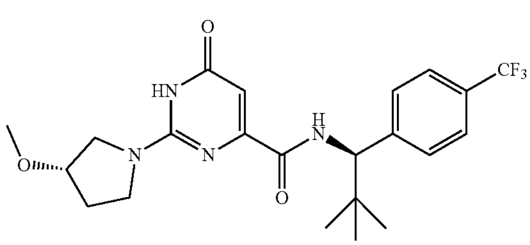 [SMILES: CO[C@H]1CCN(c2nc(C(=O)N[C@@H](c3ccc(C(F)(F)F)cc3)C(C)(C)C)cc(=O)[nH]2)C1] | N-{(1R)-2,2-dimethyl-1-[4-(trifluoromethyl)phenyl]propyl}-2-[(3S)-3-methoxypyrrolidin-1-yl]-6-oxo-1,6-dihydropyrimidine-4-carboxamide | Calc'd 453.2, found 452.9 |

TABLE 9-continued

Examples 159-171 in the following table were prepared using similar conditions as described in Example 13 and Scheme L from appropriate starting materials. The amine starting materials for Examples 159 and 161 were prepared according to methods described in WO2006/127530 and WO2007097931. The amine starting material for Example 160 can be prepared from methods described in the literature, such as Chemische Berichte, 1902, 35, 2845; Bioorg. Med. Chem. Lett., 2003, 13(23), 4173, or U.S. Pat. No. 5,312,823 May 17, 1994. The amine used in the substitution reaction for Example 166 was O-protected derivative (R)-3-((tert-butyldimethylsilyl)oxy)pyrrolidine. The TBDMS protecting group was lost during the reaction in situ.

| Example Number | Structure | IUPAC Name | Exact Mass [M + H]+ |
|---|---|---|---|
| 171 | 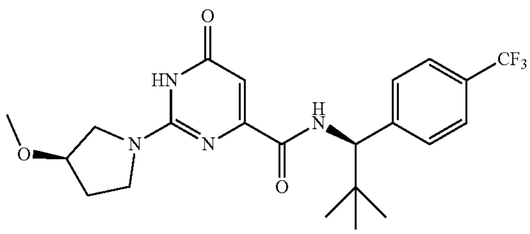 [SMILES: CO[C@@H]1CCN(c2nc(C(=O)N[C@@H](c3ccc(C(F)(F)F)cc3)C(C)(C)C)cc(=O)[nH]2)C1] | N-{(1R)-2,2-dimethyl-1-[4-(trifluoromethyl)phenyl]propyl}-2-[(3R)-3-methoxypyrrolidin-1-yl]-6-oxo-1,6-dihydropyrimidine-4-carboxamide | Calc'd 453.2, found 453.1 |

TABLE 10

Examples 172-177 in table below were obtained by chiral chromatographic resolutions of racemic compounds using chiral columns specified in the table. The racemates for Examples 172/173 and 176/177 have been described above. The racemic cyclopropylamine starting material for Examples 674 and 675 was obtained from ASW MedChem, Inc. (New Brunswick, New Jersey, USA) with unknown relative stereochemistry. NMR studies indicated that it is mostly cis isomer. The coupling reaction with the acid was carried out using conditions similar to those used for Example 2 shown in Scheme B.

| Example Number | Structure | IUPAC Name | Exact Mass [M + H]+ | Scheme and Chiral Column |
|---|---|---|---|---|
| 172 | 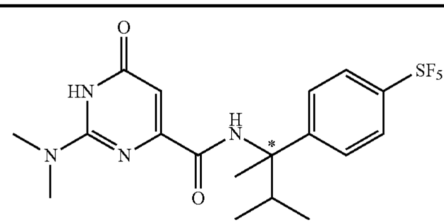 | (R)- or (S)-2-dimethylamino)-N-{1,2-dimethyl-1-[4-(pentafluoro-$\lambda^6$-sulfanyl)phenyl]propyl}-6-oxo-1,6-dihydropyrimidine-4-carboxamide | Calc'd 455.2, found 454.9 | Scheme B Isomer A from OD |
| 173 | 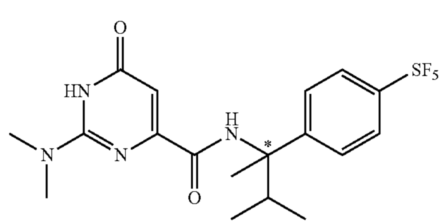 | (S)- or (R)-2-(dimethylamino)-N-{1,2-dimethyl-1-[4-(pentafluoro-$\lambda^6$-sulfanyl)phenyl]propyl}-6-oxo-1,6-dihydropyrimidine-4-carboxamide | Calc'd 455.2, found 455.0 | Scheme B Isomer B from OD |
| 174 | 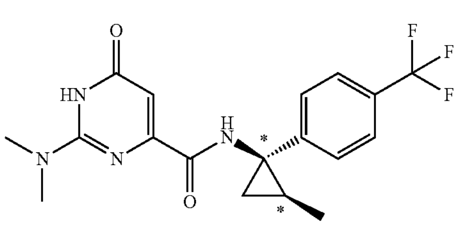 [SMILES: C[C@H]1C[C@]1(NC(=O)c1cc(=O)[nH]c(N(C)C)n1)c1ccc(C(F)(F)F)cc1] | 2-(dimethylamino)-N-{2-methyl-1-[4-(trifluoromethyl)phenyl]cyclopropyl}-6-oxo-1,6-dihydropyrimidine-4-carboxamide (cis, enantiomer A) | Calc'd 381.2, found 381.1 | Scheme B A from IC |

TABLE 10-continued

Examples 172-177 in table below were obtained by chiral chromatographic resolutions of racemic compounds using chiral columns specified in the table. The racemates for Examples 172/173 and 176/177 have been described above. The racemic cyclopropylamine starting material for Examples 674 and 675 was obtained from ASW MedChem, Inc. (New Brunswick, New Jersey, USA) with unknown relative stereochemistry. NMR studies indicated that it is mostly cis isomer. The coupling reaction with the acid was carried out using conditions similar to those used for Example 2 shown in Scheme B.

| Example Number | Structure | IUPAC Name | Exact Mass [M + H]⁺ | Scheme and Chiral Column |
|---|---|---|---|---|
| 175 | 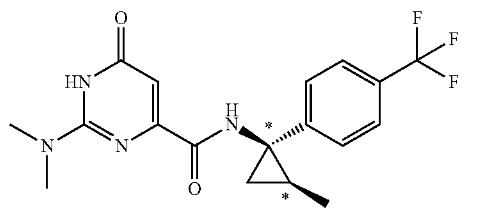 [SMILES: C[C@H]1C[C@]1(NC(=O)c1cc(=O)[nH]c(N(C)C)n1)c1ccc(C(F)(F)F)cc1] | 2-(dimethylamino)-N-{2-methyl-1-[4-(trifluoromethyl)phenyl]cyclopropyl}-6-oxo-1,6-dihydropyrimidine-4-carboxamide (cis, enantiomer B) | Calc'd 381.2, found 381.1 | Scheme B Isomer A from IC |
| 176 | 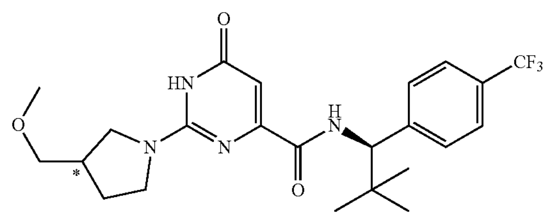 [SMILES: COCC1CCN(c2nc(C(=O)N[C@@H](c3ccc(C(F)(F)F)cc3)C(C)(C)C)cc(=O)[nH]2)C1] | (R)- or (S)-N-{(1R)-2,2-dimethyl-1-[4-(trifluoromethyl)phenyl]propyl}-2-[3-(methoxymethyl)pyrrolidin-1-yl]-6-oxo-1,6-dihydropyrimidine-4-carboxamide | Calc'd 467.2, found 467.0 | Scheme M Isomer A from OJ |
| 177 | 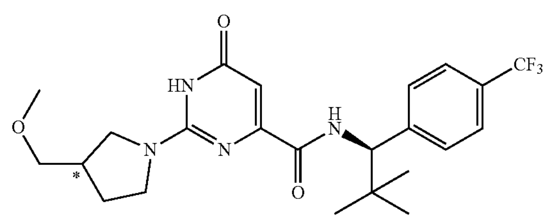 [SMILES: COCC1CCN(c2nc(C(=O)N[C@@H](c3ccc(C(F)(F)F)cc3)C(C)(C)C)cc(=O)[nH]2)C1] | (S)- or (R)-N-{(1R)-2,2-dimethyl-1-[4-(trifluoromethyl)phenyl]propyl}-2-[3-(methoxymethyl)pyrrolidin-1-yl]-6-oxo-1,6-dihydropyrimidine-4-carboxamide | Calc'd 467.2, found 467.1 | Scheme M Isomer B from OJ |

TABLE 11

Examples 178 to 194 in the following table were prepared using procedure described in Example 21 and Scheme S.

| Example Number | Structure | IUPAC Name | Exact Mass [M + H]⁺ |
|---|---|---|---|
| 178 | 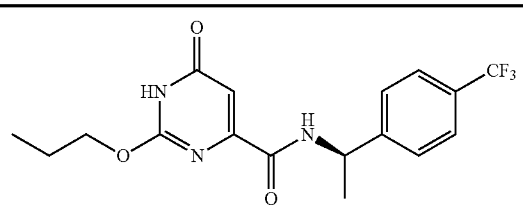 | 6-oxo-2-propoxy-N-{(1R)-1-[4-(trifluoromethyl)phenyl]ethyl}-1,6-dihydropyrimidine-4-carboxamide | 370.1 |
| 179 | 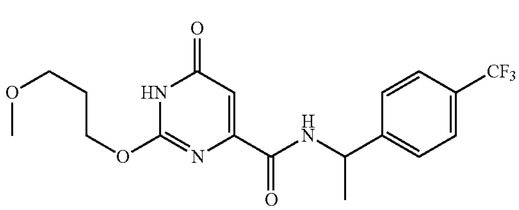 [SMILES: COCCCOc1nc(C(=O)NC(C)c2ccc(C(F)(F)F)cc2)cc(=O)[nH]1] | 2-(3-methoxypropoxy)-6-oxo-N-{1-[4-(trifluoromethyl)phenyl]ethyl}-1,6-dihydropyrimidine-4-carboxamide | 400.3 |

TABLE 11-continued

Examples 178 to 194 in the following table were prepared using procedure described in Example 21 and Scheme S.

| Example Number | Structure | IUPAC Name | Exact Mass [M + H]+ |
|---|---|---|---|
| 180 | 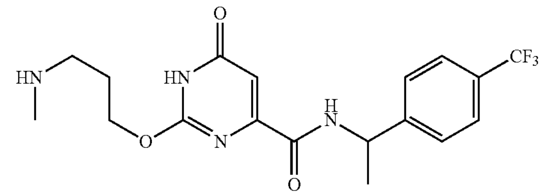 [SMILES: CNCCCOc1nc(C(=O)NC(C)c2ccc(C(F)(F)F)cc2)cc(=O)[nH]1] | 2-[3-(methylamino)propoxy]-6-oxo-N-{1-[4-(trifluoromethyl)phenyl]ethyl}-1,6-dihydropyrimidine-4-carboxamide | 399.2 |
| 181 | 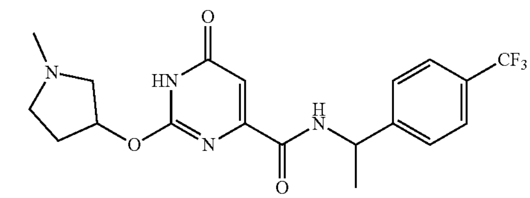 [SMILES: CC(NC(=O)c1cc(=O)[nH]c(OC2CCN(C)C2)n1)c1ccc(C(F)(F)F)cc1] | 2-[(1-methylpyrrolidin-3-yl)oxy]-6-oxo-N-{1-[4-(trifluoromethyl)phenyl]ethyl}-1,6-dihydropyrimidine-4-carboxamide | 411.2 |
| 182 | 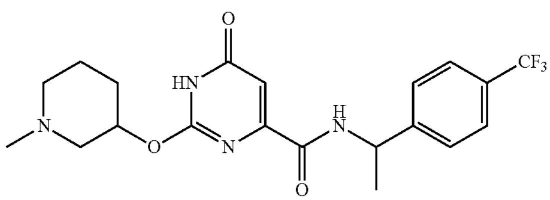 [SMILES: CC(NC(=O)c1cc(=O)[nH]c(OC2CCCN(C)C2)n1)c1ccc(C(F)(F)F)cc1] | 2-[(1-methylpiperidin-3-yl)oxy]-6-oxo-N-{1-[4-(trifluoromethyl)phenyl]ethyl}-1,6-dihydropyrimidine-4-carboxamide | 425.3 |
| 183 | 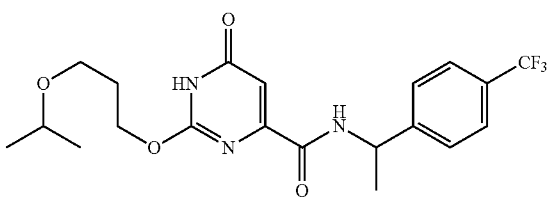 [SMILES: CC(C)OCCCOc1nc(C(=O)NC(C)c2ccc(C(F)(F)F)cc2)cc(=O)[nH]1] | 2-[3-(1-methylethoxy)propoxy]-6-oxo-N-{1-[4-(trifluoromethyl)phenyl]ethyl}-1,6-dihydropyrimidine-4-carboxamide | 428.3 |
| 184 | 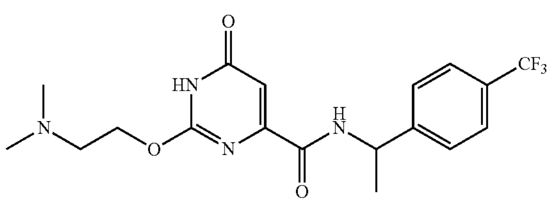 [SMILES: CC(NC(=O)c1cc(=O)[nH]c(OCCN(C)C)n1)c1ccc(C(F)(F)F)cc1] | 2-[2-(dimethylamino)ethoxy]-6-oxo-N-{1-[4-(trifluoromethyl)phenyl]ethyl}-1,6-dihydropyrimidine-4-carboxamide | 399.2 |
| 185 | 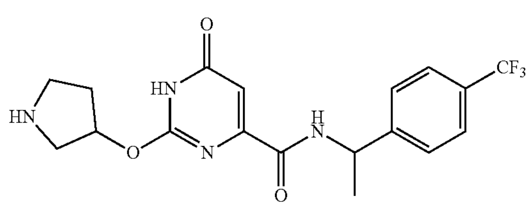 [SMILES: CC(NC(=O)c1cc(=O)[nH]c(OC2CCNC2)n1)c1ccc(C(F)(F)F)cc1] | 6-oxo-2-(pyrrolidin-3-yloxy)-N-{1-[4-(trifluoromethyl)phenyl]ethyl}-1,6-dihydropyrimidine-4-carboxamide | 397.2 |
| 186 | 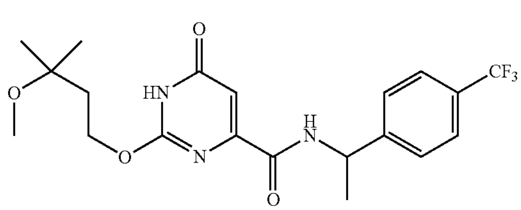 [SMILES: COC(C)(C)CCOc1nc(C(=O)NC(C)c2ccc(C(F)(F)F)cc2)cc(=O)[nH]1] | 2-(3-methoxy-3-methylbutoxy)-6-oxo-N-{1-[4-(trifluoromethyl)phenyl]ethyl}-1,6-dihydropyrimidine-4-carboxamide | 428.2 (M + 1) 450.3 (M + Na) |

TABLE 11-continued

Examples 178 to 194 in the following table were prepared using procedure described in Example 21 and Scheme S.

| Example Number | Structure | IUPAC Name | Exact Mass [M + H]+ |
|---|---|---|---|
| 187 | 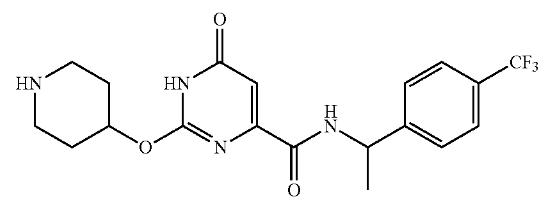 [SMILES: CC(NC(=O)c1cc(=O)[nH]c(OC2CCNCC2)n1)c1ccc(C(F)(F)F)cc1] | 6-oxo-2-(piperidin-4-yloxy)-N-{1-[4-(trifluoromethyl)phenyl]ethyl}-1,6-dihydropyrimidine-4-carboxamide | 411.2 (M + 1) 433.3 (M + Na) |
| 188 | 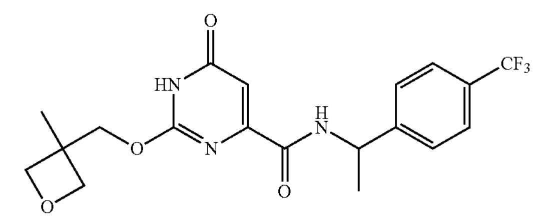 [SMILES: CC(NC(=O)c1cc(=O)[nH]c(OCC2(C)COC2)n1)c1ccc(C(F)(F)F)cc1] | 2-[(3-methyloxetan-3-yl)methoxy]-6-oxo-N-{1-[4-(trifluoromethyl)phenyl]ethyl}-1,6-dihydropyrimidine-4-carboxamide | 412.2 (M + 1) 434.3 (M + Na) |
| 189 | 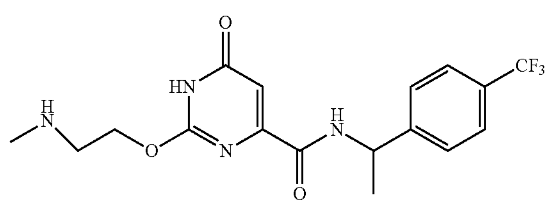 [SMILES: CNCCOc1nc(C(=O)NC(C)c2ccc(C(F)(F)F)cc2)cc(=O)[nH]1] | 2-[2-(methylamino)ethoxy]-6-oxo-N-{1-[4-(trifluoromethyl)phenyl]ethyl}-1,6-dihydropyrimidine-4-carboxamide | 385.2 |
| 190 | 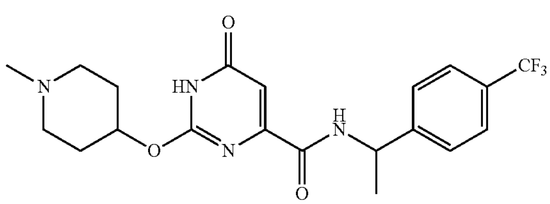 [SMILES: CC(NC(=O)c1cc(=O)[nH]c(OC2CCN(C)CC2)n1)c1ccc(C(F)(F)F)cc1] | 2-[(1-methylpiperidin-4-yl)oxy]-6-oxo-N-{1-[4-(trifluoromethyl)phenyl]ethyl}-1,6-dihydropyrimidine-4-carboxamide | 425.3 |
| 191 | 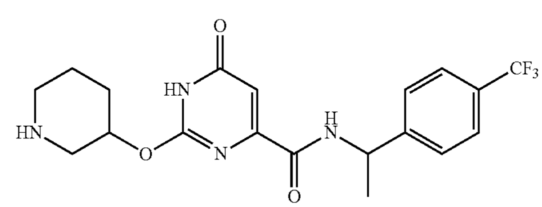 [SMILES: CC(NC(=O)c1cc(=O)[nH]c(OC2CCCNC2)n1)c1ccc(C(F)(F)F)cc1] | 6-oxo-2-(piperidin-3-yloxy)-N-{1-[4-(trifluoromethyl)phenyl]ethyl}-1,6-dihydropyrimidine-4-carboxamide | 411.3 (M + 1) 433.2 (M + Na) |
| 192 | 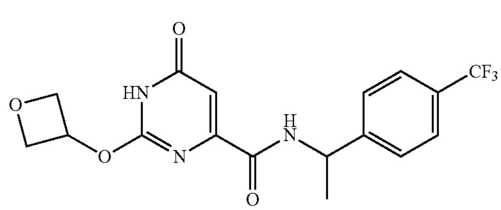 [SMILES: CC(NC(=O)c1cc(=O)[nH]c(OC2COC2)n1)c1ccc(C(F)(F)F)cc1] | 2-(oxetan-3-yloxy)-6-oxo-N-{1-[4-(trifluoromethyl)phenyl]ethyl}-1,6-dihydropyrimidine-4-carboxamide | 384.1 |
| 193 | 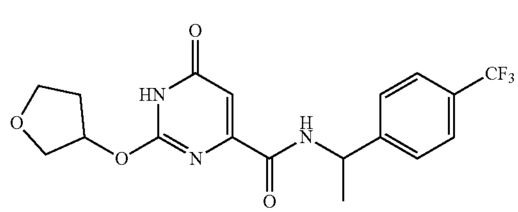 [SMILES: CC(NC(=O)c1cc(=O)[nH]c(OC2CCOC2)n1)c1ccc(C(F)(F)F)cc1] | 6-oxo-2-(tetrahydrofuran-3-yloxy)-N-{1-[4-(trifluoromethyl)phenyl]ethyl}-1,6-dihydropyrimidine-4-carboxamide | 398.2 (M + 1) 420.2 (M + Na) |

TABLE 11-continued

Examples 178 to 194 in the following table were prepared using procedure described in Example 21 and Scheme S.

| Example Number | Structure | IUPAC Name | Exact Mass [M + H]⁺ |
| --- | --- | --- | --- |
| 194 | 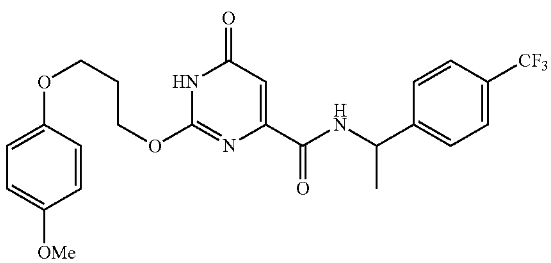 [SMILES: COc1ccc(OCCCOc2nc(C(=O)NC(C)c3ccc(C(F)(F)F)cc3)cc(=O)[nH]2)cc1] | 2-[3-(4-methoxyphenoxy)propoxy]-6-oxo-N-{1-[4-(trifluoromethyl)phenyl]ethyl}-1,6-dihydropyrimidine-4-carboxamide | 492.2 (M + 1) 514.3 (M + Na) |

The following compounds in Table 12 were prepared using procedure described for Example 3 and Scheme C from appropriate starting materials.

| Example Number | Structure | IUPAC Name | Exact Mass [M + H]⁺ |
| --- | --- | --- | --- |
| 195 | 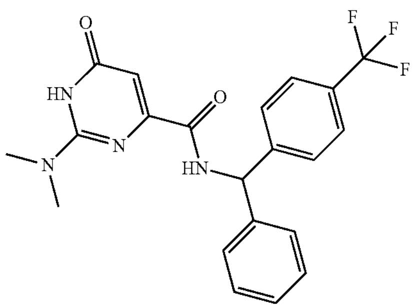 [SMILES: CN(C)c1nc(C(=O)NC(c2ccccc2)c2ccc(C(F)(F)F)cc2)cc(=O)[nH]1] | 2-(dimethylamino)-6-oxo-N-{phenyl[4-(trifluoromethyl)phenyl]methyl}-1,6-dihydropyrimidine-4-carboxamide | Calc'd 417.2, found 417.2 |
| 196 | 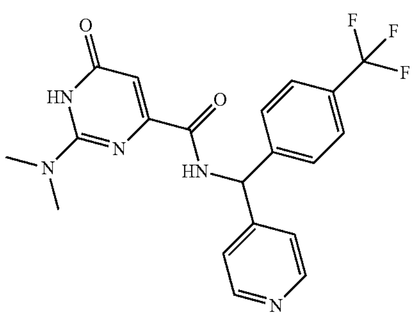 [SMILES: CN(C)c1nc(C(=O)NC(c2ccncc2)c2ccc(C(F)(F)F)cc2)cc(=O)[nH]1] | 2-(dimethylamino)-6-oxo-N-{pyridin-4-yl[4-(trifluoromethyl)phenyl]methyl}-1,6-dihydropyrimidine-4-carboxamide | Calc'd 418.1, found 417.9 |
| 197 | 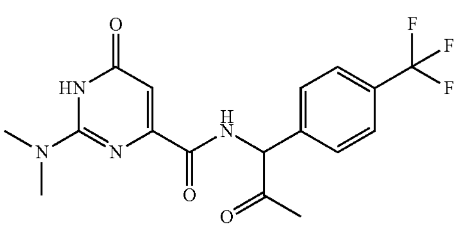 [SMILES: CC(=O)C(NC(=O)c1cc(=O)[nH]c(N(C)C)n1)c1ccc(C(F)(F)F)cc1] | 2-(dimethylamino)-6-oxo-N-{2-oxo-1-[4-(trifluoromethyl)phenyl]propyl}-1,6-dihydropyrimidine-4-carboxamide | Calc'd 383.1, found 382.8 |
| 198 | 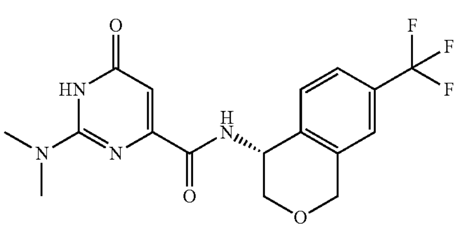 [SMILES: CN(C)c1nc(C(=O)N[C@H]2COCc3cc(C(F)(F)F)ccc32)cc(=O)[nH]1] | 2-(dimethylamino)-6-oxo-N-[(4R)-7-(trifluoromethyl)-3,4-dihydro-1H-isochromen-4-yl]-1,6-dihydropyrimidine-4-carboxamide | Calc'd 383.1, found 383.2 |

The following compounds in Table 12 were prepared using procedure described for Example 3 and Scheme C from appropriate starting materials.

| Example Number | Structure | IUPAC Name | Exact Mass [M + H]+ |
|---|---|---|---|
| 199 | 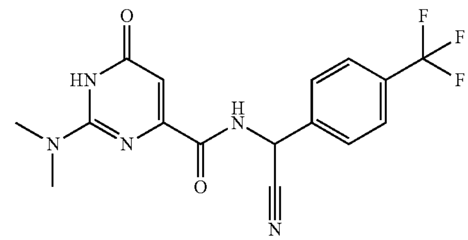 [SMILES: CN(C)c1nc(C(=O)NC(C#N)c2ccc(C(F)(F)F)cc2)cc(=O)[nH]1] | N-{cyano[4-(trifluoromethyl)phenyl]methyl}-2-(dimethylamino)-6-oxo-1,6-dihydropyrimidine-4-carboxamide | Calc'd 366.1, found 366.1 |
| 200 | 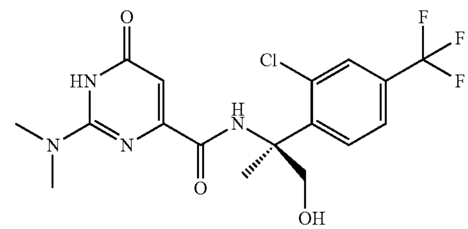 [SMILES: CN(C)c1nc(C(=O)N[C@](C)(CO)c2ccc(C(F)(F)F)cc2Cl)cc(=O)[nH]1] | N-{(1S)-1-[2-chloro-4-(trifluoromethyl)phenyl]-2-hydroxy-1-methylethyl}-2-(dimethylamino)-6-oxo-1,6-dihydropyrimidine-4-carboxamide | Calc'd 419.1, found 418.8 |
| 201 | 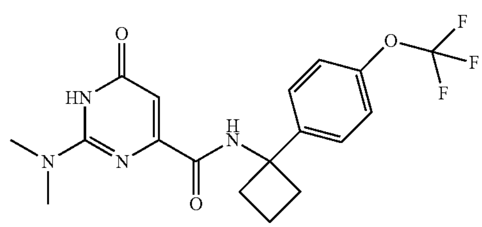 [SMILES: CN(C)c1nc(C(=O)NC2(c3ccc(OC(F)(F)F)cc3)CCC2)cc(=O)[nH]1] | 2-(dimethylamino)-6-oxo-N-{1-[4-(trifluoromethoxy)phenyl]cyclobutyl}-1,6-dihydropyrimidine-4-carboxamide | Calc'd 397.1, found 397.2 |
| 202 | 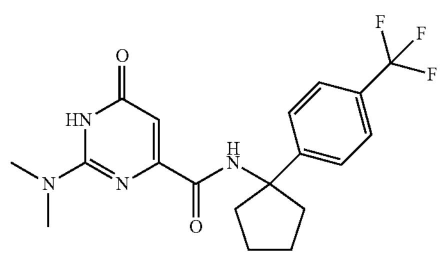 [SMILES: CN(C)c1nc(C(=O)NC2(c3ccc(C(F)(F)F)cc3)CCCC2)cc(=O)[nH]1] | 2-(dimethylamino)-6-oxo-N-{1-[4-(trifluoromethyl)phenyl]cyclopentyl}-1,6-dihydropyrimidine-4-carboxamide | Calc'd 395.2, found 395.2 |
| 203 | 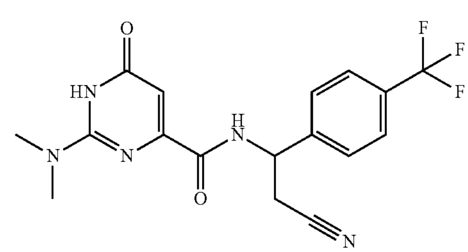 [SMILES: CN(C)c1nc(C(=O)NC(CC#N)c2ccc(C(F)(F)F)cc2)cc(=O)[nH]1] | N-{2-cyano-1-[4-(trifluoromethyl)phenyl]ethyl}-2-(dimethylamino)-6-oxo-1,6-dihydropyrimidine-4-carboxamide | Calc'd 380.1, found 379.9 |
| 204 | 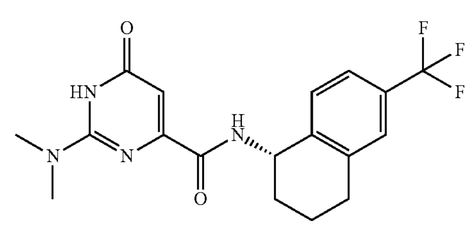 [SMILES: CN(C)c1nc(C(=O)N[C@H]2CCCc3cc(C(F)(F)F)ccc32)cc(=O)[nH]1] | 2-(dimethylamino)-6-oxo-N-[(1S)-6-(trifluoromethyl)-1,2,3,4-tetrahydronaphthalen-1-yl]-1,6-dihydropyrimidine-4-carboxamide | Calc'd 381.2, found 380.0 |

The following compounds in Table 12 were prepared using procedure described for Example 3 and Scheme C from appropriate starting materials.

| Example Number | Structure | IUPAC Name | Exact Mass [M + H]⁺ |
|---|---|---|---|
| 205 | 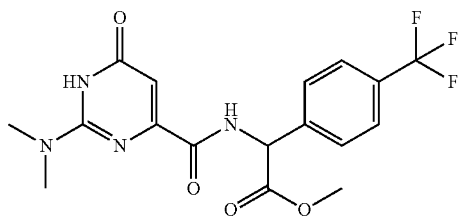 [SMILES: COC(=O)C(NC(=O)c1cc(=O)[nH]c(N(C)C)n1)c1ccc(C(F)(F)F)cc1] | methyl ({[2-(dimethylamino)-6-oxo-1,6-dihydropyrimidin-4-yl]carbonyl}amino)[4-(trifluoromethyl)phenyl]acetate | Calc'd 399.1, found 398.9 |
| 206 | 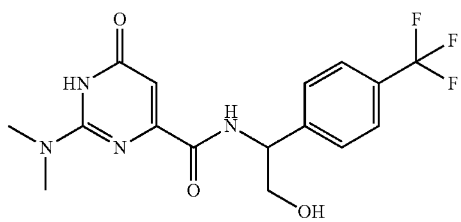 [SMILES: CN(C)c1nc(C(=O)NC(CO)c2ccc(C(F)(F)F)cc2)cc(=O)[nH]1] | 2-(dimethylamino)-N-{2-hydroxy-1-[4-(trifluoromethyl)phenyl]ethyl}-6-oxo-1,6-dihydropyrimidine-4-carboxamide | Calc'd 371.1, found 370.9 |
| 207 | 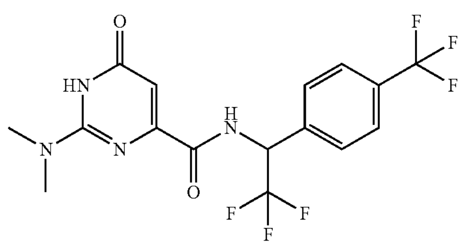 [SMILES: CN(C)c1nc(C(=O)NC(c2ccc(C(F)(F)F)cc2)C(F)(F)F)cc(=O)[nH]1] | 2-(dimethylamino)-6-oxo-N-{2,2,2-trifluoro-1-[4-(trifluoromethyl)phenyl]ethyl}-1,6-dihydropyrimidine-4-carboxamide | Calc'd 409.1, found 408.8 |
| 208 | 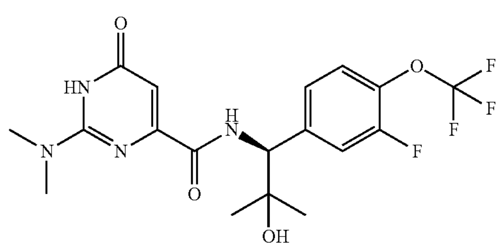 [SMILES: CN(C)c1nc(C(=O)N[C@@H](c2ccc(OC(F)(F)F)c(F)c2)C(C)(C)O)cc(=O)[nH]1] | 2-(dimethylamino)-N-{(1S)-1-[3-fluoro-4-(trifluoromethoxy)phenyl]-2-hydroxy-2-methylpropyl}-6-oxo-1,6-dihydropyrimidine-4-carboxamide | Calc'd 433.1, found 432.8 |
| 209 | 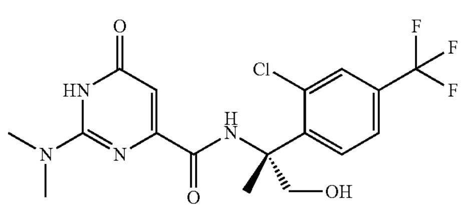 [SMILES: CN(C)c1nc(C(=O)N[C@@](C)(CO)c2ccc(C(F)(F)F)cc2Cl)cc(=O)[nH]1] | N-{(1R)-1-[2-chloro-4-(trifluoromethyl)phenyl]-2-hydroxy-1-methylethyl}-2-(dimethylamino)-6-oxo-1,6-dihydropyrimidine-4-carboxamide | Calc'd 419.1, found 418.8 |
| 210 | 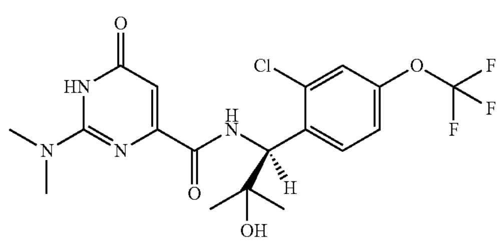 [SMILES: CN(C)c1nc(C(=O)N[C@@H](c2ccc(OC(F)(F)F)cc2Cl)C(C)(C)O)cc(=O)[nH]1] | N-{(1S)-1-[2-chloro-4-(trifluoromethoxy)phenyl]-2-hydroxy-2-methylpropyl}-2-(dimethylamino)-6-oxo-1,6-dihydropyrimidine-4-carboxamide | Calc'd 449.1, found 448.8 |

The following compounds in Table 12 were prepared using procedure described for Example 3 and Scheme C from appropriate starting materials.

| Example Number | Structure | IUPAC Name | Exact Mass [M + H]⁺ |
|---|---|---|---|
| 211 | 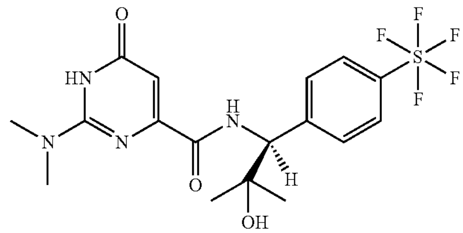 [SMILES: CN(C)c1nc(C(=O)N[C@@H](c2ccc(S(F)(F)(F)(F)F)cc2)C(C)(C)O)cc(=O)[nH]1] | 2-(dimethylamino)-N-{(1S)-2-hydroxy-2-methyl-1-[4-(pentafluoro-λ⁶-sulfanyl)phenyl]propyl}-6-oxo-1,6-dihydropyrimidine-4-carboxamide | Calc'd 457.1, found 456.8 |
| 212 | 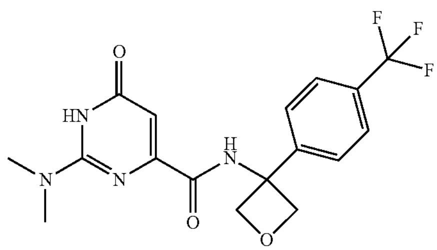 [SMILES: CN(C)c1nc(C(=O)NC2(c3ccc(C(F)(F)F)cc3)COC2)cc(=O)[nH]1] | 2-(dimethylamino)-6-oxo-N-{3-[4-(trifluoromethyl)phenyl] oxetan-3-yl}-1,6-dihydropyrimidine-4-carboxamide | Calc'd 383.1, found 382.9 |

ASSAY

The activity of the compounds in accordance with the present invention as PDE2 inhibitors may be readily determined using a fluorescence polarization (FP) methodology (Huang, W., et al., J. Biomol Screen, 2002, 7: 215). In particular, the compounds of the following examples had activity in reference assays by exhibiting the ability to inhibit the hydrolysis of the phosphate ester bond of a cyclic nucleotide. Any compound exhibiting a Ki (inhibitory constant) of about 50 µM or below would be considered a PDE2 inhibitor as defined herein.

The PDE2 inhibitory activity of the compounds of the present invention was determined in accordance with the following experimental method. Rhesus PDE2A3 was amplified from rhesus macaque brain cDNA (Biochain Institute, Hayward, Calif.) using primers based on human PDE2A sequence (accession NM_002599.3) where the forward primer containing a Kozak consensus was 5'-gccaccatggggcaggcatgtggc-3' and the reverse primer was 5'-tcactcagcatcaaggctgca-3'. Amplification with Easy-A High-Fidelity PCR cloning enzyme (Stratagene, La Jolla, Calif.) was 95° C. for 2 minutes followed by thirty three cycles of 95° C. for 40 seconds, 52° C. for 30 seconds, and 72° C. for 2 minutes 48 seconds. Final extension was 72° C. for 7 minutes. The PCR product was TA cloned into pcDNA3.3-TOPO (Invitrogen, Carlsbad, Calif.) according to standard protocol. A consensus sequence was developed from multiple clones and then deposited into GenBank (EU812167). AD293 cells (Stratagene, La Jolla, Calif.) with 70-80% confluency were transiently transfected with rhesus PDE2A3/pcDNA3.3-TOPO using Lipofectamine 2000 according to manufacturer specifications (Invitrogen, Carlsbad, Calif.). Cells were harvested 48 hours post-transfection and lysed by sonication (setting 3, 10×5 sec pulses) in a buffer containing 20 mM HEPES pH 7.4, 1 mM EDTA and Complete Protease Inhibitor Cocktail Tablets (Roche, Indianapolis, Ind.). Lysate was collected by centrifugation at 75,000×g for 20 minutes at 4° C. and supernatant utilized for evaluation of PDE2 activity. The fluorescence polarization assay for cyclic nucleotide phosphodiesterases was performed using an IMAP® FP kit supplied by Molecular Devices, Sunnyvale, Calif. (product #R8139). IMAP® technology has been applied previously to examine the effects of phosphodiesterase inhibitors (Huang, W., et al., J. Biomol Screen, 2002, 7: 215). Assays were performed at room temperature in 384-well microtiter plates with an incubation volume of 20.2 µL. Solutions of test compounds were prepared in DMSO and serially diluted with DMSO to yield 8 µL of each of 10 solutions differing by 3-fold in concentration, at 32 serial dilutions per plate. 100% inhibition is determined using a known PDE2 inhibitor, which can be any compound that is present at 5,000 times its Ki value in the assay described below, such as Bay 60-7550 (Ki-~0.2 nM) at 1 µM concentration for 100% inhibition. Bay 60-7550 was obtained from Axxora via Fisher Scientific (cat# ALX-270-421-M025/cat# NC9314773). Put another way, any compound with Ki of ~0.2 to about 2 nM could be used at 1 to 10 µM. 0% of inhibition is determined by using DMSO (1% final concentrations).

A Labcyte Echo 555 (Labcyte, Sunnyvale, Calif.) is used to dispense 200 nL from each well of the titration plate to the 384 well assay plate. Ten microliters of a solution of enzyme (1/2000 final dilution from aliquots; sufficient to produce 20% substrate conversion) was added to the assay plate. Next 10 uL of a separate solution of the substrate FAM-labeled cAMP (50 nM final concentration product # R⁷⁵⁰⁶ from Molecular Devices) and the activator cGMP (1 uM final concentration), prepared in the assay buffer (10 mM Tris HCl, pH 7.2, 10 mM MgCl₂, 0.05% NaN₃ 0.01% Tween-20, and 1 mM DTT) was added to the assay plate and shaken to mix. The reaction is allowed to proceed at room temperature for 60 minutes. A binding solution is then made from the kit components, comprised of 80% Solution A, 20% Solution B and binding reagent at a volume of 1/600 the total binding solution. The enzymatic reaction is stopped by addition of 60 µL of the binding solution to each well of the assay plates and the plates are sealed and shaken for 30 seconds. The plate was incubated at room temperature for at least one hour prior to determining the fluorescence polarization (FP). The parallel and perpendicular fluorescence of each well of the plate was measured using a Tecan Genios Pro plate reader (Tecan, Switzerland) or Perkin Elmer EnVision™ plate reader (Waltham, Mass.). Fluorescence polarization (mP) was calculated from the parallel (S) and perpendicular (P) fluorescence of each sample well and the analogous values for the median control well, containing only substrate (So and Po), using the following equation:

Polarization $(mP)=1000*(S/So-P/Po)/(S/So+P/Po)$.

Dose-inhibition profiles for each compound were characterized by fitting the mP data to a four-parameter equation given below. The apparent inhibition constant (KI), the maximum inhibition at the low plateau relative to "100% Inhibition Control" (Imax; e.g. 1=>same as this control), the minimum inhibition at the high plateau relative to the "0% Inhibition Control" (Imin, e.g. 0=>same as the no drug control) and the Hill slope (nH) are determined by a non-linear least squares fitting of the mP values as a function of dose of the compound using an in-house software based on the procedures described by Mosser et al., JALA, 2003, 8: 54-63, using the following equation:

$$mP = \frac{(0\%\ mP - 100\%\ mP)(Imax - Imin)}{1 + \left[\frac{[Drug]}{\left(10^{-pK_1}\left(1 + \frac{[Substrate]}{K_M}\right)\right)}\right]^{nH}} +$$

$$100\%\ mP + (0\%\ mP - 100\%\ mP)(1 - Imax)$$

The median signal of the "0% inhibition controls" (0% mP) and the median signal of the "100% inhibition controls" (100% mP) are constants determined from the controls located in columns 1-2 and 23-24 of each assay plate. An apparent $(K_M)$ for FAM-labeled cAMP of ~10 uM was used.

Selectivity for PDE2, as compared to other PDE families, was assessed using the IMAP® technology. Human PDE10A2 enzyme was prepared from cytosolic fractions of transiently transfected HEK cells. All other PDE's were GST Tag human enzyme expressed in insect cells and were obtained from BPS Bioscience (San Diego, Calif.): PDE1A (Cat#60010), human PDE2A1(Cat#60020), PDE3A (Cat#60030), PDE4A1A (Cat#60040), PDE5A1 (Cat#60050), PDE6C (Cat#60060), PDE7A (Cat#60070), PDE8A1 (Cat#60080), PDE9A2 (Cat#60090), PDE11A4 (Cat#60110).

Assays for PDE 1 through 11 were performed in parallel at room temperature in 384-well microtiter plates with an incubation volume of 20.2 µL. Solutions of test compounds were prepared in DMSO and serially diluted with DMSO to yield 30 µL of each of ten solutions differing by 3-fold in concentration, at 32 serial dilutions per plate. 100% inhibition was determined by adding buffer in place of the enzyme and 0% inhibition is determined by using DMSO (1% final concentrations). A Labcyte POD 810 (Labcyte, Sunnyvale, Calif.) was used to dispense 200 nL from each well of the titration plate to make eleven copies of the assay plate for each titration, one copy for each PDE enzyme. A solution of each enzyme (dilution from aliquots, sufficient to produce 20% substrate conversion) and a separate solution of FAM-labeled cAMP or FAM-labeled cGMP from Molecular Devices (Sunnyvale, Calif., product # R7506 or cGMP#R7508), at a final concentration of 50 nM were made in the assay buffer (10 mM Tris HCl, pH 7.2, 10 mM $MgCl_2$, 0.05% $NaN_3$ 0.01% Tween-20, and 1 mM DTT). Note that the substrate for PDE2 is 50 nM FAM cAMP containing 1000 nM of cGMP. The enzyme and the substrate were then added to the assay plates in two consecutive additions of 10 µL and then shaken to mix. The reaction was allowed to proceed at room temperature for 60 minutes. A binding solution was then made from the kit components, comprised of 80% Solution A, 20% Solution B and binding reagent at a volume of 1/600 the total binding solution. The enzymatic reaction was stopped by addition of 60 µL of the binding solution to each well of the assay plate. The plates were sealed and shaken for 10 seconds. The plates were incubated at room temperature for one hour, then the parallel and perpendicular fluorescence was measured using a Tecan Genios Pro plate reader (Tecan, Switzerland). The apparent inhibition constants for the compounds against all 11 PDE's was determined from the parallel and perpendicular fluorescent readings as described for PDE10 FP assay using the following apparent $K_M$ values for each enzyme and substrate combination: PDE1A (FAM cGMP) 70 nM, human PDE2A1 (FAM cAMP) 10,000 nM, PDE3A (FAM cAMP) 50 nM, PDE4A1A (FAM cAMP) 1500 nM, PDE5A1 (FAM cGMP) 400 nM, PDE6C (FAM cGMP) 700 nM, PDE7A (FAM cAMP) 150 nM, PDE8A1 (FAM cAMP) 50 nM, PDE9A2 (FAM cGMP) 60 nM, PDE10A2 (FAM cAMP) 150 nM, PDE11A4 (FAM cAMP) 1000 nM. The intrinsic PDE2 inhibitory activity of a compound which may be used in accordance with the present invention may be determined by these assays.

The compounds of the following examples had activity in inhibiting the human PDE2 enzyme in the aforementioned assays with a Ki of less than about 50 µM. Many of compounds within the present invention had activity in inhibiting the human PDE2 enzyme in the aforementioned assays, with a Ki of less than about 1 µM, preferably less than or about 0.1 µM. Additional data is provided in the following Examples. Such a result is indicative of the intrinsic activity of the compounds in use as inhibitors of the PDE2 enzyme. In general, one of ordinary skill in the art would appreciate that a substance is considered to effectively inhibit PDE2 activity if it has a Ki of less than or about 1 µM, preferably less than or about 0.1 µM. The present invention also includes compounds within the generic scope of the invention which possess activity as inhibitors of other phosphodiesterase enzymes.

In the following tables representative data for the compounds of formula I and II as PDE2 inhibitors as determined by the foregoing assays as conducted in laboratory (Lab) A or B are shown. The PDE2 Ki is a measure of the ability of the test compound to inhibit the action of the PDE2 enzyme.

TABLE 13

PDE2 Ki's or % inhibition at a given concentration (ND: not determined).

| Example No. | Rhesus PDE2 Ki (nM) - Lab A | Rhesus PDE2 Ki (nM) - Lab B | Human PDE2 Ki (nM) - Lab A | Human PDE2 Ki (nM) - Lab B |
|---|---|---|---|---|
| 1 | 1.3 | ND | 0.48 | ND |
| 2 | ND | 0.11 | ND | 0.15 |
| 3 | 0.82 | 1.5 | ND | 1.6 |

TABLE 13-continued

PDE2 Ki's or % inhibition at a given concentration (ND: not determined).

| Example No. | Rhesus PDE2 Ki (nM) - Lab A | Rhesus PDE2 Ki (nM) - Lab B | Human PDE2 Ki (nM) - Lab A | Human PDE2 Ki (nM) - Lab B |
|---|---|---|---|---|
| 4 | ND | 1.2 | ND | 1.0 |
| 5 | 0.69 | 1.5 | ND | 1.3 |
| 6 | 2.5 | ND | 1.7 | ND |
| 7 | 25% @ 1 μM | ND | ND | ND |
| 8 | 30% @ 1 μM | ND | ND | ND |
| 9 | 26% @ 1 μM | ND | ND | ND |
| 10 | 8.5 | ND | 8.2 | ND |
| 11 | 30 | ND | 18 | ND |
| 12 | 4.5 | ND | 1.8 | ND |
| 13 | 13 | ND | 9.2 | ND |
| 14 | ND | 0.41 | ND | 0.34 |
| 15 | 46 | ND | 31 | ND |
| 16 | 13350 | ND | ND | ND |
| 17 | 130 | ND | 115 | ND |
| 18 | 63 | ND | 72 | ND |
| 19 | 2933 | ND | ND | ND |
| 20 | ND | ND | ND | 329 |
| 21 | 657 | ND | ND | ND |
| 22 | 727 | ND | 988 | ND |
| 23 | 27 | ND | 16 | ND |
| 24 | 79 | ND | 40 | ND |
| 25 | 0.85 | ND | 0.37 | ND |
| 26 | 1.4 | ND | 0.34 | ND |
| 27 | 0.58 | ND | 0.21 | ND |
| 28 | 1.3 | ND | 0.45 | ND |
| 29 | 0.56 | ND | 0.22 | ND |
| 30 | 0.19 | 0.22 | ≤5.1 | 0.37 |
| 31 | ND | 0.42 | ND | 0.51 |
| 32 | ND | 6.4 | ND | 5.3 |
| 33 | ND | 2.7 | ND | 2.0 |
| 34 | ND | 0.46 | ND | 0.39 |
| 35 | ND | 0.12 | ND | 0.11 |
| 36 | ND | 4.9 | ND | 7.7 |
| 37 | ND | 0.11 | ND | 0.13 |
| 38 | ND | 0.11 | ND | 0.14 |
| 39 | ND | 8.7 | ND | 12 |
| 40 | ND | 0.87 | ND | 1.02 |
| 41 | ND | 0.31 | ND | 0.36 |
| 42 | ND | 0.45 | ND | 0.44 |
| 43 | ND | 0.23 | ND | 0.32 |
| 44 | ND | 1.6 | ND | 1.5 |
| 45 | ND | 2.1 | ND | 1.7 |
| 46 | ND | 3.4 | ND | 3.6 |
| 47 | ND | 0.43 | ND | 0.44 |
| 48 | ND | 1.9 | ND | 1.7 |
| 49 | ND | ND | ND | 2.7 |
| 50 | ND | ND | ND | 27 |
| 51 | ND | ND | ND | 9.7 |
| 52 | ND | ND | ND | 11 |
| 53 | ND | ND | ND | 4.0 |
| 54 | ND | 0.32 | ND | 0.38 |
| 55 | ND | 1.4 | ND | 0.98 |
| 56 | ND | 0.71 | ND | 0.51 |
| 57 | ND | 0.28 | ND | 0.31 |
| 58 | ND | 0.10 | ND | 0.03 |
| 59 | ND | ND | ND | 2.0 |
| 60 | ND | 0.42 | ND | 0.29 |
| 61 | ND | 0.82 | ND | 0.75 |
| 62 | ND | 0.55 | ND | 0.52 |
| 63 | ND | ND | ND | 1.9 |
| 64 | ND | ND | ND | 7.4 |
| 65 | ND | ND | ND | 2.2 |
| 66 | ND | ND | ND | 5.0 |
| 67 | ND | ND | ND | 6.9 |
| 68 | ND | ND | ND | 12 |
| 69 | ND | ND | ND | 10 |
| 70 | ND | ND | ND | 9.7 |
| 71 | ND | 0.23 | ND | 0.21 |
| 72 | ND | ND | ND | 17 |
| 73 | ND | 0.26 | ND | 0.17 |
| 74 | ND | ND | ND | 3.9 |
| 75 | ND | ND | ND | 0.39 |
| 76 | ND | 0.11 | ND | 0.12 |
| 77 | ND | 0.21 | ND | 0.19 |
| 78 | ND | 2.3 | ND | 2.2 |

TABLE 13-continued

PDE2 Ki's or % inhibition at a given concentration (ND: not determined).

| Example No. | Rhesus PDE2 Ki (nM) - Lab A | Rhesus PDE2 Ki (nM) - Lab B | Human PDE2 Ki (nM) - Lab A | Human PDE2 Ki (nM) - Lab B |
|---|---|---|---|---|
| 79 | ND | 6.4 | ND | 7.7 |
| 80 | ND | 0.65 | ND | 0.79 |
| 81 | ND | ND | ND | 21 |
| 82 | ND | 2.0 | ND | 2.5 |
| 83 | ND | 2.3 | ND | 2.4 |
| 84 | ND | 3.5 | ND | 2.5 |
| 85 | 2.0 | 4.9 | ND | 3.6 |
| 86 | 0.54 | 2.1 | ND | 1.7 |
| 87 | 1.1 | ND | 0.74 | ND |
| 88 | 0.61 | 0.51 | 5.055 | 0.69 |
| 89 | 1.1 | ND | 0.41 | ND |
| 90 | 0.69 | ND | 0.28 | ND |
| 91 | 0.64 | ND | 0.19 | ND |
| 92 | 2.5 | ND | 1.8 | ND |
| 93 | 4.0 | ND | 3.8 | ND |
| 94 | 1.2 | 0.80 | 0.90 | 0.96 |
| 95 | 0.39 | ND | 0.18 | ND |
| 96 | 0.36 | ND | 0.20 | ND |
| 97 | 0.62 | ND | 0.34 | ND |
| 98 | 0.54 | ND | 0.23 | ND |
| 99 | ND | 1.1 | ND | 1.1 |
| 100 | ND | 0.17 | ND | 0.21 |
| 101 | ND | 0.14 | ND | 0.12 |
| 102 | ND | 0.18 | ND | 0.20 |
| 103 | ND | 0.12 | ND | 0.12 |
| 104 | 0.56 | 1.1 | ND | 1.1 |
| 105 | 1.0 | 1.8 | ND | 1.6 |
| 106 | 0.81 | 1.4 | ND | 1.3 |
| 107 | 0.93 | 2.2 | ND | 1.7 |
| 108 | 0.66 | 1.3 | ND | 1.8 |
| 109 | 0.91 | 1.4 | ND | 1.9 |
| 110 | 0.48 | 0.96 | ND | 1.3 |
| 111 | 0.41 | 0.80 | ND | 0.90 |
| 112 | 0.27 | 0.44 | ND | 0.55 |
| 113 | 0.36 | 0.65 | ND | 0.63 |
| 114 | 0.94 | 1.5 | ND | 1.5 |
| 115 | ND | 1.0 | ND | 0.76 |
| 116 | ND | ND | ND | 749 |
| 117 | ND | 2.5 | ND | 2.1 |
| 118 | ND | 224 | ND | 140 |
| 119 | ND | ND | ND | 49% @ 3 μM |
| 120 | ND | 1.8 | ND | 1.9 |
| 121 | ND | ND | ND | 15% @ 3 μM |
| 122 | ND | ND | ND | 34 |
| 123 | ND | ND | ND | 167 |
| 124 | ND | 0.45 | ND | 0.34 |
| 125 | ND | ND | ND | 38% @ 3 μM |
| 126 | ND | ND | ND | 16 |
| 127 | ND | ND | ND | 527 |
| 128 | ND | 0.22 | ND | 0.15 |
| 129 | ND | ND | ND | 5.5 |
| 130 | ND | 1.2 | ND | 0.89 |
| 131 | 32 | ND | 24 | ND |
| 132 | 60 | ND | 30 | ND |
| 133 | 2.5 | 2.8 | 2.0 | 2.3 |
| 134 | 272 | ND | 144 | ND |
| 135 | 36 | ND | 27 | ND |
| 136 | 610 | ND | 491 | ND |
| 137 | 843 | ND | ND | ND |
| 138 | 67 | ND | 38 | ND |
| 139 | 109 | ND | 56 | ND |
| 140 | 54 | ND | 51 | ND |
| 141 | 10.3 | ND | 6.0 | ND |
| 142 | 23 | ND | 16 | ND |
| 143 | 0.57 | 0.61 | 0.32 | 0.82 |
| 144 | 5.7 | ND | 3.4 | ND |
| 145 | 35 | ND | 23 | ND |
| 146 | 0.43 | ND | 0.36 | ND |
| 147 | 0.19 | 0.15 | ND | 0.26 |
| 148 | 0.42 | ND | 0.20 | ND |
| 149 | 0.48 | 0.51 | ND | 0.42 |
| 150 | 0.24 | 0.29 | ND | 0.29 |
| 151 | 4.7 | ND | 2.8 | ND |
| 152 | 33 | ND | 19 | ND |
| 153 | ND | ND | ND | ND |

TABLE 13-continued

PDE2 Ki's or % inhibition at a given concentration (ND: not determined).

| Example No. | Rhesus PDE2 Ki (nM) - Lab A | Rhesus PDE2 Ki (nM) - Lab B | Human PDE2 Ki (nM) - Lab A | Human PDE2 Ki (nM) - Lab B |
|---|---|---|---|---|
| 154 | 18 | ND | 9.9 | ND |
| 155 | 4.3 | ND | 1.2 | ND |
| 156 | 24 | ND | 10 | ND |
| 157 | ND | ND | ND | 6.3 |
| 158 | ND | ND | ND | 0.85 |
| 159 | 18 | ND | 11 | ND |
| 160 | 1.6 | ND | 1.0 | ND |
| 161 | 5.1 | ND | 5.0 | ND |
| 162 | 0.51 | ND | ND | 0.61 |
| 163 | 4.1 | 5.0 | ND | 4.2 |
| 164 | 2.4 | 4.0 | ND | 3.9 |
| 165 | 0.33 | 0.50 | ND | 0.45 |
| 166 | ND | ND | 1.3 | ND |
| 167 | ND | 1.4 | ND | 2.3 |
| 168 | ND | 0.50 | ND | 0.47 |
| 169 | ND | 0.14 | ND | 0.17 |
| 170 | ND | ND | ND | 0.11 |
| 171 | ND | ND | ND | 1.4 |
| 172 | ND | 154 | ND | ND |
| 173 | ND | 6.6 | ND | 6.5 |
| 174 | ND | ND | ND | 2.7 |
| 175 | ND | ND | ND | 0.92 |
| 176 | ND | ND | ND | 0.38 |
| 177 | ND | ND | ND | 0.46 |
| 178 | 58 | ND | 52 | ND |
| 179 | 108 | ND | 75 | ND |
| 180 | 86000 | ND | ND | ND |
| 181 | >100000 | ND | ND | ND |
| 182 | 55000 | ND | ND | ND |
| 183 | 29 | ND | 23 | ND |
| 184 | 72000 | ND | ND | ND |
| 185 | >100000 | ND | ND | ND |
| 186 | 352 | ND | ND | ND |
| 187 | >100000 | ND | ND | ND |
| 188 | 12650 | ND | ND | ND |
| 189 | 9311 | ND | ND | ND |
| 190 | >100000 | ND | ND | ND |
| 191 | >100000 | ND | ND | ND |
| 192 | 11480 | ND | ND | ND |
| 193 | 1065 | ND | ND | ND |
| 194 | ~5.2 | ND | 4.4 | ND |
| 195 | ND | ND | ND | 81 |
| 196 | ND | ND | ND | 91 |
| 197 | ND | ND | ND | 3.6 |
| 198 | ND | ND | ND | 863 |
| 199 | ND | ND | ND | 27 |
| 200 | ND | ND | ND | 0.52 |
| 201 | ND | ND | ND | 18 |
| 202 | ND | ND | ND | 5.4 |
| 203 | ND | ND | ND | 22 |
| 204 | ND | ND | ND | 129 |
| 205 | ND | ND | ND | 49 |
| 206 | ND | ND | ND | 7.2 |
| 207 | ND | ND | ND | 2.9 |
| 208 | ND | ND | ND | 0.12 |
| 209 | ND | ND | ND | 3.9 |
| 210 | ND | ND | ND | 0.54 |
| 211 | ND | ND | ND | 0.073 |
| 212 | ND | ND | ND | 9.2 |

It is well known that for CNS targeting compounds, it is highly preferred that the compounds are not substrates for certain transporter proteins such as P-glycoprotein (P-gp). See Doan et al. "Passive permeability and P-glycoprotein-mediated efflux differentiate central nervous system (CNS) and non-CNS marketed drugs", J. Pharm. Exper. Ther. (2002), 303(3), 1029-1037. Table 14 listed experimental BA/AB ratios, which are measures of propensity for a compound being a substrate of P-gp, for compounds of the current invention using published procedures except 1 µM substrate concentration and rat LLC-Mdr1a were used instead of mouse LLC-Mdr1a referred to in the reference (See He et al. "Utility of unbound plasma drug levels and P-glycoprotein transport data in prediction of central nervous system exposure", Xenobiotica, (2009), 39(9), 687-693). In general, BA/AB ratio of greater than 2.0~2.5 indicates that the compound in question is a substrate of P-gp. Desirable human BA/AB ratio is less than 2.0. In addition to experimental determinations, a number of computational methods have been published to predict P-pg ratios of compounds based on chemical structure and other molecular properties. See, for example, Desai, et al. Integration of in Silico and in Vitro Tools for Scaffold Optimization during Drug Discovery: Predicting P-glycoprotein Efflux" Mol. Pharmac. (2013), 10(4), 1249-1261; and Stouch, et al. "Prediction of PGP transporter activity using calculated molecular properties", Abstracts of Papers, 221$^{st}$ ACS National Meeting, San Diego, Calif., Apr. 1-5, 2001, BTEC-037. Table 14 also listed calculated BA/AB ratios of the compounds of this invention based on another computational method for predicting P-gp BA/AB ratios. See Hochman, et al. "Establishment of P-glycoprotein structure-transport relationships to optimize CNS exposure to drug discovery" in Blood-Brain Barriers in Drug Discovery: Optimizing Brain Exposure of CNS Drugs and Minimizing Brain Side Effects for Peripheral Drugs; Li Di and E. H. Kerns (Editors), Part 2, Chapter 6, Wikey, February 2015 and Ha et al. "Mini review on molecular modeling of P-glycoprotein (Pgp)" Curr. Top Med Chem 7, 1525-9, 2007. In addition, it is well known that polar surface area (PSA), an easily calculated molecular property, is closely correlated with BA/AB ratio of the compound (Clark, "Rapid Calculation of Polar Molecular Surface Area and Its Application to the Prediction of Transport Phenomena. 2. Prediction of Blood-Brain Barrier Penetration" J. Pharm. Sci. (1999), 88(8), 815-821). Therefore, Table 14 also listed calculated PSA of the compounds of this invention.

TABLE 14

Experimental and Predicted Properties Related to P-gp

| Example # | Experimental BA/AB ratio human | Experimental BA/AB ratio rat | Calculated BA/AB ratio human | Calculated BA/AB ratio rat | PSA |
|---|---|---|---|---|---|
| 1 | 0.8 | 7.2 | 0.8 | 7.1 | 79.3 |
| 2 | 0.6 | 2.6 | 0.9 | 3.5 | 72.5 |
| 3 | NA | NA | 0.5 | 2.7 | 86.9 |
| 4 | 0.6 | 3.1 | 0.5 | 2.0 | 70.3 |
| 5 | 0.5 | 3.6 | 0.5 | 3.1 | 69.5 |
| 6 | 0.5 | 3.2 | 0.5 | 3.9 | 77.3 |
| 7 | NA | NA | 1.1 | 5.3 | 93.4 |
| 8 | NA | NA | 1.0 | 4.1 | 93.0 |
| 9 | NA | NA | 1.1 | 3.8 | 93.9 |
| 10 | 0.5 | 3.1 | 0.5 | 3.2 | 80.3 |
| 11 | NA | NA | 0.8 | 10 | 77.6 |
| 12 | 0.7 | 9.0 | 0.8 | 10 | 77.5 |
| 13 | 0.6 | 5.9 | 0.6 | 7.5 | 77.5 |
| 14 | NA | NA | 3.3 | 11 | 84.3 |
| 15 | NA | NA | 0.5 | 2.0 | 74.8 |
| 16 | NA | NA | 0.5 | 2.0 | 74.3 |
| 17 | NA | NA | 0.7 | 2.7 | 87.8 |
| 18 | NA | NA | 0.7 | 3.2 | 86.1 |
| 19 | NA | NA | 1.4 | 7.0 | 90.6 |
| 20 | NA | NA | 1.5 | 3.3 | 98.4 |
| 21 | NA | NA | 0.9 | 4.8 | 100.0 |
| 22 | NA | NA | 2.8 | 8.3 | 107.9 |
| 23 | 1.4 | 7.6 | 0.8 | 7.8 | 81.0 |
| 24 | NA | NA | 0.6 | 5.8 | 80.7 |
| 25 | NA | NA | 0.7 | 6.3 | 88.1 |
| 26 | 0.9 | 4.5 | 0.7 | 4.6 | 77.3 |
| 27 | 0.8 | 7.0 | 0.6 | 5.6 | 77.4 |
| 28 | NA | NA | 0.6 | 3.3 | 90.6 |
| 29 | NA | NA | 1.0 | 6.2 | 77.9 |
| 30 | 0.4 | 2.6 | 0.5 | 3.4 | 74.8 |
| 31 | 1.5 | 9.7 | 1.3 | 8.0 | 72.0 |
| 32 | 1.1 | NA | 0.8 | 4.1 | 86.5 |
| 33 | 1.3 | NA | 1.3 | 6.2 | 86.5 |
| 34 | 2.0 | 12.7 | 1.4 | 8.5 | 84.6 |
| 35 | 0.5 | 3.6 | 0.8 | 4.2 | 73.1 |
| 36 | NA | NA | 0.5 | 3.1 | 76.2 |
| 37 | 1.0 | 1.2 | 0.9 | 4.7 | 71.4 |
| 38 | 1.0 | NA | 1.0 | 3.1 | 69.3 |
| 39 | NA | NA | 0.8 | 3.9 | 68.2 |
| 40 | 0.5 | 2.4 | 0.5 | 2.9 | 77.4 |
| 41 | 0.4 | 3.6 | 0.9 | 4.7 | 75.5 |
| 42 | 0.7 | 3.0 | 0.7 | 3.3 | 73.4 |
| 43 | 0.7 | 2.3 | 0.7 | 2.3 | 72.8 |

TABLE 14-continued

Experimental and Predicted Properties Related to P-gp

| Example # | Experimental BA/AB ratio human | Experimental BA/AB ratio rat | Calculated BA/AB ratio human | Calculated BA/AB ratio rat | PSA |
|---|---|---|---|---|---|
| 44 | 0.7 | 2.1 | 0.8 | 2.2 | 72.8 |
| 45 | 0.6 | 10.1 | 0.6 | 3.2 | 75.8 |
| 46 | NA | NA | 0.8 | 2.7 | 76.4 |
| 47 | 0.6 | 2.1 | 0.6 | 3.1 | 74.9 |
| 48 | 1.5 | 6.4 | 1.4 | 6.2 | 86.1 |
| 49 | NA | NA | 0.7 | 3.2 | 76.5 |
| 50 | NA | NA | 1.0 | 3.4 | 85.1 |
| 51 | NA | NA | 1.0 | 3.5 | 75.3 |
| 52 | NA | NA | 0.9 | 3.6 | 88.0 |
| 53 | NA | NA | 0.7 | 4.5 | 86.2 |
| 54 | 1.4 | 4.8 | 1.3 | 6.4 | 84.6 |
| 55 | 0.6 | 3.4 | 0.7 | 4.3 | 84.0 |
| 56 | 0.3 | 1.7 | 0.5 | 4.0 | 74.9 |
| 57 | 1.7 | 0.7 | 0.9 | 1.3 | 69.5 |
| 58 | 1.3 | 4.7 | 1.0 | 4.5 | 72.8 |
| 59 | 0.8 | 4.2 | 0.8 | 4.5 | 73.0 |
| 60 | 0.8 | 4.3 | 0.9 | 4.7 | 72.9 |
| 61 | 1.6 | 12.3 | 0.8 | 3.8 | 72.7 |
| 62 | 1.2 | 5.2 | 1.0 | 4.9 | 73.0 |
| 63 | 1.7 | 10.2 | 1.1 | 6.6 | 75.0 |
| 64 | 0.8 | 5.6 | 0.6 | 4.4 | 75.4 |
| 65 | NA | NA | 1.0 | 5.5 | 74.6 |
| 66 | 0.8 | 6.1 | 0.6 | 4.9 | 75.3 |
| 67 | NA | NA | 0.5 | 3.9 | 76.0 |
| 68 | NA | NA | 0.6 | 4.2 | 75.9 |
| 69 | NA | NA | 0.5 | 4.2 | 73.2 |
| 70 | NA | NA | 0.6 | 4.6 | 76.0 |
| 71 | 0.3 | 4.8 | 0.7 | 3.0 | 72.8 |
| 72 | NA | NA | 0.9 | 3.5 | 73.6 |
| 73 | 1.2 | 6.9 | 1.0 | 5.7 | 71.4 |
| 74 | NA | NA | 0.5 | 2.1 | 77.4 |
| 75 | NA | NA | 0.8 | 3.6 | 75.5 |
| 76 | 1.6 | 4.5 | 1.1 | 3.6 | 72.1 |
| 77 | 1.1 | 7.3 | 0.9 | 5.3 | 75.2 |
| 78 | NA | NA | 0.5 | 2.9 | 71.6 |
| 79 | 0.9 | 6.2 | 0.8 | 6.2 | 78.5 |
| 80 | 0.4 | 1.7 | 0.5 | 2.9 | 71.2 |
| 81 | NA | NA | 0.7 | 3.1 | 84.7 |
| 82 | NA | NA | 0.5 | 2.8 | 73.6 |
| 83 | NA | NA | 0.5 | 3.1 | 89.1 |
| 84 | NA | NA | 0.5 | 2.9 | 78.7 |
| 85 | NA | NA | 0.5 | 3.4 | 85.6 |
| 86 | NA | NA | 0.7 | 5.5 | 85.7 |
| 87 | 0.5 | 2.2 | 0.5 | 2.3 | 89.9 |
| 88 | 0.3 | 1.8 | 0.4 | 2.4 | 77.0 |
| 89 | 0.4 | 2.9 | 0.5 | 2.8 | 74.7 |
| 90 | 0.5 | 2.7 | 0.5 | 2.6 | 89.3 |
| 91 | 0.6 | 5.1 | 0.6 | 4.5 | 85.8 |
| 92 | 0.4 | 1.7 | 0.6 | 3.2 | 78.3 |
| 93 | 0.3 | 1.9 | 0.4 | 2.6 | 74.3 |
| 94 | 0.5 | 2.6 | 0.5 | 2.9 | 76.2 |
| 95 | 1.0 | 4.5 | 0.9 | 4.9 | 76.8 |
| 96 | 0.5 | 2.5 | 0.5 | 2.6 | 78.6 |
| 97 | 0.4 | 1.8 | 0.5 | 2.2 | 77.8 |
| 98 | 0.4 | 3.0 | 0.4 | 3.1 | 76.8 |
| 99 | 0.7 | 5.8 | 0.8 | 4.1 | 72.2 |
| 100 | 0.7 | 2.9 | 0.8 | 4.9 | 83.4 |
| 101 | 1.7 | 10.1 | 1.1 | 8.6 | 83.1 |
| 102 | 1.4 | 5.7 | 1.0 | 4.7 | 72.9 |
| 103 | 2.2 | 8.2 | 1.1 | 7.1 | 72.3 |
| 104 | 0.6 | 4.2 | 0.5 | 3.7 | 87.3 |
| 105 | 0.5 | 3.7 | 0.5 | 3.2 | 87.9 |
| 106 | 0.5 | 3.5 | 0.5 | 3.1 | 77.8 |
| 107 | 0.4 | 2.2 | 0.5 | 2.7 | 86.2 |
| 108 | 0.4 | 1.9 | 0.5 | 2.2 | 75.5 |
| 109 | 0.5 | 2.5 | 0.5 | 2.8 | 75.4 |
| 110 | 0.5 | 3.5 | 0.5 | 3.5 | 86.0 |
| 111 | 0.3 | 2.0 | 0.4 | 1.9 | 76.9 |
| 112 | 0.7 | 4.7 | 0.7 | 4.2 | 74.3 |
| 113 | 0.4 | 3.9 | 0.5 | 4.2 | 77.2 |
| 114 | 0.5 | 4.0 | 0.5 | 4.3 | 88.4 |
| 115 | 0.3 | NA | 0.5 | 3.3 | 76.7 |
| 116 | NA | NA | 0.6 | 3.1 | 74.5 |

TABLE 14-continued

Experimental and Predicted Properties Related to P-gp

| Example # | Experimental BA/AB ratio human | Experimental BA/AB ratio rat | Calculated BA/AB ratio human | Calculated BA/AB ratio rat | PSA |
|---|---|---|---|---|---|
| 117 | NA | NA | 0.6 | 3.1 | 74.4 |
| 118 | NA | NA | 0.5 | 3.0 | 70.7 |
| 119 | NA | NA | 0.9 | 3.6 | 73.7 |
| 120 | 27.3 | 47.2 | 0.9 | 3.6 | 72.8 |
| 121 | NA | NA | 0.7 | 2.3 | 76.5 |
| 122 | NA | NA | 0.7 | 2.3 | 76.6 |
| 123 | NA | NA | 1.0 | 5.0 | 72.1 |
| 124 | NA | NA | 1.0 | 5.0 | 73.1 |
| 125 | NA | NA | 0.6 | 2.6 | 76.8 |
| 126 | NA | NA | 0.6 | 2.6 | 76.9 |
| 127 | NA | NA | 1.1 | 4.9 | 70.0 |
| 128 | 1.4 | 4.8 | 1.1 | 4.9 | 71.5 |
| 129 | NA | NA | 0.7 | 3.0 | 71.0 |
| 130 | 0.6 | 1.3 | 0.7 | 3.0 | 70.6 |
| 131 | 0.3 | 1.5 | 0.7 | 6.5 | 74.6 |
| 132 | NA | NA | 1.0 | 5.1 | 88.3 |
| 133 | 0.5 | 1.8 | 0.5 | 2.1 | 77.3 |
| 134 | NA | NA | 2.4 | 11 | 106.6 |
| 135 | 2.7 | 11.4 | 3.3 | 15 | 90.9 |
| 136 | NA | NA | 2.1 | 14 | 99.3 |
| 137 | NA | NA | 5.0 | 10 | 138.8 |
| 138 | 1.2 | 29.8 | 1.6 | 19 | 87.3 |
| 139 | NA | NA | 1.7 | 19 | 87.1 |
| 140 | NA | NA | 1.9 | 12 | 90.5 |
| 141 | NA | NA | 0.5 | 2.8 | 75.0 |
| 142 | NA | NA | 0.5 | 3.4 | 72.4 |
| 143 | 0.5 | 2.5 | 0.5 | 2.3 | 77.4 |
| 144 | 3.3 | 14.2 | 3.4 | 13 | 91.9 |
| 145 | 3.2 | 28.9 | 4.0 | 21 | 106.8 |
| 146 | 0.9 | 5.4 | 0.7 | 5.6 | 77.2 |
| 147 | 0.7 | 5.9 | 0.8 | 6.7 | 75.1 |
| 148 | 1.3 | 9.5 | 0.8 | 7.5 | 78.7 |
| 149 | NA | NA | 0.8 | 5.8 | 85.3 |
| 150 | 1.1 | 4.4 | 0.8 | 4.3 | 74.8 |
| 151 | 6.5 | 18.7 | 6.6 | 10 | 100.8 |
| 152 | 11.6 | 29.2 | 8.2 | 21 | 114.4 |
| 153 | NA | NA | 4.6 | 16 | 85.5 |
| 154 | 10.4 | 24.7 | 7.1 | 29 | 101.8 |
| 155 | 4.2 | 9.0 | 4.3 | 14 | 89.5 |
| 156 | 11.1 | 11.3 | 6.9 | 25 | 103.7 |
| 157 | 13.9 | 34.0 | 5.4 | 20 | 101.1 |
| 158 | 7.8 | 24.4 | 5.9 | 24 | 86.6 |
| 159 | NA | NA | 2.7 | 9.2 | 105.7 |
| 160 | 17.1 | 28.8 | 2.0 | 7.6 | 93.0 |
| 161 | 14.6 | 23.7 | 2.2 | 6.0 | 107.5 |
| 162 | 2.5 | 17.9 | 1.5 | 17 | 85.3 |
| 163 | 0.7 | 15.8 | 1.5 | 17 | 83.7 |
| 164 | 2.6 | 7.5 | 1.9 | 10 | 90.1 |
| 165 | 3.6 | 20.1 | 3.2 | 14 | 75.8 |
| 166 | NA | NA | 1.8 | 12 | 109.7 |
| 167 | 1.9 | 27.4 | 1.2 | 18 | 76.3 |
| 168 | 4.1 | 21.2 | 2.5 | 18 | 75.4 |
| 169 | 2.5 | 9.8 | 1.5 | 14 | 72.8 |
| 170 | 5.6 | 10.7 | 2.1 | 15 | 84.8 |
| 171 | 3.1 | 24.4 | 2.1 | 15 | 85.2 |
| 172 | NA | NA | 0.8 | 3.9 | 68.2 |
| 173 | 0.8 | 3.6 | 0.8 | 3.9 | 68.2 |
| 174 | NA | NA | 0.6 | 3.5 | 77.4 |
| 175 | NA | NA | 0.6 | 3.5 | 77.4 |
| 176 | 5.4 | 19.1 | 3.3 | 11 | 84.4 |
| 177 | NA | NA | 3.3 | 11 | 84.3 |
| 178 | 0.4 | 1.0 | 0.8 | 5.5 | 85.4 |
| 179 | NA | NA | 1.0 | 6.9 | 100.3 |
| 180 | NA | NA | 2.9 | 8.0 | 103.9 |
| 181 | NA | NA | 1.9 | 9.6 | 90.4 |
| 182 | NA | NA | 2.1 | 10 | 90.0 |
| 183 | 1.2 | 7.9 | 1.3 | 7.0 | 97.5 |
| 184 | NA | NA | 1.6 | 5.7 | 92.5 |
| 185 | NA | NA | 2.7 | 10 | 102.8 |
| 186 | NA | NA | 1.3 | 7.4 | 95.9 |
| 187 | NA | NA | 3.8 | 8.3 | 100.3 |
| 188 | NA | NA | 1.1 | 9.3 | 101.9 |
| 189 | NA | NA | 3.1 | 6.5 | 103.1 |
| 190 | NA | NA | 2.5 | 8.6 | 90.5 |
| 191 | NA | NA | 3.3 | 12 | 100.5 |
| 192 | NA | NA | 1.1 | 4.7 | 102.7 |
| 193 | NA | NA | 1.1 | 9.4 | 98.4 |
| 194 | 1.0 | 8.4 | 2.0 | 8.7 | 109.6 |
| 195 | NA | NA | 1.2 | 4.2 | 77.6 |
| 196 | NA | NA | 1.4 | 5.8 | 92.2 |
| 197 | NA | NA | 0.9 | 4.2 | 98.2 |
| 198 | NA | NA | 0.7 | 3.8 | 91.2 |
| 199 | NA | NA | 0.6 | 2.5 | 105.0 |
| 200 | NA | NA | 1.3 | 7.2 | 93.7 |
| 201 | NA | NA | 0.8 | 3.1 | 84.6 |
| 202 | NA | NA | 0.7 | 3.1 | 74.3 |
| 203 | NA | NA | 0.9 | 3.2 | 104.3 |
| 204 | NA | NA | 0.7 | 3.3 | 76.1 |
| 205 | NA | NA | 1.0 | 3.5 | 108.1 |
| 206 | NA | NA | 1.5 | 4.2 | 99.9 |
| 207 | NA | NA | 0.5 | 2.3 | 77.8 |
| 208 | NA | NA | 2.3 | 7.9 | 103.7 |
| 209 | NA | NA | 1.3 | 7.2 | 93.9 |
| 210 | NA | NA | 1.6 | 7.0 | 102.8 |
| 211 | NA | NA | 3.1 | 4.4 | 91.1 |
| 212 | NA | NA | 0.7 | 4.7 | 90.1 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound represented by structural formula I:

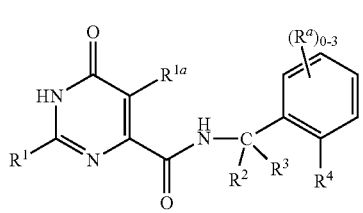

or a pharmaceutically acceptable salt thereof, wherein:

$R^1$ is linked to the pyrimidinone via an atom other than carbon and is selected from the group consisting of halo, —OR, $O(CH_2)_{1-3}OR$, $O(CH_2)_{1-3}N(R)_2$, $O(CH_2)_n C(R)_2 OR$, O-$(CH_2)_n C_{4-10}$heterocyclyl, O-$(CH_2)_{1-3} OC_{6-10}$aryl, O—$C_{6-10}$aryl, $N(R^x)_2$, —$NRC_{5-10}$heterocyclyl, —$NRC_{6-10}$aryl, —$NRC_{3-10}$cycloalkyl, SR, said alkyl, cycloalkyl, heterocyclyl and aryl optionally substituted with one to three groups of $R^a$;

$R^{1a}$ represents H, or $C_{1-6}$ alkyl, said alkyl optionally substituted with OH or halo, $R^2$ and $R^3$ are independently selected from the group consisting of hydrogen, $C_{1-6}$alkyl, $(CH_2)_n CN$, C(O)R, C(O)OR, $CF_3$, —$C_{3-10}$ cycloalkyl, $C_{6-10}$aryl, $C_{5-10}$heteroaryl, said alkyl, cycloalkyl, aryl and heteroaryl optionally substituted with one to three groups of $R^b$;

$R^2$ and $R^3$ can combine with the carbon atom to which they are attached to form a $C_{3-6}$ cycloalkyl, said cycloalkyl optionally interrupted with 1-2 heteroatoms selected from O, S, or N and optionally substituted with one to three groups of $R^b$ $R^4$ represents hydrogen, halo, or $C_{1-6}$ alkyl; or alternatively, $R^2$ and $R^3$ along with the carbon atom to which they are attached and the $R^4$ on the phenyl ring can combine to form a C6-10 bicyclic ring which includes the phenyl ring, said bicyclic ring optionally interrupted with 1-2 heteroatoms selected from O, S, and N and optionally substituted with one to three groups of $R^b$;

R represents H, or $C_{1-6}$ alkyl;

$R^a$ is selected from the group consisting of H, halo, CN, $C_{1-6}$alkyl, $(CH_2)_nOR$, $(O)_pC_{1-4}$haloalkyl, $S(O)_sCF_3$, $S(O)_sR$, $SF_5$, $C_{3-10}$cycloalkyl, said alkyl and cycloalkyl optionally substituted with one to three groups of $R^b$;

$R^b$ is selected from the group consisting of H, halo, $C_{1-6}$alkyl, $SO_2C_{1-6}$alkyl, and $(O)_pC_{1-4}$haloalkyl;

each occurring $R^x$ independently represents H, or $C_{1-6}$ alkyl, or two adjacent $R^x$ groups can combined together with the nitrogen atom to which they are attached to form a $C_{4-10}$heterocyclyl optionally substituted with one to three groups of $R^b$;

n represents 0, 1, 2, 3, or 4;

s represents 0, 1, or 2; and p represents 0 or 1.

2. The compound according to claim 1 or a pharmaceutically acceptable salt thereof wherein $R^{1a}$ is hydrogen.

3. The compound according to claim 1 or a pharmaceutically acceptable salt thereof, wherein $R^1$ is selected from the group consisting of OR, $O(CH_2)_{1-3}OR$, $O(CH_2)_nC(R)_2$ OR, and $O(CH_2)_{1-3}N(R)_2$ and optionally substituted $O-(CH_2)_nC_{4-10}$heterocyclyl said heterocyclyl is selected from the group consisting of oxetanyl, tetrahydrofuranyl, piperidinyl, pyrrolidinyl, morpholinyl, dihydropyrrolopyrazolyl, dihydropyrrolopyrimindyl, tetrahydropyranyl, pyrazolyl, and azetidinyl.

4. The compound according to claim 1 or a pharmaceutically acceptable salt thereof, wherein $R^1$ is selected from the group $N(R^x)_2$, $-NRC_{5-10}$heterocyclyl, $-NRC_{6-10}$aryl, and $NRC_{3-10}$cycloalkyl, said cycloalkyl, aryl and heterocyclyl optionally substituted with one to three groups of $R^a$.

5. The compound according to claim 4 or a pharmaceutically acceptable salt thereof wherein $R^1$ is $N(R^x)_2$ and the two adjacent $R^x$ groups are combined together with the nitrogen atom to which they are attached to form a $C_{4-10}$ heterocyclyl selected from the group consisting of optionally substituted pyrrolidinyl, pyrazolyl, azetidinyl, piperidinyl, morpholinyl, dihydropyrrolopyrazolyl, dihydropyrrolopyrimidinyl, and dihydropyrrolopyridinyl.

6. The compound according to claim 3 or a pharmaceutically acceptable salt thereof wherein $R^1$ is $O-(CH_2)_nC_{4-10}$heterocyclyl, said heterocyclyl optionally substituted with one to three groups of $R^a$.

7. The compound according to claim 1 or a pharmaceutically acceptable salt thereof wherein $R^1$ is selected from the group consisting of $SCH_3$, $-N(CH_3)_2$, $N(CH_3)(CH_2CH_3)$, $N(CH_2CH_3)_2$, $-NH_2$, $-NHCH_3$, NH-cyclobutyl, NH-cyclopentyl, NH-cyclopropyl, NH-pyridyl, $-OR$, $-O$-phenyl, $-O(CH_2)_2OCH_3$, $-O(CH_2)_3OCH_3$, $-O(CH_2)_3OCH(CH_3)_2$, $-O(CH_2)_2N(CH_3)_2$, $-O(CH_2)_2C(CH_3)_2OCH_3$, $-OCH_2$oxetanyl, $-O(CH_2)_4OCH_3$, $-O(CH_2)_3NHCH_3$, $-O$-tetrahydrofuranyl, $-O$-piperidinyl, $-O$-oxetanyl, $-O(CH_2)_3O$phenyl, $O(CH_2)_2CH(CH_3)OCH_3$, $-O$-tetrahydropyranyl, O-pyrrolidinyl, N linked pyrazolyl, N linked azetidinyl, N linked pyrrolidinyl, and N linked piperidinyl, said cyclobutyl, cyclopentyl, cyclopropyl, phenyl, oxetanyl, tetrahydrofuranyl, piperidinyl, tetrahydropyranyl, pyrollidinyl, pyrazolyl, and azetidinyl optionally substituted with one to three groups of $R^a$.

8. The compound according to claim 7 or a pharmaceutically acceptable salt thereof wherein $R^1$ is selected from $N(CH_3)_2$, $N(CH_3)(CH_2CH_3)$, $N(CH_2CH_3)_2$, $-NH_2$, $-NHCH_3$, and optionally substitiuted NH-cyclobutyl, NH-cyclopentyl, NH-cyclopropyl, and NH-pyridyl.

9. The compound according to claim 8 or a pharmaceutically acceptable salt thereof wherein $R^1$ is selected from $N(CH_3)_2$.

10. The compound according to claim 1 or a pharmaceutically acceptable salt thereof wherein one of $R^2$ and $R^3$ is hydrogen or $CH_3$ and the other is $C_{1-6}$alkyl or $C_{3-10}$ cycloalkyl, said alkyl and cycloalkyl optionally substituted with one to three groups of $R^b$.

11. The compound according to claim 10 or a pharmaceutically acceptable salt thereof wherein the $C_{1-6}$ alkyl is selected from the group consisting of $CH_3$, $CH(CH_3)_2$, $CH_2CH_3$, $C(CH_3)_3$ and the optionally substituted $C_{3-10}$ cycloalkyl is selected from cyclopropyl, cyclobutyl, and cyclopentyl.

12. The compound according to claim 11 or a pharmaceutically acceptable salt thereof wherein the $C_{1-6}$ alkyl is selected from the group consisting of $CH_3$, $CH(CH_3)_2$, and $CH_2CH_3$, and the optionally substituted $C_{3-10}$ cycloalkyl is cyclopropyl.

13. The compound according to claim 1 or a pharmaceutically acceptable salt thereof wherein $R^2$ and $R^3$ combine with the carbon atom to which they are attached to form a $C_{3-10}$ cycloalkyl, said cycloalkyl optionally substituted with one to three groups of $R^b$.

14. The compound according to claim 13 wherein the $C_{3-10}$ cycloalkyl is selected from the group consisting of cyclopropyl, cyclobutyl, and cyclopentyl.

15. The compound according to claim 1 or a pharmaceutically acceptable salt thereof wherein $R^a$ is selected from OH, halo, $CH_3$, optionally substituted cyclopropyl, $(CH_2)_n$ $OCH_3$, $CH_2F$, $(CH_2)_nCF_3$, $OCHF_2$, $OCF_3$, $SCH_3$, $SCF_3$, $SF_5$, $SOCF_3$, $SO_2CF_3$, $SO_2CH_3$, $CH_2NH_2$, and $(CH_2)_nN(CH_3)_2$.

16. The compound according claim 1 or a pharmaceutically acceptable salt thereof represented by structural formula II:

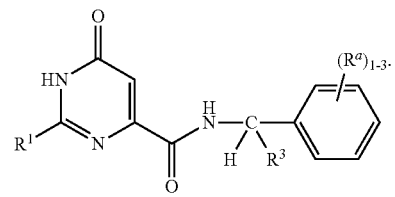

wherein $R^1$ is selected from the group consisting of $-N(CH_3)_2$, $NH_2$, $NHCH_3$, $O(CH_2)_3NHCH_3$, and optionally substituted O-tetrahydrofuranyl, N linked pyrazolyl, N linked pyrrolidinyl, O-pyrrolidinyl, or O-piperidinyl, $R^3$ is selected from the group consisting of $CH_3$, $CH(CH_3)_2$, $CH_2CH_3$, $C(CH_3)_3$ and optionally substituted cyclopropyl, and $R^a$ is selected from the group consisting of $SCF_3$, $CF_3$, $OCF_2$, $OCF_3$, and $CH_2CF_3$.

17. A compound which is:
N-(1-(3-fluoro-4-(trifluoromethyl)phenyl)cyclopropyl)-6-oxo-2-(pyrrolidin-1-yl)-1,6-dihydropyrimidine-4-carboxamide,
(R)-N-(2,2-dimethyl-1-(4-(trifluoromethyl)phenyl)propyl)-2-(dimethylamino)-6-oxo-1,6-dihydropyrimidine-4-carboxamide,
(R)-N-(1-(3-chloro-4-(trifluoromethoxy)phenyl)ethyl)-2-(dimethylamino)-6-oxo-1,6-dihydropyrimidine-4-carboxamide,
(R)-N-(cyclopropyl(4-(pentafluoro-$\lambda^6$-sulfanyl)phenyl)methyl)-2-(dimethylamino)-6-oxo-1,6-dihydropyrimidine-4-carboxamide,
(R)-2-(dimethylamino)-6-oxo-N-(1-(4-(pentafluoro-$\lambda^6$-sulfanyl)phenyl)propyl)-1,6-dihydropyrimidine-4-carboxamide,
(R)-6-oxo-2-(pyrrolidin-1-yl)-N-(1-(4-(trifluoromethyl)phenyl)ethyl)-1,6-dihydropyrimidine-4-carboxamide,
(R)-2-(4-methyl-1H-pyrazol-1-yl)-6-oxo-N-(1-(4-(trifluoromethyl)phenyl)ethyl)-1,6-dihydropyrimidine-4-carboxamide,
(R)-2-(3-methyl-1H-pyrazol-1-yl)-6-oxo-N-(1-(4-(trifluoromethyl)phenyl)ethyl)-1,6-dihydropyrimidine-4-carboxamide,
(R)-6-oxo-2-(1H-pyrazol-1-yl)-N-(1-(4-(trifluoromethyl)phenyl)ethyl)-1,6-dihydropyrimidine-4-carboxamide,
(R)-2-(azetidin-1-yl)-6-oxo-N-(1-(4-(trifluoromethyl)phenyl)ethyl)-1,6-dihydropyrimidine-4-carboxamide,
2-((R)-3-fluoropyrrolidin-1-yl)-6-oxo-N-((R)-1-(4-(trifluoromethyl)phenyl)ethyl)-1,6-dihydropyrimidine-4-carboxamide,
2-((S)-3-fluoropyrrolidin-1-yl)-6-oxo-N-((R)-1-(4-(trifluoromethyl)phenyl)ethyl)-1,6-dihydropyrimidine-4-carboxamide,
(R)-2-(3,3-difluoropyrrolidin-1-yl)-6-oxo-N-(1-(4-(trifluoromethyl)phenyl)ethyl)-1,6-dihydropyrimidine-4-carboxamide,
N-((R)-2,2-dimethyl-1-(4-(trifluoromethyl)phenyl)propyl)-2-(3-(methoxymethyl)pyrrolidin-1-yl)-6-oxo-1,6-dihydropyrimidine-4-carboxamide,
(R)-2-(methylthio)-6-oxo-N-(1-(4-(trifluoromethyl)phenyl)ethyl)-1,6-dihydropyrimidine-4-carboxamide,
(S)-2-(methylthio)-6-oxo-N-(1-(4-(trifluoromethyl)phenyl)ethyl)-1,6-dihydropyrimidine-4-carboxamide,
(R)-2-methoxy-6-oxo-N-(1-(4-(trifluoromethyl)phenyl)ethyl)-1,6-dihydropyrimidine-4-carboxamide,
(R)-2-ethoxy-6-oxo-N-(1-(4-(trifluoromethyl)phenyl)ethyl)-1,6-dihydropyrimidine-4-carboxamide,
(R)-6-oxo-2-phenoxy-N-(1-(4-(trifluoromethyl)phenyl)ethyl)-1,6-dihydropyrimidine-4-carboxamide,
(R)-2-hydroxy-N-(2-methyl-1-(4-((trifluoromethyl)thio)phenyl)propyl)-6-oxo-1,6-dihydropyrimidine-4-carboxamide,
2-(2-Methoxyethoxy)-6-oxo-N-(1-(4-(trifluoromethyl)phenyl)ethyl)-1,6-dihydropyrimidine-4-carboxamide,
(R)-2-(3,4-dimethoxyphenoxy)-6-oxo-N-(1-(4-(trifluoromethyl)phenyl)ethyl)-1,6-dihydropyrimidine-4-carboxamide,
2-(3-Fluoroazetidin-1-yl)-6-oxo-N-{(1R)-1[4-(trifluoromethyl)phenyl]ethyl}-1,6-dihydropyrimidine-4-carboxamide,
2-(3,3-Difluoroazetidin-1-yl)-6-oxo-N-{(1R)-1-[4-(trifluoromethyl)phenyl]ethyl}-1,6-dihydropyrimidine-4-carboxamide,
N-{(R)-cyclopropyl[3-fluoro-4-(trifluoromethoxy)phenyl]methyl}-6-oxo-2-pyrrolidin-1-yl-1,6-dihydropyrimidine-4-carboxamide,
N-{(R)-cyclopropyl[4-(trifluoromethyl)phenyl]methyl}-6-oxo-2-pyrrolidin-1-yl-1,6-dihydropyrimidine-4-carboxamide,
N-[(R)-cyclopropyl{4-[(trifluoromethyl)sulfanyl]phenyl}methyl]-6-oxo-2-pyrrolidin-1-yl-1,6-dihydropyrimidine-4-carboxamide,
6-oxo-2-pyrrolidin-1-yl-N-{(1R)-1-[4-(trifluoromethoxy)phenyl]ethyl}-1,6-dihydropyrimidine-4-carboxamide,
N-[(1R)-1-{3-fluoro-4-[(trifluoromethyl)sulfanyl]phenyl}propyl]-6-oxo-2-pyrrolidin-1-yl-1,6-dihydropyrimidine-4-carboxamide,
2-(dimethylamino)-N-[(1R)-2-methyl-1-{4-[(trifluoromethyl)sulfanyl]phenyl}propyl]-6-oxo-1,6-dihydropyrimidine-4-carboxamide,
2-(dimethylamino)-N-{(1R)-2,2-dimethyl-1-[4-(2,2,2-trifluoroethyl)phenyl]propyl}-6-oxo-1,6-dihydropyrimidine-4-carboxamide,
N-{(R)-cyclopropyl[4-(difluoromethoxy)phenyl]methyl}-2-(dimethylamino)-6-oxo-1,6-dihydropyrimidine-4-carboxamide,
N-{(1R)-1-[4-(difluoromethoxy)phenyl]-2-methylpropyl}-2-(dimethylamino)-6-oxo-1,6-dihydropyrimidine-4-carboxamide,
N-{(1R)-1-[4-(difluoromethoxy)phenyl]-2,2-dimethylpropyl}-2-(dimethylamino)-6-oxo-1,6-dihydropyrimidine-4-carboxamide,
N-[(1R)-1-(4-cyclopropylphenyl)-2,2-dimethylpropyl]-2-(dimethylamino)-6-oxo-1,6-dihydropyrimidine-4-carboxamide,
N-{(1R)-1-[2,5-difluoro-4-(trifluoromethyl)phenyl]ethyl}-2-(dimethylamino)-6-oxo-1,6-dihydropyrimidine-4-carboxamide,
2-(dimethylamino)-N-{(1R)-1-[2-fluoro-4-(trifluoromethyl)phenyl]-2,2-dimethylpropyl}-6-oxo-1,6-dihydropyrimidine-4-carboxamide,
2-(dimethylamino)-N-{(1R)-2,2-dimethyl-1-[4-(pentafluoro-$\lambda^6$-sulfanyl)phenyl]propyl}-6-oxo-1,6-dihydropyrimidine-4-carboxamide,
2-(dimethylamino)-N-{1,2-dimethyl-1-[4-(pentafluoro-$\lambda^6$-sulfanyl)phenyl]propyl}-6-oxo-1,6-dihydropyrimidine-4-carboxamide,
N-[(1R)-1-(4-cyclopropyl-3-fluorophenyl)ethyl]-2-(dimethylamino)-6-oxo-1,6-dihydropyrimidine-4-carboxamide,
2-(dimethylamino)-N-[(R)-[3-fluoro-4-(trifluoromethyl)phenyl](1-methylcyclopropyl)methyl]-6-oxo-1,6-dihydropyrimidine-4-carboxamide,
2-(dimethylamino)-N-{(R)-(1-methylcyclopropyl)[4-(trifluoromethyl)phenyl]methyl}-6-oxo-1,6-dihydropyrimidine-4-carboxamide,
N-[(R)-(4-tert-butylphenyl)(1-methylcyclopropyl)methyl]-2-(dimethylamino)-6-oxo-1,6-dihydropyrimidine-4-carboxamide,
2-(dimethylamino)-6-oxo-N-{1-[4-(pentafluoro-$\lambda^6$-sulfanyl)phenyl]cyclopropyl}-1,6-dihydropyrimidine-4-carboxamide,
N-[1-(4-tert-butylphenyl)cyclopropyl]-2-(dimethylamino)-6-oxo-1,6-dihydropyrimidine-4-carboxamide,
2-(dimethylamino)-N-{(1R)-2-methyl-1-[4-(trifluoromethyl)phenyl]propyl}-6-oxo-1,6-dihydropyrimidine-4-carboxamide,
N-{(1R)-1-[4-(difluoromethoxy)-3-fluorophenyl]-2-methylpropyl}-2-(dimethylamino)-6-oxo-1,6-dihydropyrimidine-4-carboxamide,
2-(dimethylamino)-N-{1-[2-fluoro-4-(trifluoromethyl)phenyl]cyclopropyl}-6-oxo-1,6-dihydropyrimidine-4-carboxamide, N-[1-(4-tert-butoxyphenyl)cyclopropyl]-2-(dimethylamino)-6-oxo-1,6-dihydropyrimidine-4-carboxamide, 2-(dimethylamino)-6-oxo-N-{1-[4-(2,2,2-trifluoroethyl)phenyl]cyclopropyl}-1,6-dihydropyrimidine-4-carboxamide, N-{1-[4-(difluoromethoxy)phenyl]cyclopropyl}-2-(dimethylamino)-6-oxo-1,6-dihydropyrimidine-4-carboxamide, N-{(R)-cyclopropyl[4-(difluoromethoxy)-3-fluorophenyl]methyl}-2-(dimethylamino)-6-oxo-1,6-dihydropyrimidine-4-carboxamide, N-{(1R)-1-[4-(difluoromethoxy)-3-fluorophenyl]-2,2-dimethylpropyl}-2-(dimethylamino)-6-oxo-1,6-dihydropyrimidine-4-carboxamide, N-[(R)-[4-(difluoromethoxy)-3-fluorophenyl](1-methylcyclopropyl)methyl]-2-(dimethylamino)-6-oxo-1,6-dihydropyrimidine-4-carboxamide, N-[(R)-cyclopropyl(4-cyclopropyl-3-fluorophenyl)methyl]-2-(dimethylamino)-6-oxo-1,6-dihydropyrimidine-4-carboxamide, 2-(dimethylamino)-N-{(R)-(1-methylcyclopropyl)[4-(pentafluoro-$\lambda^6$-sulfanyl)phenyl]methyl}-6-oxo-1,6-dihydropyrimidine-4-carboxamide, N-[(1R)-1-(4-cyclopropyl-3-fluorophenyl)-2,2-dimethylpropyl]-2-(dimethylamino)-6-oxo-1,6-dihydropyrimidine-4-carboxamide, N-[(R)-[4-(difluoromethyl)-3-fluorophenyl](1-methylcyclopropyl)methyl]-2-(dimethylamino)-6-oxo-1,6-dihydropyrimidine-4-carboxamide, N-{(1R)-1-[4-(difluoromethyl)phenyl]-2,2-dimethylpropyl}-2-(dimethylamino)-6-oxo-1,6-dihydropyrimidine-4-carboxamide, N-[(R)-[4-(difluoromethyl)phenyl](1-methylcyclopropyl)methyl]-2-(dimethylamino)-6-oxo-1,6-dihydropyrimidine-4-carboxamide, N-{(1R)-1-[4-(difluoromethyl)-3-fluorophenyl]-2,2-dimethylpropyl}-2-(dimethylamino)-6-oxo-1,6-dihydropyrimidine-4-carboxamide, N-{(1R)-1-[4-(difluoromethyl)phenyl]-2-methylpropyl}-2-(dimethylamino)-6-oxo-1,6-dihydropyrimidine-4-carboxamide, N-{(R)-cyclopropyl[4-(difluoromethyl)phenyl]methyl}-2-(dimethylamino)-6-oxo-1,6-dihydropyrimidine-4-carboxamide, N-{(1R)-1-[4-(difluoromethyl)-3-fluorophenyl]-2-methylpropyl}-2-(dimethylamino)-6-oxo-1,6-dihydropyrimidine-4-carboxamide, N-{(R)-cyclopropyl[4-(difluoromethyl)-3-fluorophenyl]methyl}-2-(dimethylamino)-6-oxo-1,6-dihydropyrimidine-4-carboxamide, N-{(1R)-1-[4-(difluoromethyl)phenyl]propyl}-2-(dimethylamino)-6-oxo-1,6-dihydropyrimidine-4-carboxamide, N-{(1R)-1-[4-(difluoromethyl)-3-fluorophenyl]propyl}-2-(dimethylamino)-6-oxo-1,6-dihydropyrimidine-4-carboxamide, N-{1-[4-(difluoromethyl)-3-fluorophenyl]-1-methylethyl}-2-(dimethylamino)-6-oxo-1,6-dihydropyrimidine-4-carboxamide, N-{1-[4-(difluoromethyl)-3-fluorophenyl]cyclopropyl}-2-(dimethylamino)-6-oxo-1,6-dihydropyrimidine-4-carboxamide, N-[(R)-(4-cyclopropylphenyl)(1-methylcyclopropyl)methyl]-2-(dimethylamino)-6-oxo-1,6-dihydropyrimidine-4-carboxamide, 2-(dimethylamino)-N-{(1S)-2,2-dimethyl-1-[4-(trifluoromethyl)phenyl]propyl}-6-oxo-1,6-dihydropyrimidine-4-carboxamide, N-{(1R)-1-[4-(difluoromethyl)-2-fluorophenyl]-2,2-dimethylpropyl}-2-(dimethylamino)-6-oxo-1,6-dihydropyrimidine-4-carboxamide, N-{(1R)-1-[4-(1,1-difluoroethyl)phenyl]ethyl}-2-(dimethylamino)-6-oxo-1,6-dihydropyrimidine-4-carboxamide, N-{(1R)-1-[4-(1,1-difluoroethyl)phenyl]-2-methylpropyl}-2-(dimethylamino)-6-oxo-1,6-dihydropyrimidine-4-carboxamide, N-{(1R)-1-[4-(1,1-difluoroethyl)phenyl]-2,2-dimethylpropyl}-2-(dimethylamino)-6-oxo-1,6-dihydropyrimidine-4-carboxamide, N-{(1R)-1-[4-(1,1-difluoroethyl)-3-fluorophenyl]-2-methylpropyl}-2-(dimethylamino)-6-oxo-1,6-dihydropyrimidine-4-carboxamide, 2-(dimethylamino)-N-{1-methyl-1-[2-methyl-4-(trifluoromethyl)phenyl]ethyl}-6-oxo-1,6-dihydropyrimidine-4-carboxamide, 2-(dimethylamino)-N-{1-[2-methoxy-4-(trifluoromethyl)phenyl]-1-methylethyl}-6-oxo-1,6-dihydropyrimidine-4-carboxamide, N-{1-[2-chloro-4-(trifluoromethyl)phenyl]-1-methylethyl}-2-(dimethylamino)-6-oxo-1,6-dihydropyrimidine-4-carboxamide, 2-(dimethylamino)-N-{1-[2-fluoro-4-(trifluoromethoxy)phenyl]-1-methylethyl}-6-oxo-1,6-dihydropyrimidine-4-carboxamide, 2-(dimethylamino)-N-{1-[2-fluoro-4-(trifluoromethyl)phenyl]-1-methylethyl}-6-oxo-1,6-dihydropyrimidine-4-carboxamide, 2-(dimethylamino)-N-{(1R)-1-[2-fluoro-4-(trifluoromethoxy)phenyl]ethyl}-6-oxo-1,6-dihydropyrimidine-4-carboxamide, N-{(1R)-1-[2,3-difluoro-4-(trifluoromethyl)phenyl]ethyl}-2-(dimethylamino)-6-oxo-1,6-dihydropyrimidine-4-carboxamide, N-[(R)-[3-chloro-4-(trifluoromethoxy)phenyl](cyclopropyl)methyl]-2-(dimethylamino)-6-oxo-1,6-dihydropyrimidine-4-carboxamide, N-{(1R)-1-[3-chloro-4-(trifluoromethoxy)phenyl]-2-methylpropyl}-2-(dimethylamino)-6-oxo-1,6-dihydropyrimidine-4-carboxamide, 2-(dimethylamino)-6-oxo-N-{(1R)-1-[4-(trifluoromethoxy)phenyl]ethyl}-1,6-dihydropyrimidine-4-carboxamide, 2-(dimethylamino)-6-oxo-N-[(1R)-1-{4-[(trifluoromethyl)sulfanyl]phenyl}propyl]-1,6-dihydropyrimidine-4-carboxamide, 2-(dimethylamino)-6-oxo-N-{(1R)-1-[4-(pentafluoro-$\lambda^6$-sulfanyl)phenyl]ethyl}-1,6-dihydropyrimidine-4-carboxamide, 2-(dimethylamino)-N-{(1R)-1-[3-fluoro-4-(trifluoromethoxy)phenyl]ethyl}-6-oxo-1,6-dihydropyrimidine-4-carboxamide, 2-(dimethylamino)-N-{(1R)-2-methyl-1-[4-(trifluoromethoxy)phenyl]propyl}-6-oxo-1,6-dihydropyrimidine-4-carboxamide, 2-(dimethylamino)-6-oxo-N-(1-{4-[(trifluoromethyl)sulfanyl]phenyl}cyclopropyl)-1,6-dihydropyrimidine-4-carboxamide, 2-(dimethylamino)-N-{1-[3-fluoro-4-(trifluoromethyl)phenyl]-1-methylethyl}-6-oxo-1,6-dihydropyrimidine-4-carboxamide, 2-(dimethylamino)-N-{1-[3-fluoro-4-(trifluoromethyl)phenyl]cyclopropyl}-6-oxo-1,6-dihydropyrimidine-4-carboxamide, N-{(1R)-2-methyl-1-[4-(trifluoromethyl)phenyl]propyl}-6-oxo-2-pyrrolidin-1-yl-1,6-dihydropyrimidine-4-carboxamide, 2-(dimethylamino)-N-[(1R)-1-{3-fluoro-4-[(trifluoromethyl)sulfanyl]phenyl}ethyl]-6-oxo-1,6-dihydropyrimidine-4-carboxamide, N-[(R)-cyclopropyl{3-fluoro-4-[(trifluoromethyl)sulfanyl]phenyl}methyl]-2-(dimethylamino)-6-oxo-1,6-dihydropyrimidine-4-carboxamide, 2-(dimethylamino)-N-[(1R)-1-{3-fluoro-4-[(trifluoromethyl)sulfanyl]phenyl}propyl]-6-oxo-1,6-dihydropyrimidine-4-carboxamide, N-{(R)-cyclopropyl[4-(pentafluoro-$\lambda^6$-sulfanyl)phenyl]methyl}-6-oxo-2-pyrrolidin-1-yl-1,6-dihydropyrimidine-4-carboxamide, 2-(dimethylamino)-N-{(1R)-2,2-dimethyl-1-[4-(trifluoromethoxy)phenyl]propyl}-6-oxo-1,6-dihydropyrimidine-4-carboxamide, 2-(dimethylamino)-N-{(1R)-1-[3-fluoro-4-(trifluoromethoxy)phenyl]-2,2-dimethylpropyl}-6-oxo-1,6-dihydropyrimidine-4-carboxamide, 2-(dimethylamino)-N-{(1R)-1-[3-fluoro-4-(trifluoromethyl)phenyl]-2,2-dimethylpropyl}-6-oxo-1,6-dihydropyrimidine-4-carboxamide, 2-(dimethylamino)-N-[(1R)-2,2-dimethyl-1-{4-[(trifluoromethyl)sulfanyl]phenyl}propyl]-6-oxo-1,6-dihydropyrimidine-4-carboxamide, 2-(dimethylamino)-N-{(1R)-1-[3-fluoro-4-(trifluoromethoxy)phenyl]propyl}-6-oxo-1,6-dihydropyrimidine-4-carboxamide, 2-(dimethylamino)-6-oxo-N-{(1R)-1-[4-(trifluoromethoxy)phenyl]propyl}-1,6-dihydropyrimidine-4-carboxamide, 2-(dimethylamino)-N-{(1R)-1-[3-fluoro-4-(trifluoromethyl)phenyl]propyl}-6-oxo-1,6-dihydropyrimidine-4-carboxamide, N-{(R)-cyclopropyl[4-(trifluoromethoxy)phenyl]methyl}-2-(dimethylamino)-6-oxo-1,6-dihydropyrimidine-4-carboxamide, N-{(R)-cyclopropyl[4-(trifluoromethyl)phenyl]methyl}-2-(dimethylamino)-6-oxo-1,6-dihydropyrimidine-4-carboxamide, N-{(R)-cyclopropyl[3-fluoro-4-(trifluoromethyl)phenyl]methyl}-2-(dimethylamino)-6-oxo-1,6-dihydropyrimidine-4-carboxamide, N-{(R)-cyclopropyl[3-fluoro-4-(trifluoromethoxy)phenyl]methyl}-2-(dimethylamino)-6-oxo-1,6-dihydropyrimidine-4-carboxamide, N-[(R)-cyclopropyl{4-[(trifluoromethyl)sulfanyl]phenyl}methyl]-2-(dimethylamino)-6-oxo-1,6-dihydropyrimidine-4-carboxamide, 2-(dimethylamino)-N-{(1R)-1-[3-fluoro-4-(trifluoromethyl)phenyl]-2-methylpropyl}-6-oxo-1,6-dihydropyrimidine-4-carboxamide, N-[(R)-cyclopropyl(4-cyclopropylphenyl)methyl]-6-oxo-2-pyrrolidin-1-yl-1,6-dihydropyrimidine-4-carboxamide, N-{(R)-cyclopropyl[4-(trifluoromethoxy)phenyl]methyl}-6-oxo-2-pyrrolidin-1-yl-1,6-dihydropyrimidine-4-carboxamide, N-[(R)-cyclopropyl(4-cyclopropylphenyl)methyl]-2-(dimethylamino)-6-oxo-1,6-dihydropyrimidine-4-carboxamide, (R)-2-(dimethylamino)-N-(1-(4-(pentafluorothio)-2-fluorophenyl)ethyl)-6-oxo-1,6-dihydrop-yrimidine-4-carboxamide, (S)-2-(dimethylamino)-N-(1-(4-(pentafluorothio)-2-fluorophenyl)ethyl)-6-oxo-1,6-dihydropy-rimidine-4-carboxamide, 2-(Dimethylamino)-N-{1-methyl-1-[4-(pentafluoro-$\lambda^6$-sulfanyl)phenyl]ethyl}-6-oxo-1,6-dihydropyrimidine-4-carboxamide, (S)-2-(dimethylamino)-N-[{3-fluoro-4-[(trifluoromethyl)sulfanyl]phenyl}(1-methylcyclopropyl)methyl]-6-oxo-1,6-dihydropyrimidine-4-carboxamide, (R)-2-(dimethylamino)-N-[{3-fluoro-4-[(trifluoromethyl)sulfanyl]phenyl}(1-methylcyclopropyl)methyl]-6-oxo-1,6-dihydropyrimidine-4-carboxamide, (S)-2-(dimethylamino)-6-oxo-N-{1-[4-(2,2,2-trifluoro-1,1-dimethylethyl)phenyl]ethyl}-1,6-dihydropyrimidine-4-carboxamide, (R)-2-(dimethylamino)-6-oxo-N-{1-[4-(2,2,2-trifluoro-1,1-dimethylethyl)phenyl]ethyl}-1,6-dihydropyrimidine-4-carboxamide, (S)-2-(dimethylamino)-N-{1-[3-fluoro-4-(1-methylcyclopropyl)phenyl]-2,2-dimethylpropyl}-6-oxo-1,6-dihydropyrimidine-4-carboxamide, (R)-2-(dimethylamino)-N-{1-[3-fluoro-4-(1-methylcyclopropyl)phenyl]-2,2-dimethylpropyl}-6-oxo-1,6-dihydropyrimidine-4-carboxamide, (S)-2-(dimethylamino)-6-oxo-N-[1-{4-[1-(trifluoromethyl)cyclopropyl]phenyl}ethyl]-1,6-dihydropyrimidine-4-carboxamide, (R)-2-(dimethylamino)-6-oxo-N-[1-{4-[1-(trifluoromethyl)cyclopropyl]phenyl}ethyl]-1,6-dihydropyrimidine-4-carboxamide, (S)-2-(dimethylamino)-N-{1-[2-fluoro-4-(pentafluoro-$\lambda^6$-sulfanyl)phenyl]-2,2-dimethylpropyl}-6-oxo-1,6-dihydropyrimidine-4-carboxamide, (R)-2-(dimethylamino)-N-{1-[2-fluoro-4-(pentafluoro-$\lambda^6$-sulfanyl)phenyl]-2,2-dimethylpropyl}-6-oxo-1,6-dihydropyrimidine-4-carboxamide, (S)-2-(dimethylamino)-N-{1-[2-fluoro-4-(trifluoromethyl)phenyl]-1-methylpropyl}-6-oxo-1,6-dihydropyrimidine-4-carboxamide, (R)-2-(dimethylamino)-N-{1-[2-fluoro-4-(trifluoromethyl)phenyl]-1-methylpropyl}-6-oxo-1,6-dihydropyrimidine-4-carboxamide, 6-oxo-2-piperidin-1-yl-N-{(1R)-1-[4-(trifluoromethyl)phenyl]ethyl}-1,6-dihydropyrimidine-4-carboxamide, 2-morpholin-4-yl-6-oxo-N-{(1R)-1-[4-(trifluoromethyl)phenyl]ethyl}-1,6-dihydropyrimidine-4-carboxamide, 2-(dimethylamino)-6-oxo-N-{(1R)-1-[4-(trifluoromethyl)phenyl]ethyl}-1,6-dihydropyrimidine-4-carboxamide, 2-amino-6-oxo-N-{(1R)-1-[4-(trifluoromethyl)phenyl]ethyl}-1,6-dihydropyrimidine-4-carboxamide, 2-(methylamino)-6-oxo-N-{(1R)-1-[4-(trifluoromethyl)phenyl]ethyl}-1,6-dihydropyrimidine-4-carboxamide, 6-oxo-2-(pyridin-2-ylamino)-N-{(1R)-1-[4-(trifluoromethyl)phenyl]ethyl}-1,6-dihydropyrimidine-4-carboxamide, 2-[2-(methylsulfonyl)-2,6-dihydropyrrolo[3,4-c]pyrazol-5(4H)-yl]-6-oxo-N-{(1R)-1-[4-(trifluoromethyl)phenyl]ethyl}-1,6-dihydropyrimidine-4-carboxamide, 2-(cyclobutylamino)-6-oxo-N-{(1R)-1-[4-(trifluoromethyl)phenyl]ethyl}-1,6-dihydropyrimidine-4-carboxamide, 2-(cyclopentylamino)-6-oxo-N-{(1R)-1-[4-(trifluoromethyl)phenyl]ethyl}-1,6-dihydropyrimidine-4-carboxamide, 2-(cyclopropylamino)-6-oxo-N-{(1R)-1-[4-(trifluoromethyl)phenyl]ethyl}-1,6-dihydropyrimidine-4-carboxamide, 2-[ethyl(methyl)amino]-6-oxo-N-{(1R)-1-[4-(trifluoromethyl)phenyl]ethyl}-1,6-dihydropyrimidine-4-carboxamide, 2-(diethylamino)-6-oxo-N-{(1R)-1-[4-(trifluoromethyl)phenyl]ethyl}-1,6-dihydropyrimidine-4-carboxamide, 2-(dimethylamino)-6-oxo-N-[(1R)-1-{4-[(trifluoromethyl)sulfanyl]phenyl}ethyl]-1,6-dihydropyrimidine-4-carboxamide, 2-(methylamino)-6-oxo-N-[(1R)-1-{4-[(trifluoromethyl)sulfanyl]phenyl}ethyl]-1,6-dihydropyrimidine-4-carboxamide, 2-amino-6-oxo-N-[(1R)-1-{4-[(trifluoromethyl)sulfanyl]phenyl}ethyl]-1,6-dihydropyrimidine-4-carboxamide, 6-oxo-2-pyrrolidin-1-yl-N-[(1R)-1-{4-[(trifluoromethyl)sulfanyl]phenyl}ethyl]-1,6-dihydropyrimidine-4-carboxamide, N-[(1R)-2-methyl-1-{4-[(trifluoromethyl)sulfanyl]phenyl}propyl]-6-oxo-2-pyrrolidin-1-yl-1,6-dihydropyrimidine-4-carboxamide, 2-azetidin-1-yl-N-[(1R)-2-methyl-1-{4-[(trifluoromethyl)sulfanyl]phenyl}propyl]-6-oxo-1,6-dihydropyrimidine-4-carboxamide, 2-(dimethylamino)-N-{(1R)-1-[3-fluoro-4-(trifluoromethoxy)phenyl]-2-methylpropyl}-6-oxo-1,6-dihydropyrimidine-4-carboxamide, 2-(dimethylamino)-N-[(1R)-1-{3-fluoro-4-[(trifluoromethyl)sulfanyl]phenyl}-2-methylpropyl]-6-oxo-1,6-dihydropyrimidine-4-carboxamide, N-{(1R)-1-[3-fluoro-4-(trifluoromethoxy)phenyl]-2-methylpropyl}-2-(methylamino)-6-oxo-1,6-dihydropyrimidine-4-carboxamide, 2-amino-N-{(1R)-1-[3-fluoro-4-(trifluoromethoxy)phenyl]-2-methylpropyl}-6-oxo-1,6-dihydropyrimidine-4-carboxamide, 2-(methylamino)-N-[(1R)-2-methyl-1-{4-[(trifluoromethyl)sulfanyl]phenyl}propyl]-6-oxo-1,6-dihydropyrimidine-4-carboxamide, 2-amino-N-[(1R)-2-methyl-1-{4-[(trifluoromethyl)sulfanyl]phenyl}propyl]-6-oxo-1,6-dihydropyrimidine-4-carboxamide, N-[(1R)-1-{3-fluoro-4-[(trifluoromethyl)sulfanyl]phenyl}-2-methylpropyl]-2-(methylamino)-6-oxo-1,6-dihydropyrimidine-4-carboxamide, 2-amino-N-[(1R)-1-{3-fluoro-4-[(trifluoromethyl)sulfanyl]phenyl}-2-methylpropyl]-6-oxo-1,6-dihydropyrimidine-4-carboxamide, 2-amino-N-{(1R)-2,2-dimethyl-1-[4-(trifluoromethyl)phenyl]propyl}-6-oxo-1,6-dihydropyrimidine-4-carboxamide, N-{(1R)-2,2-dimethyl-1-[4-(trifluoromethyl)phenyl]propyl}-2-(methylamino)-6-oxo-1,6-dihydropyrimidine-4-carboxamide, 2-(2-methyl-5,7-dihydro-6H-pyrrolo[3,4-d]pyrimidin-6-yl)-6-oxo-N-{(1R)-1-[4-(trifluoromethyl)phenyl]ethyl}-1,6-dihydropyrimidine-4-carboxamide, 2-(1,3-dihydro-2H-pyrrolo[3,4-c]pyridin-2-yl)-6-oxo-N-{(1R)-1-[4-(trifluoromethyl)phenyl]ethyl}-1,6-dihydropyrimidine-4-carboxamide, 2-(5,7-dihydro-6H-pyrrolo[3,4-d]pyrimidin-6-yl)-6-oxo-N-{(1R)-1-[4-(trifluoromethyl)phenyl]ethyl}-1,6-dihydropyrimidine-4-carboxamide, 2-[(3S)-3-fluoropyrrolidin-1-yl]-N-{(1R)-1-[3-fluoro-4-(trifluoromethoxy)phenyl]-2-methylpropyl}-6-oxo-1,6-dihydropyrimidine-4-carboxamide, 2-[(3R)-3-fluoropyrrolidin-1-yl]-N-{(1R)-1-[3-fluoro-4-(trifluoromethoxy)phenyl]-2-methylpropyl}-6-oxo-1,6-dihydropyrimidine-4-carboxamide, 2-(3-fluoroazetidin-1-yl)-N-{(1R)-1-[3-fluoro-4-(trifluoromethoxy)phenyl]-2-methylpropyl}-6-oxo-1,6-dihydropyrimidine-4-carboxamide, 2-[(3S)-3-fluoropyrrolidin-1-yl]-N-{(1R)-1-{3-fluoro-4-[(trifluoromethyl)sulfanyl]phenyl}-2-methylpropyl]-6-oxo-1,6-dihydropyrimidine-4-carboxamide, N-{(1R)-1-[3-fluoro-4-(trifluoromethoxy)phenyl]-2-methylpropyl}-2-[(3R)-3-hydroxypyrrolidin-1-yl]-6-oxo-1,6-dihydropyrimidine-4-carboxamide, N-{(R)-cyclopropyl[4-(trifluoromethyl)phenyl]methyl}-2-[(3S)-3-fluoropyrrolidin-1-yl]-6-oxo-1,6-dihydropyrimidine-4-carboxamide, 2-[(3S)-3-fluoropyrrolidin-1-yl]-N-{(1R)-1-[3-fluoro-4-(trifluoromethyl)phenyl]-2-methylpropyl}-6-oxo-1,6-dihydropyrimidine-4-carboxamide, N-{(1R)-2,2-dimethyl-1-[4-(trifluoromethyl)phenyl]propyl}-2-[(3S)-3-fluoropyrrolidin-1-yl]-6-oxo-1,6-dihydropyrimidine-4-carboxamide, N-{(1R)-2,2-dimethyl-1-[4-(trifluoromethyl)phenyl]propyl}-2-[(3S)-3-methoxypyrrolidin-1-yl]-6-oxo-1,6-dihydropyrimidine-4-carboxamide, N-{(1R)-2,2-dimethyl-1-[4-(trifluoromethyl)phenyl]propyl}-2-[(3R)-3-methoxypyrrolidin-1-yl]-6-oxo-1,6-dihydropyrimidine-4-carboxamide, (R)-2-(dimethylamino)-N-{1,2-dimethyl-1-[4-(pentafluoro-$\lambda^6$-sulfanyl)phenyl]propyl}-6-oxo-1,6-dihydropyrimidine-4-carboxamide, (S)-2-(dimethylamino)-N-{1,2-dimethyl-1-[4-(pentafluoro-$\lambda^6$-sulfanyl)phenyl]propyl}-6-oxo-1,6-dihydropyrimidine-4-carboxamide, 2-(dimethylamino)-N-{2-methyl-1-[4-(trifluoromethyl)phenyl]cyclopropyl}-6-oxo-1,6-dihydropyrimidine-4-carboxamide (cis, enantiomer A), 2-(dimethylamino)-N-{2-methyl-1-[4-(trifluoromethyl)phenyl]cyclopropyl}-6-oxo-1,6-dihydropyrimidine-4-carboxamide (cis, enantiomer B), (R)-N-{(1R)-2,2-dimethyl-1-[4-(trifluoromethyl)phenyl]propyl}-2-[3-(methoxymethyl)pyrrolidin-1-yl]-6-oxo-1,6-dihydropyrimidine-4-carboxamide, (S)-N-{(1R)-2,2-dimethyl-1-[4-(trifluoromethyl)phenyl]propyl}-2-[3-(methoxymethyl)pyrrolidin-1-yl]-6-oxo-1,6-dihydropyrimidine-4-carboxamide, 6-oxo-2-propoxy-N-{(1R)-1-[4-(trifluoromethyl)phenyl]ethyl}-1,6-dihydropyrimidine-4-carboxamide, 2-(3-methoxypropoxy)-6-oxo-N-{1-[4-(trifluoromethyl)phenyl]ethyl}-1,6-dihydropyrimidine-4-carboxamide, 2-[(1-methylpiperidin-3-yl)oxy]-6-oxo-N-{1-[4-(trifluoromethyl)phenyl]ethyl}-1,6-dihydropyrimidine-4-carboxamide, 2-[3-(1-methylethoxy)propoxy]-6-oxo-N-{1-[4-(trifluoromethyl)phenyl]ethyl}-1,6-dihydropyrimidine-4-carboxamide, 2-(3-methoxy-3-methylbutoxy)-6-oxo-N-{1-[4-(trifluoromethyl)phenyl]ethyl}-1,6-dihydropyrimidine-4-carboxamide, 2-[2-(methylamino)ethoxy]-6-oxo-N-{1-[4-(trifluoromethyl)phenyl]ethyl}-1,6-dihydropyrimidine-4-carboxamide, 6-oxo-2-(tetrahydrofuran-3-yloxy)-N-{1-[4-(trifluoromethyl)phenyl]ethyl}-1,6-dihydropyrimidine-4-carboxamide, 2-[3-(4-methoxyphenoxy)propoxy]-6-oxo-N-{1-[4-(trifluoromethyl)phenyl]ethyl}-1,6-dihydropyrimidine-4-carboxamide, N-[(1R)-1-(4-cyclopropyl-3-fluorophenyl)-2-methylpropyl]-2-(dimethylamino)-6-oxo-1,6-dihydropyrimidine-4-carboxamide, 2-(dimethylamino)-6-oxo-N-{phenyl[4-(trifluoromethyl)phenyl]methyl}-1,6-dihydropyrimidine-4-carboxamide, 2-(dimethylamino)-6-oxo-N-{pyridin-4-yl[4-(trifluoromethyl)phenyl]methyl}-1,6-dihydropyrimidine-4-carboxamide, 2-(dimethylamino)-6-oxo-N-{2-oxo-1-[4-(trifluoromethyl)phenyl]propyl}-1,6-dihydropyrimidine-4-carboxamide, 2-(dimethylamino)-6-oxo-N-[(4R)-7-(trifluoromethyl)-3,4-dihydro-1H-isochromen-4-yl]-1,6-dihydropyrimidine-4-carboxamide, N-{cyano[4-(trifluoromethyl)phenyl]methyl}-2-(dimethylamino)-6-oxo-1,6-dihydropyrimidine-4-carboxamide, 2-(dimethylamino)-6-oxo-N-{1-[4-(trifluoromethoxy)phenyl]cyclobutyl}-1,6-dihydropyrimidine-4-carboxamide, 2-(dimethylamino)-6-oxo-N-{1-[4-(trifluoromethyl)phenyl]cyclopentyl}-1,6-dihydropyrimidine-4-carboxamide, N-{2-cyano-1-[4-(trifluoromethyl)phenyl]ethyl}-2-(dimethylamino)-6-oxo-1,6-dihydropyrimidine-4-carboxamide, 2-(dimethylamino)-6-oxo-N-[(1S)-6-(trifluoromethyl)-1,2,3,4-tetrahydronaphthalen-1-yl]-1,6-dihydropyrimidine-4-carboxamide, methyl({[2-(dimethylamino)-6-oxo-1,6-dihydropyrimidin-4-yl]carbonyl}amino)[4-(trifluoromethyl)phenyl]acetate, 2-(dimethylamino)-6-oxo-N-{2,2,2-trifluoro-1-[4-(trifluoromethyl)phenyl]ethyl}-1,6-dihydropyrimidine-4-carboxamide, 2-(dimethylamino)-6-oxo-N-{3-[4-(trifluoromethyl)phenyl]oxetan-3-yl}-1,6-dihydropyrimidine-4-carboxamide, or a pharmaceutically acceptable salt thereof.

18. A pharmaceutical composition which comprises a pharmaceutically acceptable carrier and a compound of claim 1 or a pharmaceutically acceptable salt or solvate thereof.

\* \* \* \* \*